(12) United States Patent
Ducat et al.

(10) Patent No.: US 11,168,329 B2
(45) Date of Patent: *Nov. 9, 2021

(54) GENETIC CONTROL OF CELL SIZE

(71) Applicant: Board of Trustees of Michigan State University, East Lansing, MI (US)

(72) Inventors: Daniel Christopher Ducat, Lansing, MI (US); Katherine Osteryoung, Williamston, MI (US); Joshua Scott MacCready, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/783,380

(22) Filed: Feb. 6, 2020

(65) Prior Publication Data

US 2020/0181628 A1 Jun. 11, 2020

Related U.S. Application Data

(63) Continuation of application No. 15/683,411, filed on Aug. 22, 2017, now Pat. No. 10,590,426.

(60) Provisional application No. 62/377,964, filed on Aug. 22, 2016.

(51) Int. Cl.
| | |
|---|---|
| *A61K 39/02* | (2006.01) |
| *C12N 15/74* | (2006.01) |
| *C07K 14/195* | (2006.01) |

(52) U.S. Cl.
CPC .......... *C12N 15/74* (2013.01); *C07K 14/195* (2013.01)

(58) Field of Classification Search
None
See application file for complete search history.

(56) References Cited

U.S. PATENT DOCUMENTS

| | | | |
|---|---|---|---|
| 4,551,433 | A | 11/1985 | DeBoer |
| 4,689,406 | A | 8/1987 | Banks et al. |
| 4,738,921 | A | 4/1988 | Belagaje et al. |
| 6,316,224 | B1 | 11/2001 | Xia |
| 2018/0051293 | A1 | 2/2018 | Ducat et al. |

FOREIGN PATENT DOCUMENTS

| | | | |
|---|---|---|---|
| EP | 036776 | | 9/1981 |
| EP | 121775 | | 10/1984 |
| EP | 267851 | | 5/1988 |
| WO | WO 2008/066931 | * | 6/2008 |

OTHER PUBLICATIONS

Perry et al (J. Bacteriol. 188:6039-6043(2006) The Bacillus subtilis DivIVA protein has a sporulation-specific proximity to Spo0J).*

Perry et al (Identification of a polar targeting determinant for Bacillus subtilis DivIVA Mol. Microbiol. 54:1237-1249(2004) I.*
"U.S. Appl. No. 15/683,411, Non Final Office Action dated Jun. 10, 2019", 15 pgs.
"U.S. Appl. No. 15/683,411, Notice of Allowance dated Nov. 6, 2019", 6 pgs.
"U.S. Appl. No. 15/683,411, Response filed Feb. 22, 2019 to Restriction Requirement dated Dec. 4, 2018", 7 pgs.
"U.S. Appl. No. 15/683,411, Response filed Oct. 9, 2019 to Non-Final Office Action dated Jun. 10, 2019", 9 pgs.
"U.S. Appl. No. 15/683,411, Restriction Requirement dated Dec. 4, 2018", 5 pgs.
Amann, Egon, et al., "Vectors Bearing a Hybrid trp-lac Promoter Useful for Regulated Expression of Cloned Genes in *Escherichia coli*", Gene, 25(2-3), (1983), 167-178.
Beaucage, S. L., et al., "Deoxynucleoside Phosphoramidites—A New Class of Key Intermediate for Deoxypoiynucleotide Synthesis", Tetrahedron Letters, 22, (1981), 1859-1862.
Bonny, Mike, et al., "Membrane Binding of MinE Allows for a Comprehensive Description of Min-Protein Pattern Formation", PLoS Computational Biology, 9(12): e1003347, (Dec. 2013), 1-12.
Copeland, et al., "Complete sequence of chromosome 1 of Synechococcus elongatus PCC 7942", Accession No. Q31LN3, Submitted (Aug. 2005) to the EMBL/GenBank/DDBJ databases), (Aug. 2005).
De Boer, Herman A., et al., "The tac promoter: A functional hybrid derived from the trp and lac promoters", Proc. Natl. Acad. Sci. USA, 80(1), (1983), 21-25.
De Boer, Piet A. J., et al., "A Division Inhibitor and a Topological Specificity Factor Coded for by the Minicell Locus Determine Proper Placement of the Division Septum in *E. coli*", Cell, 56(4), (1989), 641-649.
De Boer, Piet A. J., et al., "Central role for the *Escherichia coli* minC ene product in two different cell division-inhibition systems", Proc. Natl. Acad. Sci. USA, 87(3), (1990), 1129-1133.
Drozdetskiy, Alexey, et al., "JPred4: a protein secondary structure prediction server", Nucleic Acids Research, vol. 43, (2015), W389-W394.
Edwards, David H., et al., "The Bacillus subtilis DivIVA protein targets to the division septum and controls the site specificity of cell division", Molecular Microbiology, 24(5), (1997), 905-915.
Eswaramoorthy, Prahathees, et al., "Cellular Architecture Mediates DivIVA Ultrastructure and Regulates Min Activity in Bacillus subtilis", mBio, 2(6): e00257-11, (2011), 1-9.
Fange, David, et al., "Noise-Induced Min Phenotypes in *E. coli*", PLoS Computational Biology, 2(6): e80, (Jun. 2006), 0637-0648.
Ghosal, Debnath, et al., "MinCD cell division proteins form alternating copolymeric cytomotive filaments", Nature Communications, 5, (2014), 1-11.
Goeddel, D. V., et al., "Synthesis of Human Fibroblast Interferon by *E. coli*", Nucleic Acids Research, 8(18), (1980), 4057-4074.
Guan, Chu Di, et al., "Vectors that facilitate the expression and purification of foreign peptides in *Escherichia coli* by fusion to maltose-binding protein", Gene, 67, (1997), 21-30.
Hoffmann, Max, "Oscillations of Min-proteins in micropatterned environments: a three-dimensional particle-based stochastic simulation approach", Soft Matter, 10, (2014), 2388-2396.

(Continued)

*Primary Examiner* — Jennifer E Graser
(74) *Attorney, Agent, or Firm* — Schwegman Lundberg & Woessner, P.A.

(57) ABSTRACT

Described herein are mutant cyanobacterial cell populations that have a smaller mean cell length than wild type cyanobacterial cell populations of the same species.

22 Claims, 32 Drawing Sheets

Specification includes a Sequence Listing.

(56) References Cited

OTHER PUBLICATIONS

Hsieh, Cheng-Wei, et al., "Direct MinE-membrane interaction contributes to the proper localization of MinDE in *E. coli*", Molecular Microbiology, 75(2), (2010), 499-512.
Kelley, Lawrence A., et al., "The Phyre2 web portal for protein modeling, prediction and analysis", Nature Protocols, 10(6), (2015), 845-858.
Kerr, Rex A., et al., "Division accuracy in a stochastic model of Min oscillations in *Escherichia coli*.", Proc Natl Acad Sci USA, 103(2), (2006), 347-352.
King, Glenn F., et al., "Structural basis for the topological specificity function of minE", Nat Struct Biol., 7(11), (2000), 1013-1017.
Kruse, Karsten, et al., "An experimentalist's guide to computational modelling of the Min system", Molecular Microbiology, 63(5), (2007), 1279-1284.
Leger, Michelle M., et al., "An ancestral bacterial division system is widespread in eukaryotic mitochondria", Proc. Natl. Acad. Sci. USA, 112(33), (2015), 10239-10246.
Loose, Martin, et al., "Protein Self-Organization: Lessons from the Min System", Annual Review of Biophysics, 40, (Jun. 2011), 315-336.
Loose, Martin, et al., "Spatial Regulators for Bacterial Cell Division Self-Organize into Surface Waves in Vitro", Science, 320(5877), (2008), 789-792.
Lutkenhaus, Joe, et al., "Assembly Dynamics of the Bacterial MinCDE System and Spatial Regulation of the Z Ring", Annual Review of Biochemistry, 76, (2007), 539-562.
MacCready, Joshua S., et al., "Robust Min-system oscillation in the presence of internal photosynthetic membranes in cyanobacteria", Molecular Microbiology, 103(3), (2016), 483-503.
Marston, Adele L., et al., "Polar localization of the MinD protein of Bacillus subtilis and its role in selection of the mid-cell division site", Genes Dev.,12(21), (1998), 3419-3430.
Marston, Adele L., et al., "Selection of the midcell division site in Bacillus subtilis through MinD-dependent polar localization and activation of MinC", Molecular Microbiology, 33(1), (1999), 84-96.
Mazouni, Khalil, et al., "Molecular analysis of the key cytokinetic components of cyanobacteria: FtsZ, ZipN and MinCDE", Molecular Microbiology, 52(4), (2004), 1145-1158.
Meinhardt, Hans, et al., "Pattern formation in *Escherichia coli*: A model for the pole-to-pole oscillations of Min proteins and the localization of the division site", Proc. Natl. Acad. Sci. USA, 98(25), (2001), 14202-14207.
Miller, Melissa B., et al., "Quorum sensing in bacteria", Annual Reviews in Microbiology, 55(1), (2001), 165-199.
Miyagishima, Shin-Ya, et al., "Identification of cyanobacterial cell division genes by comparative and mutational analyses", Mol. Microbiol., 56(1), (2005), 126-143.
Nakahira, Yoichi, et al., "Theophylline-dependent riboswitch as a novel genetic tool for strict regulation of protein expression in Cyanobacterium Synechococcus elongatus PCC 7942", Plant Cell Physiol., 54(10), Ogawa_2013, (2013), 1724-1735.
Nakanishi, Hiromitsu, et al., "Conservation and differences of the Min system in the chloroplast and bacterial division site placement", Commun Integr Biol 2(5), (2009), 400-402.
Needham-Vandevanter, D. R., et al., "Characterization of an adduct between CC-1065 and a defined oligodeoxynucleotide duplex.", Nucleic Acids Research, 12(15), (1984), 6159-6168.
Nevo, R., et al., "Thylakoid membrane perforations and connectivity enable intracellular traffic in cyanobacteria", EMBO Journal, 26(5), (2007), 1467-1473.
Nevo, Reinat, et al., "Chapter 14—Architecture of Thylakoid Membrane Networks", In: Lipids in Photosynthesis: Essential and Regulatory Functions, Advances of Photosynthesis and Respiration, vol. 30, Govindjee, Series Editor, (2009), 295-328.

Oliva, Maria A., et al., "Features critical for membrane binding revealed by DivIVA crystal structure", EMBO Journal, 29(12), (2010), 1988-2001.
Osteryoung, Katherine W., et al., "Division and Dynamic Morphology of Plastids", Annual Review of Plant Biology, vol. 65, (2014), 443-472.
Park, Kyung-Tae T., "The Min Oscillator Uses MinD-Dependent Conformational Changes in MinE to Spatially Regulate Cytokinesis.", (with Supplemental Information), Cell, 146(3), (2011), 396-407 (19 pgs.).
Petrasek, Zdenek, et al., "Simple membrane-based model of the Min oscillator", New Journal of Physics, 17: 043023, (2015), 14 pgs.
Raibaud, Olivier, et al., "Positive control of transcription initiation in bacteria", Annu Rev Genet., 18, (1984), 173-206.
Ramirez-Arcos, S., et al., "Conserved Glycines in the C Terminus of MinC Proteins Are Implicated in Their Functionality as Cell Division Inhibitors", J. Bacteriol. 186(9), (2004), 2841-2855.
Raskin, David M., et al., "Rapid pole-to-pole oscillation of a protein required for directing division to the middle of *Escherichia coli*", Proc. Natl. Acad. Sci. USA, 96(9), (1999), 4971-4976.
Raskin, David M., et al., "The MinE Ring: An FtsZ-Independent Cell Structure Required for Selection of the Correct Division Site in *E. coli*", Cell, 91, (1997), 685-694.
Shaner, Nathan C., et al., "A bright monomeric green fluorescent protein derived from Branchiostoma lanceolatum", Nat Meth., 10(5), (2013), 407-409.
Shimatake, H., et al., "Purified lambda regulatory protein cII positively activates promoters for lysogenic development.", Nature, 292(5819), (1981), 128-132.
Shine, J., et al., "Determinant of cistron specificity in bacterial ribosomes.", Nature, 254(5495), (1975), 34-38.
Steitz, Joan A., et al., "Chapter 9—Genetic Signals and Nucleotide Sequences in Messenger RNA", In: Biological Regulation and Development, vol. 1: Gene Expression, Goldberger, R. F., Editor, Plenum Press, New York, NY, (1979), 349-399.
Studier, F. William, et al., "Use of Bacteriophage T7 RNA Polymerase to Direct Selective High-Level Expression of Cloned Genes", Journal of Molecular Biology, 189(1), (1986), 113-130.
Sugita, et al., "Complete Nucleotide Sequence of the Freshwater Unicellular Cyanobacterium Synechococcus Elongatus PCC 6301 Chromosome: Gene Content And Organization", Accession No. A0A0H3KBP3, Photosyn, Res. 93, (2007), 55-67.
Szeto, Tim H., et al., "Membrane localization of MinD is mediated by a C-terminal motif that is conserved across eubacteria, archaea, and chloroplasts", Proc. Natl. Acad. Sci. USA, 99(24), (2004), 15693-15698.
Tabor, Stanley, et al., "A bacteriophage T7 RNA polymerase/promoter system for controlled exclusive expression of specific genes.", Proc. Natl. Acad. Sci. USA, 82(4), 1074-1078.
Varley, A. W., et al., "The divIVB Region of the Bacillus subtilis Chromosome Encodes Homologs of *Escherichia coli* Septum Placement (MinCD) and Cell Shape (MreBCD) Determinants", J. Bacterio. 174(21), (Nov. 1992), 6729-6742.
Varma, Archana, et al., "The Min System as a General Cell Geometry Detection Mechanism: Branch Lengths in Y-Shaped *Escherichia coli* Cells Affect Min Oscillation Patterns and Division Dynamics", J. Bacteriol., 190(6), (Mar. 2008), 2106-2117.
Waters, Christopher M., et al., "Quorum sensing: cell-to-cell communication in bacteria", Annu. Rev. Cell Dev. Biol., 21, (2005), 319-346.
Wu, F, et al., "Symmetry and scale orient Min protein patterns in shaped bacterial sculptures", Nature Nanotechnology, 10, (2015), 1-10.
Yelverton, E., et al., "Bacterial Synthesis of a Novel Human Leukocyte Interferon", Nucleic Acids Research, 9(3), (1981), 731-741.
Zieske, Katja, et al., "Reconstitution of self-organizing protein gradients as spatial cues in cell-free systems", eLife, 3:e03949, (2014), 19 pgs.

* cited by examiner

MinC Locus

Native ΔminC

Native mNG-MinC

Neutral Site 2 Ptrc::RS::mNG-MinC

MinDE Operon

Native ΔminD

Native ΔminE

Neutral Site 2 Ptrc::RS::mNG-MinD

GENETIC CONTROL OF CELL SIZE

This application is a continuation of U.S. application Ser. No. 15/683,411, filed Aug. 22, 2017, which claims benefit of priority to the filing date of U.S. Provisional Application Ser. No. 62/377,964, filed Aug. 22, 2016, the contents of which are specifically incorporated herein by reference in their entity.

FEDERAL FUNDING

This invention was made with government support under MCB1517241 awarded by the National Science Foundation. The government has certain rights in the invention.

BACKGROUND OF THE INVENTION

Despite the importance of cyanobacteria as the base of many ecological systems, their biotechnological applications, and their evolutionary relationship to plant and algal chloroplasts, molecular mechanisms of cyanobacterial division have remained largely unstudied. While cyanobacteria may share some division factors with other bacteria, several unique cyanobacterial features, including thylakoid membranes, multiple chromosome copies, and lack of nucleoid occlusion, distinguish them from classic prokaryotic model organisms and complicate extrapolation of their division mechanisms.

Cyanobacteria have been employed for the production of sustainable biofuels, pharmaceuticals, and chemicals due to their: (i) photosynthetic efficiency; (ii) low nutrient requirements; (iii) capacity to grow on non-arable landmass and with water supplies unfit for traditional agriculture; and (iv) ease of genetic manipulation. Despite the advantages of cyanobacteria, current practices for the cultivation, harvesting, and processing of cyanobacterial "crops" are expensive and infrastructure-intensive. These costs represent a significant economic barrier to cyanobacterial bioproduction, regardless of the specific target product. While research efforts have placed focus on improving photosynthetic efficiency or metabolic engineering in order to achieve higher total yields, there has been little progress on engineering cyanobacteria in order to relieve these harvesting/processing costs that currently prohibit widespread adoption.

SUMMARY

New strains of cyanobacteria and bacteria are described herein with modifications to the genes/proteins that provide control over cellular division and cellular morphology. The methods and new strains are useful for improving cyanobacterial/bacterial harvest and cellular lysis.

Cyanobacteria and other types of bacteria are emerging as alternative crop species for the production of fuels, chemicals, and biomass. Yet, the success of these microbes depends upon the development of cost-effective technologies that permit scaled cultivation and cell harvesting.

Three of the most significant costs associated with cyanobacterial cultivation are related to mixing cultures, recovering and dewatering cell biomass, and lysis of cyanobacterial cells to obtain intracellular metabolites. These processes can account for up to 40% of operating costs. There are intrinsic properties of cyanobacterial cells that can influence the costs associated with each of these processes, but optimal cyanobacteria properties vary with the stage of cultivation. For example, during growth of a culture, cyanobacterial cells are ideally buoyant and small so that the mixing costs required to keep them in suspension are minimized. Yet, small, buoyant cells are difficult to harvest, typically requiring centrifugation or filtration processes where the volume of liquid that to be handled can be large. Therefore, at the harvesting stage an ideal cyanobacterium would be large, and dense relative to most wild type cyanobacteria cells. Such large cell sizes facilitate accumulation of useful products within the cell and allow for spontaneous (gravity) precipitation from solution during harvest, thereby increasing product yield and reducing energy expenditure required to recover cell mass. Finally, processing cyanobacterial cell mass can involve lysing the cells to recover internal products. An ideal cyanobacterium would be readily lysed by standard procedures following harvest, but would not be sickly or have an otherwise compromised cell wall while being actively grown.

As illustrated herein, altered expression of several types of genes can lead to cell elongation through disruption of FtsZ assembly and cell division. FtsZ is a cytoskeletal polymer that is needed for establishment of the divisome and the regulation of cell division. The Min system regulates FtsZ assembly and positioning. MinC and Cdv3 are two proteins that are components of the cyanobacterial Min system. Cyanobacterial strains overexpressing MinC, MinD, cdv3, or Ftn2 exhibit delayed/impaired divisome formation and therefore continue to rapidly grow but do not divide, becoming elongated relative to unmodified strains. Cyanobacterial cells that overexpress MinC, MinD, cdv3, or Ftn2 can have cell sizes that are 2-fold to 20000-fold larger than unmodified wild type strains. Hyper-elongated cells exhibit increased rates of sedimentation under low centrifugal forces or by gravity-assisted settling. Furthermore, hyper-elongated cells are also more susceptible to lysis through the application of mild physical strain.

Altering the activity of other FtsZ-regulatory genes such as MinE or MinD can also alter the morphology and length of cyanobacterial cells. Overexpression of MinE decreases cell size. Overexpression of MinD generates a distribution of both large and small cells.

Methods are described herein that allow cyanobacterial cell size to be tuned and controlled so that the sedimentation rate, susceptibility to cell lysis, and resistance to sheer forces of the cells are ideally suited for growth, harvesting, and recovery of commercially useful components from the cells. In some embodiments, expression of MinC protein, MinD protein, MinE protein, Cdv3 (DivIVA) protein, FtsZ protein, Ftn2 protein, or a combination thereof in a cyanobacteria is from a heterologous promoter. In some cases, one or more native genes encoding one or more MinC protein, MinD protein, MinE protein, Cdv3 (DivIVA) protein, FtsZ protein, or Ftn2 protein can be mutated or deleted. Such mutant cells can be smaller than wild type cells.

In some cases, one or more native genes encoding one or more MinC protein, MinD protein, MinE protein, Cdv3 (DivIVA) protein, FtsZ protein, or Ftn2 protein can be mutated or deleted so that expression of MinC protein, MinD protein, MinE protein, Cdv3 (DivIVA) protein, FtsZ protein, Ftn2 protein, or a combination is from the heterologous promoter. The average size of cells in the population can be modulated by turning on or off such an inducible promoter.

New strains of cyanobacteria are described herein where the cell size can be modulated to facilitate growth, harvesting of cells, and processing of products made by the cells.

DESCRIPTION OF THE FIGURES

The patent or application file contains at least one drawing executed in color. Copies of this patent or patent application publication with color drawing(s) will be provided by the Office upon request and payment of the necessary fee.

FIG. 1A schematically illustrates established *Bacillus subtilis* and *Escherichia coli* Min system models (Lukenhaus, Annu Rev Biochem 76:539-62 (2007); Eswaramoorthy et al., mBio 2: e00257-11 (2011)). FIG. 1B illustrates the operon organization and genomic context of MinC, MinD, and MinE in *S. elongatus*. FIG. 1C illustrates some of the structural features of *S. elongatus* (Se) MinC that are conserved compared to the *E. coli* (Ec) and/or *B. subtilis* (Bs) MinC (SEQ ID NOs: 105-107). FIG. 1D illustrates some of the structural features of *S. elongatus* (Se) MinD that are conserved compared to the *E. coli* (Ec) and/or *B. subtilis* (Bs) MinD (SEQ ID NOs: 108-110). FIG. 1E illustrates some of the structural features of *S. elongatus* (Se) MinE that are conserved compared to the *E. coli* (Ec) and/or *B. subtilis* (Bs) MinE (SEQ ID NOs: 111-112). Red bars above the alignments show the positions of the indicated α-helices, including membrane targeting sequences (MTS) and MinE contact helix, in the *E. coli* proteins. Red letter sequences indicate equivalent predicted structures in *B. subtilis* and *S. elongatus* homologs. Blue in FIG. 1E shows that the β1 sheet within the *E. coli* MinE contact helix is also predicted in *S. elongatus* MinE. FIG. 1F is a schematic illustration of construct designs. In *S. elongatus*, MinC and DivIVA are expressed individually, whereas MinD and MinE are in the same operon with a putative ferredoxin-like gene (blue) of unknown function. In mNG-MinC, MinC was codon-optimized (CO) to increase transformation frequency. FIG. 1G shows PCR verification of Min gene deletions.

FIG. 2A shows histograms of *S. elongatus* cell sizes measured in deletion (green) or overexpression (blue) strains of MinC, MinD, and MinE relative to the wild type (WT; red) distribution (n=1000 cells per condition). Mean±standard deviation reported in parentheses for each strain. FIG. 2B illustrates that FtsZ (white) localization is altered in Min deletion (Δ) or overexpression (OE) cell lines as visualized by immunofluorescence. Chlorophyll a fluorescence is shown in red; Z rings are shown by yellow arrowheads; FtsZ helical filaments are shown by blue arrowheads. Scale bars 5 μm. FIG. 2C shows additional wide-field images of MinCDE and Cdv3 deletion and overexpression strains stained with anti-FtsZ. Chlorophyll fluorescence shown in red; FtsZ staining in white. FIG. 2D illustrates the extreme cell filamentation in Cdv3 overexpression strains. FIG. 2E illustrates the quantity of MinC expression as induced by increasing concentrations of theophylline. FIG. 2F illustrates the quantity of Cdv3 expression as induced by increasing concentrations of theophylline. FIG. 2G graphically illustrates the cyanobacterial growth rate in response to increasing theophylline inducer. Wild-type *S. elongatus* was incubated with increasing concentrations of theophylline and monitored for growth over 24 hours by optical density at 750 nm ($OD_{750}$). Doubling time was calculated for n≥4 independent day experiments. Error bars represent standard deviation and the p value for the only significant (p<0.05) change in doubling time is denoted, as determined from pairwise unequal variances t-tests.

FIG. 3A schematically illustrates constructs where mNG-MinC (mNG, light green) fusions are expressed from the MinC promoter (P, yellow) but a specR replacement of the *S. elongatus* MinC coding region eliminates MinC expression (ΔminC). The segment encoding the MinC fusion partner was codon-optimized (CO) to increase transformation frequency. When mNG-MinC was expressed from Neutral Site 2 (NS2), a 5' synthetic riboswitch (RS, brown) was operably linked to control translation. FIG. 3B illustrates that native MinD (red) and native MinE (dark green) coding regions are in the same operon along with a putative ferredoxin-like gene (orange) of unknown function. Replacement of the *S. elongatus* MinD (ΔminD) or MinE (ΔminE) coding region eliminates MinD or MinE expression. Moreover, ΔminD and ΔminE deletion strains were codon optimized (CO) to increase transformation frequency. Also shown is a mNG-MinD fusion construct. Native homology regions of around 1000 bp (purple) were used to fully replace at the native loci, whereas homology regions (bright blue) were used to insert at NS2. FIG. 3C also illustrates that native cdv3 is expressed from its own promoter (P, yellow) and that cdv3 is clustered with coaD (dark blue), a component of Co-enzyme A synthesis. Generation of deletion strains were performed by full replacement of the native gene (SpecR, grey) with a selectable marker, whereas fluorescent and overproduction strains had a selectable marker positioned as to not interfere with expression (KanR, grey). FIG. 3D graphically illustrates that the periodicity of mNG-MinC increases proportionally with cell length (n=10 cells per cell length). FIG. 3E illustrates time lapse imaging of the pole-to-pole oscillations of mNG-MinC and mNG-MinD when expressed from a synthetic riboswitch, as compared to natively-expressed mNG-MinC, which exhibits similar pole-to-pole oscillations. White dots indicate cell perimeters. Images taken every 30 seconds. Scale bar 1 μm. FIG. 3F illustrates that in ΔminD backgrounds, the native mNG-MinC signal is diffuse, not recruited to the membrane or midcell. Also the mNG-MinC signal does not oscillate. FIG. 3G illustrates that mNG-MinC exhibits an even distribution pattern in ΔminD background, exhibiting a loss of pole-to-pole oscillation and membrane recruitment. FIG. 3H illustrates that in ΔminE strains, the natively expressed mNG-MinC formed helical patterns along the membrane (red arrowheads) and intermittent ring-like structures (blue arrowheads). FIG. 3I illustrates that mNG-MinC localization is disrupted in strains with an incomplete minE knockout. Oscillation of mNG-MinC is lost and helix-like patterning forms along the membrane.

FIG. 4A illustrates the operon structure and genomic context of cdv3 in *S. elongatus*. The percent primary sequence identity of Cdv3 in *S. elongatus* is shown below the diagram in comparison to DivIVA of *B. subtilis*. Scale bar, 500 bp. FIG. 4B illustrates the secondary structure of *B. subtilis* DivIVA in comparison to *S. elongatus* Cdv3. Both proteins are predicted to consist largely of α-helices (red), which comprise the coiled-coil structures spanning the length of DivIVA. Delta-Blast identified a putative partial *B. subtilis* DivIVA domain (MPLTPNDIHNKTFTKSFRGYDE-DEVNEFLAQVR-KDY; SEQ ID NO:1) in *S. elongatus* Cdv3 (LDGTRVPLS-GRILVRENDLLDLLDDVRAFLPAAIQQA; SEQ ID NO:2). Within the crossed loop region required for DivIVA binding to negatively curved membranes (bottom of FIG. 4B; green), Cdv3 lacks conservation of key residues and secondary structure features. FIG. 4C illustrates that natively-expressed Cdv3-mNG concentrates into a ring-like structure at midcell in *S. elongatus*. Scale bar 5 μm. FIG. 4D illustrates the midcell localization of mNG-MinC is lost in the absence of Cdv3. Scale bar 5 μm. FIG. 4E shows histograms illustrating that deletion (green) of cdv3 influences the length of S. elongatus cells (n=1000) compared to wild type cells. The mean cell length of Δcdv3 cells was 4.54±1.41 (standard deviation) as shown in parentheses. FIG. 4F illustrates that FtsZ (white) localization is altered in Δcdv3 or cdv3 overexpression (OE) cyanobacterial lines as visualized by immunofluorescence with α-FtsZ antibodies. Chlorophyll a fluorescence, red; Z rings, yellow arrowheads; FtsZ helical filaments, blue arrowheads. Scale bars 10 μm. FIG. 4G illustrates that in the absence of cdv3, mNG-MinC oscillations are apparent. However, in elongated cells multiple mNG-MinC wave patterns are observed instead of pole-to-pole oscillations (blue arrowheads). The mid-cell localization of mNG-MinC is lost in both ΔminD and Δcdv3 strains. FIG. 4H illustrates that DivIVA (also called cdv3 in S. elongatus) localization to division planes is independent of other Min system regulators. DivIVA-mNG was imaged in ΔminC, ΔminD and ΔminE backgrounds. Upon the deletion of minC, the DivIVA signal appeared at midcell. Likewise, in ΔminD backgrounds, DivIVA localization appeared in ring-like patterns that were often observed in multiple locations and which were frequently near cell poles. These localizations are consistent with FtsZ staining in ΔminC and ΔminD cells, respectively. Interestingly, ΔminE cells displayed erratic DivIVA-mNG localization, where ring-like structures formed randomly in the cell (often at constricting sites presumed to be division planes), while also forming a helical pattern that was reminiscent of FtsZ patterning in ΔminE cells. These patterns all indicate co-localization of DivIVA and FtsZ in S. elongatus. FIG. 4I shows images of cyanobacterial cells illustrating immunolocalization of FtsZ (yellow) in representative cells with Cdv3 expression induced for the indicated number of hours. Formation of Z-rings was delayed in Cdv3-mTurq (blue) expressing lines (24 hr-OE) while multiple, mispositioned Z-rings are evident in highly elongated cells (48-72 hours post-induction) without clear indications of constriction. Scale bars for (C)=10 μm.

FIG. 5A is a schematic diagram of a cyanobacterial cell illustrating the locations of MinC, MinD, MinE, Cdv3, and FtsZ proteins, as well as the effect of overexpressing MinC protein on cell length. FIG. 5B graphically illustrates cell length upon inducing expression of MinC protein (left panel) and MinD protein (right panel) with increased amounts of the expression inducer (theophylline). As illustrated, greater concentrations of the theophylline inducer led to cyanobacterial populations with increased mean cell lengths. FIG. 5C graphically illustrates cell length upon inducing expression of MinE protein (left panel) and Cdv3 protein (right panel) with increased amounts of the expression inducer (theophylline). As illustrated, greater concentrations of the theophylline inducer led to cyanobacterial populations with increased mean cell lengths. FIG. 5D graphically illustrates cell length upon inducing expression of MinD protein (left panel) with varying amounts of the inducer (theophylline), and images of cells after 96 hours of MinD protein induction by 2 mM theophylline (right panel). As illustrated, greater concentrations of the theophylline inducer lead to cyanobacterial populations with increased mean cell lengths. FIG. 5E graphically illustrates cell length at various times after inducing expression of MinE protein (left panel) and Cdv3 protein (right panel) with varying amounts of the inducer (theophylline). As illustrated, greater concentrations of the theophylline inducer lead to cyanobacterial populations with increased mean cell lengths. FIG. 5F shows brightfield microscopy images of elongated cyanobacterial cells that have been induced to over-express Cdv3. The scale of these images was changed between panels to capture the extreme elongation that is seen in these cells.

FIG. 6A illustrates sedimentation of hyper-elongated cells that over-express Cdv3 (DivIVA) in a graduated cylinder at 0 hours and 24 hours of sedimentation without application of additional gravitational forces. FIG. 6B also illustrates sedimentation of hyper-elongated cells that overexpress Cdv3 (DivIVA at 0 hours and 24 hours of sedimentation without application of additional gravitational forces. FIG. 6C graphically illustrates sedimentation of hyper-elongated cells that overexpress Cdv3 (DivIVA compared to cells that overexpress MinE when additional gravitational forces were applied.

FIG. 7A illustrates the morphological changes that occur following overexpression of Cdv3 by the addition of theophylline, as reflected by changes in the light scattering and fluorescent properties of cells when analyzed by flow cytometry. Cdv-3 overexpression (Cdv3-OE) strains were analyzed by flow cytometry a 0 hours (top), 24 hours (middle), or 48 hours (bottom) after induction of Cdv-3 expression by addition of theophylline. An increase in the forward scatter and chlorophyll-associated red autofluorescence was observed that is correlated with the increased cell size of Cdv3-overexpressing cells. Cell counts are gated into wild type-length (blue box) and elongated (red box) to facilitate quantification. FIG. 7B shows representative experiments to illustrate the effects of increasing pressure and lytic forces from a cell disruptor when applied to both uninduced (top) and Cdv3-overexpressing (bottom) cyanobacterial cultures, as measured by flow cytometry. The proportion of elongated cells (red) relative to WT lengths (blue) is represented in pie charts for each condition. The application of even very mild sheer force results in preferential lysis of the hyperelongated cell population. FIG. 7C graphically illustrates the proportion of intact cells remaining following cell disruption with increasing pressures, as shown in 7B. FIG. 7D graphically illustrates the proportion of intact cells remaining following cell disruption as in FIG. 7C, but where only the proportion of elongated cells is tracked. FIG. 7E graphically illustrates dry cell weight of harvested control (uninduced, dark grey) and Cdv3-overexpressing (induced, light grey) cyanobacterial cells, showing that Cdv3 overexpression does not adversely affect cell biomass accumulation or recovery of biomass from harvesting. The p values displayed are from unequal variances t-tests with n=4 biological replicates.

DETAILED DESCRIPTION

While cyanobacteria and algae can offer many benefits relative to traditional land plants for production of commercially useful products, commercialization of photosynthetic crop species has been limited due to technical problems relating to scaled cultivation. Cyanobacteria exhibit rapid division times, high photosynthetic efficiencies, the capacity to be cultivated in non-potable water supplies on non-arable lands. In addition, cyanobacteria are readily genetically manipulated. These features that make them of considerable interest as alternative crop species. Yet, these advantages are overshadowed by several economic considerations that have stymied widespread cultivation of alternative microalgal crops. In contrast to the technology for plants that has been under development for millennia, the infrastructure, strains and equipment for cyanobacterial crops are still emerging.

One of the largest economic obstacles to cyanobacterial biotechnology is related to the costs of harvesting and processing cells for the recovery of biomass. Three of the most significant costs associated with cyanobacterial cultivation are related to mixing cultures, recovering and dewatering cell biomass, and lysis of cyanobacterial cells to obtain intracellular metabolites (accounting for up to ~40% of operating costs). Although the industry has attempted several procedures to overcome these problems (e.g., chemical flocculants, mechanical separation by filtration or centrifugation, etc.) such procedures can be expensive, for example, because they may introduce chemicals that need to be removed later and cannot be recycled, or because expensive equipment is required to isolate the cells.

Figure 2A:
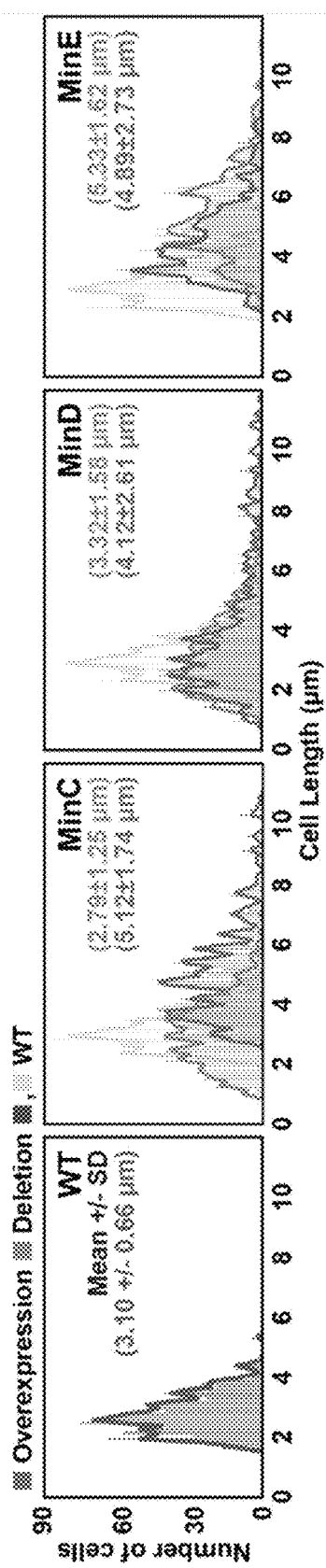
FIG. 2A-2G illustrate the effects of cyanobacterial Min Homologs on cell-size and FtsZ positioning.
Figure 2B:
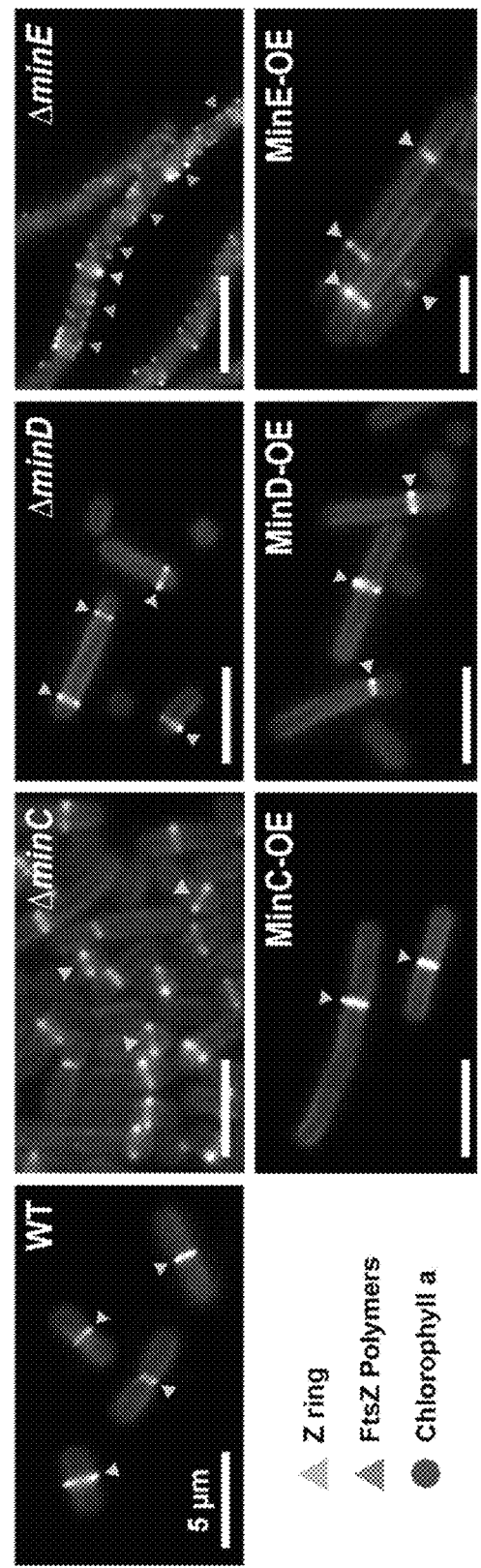

As illustrated herein, the size or length of cyanobacterial cells can be regulated by modulating the expression of minC, minD, minE, cdv3 (also called DivIVA), FtsZ, Ftn2, or combinations thereof. In wild-type (WT) cyanobacterial cells, cell sizes are within a narrow range of about 1.7-4.5 µm (mean cell length 3.10±0.66 µm; FIG. 2A-2B). However, by modulating the expression of Min genes (or transgenes), the sizes of cells can be significantly altered.

For example, the Min proteins can interact with and modulate the capacity of FtsZ to assemble into the filaments that make up the rings that ultimately divide the cell. Reduced expression and/or activity of at least one of minC, or minD generally produces cyanobacterial populations containing small cells. However, reduce expression of FtsZ can produce elongated cells. Overexpression (OE) of minC, minD, minE, cdv3 (also called DivIVA), Ftn2, or combinations thereof can disrupt divisome assembly, generally resulting in cell elongation.

By regulating cell size, the costs of cell mixing during culture and/or cell separation after culture can be reduced. For example, cell size can be regulated in an inducible manner so that the costs of cell mixing can be minimized during culture growth (e.g., by keeping cells small), and the costs of harvesting can also be minimized by inducing cell elongation to facilitate cell separation and processing.

Cyanobacterial/Bacterial Cell Division

Cyanobacteria and bacteria have several genes that are involved in cell division. Several of molecular players involved in cell division are as follows.

FtsZ: This protein is a bacterial homolog of tubulin that is needed for division of bacteria. FtsZ is able to polymerize into filaments and laterally interact with other FtsZ filaments to form an FtsZ-ring that constricts at the site of division. This ring acts as the focal point for cell division by both providing some constrictive force and by scaffolding other bacterial division machinery.

MinC: This protein directly inhibits the self-assembly of FtsZ. Therefore, FtsZ is most able to polymerize and form the FtsZ-ring in areas of the cell where MinC is least active.

MinD: This protein binds to cell membranes and also recruits MinC, thereby localizing MinC on the plasma membrane, near where FtsZ polymers would form. Through recruiting MinC, it enhances destabilization of FtsZ and also concentrates the MinC/MinD destabilization at specific sites of action.

MinE: This protein stimulates the ATPase activity of MinD, which causes MinD to dissociate from the membrane. The cooperative action of many MinE proteins leads to the removal of MinD from patches of the cell membrane. Collectively, MinE's interaction with MinD leads to emergent behaviors that effectively "chase" MinD from pole to pole, keeping the concentration of MinD (and MinC) low in the center of the cell.

Cdv3: This protein has sequence homology to the bacterial protein DivIVA and also shares some functional similarities. The precise functions of Cdv3 were previously unclear. As illustrated herein, if the levels of Cdv3 are too high (or too low), cyanobacteria are unable to properly divide. Cdv3 is recruited to the FtsZ-ring, and it can recruit a pool of MinC to the FtsZ ring.

Cyanobacteria constitute a large phylum where Min dynamics that have previously not been studied in detail. Although, the cyanobacterial Min genes share sequence homology with bacterial MinE and DivIVA (Cdv3) genes, cyanobacteria possess extensive, geometrically complex internal thylakoid membranes that could sequester MinCDE and/or complicate analysis of the role of these genes in cell division. Hence, information previously available for bacterial systems may not be applicable to cyanobacterial systems.

As described herein, the Min genes can modulate polymerization and localization of FtsZ, and the FtsZ protein is the protein that forms contractile Z rings that cause actual cell division. MinC can act as an inhibitor of Z-ring assembly. In wild type cells MinD recruits MinC onto plasma membranes. MinE and Cdv3 (also called DivIVA) function independently in positioning MinCD, and hence Z rings, in rod-shaped cyanobacteria such as Synechococcus elongatus PCC 7942.

Methods are described herein to generate cyanobacterial populations that contain larger cells than wild type cyanobacterial populations of the same species. Also described herein are cyanobacterial populations that include a significant proportion of larger cells. Such larger cell populations can have expression cassettes or expression vectors with promoters operably linked to nucleic acid segments encoding MinC, MinD, MinE, Cdv3 (DivIVA), and/or Ftn2 polypeptides.

Methods are also described herein to generate cyanobacterial populations that contain smaller cells than wild type cyanobacterial populations of the same species. Such methods can involve generating loss-of-function mutations in MinC, MinD, MinE and/or Cdv3 (DivIVA) genes to generate cyanobacterial populations that contain smaller cells than wild type cyanobacterial populations of the same species. Moreover, overexpression of FtsZ can reduce the mean cell size of cyanobacteria. Therefore, in some cases where smaller cell size is desirable, expression of FtsZ can be induced. For example, cyanobacterial populations can contain expression cassettes or expression vectors with promoters operably linked to nucleic acid segments encoding FtsZ, where the expression of FtsZ can be regulated.

The wild type species described herein do not overexpress MinC, MinD, MinE, Cdv3 (DivIVA), FtsZ and/or Ftn2 and do not have loss-of-function mutations in MinC, MinD, MinE, Cdv3 (DivIVA), FtsZ and/or Ftn2 genes.

MinC

As indicated above, MinC proteins can stimulate depolymerization of FtsZ. Therefore, FtsZ is most able to polymerize and form the FtsZ-ring in areas of the cell where MinC is least active. MinC proteins participate in pole-to-pole oscillations that position the Z ring at the cell midzone.

As illustrated herein, in wild-type (WT) cells, cell sizes fell within a narrow range of about 1.7-4.5 µm (mean cell length 3.10±0.66 µm; FIG. 2A-2B).

As also shown herein, cyanobacterial populations that overexpress MinC proteins have an increased mean cell size or length. To increase cyanobacterial or bacterial cell sizes a cell population of can be modified to include an expression cassette or vector that encodes a MinC protein. For example, the mean cell length of MinC overexpressing cyanobacterial cells is at least 150%, or at least 200%, or at least 250%, or at least 300%, or at least 500%, or at least 750%, or at least 1000%, or at least 5000%, or at least 10000%, or at least 15000%, or at least 20000% greater than a wild type population of cyanobacteria of the same species.

However, as demonstrated herein, cyanobacterial populations with loss of function MinC mutations include cyanobacterial cells that are significantly smaller than are observed in wild type cyanobacterial populations of the same species. For example, the mean cell length of MinC mutant cyanobacterial cells is at least 15%, or at least 20%, or at least 25%, or at least 30%, or at least 35%, or at least 40%, or at least 45%, or at least 50% less than the mean cell length of a wild type population of cyanobacteria of the same species.

Examples of MinC sequences are provided herein to facilitate generation of cyanobacterial populations containing significant numbers of small cells. One sequence for a *Synechococcus elongatus* MinC polypeptide has the following sequence (SEQ ID NO:4).

```
  1 MSDVDASTPS AEEAIAPDID SDSDAAVETP AAEPAIAPPI
 41 QLEAEGDRWW LRLPSAPPVG QEANADGLTW LDLQQSLQQL
 81 LQGQENFWDA GAELHLFADS WLLDGRQLEW LSQQLARADL
121 KLTRITTQRR QTAVAAVSLG LSIEQPITQA DPWQRKTSTS
161 PIAAPLYLKR TLRSGAEVRH NGSVIVVGDV NPGSSIVASG
201 DILVWGNLRG IAHAGAAGNS DATIFALSLA ATQLRIGDRL
241 ARLPSSQAAG YPETAQVIDG QIQIRRADPG GK
```

A nucleic acid that encodes the polypeptide with SEQ ID NO:4 is shown below as SEQ ID NO:5.

```
  1 ATGAGTGACG TAGACGCTTC TACCCCCTCG GCAGAGGAGG
 41 CGATCGCACC TGACATCGAC AGTGACAGCG ATGCGGCAGT
 81 TGAGACACCT GCTGCTGAAC CCGCGATCGC ACCGCCAATC
121 CAGCTCGAAG CGGAGGGCGA TCGCTGGTGG TTGAGGCTGC
161 CAAGTGCACC CCCGGTTGGT CAAGAAGCCA ATGCGGACGG
201 CTTGACTTGG CTAGATTTGC AACAGTCGCT CCAACAATTG
241 CTGCAAGGTC AGGAAAACTT CTGGGATGCG GGAGCTGAGC
281 TCCACCTCTT TGCCGATAGT TGGCTACTGG ATGGGCGTCA
321 GTTGGAATGG CTAAGCCAGC AGCTAGCGCG GGTTGACCTG
361 AAATTGACAC GGATCACAAC CCAGCGCCGG CAGACGGCAG
401 TGGCAGCCGT GAGCCTTGGG CTCTCGATTG AACAGCCAAT
441 CACCCAGGCC GATCCTTGGC AGCGCAAGAC CTCGACCAGC
481 CCCATTGCCG CGCCGCTCTA CCTCAAACGC ACCCTGCGAT
521 CGGGAGCTGA GGTACGCCAT AACGGCTCAG TGATTGTGGT
561 GGGAGATGTC AACCCCGGCA GCAGCATTGT GGCCAGTGGC
601 GACATTCTTG TTTGGGGTAA CCTGCGGGGC ATTGCCCATG
641 CGGGGGCTGC CGGTAATTCA GACGCGACAA TTTTTGCCCT
681 GTCGCTGGCG GCCACCCAAC TGCGGATTGG CGATCGTCTA
721 GCCAGACTGC CCAGTAGCCA AGCAGCCGGC TATCCCGAAA
761 CGGCCCAAGT GATTGATGGT CAAATTCAGA TTCGCCGCGC
801 CGATCCTGGC GGGAAGTAG
```

Other cyanobacterial polypeptides and nucleic acids are available with significant sequence homology to the SEQ ID NO:4 MinC protein. Such MinC-related sequences can be modified to include loss-of-function mutations.

For example, a related *Synechococcus elongatus* MinC sequence with accession number WP_050738292.1 (GI: 914820796) is available from the National Center for Biotechnology Information database (see website at ncbi.nlm.nih.gov). The sequence for this MinC polypeptide shares 99% or more sequence identity with SEQ ID NO:4 and is shown below as SEQ ID NO:6.

```
  1 MSDVDASTPS AEEAIAPDID SDSDAAVEPP AAEPAIAPPI
 41 QLEAEGDRWW LRLPSAPPVG QEANADGLTW LDLQQSLQQL
 81 LQGQENFWDA GAELHLFADS WLLDGRQLEW LSQQLARADL
121 KLTRITTQRR QTAVAAVSLG LSIEQPITQA DPWQRKTSTS
161 PIAAPLYLKR TLRSGAEVRH NGSVIVVGDV NPGSSIVASG
201 DILVWGNLRG IAHAGAAGNS DATIFALSLA ATQLPIGDRL
241 ARLPSSQAAG YPETAQVIDG QIQIRRADPG GK
```

A comparison between SEQ ID NO:4 and SEQ ID NO:6 MinC sequences is shown below. The asterisks below the comparison show which amino acids are identical.

```
99.3% identity in 272 residues overlap; Score: 1373.0; Gap frequency: 0.0%
Seq4   1 MSDVDASTPSAEEAIAPDIDSDSDAAVETPAAEPAIAPPIQLEAEGDRWWLRLPSAPPVG
Seq6   1 MSDVDASTPSAEEAIAPDIDSDSDAAVEPPAAEPAIAPPIQLEAEGDRWWLRLPSAPPVG
         ***************************  ******************************
```

```
Seq4  61 QEANADGLTWLDLQQSLQQLLQGQENFWDAGAELHLFADSWLLDGRQLEWLSQQLARVDL
Seq6  61 QEANADGLTWLDLQQSLOQLLQGQENFWDAGAELHLFADSWLLDGRQLEWLSQQLARADL
         ************************************************************ **

Seq4 121 KLTRITTQRRQTAVAAVSLGLSIEQPITQADPWQRKTSTSPIAAPLYLKRTLRSGAEVRH
Seq6 121 KLTRITTQRRQTAVAAVSLGLSIEQPITQADPWQRKTSTSPIAAPLYLKRTLRSGAEVRH
         ***********************************************************

Seq4 181 NGSVIVVGDVNPGSSIVASGDILVWGNLRGIAHAGAAGNSDATIFALSLAATQLRIGDRL
Seq6 181 NGSVIVVGDVNPGSSIVASGDILVWGNLRGIAHAGAAGNSDATIFALSLAATQLRIGDRL
         ***********************************************************

Seq4 241 ARLPSSQAAGYPETAQVIDGQIQIRRADPGGK
Seq6 241 ARLPSSQAAGYPETAQVIDGQIQIRRADPGGK
         ********************************
```

Another MinC sequence from *Leptolyngbya* sp. NIES-3755 is available from the NCBI database as accession number BAU11733.1 (GI:965632161), which has 46% sequence identity to SEQ ID NO:4, and is shown below as SEQ ID NO:7.

```
  1 MTSDTSLSPL SNDPTPISPE AVSSPDVDAD LLDLPPLETP

41 EVPKIAIEDL QVRLKAKDGV LSLILPPESE AASKVALAWG

61 ELWQQLKQLL MGREPQWQPN TIVHLIADDR LLDTRQLSAI

121 AEALTDVOLQ LKSVHTRRPQ TAVVAATAGY SVEQITAVDP

161 LAAKQETAVA MEEPLYIQMT LRSGTEIRHN GIVVVMGDLN

201 PGSTIIAEGD ILVWGRLRGV AHAGCKGNVK SLIMALQLEP

241 TQIRIADYVA RAPETPPAQY FPEVAYVSPQ GSIRIARATD

281 FSMRKDD
```

A comparison between SEQ ID NO:4 and SEQ ID NO:7 MinC sequences is shown below, with highly conserved amino acids identified. The asterisks below the comparison show which amino acids are identical.

Another MinC sequence from *Gloeocapsa* sp. PCC 7428 is available from the NCBI database as accession number WP_015191142.1 (GI:505004040), which has 46% sequence identity to SEQ ID NO:4, and is shown below as SEQ ID NO:8.

```
  1 MTDSAPPEIE TTLTPPTNIA NSNLQVRLKG EGEHLLLILP

41 TEVESSATAT TWSDLWQQLK QRLNGGDRFW QPNTIVHLMA

61 TDRLLDTRQL QAIADALSEA QLQLTHVFTS RRQTAVAAAT

121 AGYSVEQQAP ITGLNQTVNA APTPLAEPLY LQMTVRSGIE

161 IRHAGSVIVL GDLNPGGTVV ANGDILVWGR LRGVAHAGAA

201 GNSKCLIMAL QMEPTQLRIA EFVARAPTNI PSQFYPEVAY

241 VTPEGIRIAK AADFSKSQFS LPS
```

A comparison between SEQ ID NO:4 and SEQ ID NO:8 MinC sequences is shown below, with highly conserved amino acids identified. The asterisks below the comparison show which amino acids are identical.

50.2% identity in 213 residues overlap; Score: 479.0; Gap frequency 1.9%

45.1% identity in 268 residues overlap; Score: 489.0; Gap frequency: 2.6%

```
Seq4   5 DASTPSAEEAIAPDIDSD--SDAAVETPAAEPAIAPPIQLEAEGDRWWLRLPSAPPVGQE
Seq7  13 DPTPISPEAVSSPDVDADLLDLPPLETPEVPKIAIEDLQVRLKAKDGVLSL-ILPPESEA
            *  * **  *   ***          *       *  *  **

Seq4  63 ANADGLTWLDLQQSLQQLLQGQENFWDAGAELHLFADSWLLDGRQLEWLSQQLARVDLKL
Seq7  72 ASKVALAWGELWQQLKQLLMGRERQWPNTIVHLIADDRLLDTRQLSAIAEALTDVQLQL
          *   *  * * *** *** *  * *      ** ** *** ***      *   *

Seq4 123 TRITTQRRQTAVAAVSLGLSIEQPITQADPWQRKTSTS-PIAAPLYLKRTLRSGAEVRHN
Seq7 132 KSVHTRRQTAVVAATAGYSVEQ-ITAVDPLAAKQETAVAMEEPLYIQMTLRSGTEIRHN
          * ****** *    *  ** **   *       ***   ***** * *** ****

Seq4 182 GSVIVVGDVNPGSSIVASGDILVWGNLRGIAHAGAAGNSDATIFALSLAATQLRIGDRLA
Seq7 191 GTVVVMGDLNPGSTIIAEGDILVWGRLRGVAHAGCKGNVKSLIMALQLEPTQIRIADYVA
         * * ** ** ***  * * ******* *** **    **  *   ** **  **  *

Seq4 242 RLPSSQAAGY-PETAQVI-DGQIQIRRA
Seq7 251 RAPETPPAQYFPEVAYVSPQGSIRIARA
         * *      * * *  *    *  * *
```

```
Seq4  58 PVGQEANADGLTWLDLQQSLQQLLQGQENFWDAGAELHLFADSWLLDGRQLEWLSQQLAR

Seq8  40 PTEVESSATATTWSDLWQQLKQRLNGGDRFWQPNTIVHLMATDRLLDTRQLQAIADALSE
         *   *   *  ** **  * * *    **    ** *   *** ***       *

Seq4 118 VDLKLTRITTQRRQTAVAAVSLGLSIEQ--PITQADPWQRKTSTSPIAAPLYLKRTLRSG

Seq8 100 AQLQLTHVFTSRRQTAVAAATAGYSVEQQAPITGLNQTVNAAPT-PLAEPLYLQMTVRSG
         * **   * ********   * * **   ***          *  *  **** * ***

Seq4 176 AEVRHNGSVIVVGDVNPGSSIVASGDILVWGNLRGIAHAGAAGNSDATIFALSLAATQLR

Seq8 159 IEIRHAGSVIVLGDLNPGGTVVANGDILVWGRLRGVAHAGAAGNSKCLIMALQMEPTQLR
          * ** ***** ** ***  ** ******* *** ********    * **    ****

Seq4 236 IGDRLARLPSS-QAAGYPETAQVIDGQIQIRRA

Seq8 219 IAEFVARAPTNIPSQFYPEVAYVTPEGIRIAKA
         *   **  *       *** * *    *   *
```

Another MinC sequence from *Leptolyngbya boryana* IAM M-101 is available from the NCBI database as accession number BAS56644.1 (GI:932876592), which has 50% sequence identity to SEQ ID NO:4, and is shown below as SEQ ID NO:9.

```
  1    MTPDTSVSPT PIDPLSVTSD STLEKPLEAP TPSSDTPTAE
 41    NPKTDVTASS DAHASSEITD SSLSTSSELS PQTVAIADLQ
 81    VRLKTKEGEL HLILPPESEN SKIALAWVEL WQQFKQLLMG
121    QERFWQPNTP VHLVSDDRLL DTRQISAIAE ALAEVQLQLK
161    WVHTRRRQTA VVAATAGYSV EQITAASPLL PNSEPATAME
201    DPLYIQMTLR SGAEIRHNGT VVVVGDLNPG SSIIAEGDIL
241    VWGRLRGVAH AGCKGNAKCL IMALQMEPTQ IRIADYVARA
281    PETPLAQYFP EVAYVSPQGS IRIARAADFA ARKEEPNFS
```

A comparison between SEQ ID NO:4 and SEQ ID NO:9 MinC sequences is shown below, with highly conserved amino acids identified. The asterisks below the comparison show which amino acids are identical.

48.6% identity in 212 residues overlap; Score: 485.0; Gap frequency: 0.9%

Another MinC sequence from *Leptolyngbya boryana* is available from the NCBI database as accession number WP_026148713.1 (GI:648456962), which also has 50% sequence identity to SEQ ID NO:4, and is shown below as SEQ ID NO:10.

```
  1    MTDSSLSTSS ELSPQTVAIA DLQVRLKTKE GELHLILPPE
 41    SENSKIALAW VELWQQFKQL LMGQERFWQP NTPVHLVSDD
 81    RLLDTRQISA IAEALAEVQL QLKWVHTRRR QTAVVAATAG
121    YSVEQITAAS PLLPNSEPAT AMEDPLYIQM TLRSGAEIRH
161    NGTVVVVGDL NPGSSIIAEG DILVWGRLRG VAHAGCKGNA
201    KCLIMALQME PTQIRIADYV ARAPETPLAQ YFPEVAYVSP
241    QGSIRIARAA DFAARKEEPN FS
```

A comparison between SEQ ID NO:4 and SEQ ID NO:10 MinC sequences is shown below, with highly conserved amino acids identified. The asterisks below the comparison show which amino acids are identical.

48.6% identity in 212 residues overlap; Score: 485.0; Gap frequency: 0.9%

```
Seq4  58 PVGQEANADGLTWLDLQQSLQQLLQGQENFWDAGAELHLFADSWLLDGRQLEWLSQQLAR

Seq9  95 PPESENSKIALAWVELWQQFKQLLMGQERFWQPNTPVHLVSDDRLLDTRQISAIAEALAE
          *  *      * *  * *** *** ***  **    *  * *** **         **

Seq4 118 VDLKLTRITTQRRQTAVAAVSLGLSIEQPITQADPWQRKTSTSPIAAPLYLKRTLRSGAE

Seq9 155 VQLQLKWVHTRRRQTAVVAATAGYSVEQITAASPLLPNSEPATAMEDPLYIQMTLRSGAE
          * *   *  * ******  * * * **                  ***   *******

Seq4 178 VRHNGSVIVVGDVNPGSSIVASGDILVWGNLRGIAHAGAAGNSDATIFALSLAATQLRIG

Seq9 215 IRHNGTVVVVGDLNPGSSIIAEGDILVWGRLRGVAHAGCKGNAKCLIMALQMEPTQIRIA
         **** * ***** ****** * ******* *** ****  ***    ** **  *  **

Seq4 238 DRLARLPSSQAAGY-PETAQVI-DGQIQIRRA

Seq9 275 DYVARAPETPLAQYFPEVAYVSPQGSIRIARA
         *  **       *   * *  *    **  **
```

```
Seq4    58 PVGQEANADGLTWLDLQQSLQQLLQGQENFWDAGAELHLFADSWLLDGRQLEWLSQQLAR

Seq10   38 PPESENSKIALAWVELWQQFKQLLMGQERFWQPNTPVHLVSDDRLLDTRQISAIAEALAE
              *  *     * *  * *   *** *** **     ** *  *** **          **

Seq4   118 VDLKLTRITTQRRQTAVAAVSLGLSIEQPITQADPWQRKTSTSPIAAPLYLKRTLRSGAE

Seq10   98 VQLQLKWVHTRRRQTAVVAATAGYSVEQITAASPLLPNSEPATAMEDPLYIQMTLRSGAE
            * * *      * ****** *  * * **                ***   *******

Seq4   178 VRHNGSVIVVGDVNPGSSIVASGDILVWGNLRGIAHAGAAGNSDATTFALSLAATQLRIG

Seq10  158 IRHNGTVVVVGDLNPGSSIIAEGDILVWGRLRGVAHAGCKGNAKCLIMALQMEPTQIRIA
             **** * **** ****** * ******* *** **** **    *  **    ** **

Seq4   238 DRLARLPSSQAAGY-PETAQVI-DGQIQIRRA

Seq10  218 DYVARAPETPLAQYFPEVAYVSPQGSIRIARA
            *  **  *     * *  ** *    * * **
```

Any of the conserved amino acids and conserved domains illustrated by the sequence comparisons shown above can be expressed in cells (e.g., via a transgene or expression cassette introduced into a host cell) to increase the activity of the MinC proteins described herein.

Any of the conserved amino acids and conserved domains illustrated by the sequence comparisons shown above can also be deleted or mutated to reduce the activity of the (endogenous) MinC proteins described herein.

When reducing MinC expression, a wild type cyanobacterial population can have a MinC polypeptide with at least 70%, or at least 75%, or at least 80%, or at least 85%, or at least 90%, or at least 95%, or at least 97%, or at least 98%, or at least 99% sequence identity to any of SEQ ID NOs:4, 6-9, or 10.

Similarly, a cyanobacterial population can overexpress a MinC polypeptide with at least 70%, or at least 75%, or at least 80%, or at least 85%, or at least 90%, or at least 95%, or at least 97%, or at least 98%, or at least 99%, sequence identity to any of SEQ ID NOs:4, 6-9, or 10. As illustrated herein, such overexpression can increase the mean cell size or length of a cyanobacterial population.

However, cyanobacterial strains with reduced cell length can express mutant MinC polypeptides that have reduced MinC activity. Such reduced activity MinC polypeptides can have less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:4, 6-9, or 10. The mutations in mutant MinC polypeptides can, for example, have mutations in at least one conserved amino acid position, or at least two conserved amino acid positions, or at least three conserved amino acid positions, or at least five conserved amino acid positions, or at least seven conserved amino acid positions, or at least eight conserved amino acid positions, or at least ten conserved amino acid positions, or at least fifteen amino acid positions, or at least twenty conserved amino acid positions, or at least twenty-five amino acid positions. In some cases, an entire conserved MinC domain or the entire endogenous MinC gene is deleted or mutated (e.g., replaced with non-conserved sequences).

The conserved amino acids are in many cases mutated by deletion or replacement with amino acids that have dissimilar physical and/or chemical properties (see, e.g., Table 1).

Such mutations can reduce MinC expression or function and provide cyanobacterial populations with a mean cell length that is at least 10% smaller than the mean cell length of a wild type cyanobacterial population of the same species.

In addition to mutations in the coding region of the MinC gene, the endogenous promoter that drives expression of MinC proteins can be mutated to reduce or eliminate MinC protein expression. One example of a *Synechococcus elongatus* minCD promoter sequence is shown below (SEQ ID NO:11).

```
 1    AAATATTCTG AAATGAGCTG TTGACAATTA ATCATCCGGC

41    TCGTATAATG TGTGGA
```

To reduce expression of MinC protein, a promoter region with at least at least 70%, or at least 75%, or at least 80%, or at least 85%, or at least 90%, or at least 95%, or at least 97%, or at least 98%, or at least 99% sequence identity to SEQ ID NO:11 can be mutated to reduce or eliminate transcription of MinC RNA. For example, a cyanobacterial promoter with at least 75%, or at least 80%, or at least 85%, or at least 90%, or at least 95%, or at least 97%, or at least 98%, or at least 99% sequence identity to SEQ ID NO:11 can be mutated so that the promoter sequence has less than 99%, or less than 98%, or less than 95%, or less than 90%, or less than 85%, or less than 75%, or less than 60%, or less than 50%, or less than 40%, or less than 30%, or less than 20% sequence identity to SEQ ID NO:11. In some cases such a cyanobacterial promoter can have a deletion of at least one nucleotide, or at least two nucleotides, or at least three nucleotides, or at least five nucleotides, or at least ten nucleotides, or at least twenty nucleotides, or at least twenty five nucleotides, or at least thirty nucleotides. Such deletions can reduce MinC expression and provide cyanobacterial populations with a mean cell length that is at least 10% smaller than the mean cell length of a wild type cyanobacterial population of the same species.

In some cases, MinC mutations are introduced by insertion of foreign DNA into the gene of interest such as transposable elements or T-DNA. The foreign DNA not only disrupts the expression of the gene into which it is inserted but also acts as a marker for subsequent identification of the mutation. For example, the insertion of a transposon or T-DNA on the order of 5 to 25 kb in length generally produces a dramatic disruption of gene function. If a large enough population of transposon-transformed or T-DNA-transformed lines is available, one has a very good chance of finding a cyanobacteria carrying an insertion within any gene of interest.

Insertion, modification, or deletion of MinC mutations can involve use of a targeting vector that contains MinC homologous flanking sequences. For example, the following two flanking regions of the *Synechococcus elongatus* MinC gene can be employed to generate insertion, modification, or deletion MinC mutations. The first MinC flanking region is referred to as ΔminC Region 1 and is assigned SEQ ID NO:12.

```
  1  AGTCTAGGGA TCAGCATTGG GAAAAAACCT GAATGGATAG
 41  GGCTCGTGGG GTTGAGTGCT CTAAGCAGAC TCATAGGGGG
 81  TACGAACCCA ATTCGGTTTT GGATGCATCG ATCGCTGGCA
121  ATTAATCCGA ACGAGTTGCG GTGACAGGGG GTTGCGATCG
161  CCGACGAGGC TTGGGCCGAA AGGGGACCAG CAGTTCTGCC
201  TCAACAATCC GCAACTGACC GTACCGAGTC ACCTCGCAGT
241  CAAACTGCCA CCACCCTGGA CGCAGTTGCT CAGGTGCCCC
281  GCGCAATTGC AGTCGTTTGA TTTTCCAGGC TGGCTTGTCG
321  ATCTGTCCGG GTGGCGCGGC CTCATTGCGA CCAATCCAGA
361  CCTGCACGGC CCCGTTTTGA TCCTTCCAGC TTTTGACAAA
401  ACCGCAGATC CGTACCCGAC CAGCTTGTAG ATCTGCGGGA
441  GCCTGATTTT GCCAGCCCCG CAACCAAAAT TGCAGATGCT
481  TGTGGCGTTG CAGCGGCCAG CTGACCCAGT AGTGAGGGGT
521  TTGCATGAGC TGCTGCAGCT GCTGGGGATG GCGTTGTAGG
561  GTCGCTTGCA CCAATCCACT CAGCGCTACA TTCAGGCTGT
601  GATTGTCCGT AATCTGCAGA GTGGCTGTTT CTCCCTGTTG
641  GTCCCAAGCC AAGCTGCCTT GGAAACAAGC AACCGCCCGA
681  TAGGTGACGC TGTCGGGCTT CGGGGGCAGT TCCGTGCGGC
721  GGGGTGGCTT GCGGCTGGGA CGCGATCGCG ACGCAGCAGG
761  GCTAGAACGG GTGATCGGTC GCGCAGGGCG TGGACGACCA
801  CTCGGCAAAG GGGATGGGGG AGGCGTAGCC ATGGATGGCA
841  CTGGGCAAGG GCGATCACTG TTATTCTGGC GGCTCCCGCT
881  CGACTTGCCC GTACTCTTTA ATTTGTTTTG GGCTAAATAT
921  CGGGCCAAGT CTGCTTGGGC AGCGGATCTC TGGATCCATC
961  CCAGCCCAAT TGCTAACCTG CTCTCTACCC CGTGGTTCCG
```

The second MinC flanking region is referred to as ΔminC Region 2 and is assigned SEQ ID NO:13.

```
  1  GGGCACATCT TGAGACGATC GCCCGATGCG ACCGCTTCGC
 41  GGAGTGAACC TTCGACTGAA CCTTAGCGCC CGCCAAAATG
 81  CAAAACTGAC AGAGAGCCTG TCCTGCTCTG TCCTACTTCC
121  GTTTCAATAC TGTTTCACCT GCAAAGGTGC TTTTCCTAGG
161  TTGGCAGATG AGCGATCGCC CGCAGCCGGC ACCCACCGTC
201  CTGAAACGCC TGACCCAATT GGCAACGCAG GTTCAGCGAC
241  GGGCCAAGTT TGATAATCTC AACCTGCGTG ACTCTGACTC
281  AGTTCCCCAA TTGACGGTCT GTCAGGGAGA CCGCCGGCAG
321  TCTTATCCGC TGCTTGGGGA CTATTACCGC CTGGGCCGAG
361  GCCGTGACTG TGACATCCCG ATTGATAGCC CGATCGTCAG
401  CAAGCTTCAC CTCAGCCTCG GTCGCTCGGG CAAAGAGCGC
441  GGTGACTTTG TCCTGCAAGA CGAAAACTCG ACCAACGGCG
481  TCTTTTGGCG GGGCCGCCGT GTCGATCGCT TGGAATTACA
521  GCATGGCGAT CGCATCTACC TGGGGCCACC AGAGCTGACC
561  GATCGCGTTG AGCTGCTCTA TGAAAACGCT CCTCCTCTCT
601  GGCAGGACTG GCTGAAACGA GGGGTGACTA TCACTACAGC
641  TGTGGTCGGA GCGATCGCGA TCGGCATTAC CCTCGAGGCC
681  AGCCGAGTCT CCGTGCGATC GCTGGGGACG GTGCAAGGAC
721  CGATCGCTGC CTATGCCGCT GATGGCGAGC CCCTACAAAC
761  TCTGCGCAGT AGTAGCCACG TCGAATTACC GGCCCTCTCA
801  GATTTTTCGC CCGTTCTCCC CAAAGCCCTG CTTGCCTCCG
841  AAGACAGTCG CTTCTACTGG CATCTGGGTA TCGATCCCTA
881  CGGCACGGCG CGTGCGATTC TGACTAACTT CCGCAGTGGC
921  GAAGTTCGCG AAGGCGCCAG CACCCTCACC CAGCAGATTG
941  CTCGCAGCCT ATTTAGCGAC TACGTCGGGC GTGAGGACTC
```

Mutations can be generated in MinC sequences from a variety of cyanobacterial species, for example, by transforming cells from the selected cyanobacterial species with a targeting vector that includes two flanking segments, for example, SEQ ID NO:12 and 13 in *Synechococcus elongatus* and related cyanobacterial species. Such targeting vectors can be used for cyanobacterial species other than *Synechococcus elongatus*, for example, by using targeting vectors that have flanking segment sequences that have less than 100%, or less than 99%, or less than 98%, or less than 95%, or less than 90%, or less than 85%, or less than 75% sequence identity to SEQ ID NO:12 and/or 13, but still retain some sequence identity to SEQ ID NO:12 and/or 13. In some cases the targeting vectors that have flanking segment sequences that have at least 70%, or at least 75%, or at least 80%, or at least 85%, or at least 90%, or at least 95%, or at least 97%, or at least 98%, or at least 99% sequence identity to SEQ ID NOs:12 and 13.

Such mutations can reduce MinC expression or function and provide cyanobacterial populations with a mean cell length that is at least 10% smaller than the mean cell length of a wild type cyanobacterial population of the same species.

In some cases, to induce expression of MinC protein, a promoter region can be used in an expression cassette or vector where the promoter has at least at least 70%, or at least 75%, or at least 80%, or at least 85%, or at least 90%, or at least 95%, or at least 97%, or at least 98%, or at least 99% sequence identity to SEQ ID NO:11.

MinD Sequences

MinD proteins bind to the cell membrane and interact with both MinC and MinE proteins, and promote the function of MinC. As illustrated herein, cyanobacterial populations that overexpress MinD proteins have an increased mean cell size or length. For example, the mean cell length of MinD overexpressing cyanobacterial cells is at least 150%, or at least 200%, or at least 250%, or at least 300%, or at least 500%, or at least 750%, or at least 1000%, or at least 5000%, or at least 10000%, or at least 15000%, or at least 20000% greater than a wild type population of cyanobacteria of the same species.

However, as also demonstrated herein, cyanobacterial populations with loss of function MinD mutations include cyanobacterial cells that are significantly smaller than are observed in wild type cyanobacterial populations of the same species. For example, the mean cell length of MinD mutant cyanobacterial cells mean cell length is at least 15%, or at least 20%, or at least 25%, or at least 30%, or at least 35%, or at least 40%, or at least 45%, or at least 50% less than a wild type population of cyanobacteria of the same species.

Examples of MinD sequences are provided herein to facilitate generation of cyanobacterial populations containing significant numbers of large or small cells. One sequence for a *Synechococcus elongatus* MinD polypeptide has the following sequence (SEQ ID NO:14).

```
  1  MSRVIVVTSG KGGVGKTTSS ANLGMALAQL GKRLVLIDAD
 41  FGLRNLDLLL GLENRIVYTA QDVLAGNCRL EQALVKDKRQ
 81  PNLCLLPAAN NRMKESVTPQ QMEQLVTLLD GQFDVILIDS
121  PAGIEAGFQN AIAAAREAVI VTTPEIAAVR DADRVIGLLE
161  AHGITEIRLI LNRLRPAMVK ANDMMSVEDV QEILAIPLVG
201  IIPDDEQVII STNRGEPLVL AEAPSLAAKA FINVARRLSG
241  ESIDFLNLEE PQSGVLSKIR RILNKKIL
```

A nucleic acid that encodes the polypeptide with SEQ ID NO:14 has the sequence shown below as SEQ ID NO:15.

```
  1  ATGAGTCGCG TTATTGTTGT CACCTCCGGT AAGGGAGGCG
 41  TGGGCAAAAC CACCTCCAGC GCCAACTTGG GTATGGCCTT
 81  AGCCCAGCTG GGTAAACGCC TCGTGCTCAT CGATGCGGAC
121  TTTGGCTTGC GCAATCTCGA CCTGCTGCTG GGGCTGGAGA
161  ATCGGATTGT CTACACCGCT CAGGATGTTT TAGCGGGCAA
201  TTGCCGCCTC GAGCAAGCAT TGGTCAAAGA CAAGCGCCAA
241  CCGAATCTCT GCCTGCTGCC TGCGGCCAAC AACCGCATGA
281  ACCAGTCGGT GACCCCCCAG CAGATGGAGC AGTTGGTGAC
321  GCTGCTCGAT GGTCAGTTCG ACGTGATCTT GATCGACTCA
361  CCCGCTGGAA TTGAAGCCGG ATTCCAGAAT GCGATCGCGG
401  CCGCCCGCGA AGCCGTAATT GTTACGACGC CGGAGATTGC
441  GGCTGTCCGA GACGCCGATC GCGTTATTGG ATTGCTAGAA
481  GCCCATGGCA TCACAGAGAT TCGGCTGATT TTGAACCGGC
521  TGCGGCCAGC GATGGTCAAG GCCAACGACA TGATGAGTGT
561  CGAAGATGTG CAGGAAATCC TCGCGATCCC TCTTGTCGGC
601  ATCATTCCCG ATGACGAGCA GGTGATTATT TCCACCAACC
641  GTGGCGAGCC GTTGGTCCTA GCCGAGGCAC CTTCCTTGGC
681  GGCCAAGGCA TTCATCAATG TGGCGCGGCG CCTGAGTGGT
721  GAAAGCATCG ACTTCCTCAA TCTTGAGGAA CCCCAGAGCG
761  GTGTGCTCAG TAAGATTCGC CGCATCCTCA ATAAAAAAAT
801  TCTCTAG
```

Other cyanobacterial polypeptides and nucleic acids are available with significant sequence homology to the SEQ ID NO:14 MinD protein. For example, a related *Oscillatoriales cyanobacterium* JSC-12 MinD sequence with accession number WP_009769434.1 (GI:497455236) is available from the National Center for Biotechnology Information database (see website at ncbi.nlm.nih.gov). The sequence for this MinD polypeptide shares 74% or more sequence identity with SEQ ID NO:14 and is shown below as SEQ ID NO:16.

```
  1  MSRVIVVTSG KGGVGKTTTT ANLGMALAKR GRKVIVIDAD
 41  FGLRNLDLLL GLENRVVYTA VDVLAGQCRL EQALVKDKRH
 81  PNLMLLPAAQ NRTKDAVKPD QMKQLVNALA KAFNYVLVDC
121  PAGIEMGFQN AIAAAKEALI VTTPEIAAVR DADRVVGLLE
161  ANNIKQIRLI VNRLRPAMVQ ANDMMTVEDV QEILAVPLIG
201  IVPDDERVIV STNKGEPLVL AETPSLAGTA FDNIARRLEG
241  ESVEFLDFTA PNDGFFSRLR RVLTTPIGKK PSK
```

A comparison between SEQ ID NO:14 and SEQ ID NO:16 MinD sequences is shown below, with highly conserved amino acids identified. The asterisks below the comparison show which amino acids are identical.

73.8% identity in 267 residues overlap; Score: 1008.0; Gap frequency 0.0%

```
Seq14   1 MSRVIVVTSGKGGVGKTTSSANLGMALAQLGKRLVLIDADFGLRNLDLLLGLENRIVYTA

Seq16   1 MSRVIVVTSGKGGVGKTTTTANLGMALAKRGRKVIVIDADFGLRNLDLLLGLENRVVYTA
          ****************** ******* *       ******************* ****

Seq14  61 QDVLAGNCRLEQALVKDKRQPNLCLLPAANNRMKESVTPQQMEQLVTLLDGQFDVILIDS

Seq16  61 VDVLAGQCRLEQALVKDKRHPNLMLLPAAQNRTKDAVKPDQMKQLVNALAKAFNYVLVDC
           ***** ************ *** *****  **  *  * **  *  **   *  * *

Seq14 121 PAGIEAGFQNAIAAAREAVIVTTPEIAAVRDADRVIGLLEAHGITEIRLILNRLRPAMVK

Seq16 121 PAGIEMGFQNAIAAAKEALIVTTPEIAAVPDADRVVGLLEANNIKQIRLIVNRLRPAMVQ
          ***** ********* ** ********** ***** ****   *  **** *******
```

```
Seq14 181 ANDMMSVEDVQEILAIPLVGIIPDDEQVIISTNRGEPLVLAEAPSLAAKAFINVARRLSG

Seq16 181 ANDMMTVEDVQEILAVPLIGIVPDDERVIVSTNKGEPLVLAETPSLAGTAFDNIARRLEG
          ***** ********* ** ** **** ** *** ******** ****  ** * **** *

Seq14 241 ESIDFLNLEEPQSGVLSKIRRILNKKI

Seq16 241 ESVEFLDFTAPNDGFFSRLRRVLTTPI
          ** ** *   *  *  ** *
```

Another MinD sequence from *Kamptonenma* is available from the NCBI database as accession number WP_007353741.1 (GI:494595482), which has at least 72% sequence identity to SEQ ID NO:14, and is shown below as SEQ ID NO:17.

```
  1    MARIIVVTSG KGGVGKTTST ANLGMALAKL GRSVAVVDAD
 41    FGLRNLDLLL GLENRIVYTA VEVIAGECRL EQALVKDKRQ
 81    PNLVLLPAAQ NRMKDAVSAE QMKQLVNVLA EKYDYILIDS
121    PAGIEQGFQN AIAAAQEGVI VTTPEIAAVR DADRVVGLLE
161    AHNVKRIHLI VNRIRPLMVQ ANDMMSVQDV REILAIPLLG
201    VVPDDERVIV STNRGEPLVL SETPSLAGTA YENIARRLEG
241    EKVEFLELNP PQDNEFTRLR RLLTAKIM
```

A comparison between SEQ ID NO:14 and SEQ ID NO:17 MinD sequences is shown below, with highly conserved amino acids identified. The asterisks below the comparison show which amino acids are identical.
72.4% identity in 268 residues overlap; Score: 1005.0; Gap frequency: 0.0%

Another MinD sequence from *Geitlerinema* sp. PCC 7407 is available from the NCBI database as accession number WP_015173510.1 (GI:504986408), which also has at least 72% sequence identity to SEQ ID NO:14, and is shown below as SEQ ID NO:18.

```
  1    MSRVIVVTSG KGGVGKTTCT ANLGMALAQQ GRRVIVVDAD
 41    FGLRNLDLLL GLENRIVYTA LEVLAGECRL EQAIVKDKRQ
 61    NRLALLPAAQ NRTKDAVRPE QMKQLIAALT GKYDYILVDC
121    PAGIEMGFQN AIVAAREALV VTTPEISAVR DADRVVGLLE
161    AQGIKQMRLI INRIRPNMVQ VNDMMSVEDV QEILAIPLIG
201    VIPDDERVIV STNRGEPLVL SETPSMAGTA FENVARRLEG
241    QKVEFLDLNG PGDSFFSRIK RLLSTKIL
```

A comparison between SEQ ID NO:14 and SEQ ID NO:18 MinD sequences is shown below, with highly conserved amino acids identified. The asterisks below the comparison show which amino acids are identical.

```
Seq14   1 MSRVIVVTSGKGGVSKTTSSANLGMALAQLGKRLVLIDADFGLRNLDLLLGLENRIVYTA

Seq17   1 MARIIVVTSGKGGVGKTTSTANLGMALAKLGRSVAVVDADFGLRNLDLLLGLENRIVYTA
          * * ************* ******* **         ***********************

Seq14  61 QDVLAGNCRLEQALVKDKRQPNLCLLPAANNRMKESVTPQQMEQLVTLLDGQFDVILIDS

Seq17  61 VEVIAGECRLEQALVKDKRQPNLVLLPAAQNRMKDAVSAEQMKQLVNVLAEKYDYILIDS
          * ** ***************** ***** ****    *  ** ***  *  * *****

Seq14 121 PAGIEAGFQNAIAAAREAVIVTTPEIAAVRDADRVIGLLEAHGITEIRLILNRLRPAMVK

Seq17 121 PAGIEQGFQNAIAAAQEGVIVTTPEIAAVRDADRVVGLLEAHNVKRIHLIVNRIRPLMVQ
          *****  ******* *  ****************** *****   * ** ** ** **

Seq14 181 ANDMMSVEDVQEILAIPLVGIIPDDEQVIISTNRGEPLVLAEAPSLAAKAFINVARRLSG

Seq17 181 ANDMMSVQDVREILAIPLLGVVPDDERVIVSTNRGEPLVLSETPSLAGTAYENIARRIEG
          ******* ** ******* * **** ** ********** * ****   *  * **** *

Seq14 241 ESIDFLNLEEPQSGVLSKIRRILNKKIL

Seq17 241 EKVEFLELNPPQDNFFTRLRRLLTAKIM
          *  ** *   **      * ** * **
```

```
72.4% identity in 268 residues overlap; Score: 1000.0; Gap frequency: 0.0%
Seq14    1 MSRVIVVTSGKGGVGKTTSSANLGMALAOLGKRLVLIDADFGLRNLDLLLGLENRIVYTA
Seq18    1 MSRVIVVTSGKGGVGKTTCTANLGMALAQQGRRVIVVDADFGLRNLDLLLGLENRIVYTA
           ******************  *********  *    ************************

Seq14   61 QDVLAGNCRLEQALVKDKRQPNLCLLPAANNRMKESVTPQQMEQLVTLLDGQFDVILIDS
Seq18   61 LEVLAGECRLEQAIVKDKRQNRLALLPAAQNRTKDAVRPEQMKQLIAALTGKYDYILVDC
            ****  ****** ****** * *** ** ** *    **** **    * *  **  *

Seq14  121 PAGIEAGFQNAIAAAREAVIVTTPEIAAVRDADRVIGLLEAHGITEIRLILNRLRPAMVK
Seq18  121 PAGIEMGFQNAIVAAREALVVTTPEISAVRDADRVVGLLEAQGIKQMRLIINRIRPNMVQ
           ***** ****** **** ******** ******** ***** **   ** ** ** **

Seq14  181 ANDMMSVEDVQEILAIPLVGIIPDDEQVIISTNRGEPLVLAEAPSLAAKAFINVARRLSG
Seq18  181 VNDMMSVEDVQEILAIPLIGVIPDDERVIVSTNRGEPLVLSETPSMAGTAFENVARRLEG
            ***************** * ***** ** ********    **    ** ****** *

Seq14  241 ESIDFLNLEEPQSGVLSKIRRILNKYIL
Seq18  241 QKVEFLDLNGPGDSFFSRIKRLLSTKIL
             * *        * *   ***
```

Another MinD sequence from *Planktothricoides* sp. SR001 is available from the NCBI database as accession number WP_054465548.1 (GI:935599625), which has 73% sequence identity to SEQ ID NO:14, and is shown below as SEQ ID NO:19.

```
  1 MSRIIVITSG KGGVGKTTST ANLGMALAKR GRKVALIDAD

41 FGLRNLDLLL GLENRIVYTA VEVIAGQCRL EQALVKDKRQ

81 PGLALLPAAQ NRMKDAVTPD QMKQIVQQLL QKYHYVLIDS

121 PAGIEQGFQN AIAAAREALI VTTPEIAAVR DADRVIGLLE

161 AHGVRQIHLI VNRLKPQMVE ANDMMSVADV QEILAIPLIG

201 VIPDDERVIV STNRGEPLVL GEEQTLAGKA FDNIARRLEG

241 EKVELLDLSL PSDNFFSRIR KLFFTKIM
```

A comparison between SEQ ID NO:14 and SEQ ID NO:19 MinD sequences is shown below, with highly conserved amino acids identified. The asterisks below the comparison show which amino acids are identical.

```
73.1% identity in 268 residues overlap; Score: 993.0; Gap frequency: 0.0%
Seq14    1 MSRVIVVTSGKGGVGKTTSSANLGMALAQLGKRLVLIDADFGLRNLDLLLGLENRIVYTA
Seq19    1 MSRIIVITSGKGGVGKTTSTANLGMALAKRGRKVALIDADFGLRNLDLLLGLENRIVYTA
           *** ** ************ ********   *  ***************************

Seq14   61 QDVLAGNCRLEQALVKDKRQPNLCLLPAANNRMKESVTPQQMEQLVTLLDGQFDVILIDS
Seq19   61 VEVIAGQCRLEQALVKDKRQPGLALLPAAQNRMKDAVTPDQMKQIVQQLLQKYHYVLIDS
            * ***************** * ***** **** ****  **  *   *      ****

Seq14  121 PAGIEAGFQNAIAAAREAVIVTTPEIAAVRDADRVIGLLEAHGITEIRLILNRLRPAMVK
Seq19  121 PAGIEQGFQNAIAAAREALIVTTPEIAAVRDADRVIGLLEAHGVRQIHLIVNRLKPQMVE
           ***** ************ ***********************  ** ** *** * **

Seq14  181 ANDMMSVEDVQEILAIPLVGIIPDDEQVIISTNRGEPLVLAEAPSLAAKAFINVARRLSG
Seq19  181 ANDMMSVADVQEILAIPLIGVIPDDERVIVSTNRGEPLVLGEEQTLAGKAFDNIARRLEG
           ******* ********** * ***** ** ********        **  * * *** *

Seq14  241 ESIDFLNLEEPQSGVLSKIRRILNKKIL
Seq19  241 EKVELLDLSLPSDNFFSRIRKLFFTKIM
           *    * *     *   ***    **
```

Any of the conserved amino acids and conserved domains illustrated by the sequence comparisons shown above can be expressed in cells (e.g., via a transgene or expression cassette introduced into a host cell) to increase the activity of the MinD proteins described herein.

In addition, any of the conserved amino acids and conserved domains illustrated by the sequence comparisons shown above can be deleted to reduce the expression and/or activity of the (e.g., endogenous) MinD proteins described herein.

To increase cyanobacterial or bacterial cell sizes a cell population of can be modified to include an expression cassette or vector that encodes a MinD polypeptide. For example, an expression cassette or vector that encodes a MinD polypeptide can have at least 70%, or at least 75%, or at least 80%, or at least 85%, or at least 90%, or at least 95%, or at least 97%, or at least 98%, or at least 99% sequence identity to any of SEQ ID NOs:14, 16, 17, 18, or 19.

In some cases, cyanobacterial cell population can be of reduced cell sizes. For example, MinD mutations can be introduced to reduce cell size by methods that can include deletion or insertion of foreign DNA into the MinD locus. For example, this can involve the use of either transposable elements or T-DNA. The foreign DNA not only disrupts the expression of the gene into which it is inserted but also acts as a marker for subsequent identification of the mutation. If a large enough population of transposon-transformed or T-DNA-transformed lines is available, one has a very good chance of finding a cyanobacteria carrying an insertion within any gene of interest.

Any of the conserved amino acids and conserved domains illustrated by the sequence comparisons shown above can be deleted or mutated to reduce the activity of the MinD proteins described herein.

For example, a wild type cyanobacterial population can have a MinD polypeptide with at least 70%, or at least 75%, or at least 80%, or at least 85%, or at least 90%, or at least 95%, or at least 97%, or at least 98%, or at least 99% sequence identity to any of SEQ ID NOs:14, 16, 17, 18, or 19.

However, the cyanobacterial strain with reduced cell length can express mutant MinD polypeptides that have reduced MinD activity. Such MinD polypeptides that have reduced MinD activity can have less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:14, 16, 17, 18, or 19. The mutations in mutant MinC polypeptides can, for example, have mutations in at least one conserved amino acid position, or at least two conserved amino acid positions, or at least three conserved amino acid positions, or at least five conserved amino acid positions, or at least seven conserved amino acid positions, or at least eight conserved amino acid positions, or at least ten conserved amino acid positions, or at least fifteen amino acid positions, or at least twenty conserved amino acid positions, or at least twenty-five amino acid positions. In some cases, an entire conserved MinD domain or the entire endogenous MinD gene is deleted or mutated.

The conserved amino acids are in many cases mutated by deletion or replacement with amino acids that have dissimilar physical and/or chemical properties.

In addition to mutations in the coding region of the MinD gene, the endogenous promoter that drives expression of MinD proteins can be mutated to reduce or eliminate MinD protein expression. As described above, one example of a *Synechococcus elongatus* minCD promoter sequence is shown below (SEQ ID NO:20).

```
  1 AAATATTCTG AAATGAGCTG TTGACAATTA ATCATCCGGC
 41 TCGTATAATG TGTGGA
```

To reduce expression of MinD protein, a promoter region with at least at least 70%, or at least 75%, or at least 80%, or at least 85%, or at least 90%, or at least 95%, or at least 97%, or at least 98%, or at least 99% sequence identity to SEQ ID NO:20 can be mutated to reduce or eliminate transcription of MinD RNA. For example, a cyanobacterial promoter with at least 75%, or at least 80%, or at least 85%, or at least 90%, or at least 95%, or at least 97%, or at least 98%, or at least 99% sequence identity to SEQ ID NO:20 can be mutated be mutated so that the promoter sequence has less than 99%, or less than 98%, or less than 95%, or less than 90%, or less than 85%, or less than 75%, or less than 60%, or less than 50%, or less than 40%, or less than 30%, or less than 20% sequence identity to SEQ ID NO:20. In some cases such a cyanobacterial promoter can have a deletion of at least one nucleotide, or at least two nucleotides, or at least three nucleotides, or at least five nucleotides, or at least ten nucleotides, or at least twenty nucleotides, or at least twenty five nucleotides, or at least thirty nucleotides. Such deletions can reduce MinD expression and provide cyanobacterial populations with a mean cell length that is at least 10% smaller than the mean cell length of a wild type cyanobacterial population of the same species.

In some cases, MinD mutations are introduced by insertion of foreign DNA into the gene of interest. For example, this can involve the use of either transposable elements or T-DNA. The foreign DNA not only disrupts the expression of the gene into which it is inserted but also acts as a marker for subsequent identification of the mutation. The insertion of a transposon or T-DNA on the order of 5 to 25 kb in length generally produces a dramatic disruption of gene function. If a large enough population of transposon-transformed or T-DNA-transformed lines is available, one has a very good chance of finding a cyanobacteria carrying an insertion within any gene of interest.

Insertion, modification, or deletion of MinD mutations can involve use of a targeting vector that contains MinD homologous flanking sequences. For example, the following two flanking regions of the *Synechococcus elongatus* MinD gene can be employed to generate insertion, modification, or deletion MinD mutations. The first MinD flanking region is referred to as ΔminD Region 1 and assigned SEQ ID NO:21.

```
   1 GGCGGGCTTG GGCTTCTGTC AGTCCTACCT GAGCTGCCGC
  41 CGGATCCATC TCTAAAACTT GCTGCGGGGC TAGAGCTGAT
  81 TGCTGACGCG GCCAACCGAA CAGACCGTGT TGCGCGATCG
 121 CACGGACTTC TGCCGGACTG AGATTGGCTG CGATCGCCCG
 161 ACTCCCCGGC AGCAGCGGCA GCGGATCAGG TTGGAAATAA
 201 TTGAGACTCA GCTCGCAGGA ATCCGTCTGA CGAGTTGACT
 241 GCTCCAGCAG ATGGATGCCC TCAGCCTGAC ATTGAGCTTG
 281 CAGCCGTTGA ACAATCGTAG GCTCCCAACT CGACCAGATT
 321 GCAGGCGTTG CCAAGCCGAC ATCCCAACCA TGACGGGTCA
 441 GGGCTTGGGC AACTCCAATC GCGATTGTGC GATCGCCAGT
 481 AACCGTCACA GATTGCGGTT GTGGATCGGC GGTCAGTAAG
 521 TCCCAGAGCG GCGTTGCTTC TGCCCCTGTC GGTTGAGCCT
 561 GCCAGATCTG CCGCGCCTCC AGTCGGCGAT CGCTACAGTC
 601 CACCACCCGA CGCGATCGTG TCGCTTTCCA GTGACTGGCA
 641 ACAATATCAA TTCCCTGTTG CTGCAGAGCG ATCGGGCCTT
 681 GCAGTAGCTC AAGGCGTTCG TAGAGAGCCT GCCCTGAGGC
 721 CAGTGCTTCT GGCACAGAAG TGGACTTCAA CAAGCAACGC
 801 ATCAACAGGC GATCGCGATC GATCGCGCCC CAACTCTCTG
 841 GCAGATAGAT CAAGGCCACA CGAGCCTGCC AGCGCCGTGC
 881 CTGTTGTGCC AGCGCGATCG CTGCCGGTGT CGCCCCCAGA
 921 ATCAGTAAGT TATAGTCCGC TGTCATTCAA GTTGGGAGTG
 961 AAAGCCCCGC TGCATTGTCT TTCCATCGTC AGGCAGAACA
1001 GCCCTGTCAT GAAGGGTGAA TATAGAAAGC CTTTGGCAGT
1041 CTAGGGGAT TTGACGACAC GGTTTAAGAT GAGTCAGCGA
1081 TTGCCGGCTG AGCGATCGCC GCTCCTGCTC TTCGGACCCT
```

The second MinD flanking region is referred to as ΔminD Region 2 and is assigned SEQ ID NO:22.

```
   1 TAATTACTGC CTTGCCGGTG TAGCTCAGGG GTAGAGCAGC
  41 TGTTTTGTAA ACAGCCGGTC GCAGGTTCGA ATCCGGTCAC
  81 CGGCTCTGAG CTCAAACCCA GTCTTCTTGT TGGAGGCTGG
 121 GTTTTTGTTT GTCGTAGCTG ACTAGACGTT CCCTGCCGTA
 161 ACCACGGATT GCTGACTGAA TCAAGCCGCT TCAGAGATGT
 201 CATCCGTGCG AGTCAGTGTC AGGGCGTAAC GGTAGAGCGC
 241 GATCGGACGA TCGCCAACTT GAAAGTAGCT GGGGTCCTGC
```

```
281 GGCGTCAGAT AGATGGCGGT AATTTGATCC GCCGTAATCA
321 AATTCCGCCA TCGCAGCTGG TAGCGAGCTG TGGTTTCTAC
361 GCTGTTGAAC TGAGGGCGAC CCTGACCCCG AAAAATCTGG
401 CGGCTCAGTT CGCTAGCAAT GAAAACGAAG TCGGTGGGCT
441 GTTCCCAGGC TCGGCCTGTC ATCCGCATTA GCAGACTATC
481 GCCATTCACC AACTGGACGA GTTGTTGATT GGGATCAGGA
521 GCTTTGACGG TGGCAACAGC CTCCCCAAGA TAGGCGCGGG
561 CGATCGCAAG GCCATTAAAA GCGCGATCGG CGACGACGGG
601 GGCTGCTTGA GGCCGTAAAT CTGGIAGCGG TTTTGCAGCG
641 GCAGCGTAGG TCGGGGTGCC AAAGCGCACA GGAAACTCCA
681 GCGGTTGATC CAGCCAGCGG CGATTGCTGT CAAAGCCTGG
721 TGTGATGATT TCCGGCGCGA GGGGTGCTTG TAAATCCACC
761 AAGGTGCTGG TGACTTGCCA CGTTCCTGCC ATCCAATCGG
801 GGTAGGGCAG ATCCGGTGCA TTGGTTTTTA GGGATGGTGA
841 GCTTGACCAA GCCGGATACG ACGCAACGCG ATCGCTCAAG
881 GTTGCCGCCT GTGCTGGTGT GATCACAGTC AGCCAACAGC
921 CGAGGGCAAT CGCTCCGATT AACAGCGATC GCAGTAACCC
961 AACAGGAACA ACACGCACGA CAAATCAGCC AGAGATCCGC
```

Mutations can be generated in MinD sequences from a variety of cyanobacterial species, for example, by transforming cells from selected cyanobacterial species with a targeting vector that includes two flanking segments, for example, SEQ ID NO:21 and 22 in *Synechococcus elongatus* and related cyanobacterial species. Such targeting vectors can be used for cyanobacterial species other than *Synechococcus elongatus*, for example, by using targeting vectors that have flanking segment sequences that have less than 100%, or less than 99%, or less than 98%, or less than 95%, or less than 90%, or less than 85%, or less than 75% sequence identity to SEQ ID NO:21 and/or 22. In some cases the targeting vectors that have flanking segment sequences that have at least 70%, or at least 75%, or at least 80%, or at least 85%, or at least 90%, or at least 95%, or at least 97%, or at least 98%, or at least 99% sequence identity to SEQ ID NOs:21 and 22.

In some cases, to induce expression of MinD protein, a promoter region can be used in an expression cassette or vector where the promoter has at least at least 70%, or at least 75%, or at least 80%, or at least 85%, or at least 90%, or at least 95%, or at least 97%, or at least 98%, or at least 99% sequence identity to SEQ ID NO:21 or 22.

MinE

MinE proteins are antagonists of MinC proteins, so cells with loss-of-function mutations of MinE cells are longer than wild type cyanobacterial cells of the same species. One sequence for a *Synechococcus elongatus* MinE polypeptide has the following sequence (SEQ ID NO:23).

```
  1 MLADLFERLF PRQQASRDTV KQRLKLVLAH DRADLSPELL
 41 QKMRQEILEV VSRYVELDSE GMELSLENDQ RVTALVANLP
 81 IRRVKPATAE G
```

A nucleic acid that encodes the polypeptide with SEQ ID NO:23 has the sequence shown below as SEQ ID NO:24.

```
  1 ATGCTGGCTG ACTTATTCGA GCGCTTGTTC CCCCGGCAAC
 41 AGGCCAGTCG AGACACCGTG AAGCAGCGCC TTAAGCTTGT
 81 GCTGGCTCAC GATCGTGCTG ACCTCAGCCC TGAGCTGTTG
121 CAAAAGATGC GCCAAGAGAT TTTAGAAGTG GTCTCTCGCT
161 ACGTTGAGCT GGACTCTGAG GGAATGGAAC TCTCGCTAGA
201 AAATGACCAG CGAGTCACAG CACTTGTCGC CAATTTACCG
241 ATTCGTCGTG TCAAACCCGC AACTGCTGAA GGATGA
```

Other cyanobacterial polypeptides and nucleic acids are available with significant sequence homology to the SEQ ID NO:23 MinE protein. For example, a related *Synechococcus* sp. PCC 6312 MinE sequence with accession number WP_015125088.1 (GI:504937986) is available from the National Center for Biotechnology Information database (see website at ncbi.nlm.nih.gov). The sequence for this MinE polypeptide shares 72% or more sequence identity with SEQ ID NO:23 and is shown below as SEQ ID NO:25.

```
  1 MITDLLERIF PRQQTSRQQV KQRLKLVLAH DPCDLNPEIL
 41 EHLRQDILEV VSRYVELDLD ALDFSLESDQ RTTALIANLP
 81 IRRVKLPTPT EESPVPMQRD GLEL
```

A comparison between SEQ ID NO:23 and SEQ ID NO:25 MinE sequences is shown below, with highly conserved amino acids identified. The asterisks below the comparison show which amino acids are identical.

```
71.6% identity in 88 residues overlap; Score: 323.0; Gap frequency: 0.0%
Seq23    1 MLADLFERLFPRQQASRDTVKQRLKLVLAHDRADLSPELLQKMRQEILEVVSRYVELDSE
Seq25    1 MITDLLERIFPRQQTSRQQVKQRLKLVLAHDRCDLNPEILEHLRQDILEVVSRYVELDLD
           *  ** ** ***** ** ************* **  ** *   ** ************

Seq23   61 GMELSLENDQRVTALVANLPIRRVKPAT
Seq25   61 ALDFSLESDQRTTALIANLPIRRVKLPT
              *** *** *** ********* *
```

Another MinE sequence from *Leptolyngbya* sp. O-77 is available from the NCBI database as accession number BAU43948.1 (GI:984538968), which has at least 71% sequence identity to SEQ ID NO:23, and is shown below as SEQ ID NO:26.

```
  1 MLSELLDRLF PRQPEVSSRE TVKQRLQLVL AHDRTDLPPA
 41 TIEKMRQEIL EVVSRYVEID QEGTEFMLEN NQRATALIAN
 81 LPIRRIKSDV
```

A comparison between SEQ ID NO:23 and SEQ ID NO:26 MinE sequences is shown below, with highly conserved amino acids identified. The asterisks below the comparison show which amino acids are identical.

```
71.3% identity in 87 residues overlap; Score: 301.0; Gap frequency: 2.3%
Seq23     1 MLADLFERLFPRQQ--ASRDTVKQRLKLVLAHDRADLSPELLQKMRQEILEVVSRYVELD
Seq26     1 MLSELLDRLFPRQPEVSSRETVKQRLQLVLAHDRTDLPPATIEKMRQEILEVVSRYVEID
            ** *  ******    ** ****** ******* ** *   *************** *

Seq23    59 SEGMELSLENDQRVTALVANLPIRRVK
Seq26    61 QEGTEFMLENNQRATALIANLPIRRIK
             ** * *** ** *** ******* *
```

Another MinE sequence from *Lyngbya aestuarii* is available from the NCBI database as accession number WP_040483865.1 (GI:750179791), which has at least 73% sequence identity to SEQ ID NO:23, and is shown below as SEQ ID NO:27.

```
     1 MKLNELLERL FPRSTNSRED VKRRLKLVLA HDRADLTPEL

41 IEAMRQEILE VLSRYVEIDT EDSEFGLESD QRATALIANL

81 PIRRVKNTPD VNQTSPTSPD APL
```

A comparison between SEQ ID NO:23 and SEQ ID NO:27 MinE sequences is shown below, with highly conserved amino acids identified. The asterisks below the comparison show which amino acids are identical.

```
72.6% identity in 84 residues overlap; Score: 306.0; Gap frequency: 0.0%
Seq23     2 LADLFERLFPRQQASRDTVKQRLKLVLAHDRADLSPELLQKMRQEILEVVSRYVELDSEG
Seq27     3 LNELLERLFPRSTNSREDVKRRLKLVLAHDRADLTPELIEAMRQEILEVLSRYVEIDTED
            * * ******  **  ** ** ************* ***  ******** ***** * *

Seq23    62 MELSLENDQRVTALVANLPIRRVK
Seq27    63 SEFGLESDQRATALIANLPIRRVK
              ** *** *** *** *********
```

Another MinE sequence from *Calothrix* sp. PCC 7103 is available from the NCBI database as accession number WP_040483865.1 (GI:750179791), which has at least 64% sequence identity to SEQ ID NO:23, and is shown below as SEQ ID NO:28.

```
     1 MILEFIERLF SRSNDTSRSE VKRRLQLVIA HDRADLSPQM

41 IEKMRQEILE IVCRYVEVET EGLEFSLESN QRTTALIANL

81 PIRRVKESTS EEEANSEKV
```

A comparison between SEQ ID NO:23 and SEQ ID NO:28 MinE sequences is shown below, with highly conserved amino acids identified. The asterisks below the comparison show which amino acids are identical.

```
63.7% identity in 91 residues overlap; Score: 293.0; Gap frequency: 1.1%
Seq23     1 MLADLFERLFPRQQ-ASRDTVKQRLKLVLAHDRADLSPELLQKMRQEILEVVSRYVELDS
Seq28     1 MILEFIERLFSRSNDTSRSEVKRRLQLVIAHDRADLSPQMIEKMRQEILEIVCRYVEVET
            *   **** *    **  ** ** ** ** *********    ******** * ****

Seq23    60 EGMELSLENDQRVTALVANLPIRRVKPATAE
Seq28    61 EGLEFSLESNQRTTALIANLPIRRVKESTSE
            ** * ***  ** *** ********* *  *
```

Another MinE sequence from *Leptolyngbya* sp. Heron Island J is available from the NCBI database as accession number WP_023071655.1 (GI:553737423), which has at least 71% sequence identity to SEQ ID NO:23, and is shown below as SEQ ID NO:29.

```
  1    MISDFFERLF GSREPVSRDT AKQRLRFVLA HDRSDISPQN
 41    LEKLRQEILE VVSRYVELDF DGLEFSLESD QRMTALMANL
 61    PIRRVRSNPL EPDSPVEETE AKNLELTDES IALDDEVEEV
121    SETADIPLD
```

A comparison between SEQ ID NO:23 and SEQ ID NO:29 MinE sequences is shown below, with highly conserved amino acids identified. The asterisks below the comparison show which amino acids are identical.

```
70.9% identity in 86 residues overlap; Score: 303.0; Gap frequency: 1.2%
Seq23  1 MLADLFERLF-PRQQASRDTVKQRLKLVLAHDRADLSPELLQKMRQEILEVVSRYVELDS
Seq29  1 MISDFFERLFGSREPVSRDTAKQRLRFVLAHDRSDISPQNLEKLRQEILEVVSRYVELDF
         *  * *****  *    **** **** ****** *  ** * * * ***************

Seq23 60 EGMELSLENDQRVTALVANLPIRRVK
Seq29 61 DGLEFSLESDQRMTALMANLPIRRVR
         * * *** *** *** *** ********
```

Another MinE sequence from *Scytonema millei* is available from the NCBI database as accession number WP_039717520.1 (GI:748142306), which has at least 67% sequence identity to SEQ ID NO:23, and is shown below as SEQ ID NO:30.

```
  1    MFSDLFDKIF SSNPNDNNSR SQVKQRLQLV ISHDRSDLSP
 41    QTIEKMRREI LEVVGRYVEL DVEGMEFSLE NNQRATALIA
 81    NLPIRRVKTD E
```

A comparison between SEQ ID NO:23 and SEQ ID NO:30 MinE sequences is shown below, with highly conserved amino acids identified. The asterisks below the comparison show which amino acids are identical.

```
67.0% identity in 88 residues overlap; Score: 286.0; Gap frequency: 3.4%
Seq23  1 MLADLFERLF---PRQQASRDTVKQRLKLVLAHDRADLSPELLQKMRQEILEVVSRYVEL
Seq30  1 MFSDLFDKIFSSNPNDNNSRSQVKQRLQLVISHDRSDLSPQTIEKMRREILEVVGRYVEL
         * ***   *    *    **  ***** **  *** ****    *** ****** *****

Seq23 58 DSEGMELSLENDQRVTALVANLPIRRVK
Seq30 61 DVEGMEFSLENNQRATALIANLPIRRVK
         * **** **** ** *** *********
```

Another MinE sequence from *Microcoleus* sp. PCC 7113 is available from the NCBI database as accession number WP_015183206.1 (GI:504996104), which has at least 64% sequence identity to SEQ ID NO:23, and is shown below as SEQ ID NO:31.

```
  1    MISDLLERLF PWTSASNSRA EVKRRLQLVI AHDRADLTPQ
 41    MIEKMRNEIL EVVSRYVEIE TEGLEIALES NQRVTALIAN
 81    LPIRRVKEEA PVASGGVEPG IDLIG
```

A comparison between SEQ ID NO:23 and SEQ ID NO:31 MinE sequences is shown below, with highly conserved amino acids identified. The asterisks below the comparison show which amino acids are identical.

```
67.8% identity in 87 residues overlap; Score: 291.0; Gap frequency: 2.3%
Seq23   1 MLADLFERLFPRQQAS--RDTVKQRLKLVLAHDRADLSPELLQKMRQEILEVVSRYVELD
Seq31   1 MISDLLERLFPWTSASNSRAEVKRRLQLVIAHDRADLTPQMIEKMRNEILEVVSRYVEIE
          *  ** *****    **  *  ** ** ** *******  *    *** **********

Seq23  59 SEGMELSLENDQRVTALVANLPIRRVK
Seq31  61 TEGLEIALESNQRVTALIANLPIRRVK
          ** *  **  ****** ** *******
```

Another MinE-like sequence from *Synechococcus elongatus* PCC 7942 is available from the NCBI database as accession number AAA16171.1 (GI:310860), is shown below as SEQ ID NO:32.

```
  1   MTQAQSLDVL NLLEQLEESV LDGTRVPLSG RILVRENDLL
 41   DLLDDVRAGL PAAIQQAQQI LERQAQILAD AQQQAQAIVA
 81   QAQQERALLI DQNSIRLQAE RDASSSAKPF NRNVMPFGNR
121   RSRKQHKCGA RPNSSSSKSA RKPTVFASRP KPKSSSCAAK
161   LNSSYLSSAK GFWSNVRSCG GVLTAMLTKF CGTWSSD
```

Any of the Min proteins and/or their related proteins, for example with conserved domains illustrated by the sequence comparisons shown above, can be expressed in cells (e.g., via a transgene or expression cassette introduced into a host cell) to increase the activity of the MinE proteins described herein.

Figure 2C:
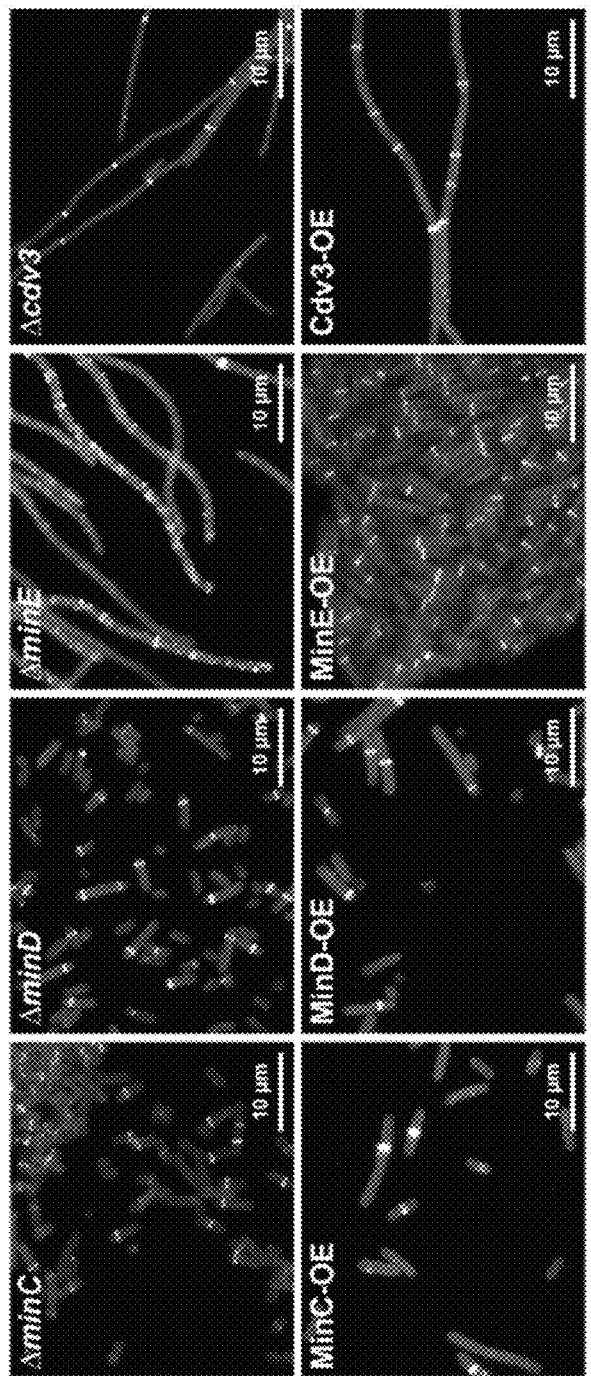

As illustrated in FIG. 2C, deletion or inactivation of MinE tends to elongate cells while overexpression of MinE does not. For example, the mean cell length of inactivated MinE mutants can be at least 150%, or at least 200%, or at least 250%, or at least 300%, or at least 500%, or at least 750%, or at least 1000%, or at least 5000%, or at least 10000%, or at least 15000%, or at least 20000% greater than a wild type population of cyanobacteria of the same species.

Complete deletion of an endogenous MinE gene may be lethal. Hence, partial deletion or inactivation of MinE function may be a better approach.

For example, MinE mutations can be introduced to increase cell size by methods that can include partial deletion or insertion of foreign DNA into the MinE locus. For example, this can involve the use of either transposable elements or T-DNA. The foreign DNA not only disrupts the expression of the gene into which it is inserted but also acts as a marker for subsequent identification of the mutation. If a large enough population of transposon-transformed or T-DNA-transformed lines is available, one has a very good chance of finding a cyanobacteria carrying an insertion within any gene of interest.

Any of the conserved amino acids and conserved domains illustrated by the sequence comparisons shown above can be deleted or mutated to reduce the activity of the MinE proteins described herein and thereby increase cell size. For example, to increase cyanobacterial cell sizes a population of cyanobacteria can include a mutation of any of SEQ ID NOs:23, 25-31, or 32.

A wild type cyanobacterial population can have a MinE polypeptide with at least 70%, or at least 75%, or at least 80%, or at least 85%, or at least 90%, or at least 95%, or at least 97%, or at least 98%, or at least 99% sequence identity to any of SEQ ID NOs:23, 25-31, or 32.

However, the cyanobacterial strain with increased cell length can express mutant MinE polypeptides that have reduced MinE activity. Such MinE polypeptides that have reduced MinE activity can have less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:23, 25-31, or 32. The mutations in mutant MinE polypeptides can, for example, have mutations in at least one conserved amino acid position, or at least two conserved amino acid positions, or at least three conserved amino acid positions, or at least five conserved amino acid positions, or at least seven conserved amino acid positions, or at least eight conserved amino acid positions, or at least ten conserved amino acid positions, or at least fifteen amino acid positions, or at least twenty conserved amino acid positions, or at least twenty-five amino acid positions. In some cases, an entire conserved MinE domain can be deleted. Alternatively, the endogenous MinE gene is partially deleted or mutated.

The conserved amino acids are in many cases mutated by deletion or replacement with amino acids that have dissimilar physical and/or chemical properties.

Cdv3 (DivIVA)

Cdv3 proteins promote cell division. Hence, cyanobacterial cells that express increased levels of the Cdv3 or DivIVA protein are larger than wild type cells with no such Cdv3 or DivIVA overexpression. Cells with loss-of-function Cdv3 or DivIVA mutations are smaller than wild type cyanobacterial cells of the same species.

For example, the mean cell length of Cdv3 overexpressing cyanobacterial cells is at least 150%, or at least 200%, or at least 250%, or at least 300%, or at least 500%, or at least 750%, or at least 1000%, or at least 5000%, or at least 10000%, or at least 15000%, or at least 20000% greater than a wild type population of cyanobacteria of the same species.

One sequence for a *Synechococcus elongatus* Cdv3 polypeptide has the following sequence (SEQ ID NO:33).

```
  1   MTQAQSLDVL NLLEQLEESV LDGTRVPLSG RILVRENDLL
 41   DLLDDVRAGL PAAIQQAQQI LERQAQILAD AQQQAQAIVA
```

```
 81  QAQQERALLI DQNSIRLQAE RDAQQLRQTL QQECDALRQQ

121  AIAEATQVRG EAQQFQLQVR QETDSLRQQT QAEIEQLRSQ

161  TQQQLSEQRQ RILVECEELR RGADSYADQV LRDMEQRLTQ

201  MMQIIRNGRQ ALNLSENTPP PAPRRRSR
```

A nucleic acid that encodes the polypeptide with SEQ ID NO:33 has the sequence shown below as SEQ ID NO:34.

```
  1  GTGACCCAAG CCCAATCACT CGATGTCTTG AACTTGCTAG

41  AGCAGCTCGA AGAGTCTGTG CTCGACGGGA CTCGCGTGCC

81  GCTTTCGGGG CGCATTCTGG TTCGAGAAAA CGACCTGCTC

121  GACCTGTTAG ATGACGTGCG TGCCGGGTTG CCCGCTGCGA

161  TTCAACAAGC TCAGCAAATC CTCGAGCGCC AAGCCCAAAT

201  TTTGGCTGAC GCCCAACAGC AAGCACAGGC GATCGTGGCG
```

```
  1  MVRQEPPIND PRLINDPRLN GQVDDVLAQQ QIGNVTPGPV

41  AGFDIQDALN QIEEAVLDSP RLPVMGRTMI NEDDLLDQLD

61  AVRLNLPGAF QEAQQLLEQR DDILSEAERY AQDIVTTAEK

121  QAAAILNETT ILRQAEQQAQ QLRLQVEQEC AALRSQTMME

161  IEQLQAQTNQ ECDEMRKSAI TECHAIQTDA DTYADQVLQR

201  METQFSEMLD VISNGRQQLY ERQQRARQTA PTPPSSASSG

241  DVPVAPLSRR PISQRPPGQQ SYIQPPPSTP PSRPQQQPPR

281  PQQPPRPQQR PPRKF
```

A comparison between SEQ ID NO:33 and SEQ ID NO:35 Cdv3 sequences is shown below, with highly conserved amino acids identified. The asterisks below the comparison show which amino acids are identical.

```
41.5% identity in 205 residues overlap; Score: 313.0; Gap frequency: 14.1%
Seq33   8 DVLNLLEQLEESVLDGTRVPLSGRILVRENDLLDLLDDVRAGLPAAIQQAQQILERQAQI
Seq35  44 DIQDALNQIEEAVLDSPRLPVMGRTMINEDDLLDQLDAVRLNLPGAFQEAQQLLEQRDDI
              *  * ** ***   * *  **    * ****  **  ** ** *  ***  **    *

Seq33  68 LADAQQQAQAIVAQAQQERALLIDQNSIRLQAERDAQQLRQTLQQECDALRQQAIAEATQ
Seq35 104 LSEAERYAQDIVTTAEKQAAAILNETTILRQAEQQAQQLRLQVEQECAALRSQ-------
          * *    ** **  *    *   *** *****     *** *** *

Seq33 128 VRGEAQQFQLQVRQETDSLRQQTQAEIEQLRSQTQQQLSEQRQRILVECEELRRGADSYA
Seq35 157 ---------------------TMMEIEQLQAQTNQECDEMRKSAITECHAIQTDADTYA
                               * *****  **    * *      **     ** **

Seq33 188 DQVLRDMEQRLTQMMQIIRNGRQAL
Seq35 195 DQVLQRMETQFSEMLDVISNGRQQL
          ****  **       *  * **** *
```

```
         -continued
241  CAGGCGCAGC AAGAACGGGC CCTGCTGATT GACCAAAACA

281  GTATTCGGCT TCAAGCTGAG CGCGATGCGC AGCAGCTCCG

321  CCAAACCCTT CAACAGGAAT GTGATGCCCT TCGGCAACAG

361  GCGATCGCGG AAGCAACACA AGTGCGGGGC GAGGCCCAAC

401  AGTTCCAGCT CCAAGTCCGC CAGGAAACCG ACAGTCTTCG

441  CCAGCAGACC CAAGCCGAAA TCGAGCAGCT GCGCAGCCAA

481  ACTCAACAGC AGCTATCTGA GCAGCGCCAA AGGATTTTGC

521  TCGAATGTGA GGAGTTGCGG CGGGGTGCTG ACAGCTATGC

561  TGACCAAGTT CTGCGGGACA TGGAGCAGCG ATTGACCCAG

601  ATGATGCAGA TCATCCGCAA TGGTCGTCAG GCCCTGAACT

641  TGAGCGAAAA TACGCCGCCC CCTGCTCCCC GTCGGCGATC

681  GCGCTAA
```

Other cyanobacterial polypeptides and nucleic acids are available with significant sequence homology to the SEQ ID NO:33 Cdv3 protein. For example, a related *Leptolyngbya* sp. Heron Island J Cdv3 sequence with accession number WP_023073979.1 (GI:553739790) is available from the National Center for Biotechnology Information database (see website at ncbi.nlm.nih.gov). The sequence for this Cdv3 polypeptide shares 41% or more sequence identity with SEQ ID NO:33 and is shown below as SEQ ID NO:35.

Another Cdv3 sequence from *Leptolyngbya* sp. PCC 7375 is available from the NCBI database as accession number WP_006517434.1 (GI:493564058), which has at least 42% sequence identity to SEQ ID NO:33, and is shown below as SEQ ID NO:36.

```
  1  MVRQEPPLND PRLVNDPRLV NDPRLNGQAA QVDDVLAQQQ

41  IGKAGPAPMA GFDIQDALNQ IEESVLDSPR LPVMGRTMIN

81  EDDLLDQLDA VRLNLPSAFQ EAQQLVEQRD DILNEAERYA

121  QNIVTAAEKQ AATILNETSI LRQAEQQAQQ LRLQVEQECA

161  ALRSQTMLEI EQLQTQTKQE CEDLRQNAIA ECHAIQTDAD

201  TYADQVLQRM ETQFSEMLGV ISNGRQQLYE RQQRARQTAP

241  PSMPAASDVV APPNPLNRCP ATQRPSSTQQ SYIQPPQQQP

281  PTRSPQQQPP TRPPQQPPRP QQRPPRKF
```

A comparison between SEQ ID NO:33 and SEQ ID NO:36 Cdv3 sequences is shown below, with highly conserved amino acids identified. The asterisks below the comparison show which amino acids are identical.

```
42.0% identity in 205 residues overlap; Score: 313.0; Gap frequency: 14.1%
Seq33    8  DVLNLLEQLEESVLDGTRVPLSGRILVRENDLLDLLDDVRAGLPAAIQQAQQILERQAQI
Seq36   53  DIQDALNQIEESVLDSPRLPVMGRTMINEDDLLDQLDAVRLNLPSAFQEAQQLVEQRDDI
             *  * ****** * * **    * **** ** **  ** * * ***  *     *

Seq33   68  LADAQQQAQAIVAQAQQERALLIDQNSIRLQAERDAQQLRQTLQQECDALRQQAIAEATQ
Seq36  113  LNEAERYAQNIVTAAEKQAATILNETSILRQAEQQAQQLRLQVEQECAALRSQ-------
             *  *   ** **  *    *    ** ***  *****    *** *** *

Seq33  128  VRGEAQQFQLQVRQETDSLRQQTQAEIEQLRSQTQQQLSEQRQRILVECEELRRGADSYA
Seq36  166  ---------------------TMLEIEQLQTQTKQECEDLRQNAIAECHAIQTDADTYA
                                    * ***** ** **    **     ** **

Seq33  188  DQVLRDMEQRLTQMMQIIRNGRQAL
Seq36  204  DQVLQRMETQFSEMLGVISNGRQQL
            **** **    *  * **** *
```

Another Cdv3 sequence from *Neosynechococcus sphagnicola* sy1 is available from the NCBI database as accession number KGF72132.1 (GI:691246400), which has at least 40% sequence identity to SEQ ID NO:33, and is shown below as SEQ ID NO:37.

```
  1   MQHPAEALDV QRELNKLEEM ILDSPRLPFS GRTLVDEEHI
 41   LDQVDLIRLS LPAAFHEAEE MVRRKDELLS QAEHYAQERI
 61   DQAERQAAQI LDEIGIIQQA EQEARQIRQR VQQECEAAQT
121   HTMAEIERMH RQAQQELEEM RRLAISECHD IQHEADVYAD
161   RVLKSMEQQL GEMMRVIRNG RQQLQPEPPP SRREQREDGT
201   TTNPGRPTPP AVHTQTQTRM PERIKG
```

A comparison between SEQ ID NO:33 and SEQ ID NO:37 Cdv3 sequences is shown below, with highly conserved amino acids identified. The asterisks below the comparison show which amino acids are identical.

```
38.6% identity in 223 residues overlap; Score: 297.0; Gap frequency: 14.3%
Seq33    4  AQSLDVLNLLEQLEESVLDGTRVPLSGRILVRENDLLDLLDDVRAGLPAAIQQAQQILER
Seq37    5  AEALDVQRELNKLEEMILDSPRLPFSGRTLVDEEHILDQVDLIRLSLPAAFHEAEEMVRR
             * ***  *  *** **   * * *** ** **  **  *  *  ****  *     *

Seq33   64  QAQILADAQQQAQAIVAQAQQERALLIDQNSIRLQAERDAQQLKTLQQECDALRQQAIA
Seq37   65  KDELLSQAEHYAQERIDQAEQAAQILDEIGIIQQAEQEARQIRQRVQQECEAAQTH---
               ** *  * ** *  *  *  ** *    *  ** * * *  * **** *  *

Seq33  124  EATQVRGEAQQFQLQVRQETDSLRQQTQAEIEQLRSQTQQQLSEQRQRILVECEELRRGA
Seq37  122  ------------------------TMAEIERMHRQAQQELEEMRRLAISECHDIQHEA
                                    * ****   * ** * **     **    *

Seq33  184  DSYADQVLRDMEQRLTQMMQIIRNGRQALNLSENTPPPAPRRR
Seq37  156  DVYADRVLKSMEQQLGEMMRVIRNGRQQL---QPEPPPSRREQ
            * *** **  *** *  ** ****** *     ***  *
```

Another Cdv3 sequence from *Planktothrix* is available from the NCBI database as accession number WP_026787539.1 (GI:652391691), which has at least 40% sequence identity to SEQ ID NO:33, and is shown below as SEQ ID NO:38.

```
  1   MLRQESTPRL EPEQNGLRVE PETTVSNSPG IDIQRELNRL
 41   EEMILDSPRI PLTRRTLVDE EQLLDQLDLI RLNLPSAFQE
 81   SDIIVRHKDE ILQEAFEYAQ EIVTMAEQRA ARILNEMGLI
```

-continued
```
121   QQAKSEADQL RQQVQNECDT LQQQTLSEIE QIRYRLQQEL
161   EEMRSRTMAE CEEIQNGADD YADHVLGSIE QQLNEMMRVI
181   RNGRQQVQGN NPTR
```

A comparison between SEQ ID NO:33 and SEQ ID NO:38 Cdv3 sequences is shown below, with highly conserved amino acids identified. The asterisks below the comparison show which amino acids are identical.

```
40.0% identity in 210 residues overlap; Score: 305.0; Gap frequency: 13.8%
Seq33    1 MTQAQSLDVLNLLEQLEESVLDGTRVPLSGRILVRENDLLDLLDDVRAGLPAAIQQAQQI
Seq38   25 VSNSPGIDIQRELNRLEEMILDSPRIPLTRRTLVDEEQLLDQLDLIRLNLPSAFQESDII
                  *    *  ***  **  * **  * ** *  *** **  *  ** * *    *

Seq33   61 LERQAQILADAQQQAQAIVAQAQQERALLIDQNSIRLQAERDAQQLRQTLQQECDALRQQ
Seq38   85 VRHKDEILQEAEEYAQEIVTMAEQRAARILNEMGLIQQAKSEADQLRQQVQNECD-----
                 **  *   ** **  * *  *          **   * ****  * ***

Seq33  121 AIAEATQVRGEAQQFQLQVRQETDSLRQQTQAEIEQLRSQTQQQLSEQRQRILVECEELR
Seq38  140 ------------------------TLQQQTLSEIEQIRYRLQQELEEMRSRTMAECEEIQ
                                    * ***  **** *   ** * * * *   ****

Seq33  181 RGADSYADQVLRDMEQRLTQMMQIIRNGRQ
Seq38  176 NGADDYADHVLGSIEQQLNEMMRVIRNGRQ
            *** *** **   ** *  **  ******
```

Another Cdv3 sequence from *Geitlerinema* sp. PCC 7105 is available from the NCBI database as accession number WP_017658745.1 (GI:516254782), which has at least 40% sequence identity to SEQ ID NO:33, and is shown below as SEQ ID NO:39.

```
  1 MLRQDSAGID PKSDSPQPQG EPAQTVAPEQ RQEGANQGSV

41 NVQQALNRLE EAILDSPRIP FTGRTLVDEE PLLDILDAIR

81 LNLPAAFQEA EEVIRQKDEI LRQAEQYGRE IVDAAEQQAA

121 SILDEMGLVR QAKVEADRLR QQVQADCEVA RERAISEIEQ
161 MQRQAQQELE EVRARALAEA EQIEAGADEY ADRVLRNIEQ
201 QLSDMMRVIR NGRQQLQQEV AYRAHQKEPK VNPNVRRY
```

A comparison between SEQ ID NO:33 and SEQ ID NO:39 Cdv3 sequences is shown below, with highly conserved amino acids identified. The asterisks below the comparison show which amino acids are identical.

```
40.1% identity in 207 residues overlap; Score: 306.0; Gap frequency: 14.0%
Seq33    6 SLDVLNLLEQLEESVLDGTRVPLSGRILVRENDLLDLLDDVRAGLPAAIQQAQQILERQA
Seq39   39 SVNVQQALNRLEEAILDSPRIPFTGRTLVDEEPLLDILDAIRLNLPAAFQEAEEVIRQKD
           *  *   *  ***  **  * *  ** ** *  *** **  *  **** * *

Seq33   66 QILADAQQQAQAIVAQAQQERALLIDQNSIRLQAERDAQQLRQTLQQECDALRQQAIAEA
Seq39   99 EILRQAEQYGREIVDAAEQQAASILDEMGLVRQAKVEADRLRQQVQADCEVARERAISE-
            ** * *    **  * *  *   *      **   *  ***  *  *   *  ** *

Seq33  126 TQVRGEAQQFQLQVRQETDSLRQQTQAEIEQLRSQTQQQLSEQRQRILVECEELRRGADS
Seq39  158 ----------------------------IEQMQRQAQQELEEVRARALAEAEQIEAGADE
                                       ***   * ** * * * * * * *    ***

Seq33  186 YADQVLRDMEQRLTQMMQIIRNGRQAL
Seq39  190 YADRVLRNIEQQLSDMMRVIRNGRQQL
           *** ***  ** *  **  ****** *
```

Any of the conserved amino acids and conserved domains illustrated by the sequence comparisons shown above can be expressed in cells (e.g., via a transgene or expression cassette introduced into a host cell) to increase the activity of the Cdv3 proteins described herein.

Figure 2D:
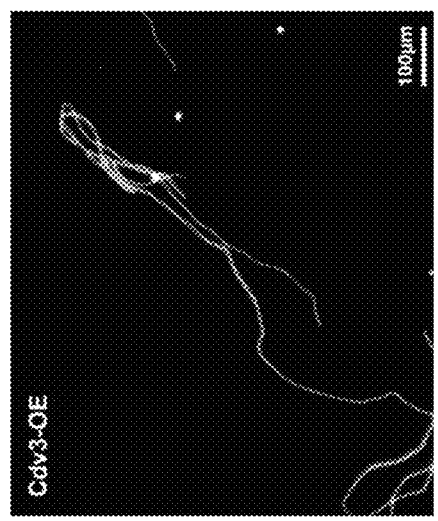
Figure 2E:
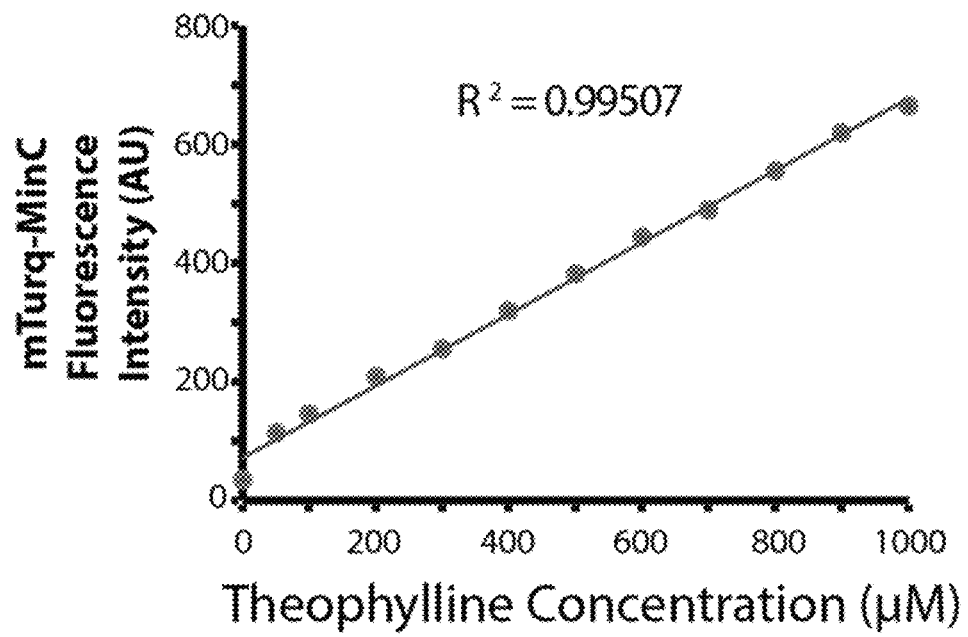
Figure 2F:
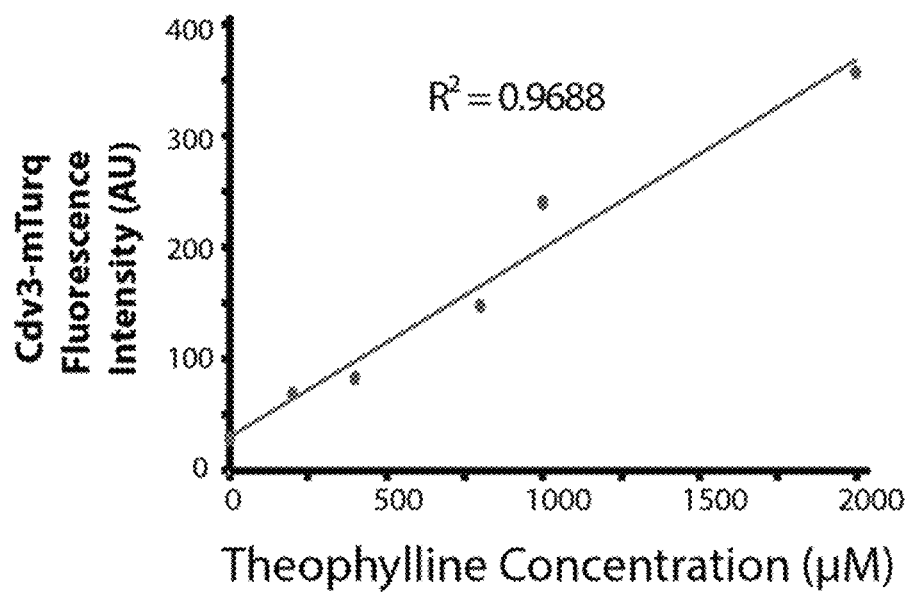

As illustrated in FIGS. 2C-2D, 2F, overexpression of Cdv3 tends to elongate cells. To increase cyanobacterial cell sizes a population of cyanobacteria can include an expression cassette or vector that encodes a Cdv3 polypeptide. For example, an expression cassette or vector that encodes can include a Cdv3 polypeptide with at least 70%, or at least 75%, or at least 80%, or at least 85%, or at least 90%, or at least 95%, or at least 97%, or at least 98%, or at least 99% sequence identity to any of SEQ ID NOs:33, 35-38, or 39.

Any of the conserved amino acids and conserved domains illustrated by the sequence comparisons shown above can be deleted in cells to reduce the expression and/or activity of the (e.g., endogenous) Cdv3 proteins described herein. As illustrated in FIG. 2C deletion of Cdv3 can also lead to elongation of cells.

For example, Cdv3 mutations can be introduced to increase cell size by methods that can include deletion of Cdv3 sequences or insertion of foreign DNA into the Cdv3 locus. For example, this can involve the use of either transposable elements or T-DNA. The foreign DNA not only disrupts the expression of the gene into which it is inserted but also acts as a marker for subsequent identification of the mutation. If a large enough population of transposon-transformed or T-DNA-transformed lines is available, one has a very good chance of finding a cyanobacteria carrying an insertion within any gene of interest.

Any of the conserved amino acids and conserved domains illustrated by the sequence comparisons shown above can be deleted or mutated to reduce the activity of the Cdv3 proteins described herein and thereby increase cell size. For example, to increase cyanobacterial cell sizes a population of cyanobacteria can include a mutation of any of SEQ ID NOs:33, 35-38, or 39.

A wild type cyanobacterial population can have a Cdv3 polypeptide with at least 70%, or at least 75%, or at least 80%, or at least 85%, or at least 90%, or at least 95%, or at least 97%, or at least 98%, or at least 99% sequence identity to any of SEQ ID NOs:33, 25-38, or 39.

However, the cyanobacterial strain with increased cell length can express mutant Cdv3 polypeptides that have reduced Cdv3 activity. Such Cdv3 polypeptides that have reduced Cdv3 activity can have less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:33, 35-38, or 39. The mutations in mutant Cdv3 polypeptides can, for example, have mutations in at least one conserved amino acid position, or at least two conserved amino acid positions, or at least three conserved amino acid positions, or at least five conserved amino acid positions, or at least seven conserved amino acid positions, or at least eight conserved amino acid positions, or at least ten conserved amino acid positions, or at least fifteen amino acid positions, or at least twenty conserved amino acid positions, or at least twenty-five amino acid positions. In some cases, an entire conserved Cdv3 domain or the entire endogenous Cdv3 gene is deleted or mutated.

The conserved amino acids are in many cases mutated by deletion or replacement with amino acids that have dissimilar physical and/or chemical properties.

FtsZ Sequences

FtsZ proteins polymerize or self-assemble to form a contractile "Z ring" (usually in the middle of the cell) that mediates actual cell division. The Min proteins modulate the self-assembly or positioning of FtsZ rings.

In some cases, cyanobacterial cells that express increased levels of the FtsZ protein can be smaller than wild type cells with no such FtsZ overexpression. Cells with loss-of-function FtsZ mutations can in some cases be larger than wild type cyanobacterial cells of the same species.

One example of a *Synechococcus elongatus* 7942 FtsZ protein sequence is shown below as SEQ ID NO:40.

```
  1 MTDPMPINNS YGFNRDGSLS GFDALGQPEE LIIPSSVARI
 41 KWIGVGGGGS NGVNRMISSD VSGVEFWALN TDAQALLHSA
 81 APKRMQLGQK LTRGLGAGGN PAIGMKAAEE SREELIAALE
121 GADLVFITAG MGGGTGTGAA PIVAEVAKEV GALTVGIVTK
161 PFTFEGRRRM KQAEEGTAAL QSSVDTLITI PNDRLLHAIS
201 EQTPIQEAFR VADDILRQGV QGISDIITIP GLVNVDFADV
241 RAVMADAGSA LMGIGSGSGK SRAREAAHAA ISSPLLESSI
281 EGARGVVFNI TGGRDMTLHE VNAAADAIYE VVDPEANIIF
321 GAVIDDRLEG ELRITVIATG FSTDRPNLNT ISTSTSQPTS
361 QPSVSPNPAS APPASGGGLD IPAFLQRKIQ NRP
```

A nucleotide sequence encoding the *Synechococcus elongatus* 7942 SEQ ID NO:40 FtsZ protein is shown below (SEQ ID NO:41).

```
  1 ATGACCGACC CTATGCCGAT CAACAATTCC TATGGCTTCA
 41 ACCGTGACGG CTCTCTGTCG GGGTTCGATG CACTAGGGCA
 81 GCCAGAAGAA CTAATCATCC CCAGCAGCGT TGCCCGCATC
121 AAAGTAATTG GCGTTGGCGG TGGCGGCAGC AACGGGGTCA
161 ACCGCATGAT TAGCAGCGAT GTCAGCGGGG TTGAATTTTG
201 GGCCCTCAAC ACTGATGCTC AAGCTTTGCT CCACTCTGCA
241 GCCCCCAAGC GGATGCAGTT GGGACAGAAA CTAACGCGAG
281 GGCTAGGCGC AGGTGGCAAC CCTGCGATCG GCATGAAAGC
321 CGCTGAAGAA TCGCGGGAAG AACTAATCGC CGCCTTGGAA
361 GGGGCTGACC TCGTCTTTAT CACGGCGGGG ATGGGCGGTG
```

```
401 GAACCGGCAC TGGAGCTGCC CCGATCGTGG CAGAAGTCGC
441 CAAAGAAGTG GGTGCGCTGA CGGTTGGGAT TGTCACCAAA
481 CCCTTCACCT TCGAAGGGCG TCGCCGAATG AAGCAGGCGG
521 AAGAAGGAAC AGCCGCACTG CAAAGCTCAG TCGACACTTT
561 GATCACTATT CCTAATGACC GCCTACTCCA CGCCATATCT
601 GAGCAGACGC CGATTCAAGA AGCTTTCCGG GTCGCCGACG
641 ATATTCTCCG GCAGGGTGTG CAAGGGATTT CTGACATCAT
681 CACGATCCCA GGTCTGGTCA ACGTCGACTT TGCCGACGTT
721 CGCGCCGTCA TGGCCGATGC TGGATCAGCC CTGATGGGCA
761 TCGGTAGCGG CTCTGGCAAG TCCCGCGCTC GGGAAGCCGC
801 TCATGCAGCC ATTAGCTCAC CGCTGCTGGA GTCTTCGATC
841 GAAGGGCGC GCGGCGTTGT CTTCAACATC ACAGGCGGCC
881 GCGATATGAC CCTGCATGAG GTCAACGCAG CAGCGGATGC
921 GATTTACGAA GTCGTCGATC CTGAAGCCAA TATCATTTTC
961 GGCGCCGTGA TTGACGATCG ATTGGAAGGA GAGCTGCGGA
1001 TCACCGTGAT CGCCACGGGC TTCAGCACCG ATCGCCCCAA
1041 CCTCAACACG ATTTCCACCA GCACGTCCCA GCCGACCAGC
1081 CAACCCAGCG TGAGTCCCAA CCCAGCTAGT GCCCCACCGG
1121 CGAGCGGCGG CGGCCTCGAC ATTCCGGCCT TCCTACAACG
1161 GAAAATTCAA AACCGACCCT AG
```

Other polypeptides and nucleic acids are available with significant sequence homology to the SEQ ID NO:40 FtsZ protein. For example, a related *Escherichia coli* str. K-12 substr. MG1655 sequence is available as SEQ ID NO:42, shown below.

```
  1 MFEPMELTND AVIKVIGVGG GGGNAVEHMV RERIEGVEFF
 41 AVNTDAQALR KTAVGQTIQI CSGITKGLGA GANPEVGRNA
 61 ADEDRDALRA ALEGADMVFI AAGMGGGTGT GAAPVVAEVA
121 KDLGILTVAV VTKPFNFEGK KRMAFAEQGI TELSKHVDSL
161 ITIPNDKLLK VLGRGISLLD AFGAANDVLK GAVQGIAELI
201 TRPGLMNVDF ADVRTVMSEM GYAMMGSGVA SGEDRAEEAA
241 EMAISSPLLE DIDLSGARGV LVNITAGFDL RLDEFETVGN
281 TIRAFASDNA TVVIGTSLDP DMNDELRVTV VATGIGMDKR
321 PEITLVTNKQ VQQPVMDRYQ QHGMAPLTQE QKPVAKVVND
361 NAPQTAKEPD YLDIPAFLRK QAD
```

The sequence for this SEQ ID NO:42 FtsZ polypeptide shares 54% or more sequence identity with SEQ ID NO:40 as illustrated below. The asterisks below the comparison show which amino acids are identical.

54.1% identity in 318 residues overlap; Score: 852.0; Gap frequency: 0.3%
```
Seq40     38 ARIKVIGVGGGGSNGVNRMISSDVSGVEFWALNTDAQALLHSAAPKRMQLGQKLTRGLGA
Seq42     11 AVIKVIGVGGGGNAVEHMVRERIEGVEFFAVNTDAQALRKTAVGQTIQIGSGITKGLGA
                ********** * *     **** * *******    *   *   * ****

Seq40     98 GGNPAIGMKAAEESREELIAALEGADLVFITAGMGGGTGTGAAPIVAEVAKEVGALTVGI
Seq42     71 GANPEVGRNAADEDRDALRAALEGADMVFIAAGMGGGTGTGAAPVVAEVAKDLGILTVAV
              * **  *  **  *  * *  ******* *** ************** ****** * ***

Seq40    158 VTKPFTFEGRRRMKQAEEGTAALQSSVDTLITIPNDRLLHAISEQTPIQEAFRVADDILR
Seq42    131 VTKPFNFEGKKRMAFAEQGITELSKHVDSLITIPNDKLLKVLGRGISLLDAFGAANDVLK
             ***** *** ** **  * **   *  ** ******* **       **   *  * *

Seq40    218 QGVQGISDIITIPGLVNVDFADVRAVMADAGSALMGIGSGSGKSRAREAAHAAISSPLLE
Seq42    191 GAVQGIAELITRPGLMNVDFADVRTVMSEMGYAMMGSGVASGEDRAEEAAEMAISSPLLE
              ****    ** *** ******** ** *    * **** * **  *** ** *******

Seq40    218 S-SIEGARGVVFNITGGRDMTLHEVNAAADAIYEVVDPEANIIFGAVIDDRLEGELRITV
Seq42    251 DIDLSGARGVLVNITAGFDLRLDEFETVGNTIRAFASDNATVVIGTSLDPDMNDELRVTV
                  ***** ***** *** *  *      *      *  *  *    *   *** **

Seq40    337 IATGFSTDRPNLNTISTS
Seq42    311 VATGIGMDKRPEITLVTN
              ***  * *  *  *
```

A nucleotide sequence encoding the SEQ ID NO:42 protein is shown below as SEQ ID NO:43.

```
   1 ATGTTTGAAC CAATGGAACT TACCAATGAC GCGGTGATTA
  41 AAGTCATCGG CGTCGGCGGC GGCGGCGGTA ATGCTGTTGA
  81 ACATATGGTG CGCGAGCGCA TTGAAGGTGT TGAATTCTTC
 121 GCGGTAAATA CCGATGCACA AGCGCTGCGT AAAACAGCGG
 161 TTGGACAGAC GATTCAAATC GGTAGCGGTA TCACCAAAGG
 201 ACTGGGCGCT GGCGCTAATC CAGAAGTTGG CCGCAATGCG
 241 GCTGATGAGG ATCGCGATGC ATTGCGTGCG GCGCTGGAAG
 281 GTGCAGACAT GGTCTTTATT GCTGCGGGTA TGGGTGGTGG
 321 TACCGGTACA GGTGCAGCAC CAGTCGTCGC TGAAGTGGCA
 361 AAAGATTTGG GTATCCTGAC CGTTGCTGTC GTCACTAAGC
 401 CTTTCAACTT TGAAGGCAAG AAGCGTATGG CATTCGCGCA
 441 GCAGGGGATC ACTGAACTGT CCAAGCATGT GGACTCTCTG
 481 ATCACTATCC CGAACGACAA ACTGCTGAAA GTTCTGGGCC
 521 GCGGTATCTC CCTGCTGGAT GCGTTTGGCG CAGCGAACGA
 561 TGTACTGAAA GGCGCTGTGC AAGGTATCGC TGAACTGATT
 601 ACTCGTCCGG GTTTGATGAA CGTGGACTTT GCAGACGTAC
 641 GCACCGTAAT GTCTGAGATG GGCTACGCAA TGATGGGTTC
 681 TGGCGTGGCG AGCGGTGAAG ACCGTGCGGA AGAAGCTGCT
 721 GAAATGGCTA TCTCTTCTCC GCTGCTGGAA GATATCGACC
 761 TGTCTGGCGC GCGCGGCGTG CTGGTTAACA TCACGGCGGG
 801 CTTCGACCTG CGTCTGGATG AGTTCGAAAC GGTAGGTAAC
 841 ACCATCCGTG CATTTGCTTC CGACAACGCG ACTGTGGTTA
 881 TCGGTACTTC TCTTGACCCG GATATGAATG ACGAGCTGCG
 921 CGTAACCGTT GTTGCGCACA GTATCGGCAT GGACAAACGT
 961 CCTGAAATCA CTCTGGTGAC CAATAAGCAG GTTCAGCAGC
1001 CAGTGATGGA TCGCTACCAG CAGCATGGGA TGGCTCCGCT
1041 GACCCAGGAG CAGAAGCCGG TTGCTAAAGT CGTGAATGAC
1081 AATGCGCCGC AAACTGCGAA AGAGCCGGAT TATCTGGATA
1121 TCCCAGCATT CCTGCGTAAG CAAGCTGATT AA
```

Another FtsZ sequence from *Planktothricoides* sp. SR001 is available from the NCBI database as accession number WP_054467071.1 (GI:935603347), which has at least 76% sequence identity to SEQ ID NO:40, and is shown below as SEQ ID NO:44.

```
   1 MTLNNSLGPV HESPHAQETT SLPPANAENS NPFNNVGLYG
  41 GQNLDPIWRE KTPPKEEPRS REIVPSSIAR IKVIGVGGGG
  81 CNAVNRMIAS EVSGVEFWGI NTDAQALTQA NAPKRLQIGQ
 121 KLTRGLGAGG NPAIGQKAAE ESRDEIAAAL DGSDLVFITA
 161 GMGGGTGTGA APIVAEAAKE VGALTVGVVT RPFNFEGRRR
 201 TSQAEEGIAA LQGRVDTLII IPNDRLLHVI SEQTPVQEAF
 241 RVADDILRQG VQGISDIITI PGMVNVDFAD VRAIMADAGS
 281 ALMGIGTGSG KSRAREAAMA AISSPLMEAS IEGAKGVVFN
 321 ITGGGDLTLH EVSAAADIIY EVVDPNANII FGAVIDERLQ
 361 GEIRMTVIAT GFSNEPQPLP QKSRTVPPPP PSFRREASAP
 401 RTVNPVEPSP QPKPPTQTGG LDIPEFLQRR RPPK
```

A comparison between SEQ ID NO:44 and SEQ ID NO:40 FtsZ sequences is shown below, with highly conserved amino acids identified. The asterisks below the comparison show which amino acids are identical.

76.6% identity in 368 residues overlap; Score: 1372.0; Gap frequency: 3.0%

```
Seq40    32 IIPSSVARIKVIGVGGGGSNGVNRMISSDVSGVEFWALNTDAQALLHSAAPKRMQLGQKL
Seq44    63 IVPSSIARIKVIGVGGGGCNAVNRMIASEVSGVEFWGINTDAQALTQANAPKRLQIGQKL
             * *** ************ *  ***** * ******* *******     **** * ****

Seq40    92 TRGLGAGGNPAIGMKAAEESREELIAALEGADLVFITAGMGGGTGTGAAPIVAEVAKEVG
Seq44   123 TRGLGAGGNPAIGQKAAEESRDEIAAALDGSDLVFITAGMGGGTGTGAAPIVAEAAKEVG
             ************* ******* * *** * ************************** *****

Seq40   152 ALTVGIVTKPFTFEGRRRMKQAEEGTAALQSSVDTLITIPNDRLLHAISEQTPIQEAFRV
Seq44   183 ALTVGVVTRPFNFEGRRRTSQAEEGIAALQGRVDTLIIIPNDRLLHVISEQTPVQEAFRV
             ***** ** ** ******   *****  ****    ****** ********* ****** ******

Seq40   212 ADDILRQGVQGISDIITIPGLVNVDFADVRAVMADAGSALMGIGSGSGKSRAREAAHAAI
Seq44   243 ADDILRQGVQGISDIITIPGMVNVDFADVRAIMADAGSALMGIGTGSGKSRAREAAMAAI
             ******************** ********** ************  ************ ***

Seq40   272 SSPLLESSIEGARGVVFNITGGRDMTLHEVNAAADAIYEVVDPEANIIFGAVIDDRLEGE
Seq44   303 SSPLMEASIEGAKGVVFNITGGGDLTLHEVSAAADIIYEVVDPNANIIFGAVIDERLQGE
             **** * ***** ********* * ****** **** ********* ************ ** **

Seq40   332 LRITVIATGFSTDRPNLNTISTST-----------SQPTSQPSVSPNPASAPPASGGGLD
Seq44   363 IRMTVIATGFSNEPQPLPQKSRTVPPPPPSFRREASAPRTVNPVEPSPQPKPPTQTGGLD
             * ********   *   *     *            *  *      * *  **     ****
```

Seq40   381 IPAFLQRK
Seq44   423 IPEFLQRR
              **

Any of the conserved amino acids and conserved domains illustrated by the sequence comparisons shown above can be expressed in cells (e.g., via a transgene or expression cassette introduced into a host cell) to increase the activity of the FtsZ proteins described herein.

Any of the conserved amino acids and conserved domains illustrated by the sequence comparisons shown above can be deleted in cells) to reduce the expression and/or activity of the (e.g., endogenous) FtsZ proteins.

Ftn2 Sequences

As illustrated herein, cyanobacterial populations that overexpress Ftn2 proteins have an increased mean cell size or length. For example, the mean cell length of Ftn2 overexpressing cyanobacterial cells is at least 150%, or at least 200%, or at least 250%, or at least 300%, or at least 500%, or at least 750%, or at least 1000%, or at least 5000%, or at least 10000%, or at least 15000%, or at least 20000% greater than a wild type population of cyanobacteria of the same species.

One sequence for a *Synechococcus elongatus* Ftn2 polypeptide has the following sequence (SEQ ID NO:45).

```
  1 VRIPLDYYRI LCVGVQASAD KLAESYRDRL NQSPSHEFSE

41 LALQARRQLL EAAIAELSDP EQRDRYDRRF FQGGLEAIEP

61 SLELEDWQRI GALLILLELG EYDRVSQLAE ELLPDYDASA

121 EVRDQFARGD IALAIALSQQ SLGRECRQQG LYEQAAQHFG

161 RSQSALADHQ RFPELSRTLH QEQGQLRPYR ILERLAQPLT

201 ADSDRQQGLL LLQAMLDDRQ GIEGPGDDGS GLTLDNFLMF

241 LQQIRGYLTL AEQQLLFESE ARRPSPAASF FACYTLIARG

281 FCDHQPSLIH RASLLLHELK SRMDVHIEQA IASLLLGQPE

321 EAEALLVQSQ DEETLSQIRA LAQGEALIVG LCRFTETWLA

361 TKVFPDFRDL KERTAPLQPY FDDPDVQTYL DAIVELPSDL

401 MPTPLPVEPL EVRSSLLAKE LPTPATPGVA PPPRRRRRDR

441 SERPARTAKR LPLPWIGLGV VVVLGGGTGV WAWRSRSNST

481 PPTPPPVVQT LPEAVPAPSP APVTVALDRA QAETVLQNWL

521 AAKAAALGPQ YDRDRLATVL TGEVLQTWQG FSSQQANTQL

561 TSQFDHKLTV DSVQLSDGDQ RAVVQAKVDE VEQVYRGDQL

601 LETRRDLGLV IRYQLVRENN IWKIASISLV R
```

A nucleic acid that encodes the polypeptide with SEQ ID NO:45 has the sequence shown below as SEQ ID NO:46.

```
  1 GTGCGTATTC CTCTCGATTA CTACCGAATT CTCTGTGTTG

41 GCGTGCAAGC CTCGGCAGAC AAACTTGCCG AAAGCTACCG

81 CGATCGCCTC AACCAATCGC CCTCCCATGA GTTTTCAGAG

121 CTGGCATTGC AGGCGCGGCG GCAACTCCTC GAAGCAGCGA

161 TTGCTGAGCT GAGTGATCCC GAACAGCGCG ATCGCTACGA

201 TCGCCGCTTT TTTCAGGGCG GTCTGGAAGC GATTGAACCA

241 AGCCTAGAAC TCGAAGACTG GCAGCGAATT GGAGCCCTGC

281 TGATCCTGCT GGAATTGGGG GAATACGATC GCGTTTCGCA

321 ACTGGCTGAG GAACTCCTGC CAGACTACGA CGCGAGCGCA

361 GAAGTACGCG ATCAGTTCGC GCGGGGTGAT ATCGCCTTGG

401 CGATCGCACT ATCCCAGCAA TCCCTCGGTC GAGAATGCCG

441 TCAGCAGGGT CTGTACGAAC AGGCCGCCCA GCACTTTGGC

481 CGCAGCCAGT CTGCCCTAGC CGATCATCAG CGCTTTCCTG

521 AACTGAGTCG AACCCTGCAC CAAGAACAAG GACAGCTACG

561 GCCCTATCGC ATTTTGGAGC GGTTGGCCCA GCCCTTGACT

601 GCCGATAGCG ATCGCCAGCA GGGTTTGCTG TTGTTGCAGG

641 CGATGTTGGA CGACCGGCAG GGCATTGAAG GCCCTGGGGA

681 TGATGGCTCG GGGCTGACCC TTGATAACTT TTTGATGTTT

721 CTCCAGCAAA TTCGCGGCTA TCTGACCCTG GCTGAACAGC
```

```
 761 AGTTGCTGTT TGAATCGGAA GCGCGTCGGC CCTCGCCGGC

801 TGCGAGCTTT TTTGCCTGCT ACACCCTGAT TGCGCGGGGC

841 TTTTGCGATC ACCAACCCTC GTTGATCCAT CGCGCCAGCT

881 TGCTCTTGCA TGAACTCAAG AGCCGCATGG ATGTGCACAT

921 CGAACAGGCG ATCGCCAGCC TATTGCTCGG ACAGCCCGAA

961 GAAGCTGAGG CGCTACTCGT CCAGAGCCAA GATGAGGAAA

1001 CCCTCAGCCA AATCCGTGCC CTAGCCCAAG GGGAAGCCCT

1121 GATCGTCGGT TTGTGCCGAT TCACGCAAAC CTGGCTAGCG

1161 ACCAAGGTAT TTCCGGATTT CCGCGACCTC AAGGAAAGGA

1201 CTGCGCCGCT GCAGCCCTAC TTTGACGACC CCGATGTCCA

1241 GACCTATCTG GATGCGATCG TGGAGTTGCC GTCCGATTTG

1281 ATGCCAACGC CGCTACCCGT TGAGCCGCTT GAGGTGCGAT

1321 CGTCGTTGCT GGCCAAGGAA CTGCCGACCC CAGCAACGCC

1361 TGGTGTAGCT CCACCCCCTC GCCGCCGTCG CCGCGATCGC

1401 TCCGAACGTC CTGCTCGCAC GGCCAAACGC TTGCCCTTGC

1441 CCTGGATTGG TTTGGGGGTT GTGGTGGTTC TCGGCGGTGG

1481 AACAGGGGTT TGGGCTTGGC GATCGCGTTC CAATTCCACC

1521 CCGCCGACCC CGCCCCCCGT GGTTCAAACG CTGCCTGAGG

1561 CGGTACCTGC CCCTTCGCCC GCGCCAGTTA CCGTTGCCCT

1601 CGATCGGGCT CAGGCTGAAA CTGTGTTGCA AAACTGGTTG

1641 GCCGCTAAAG CTGCAGCCTT GGGGCCTCAA TACGATCGCG

1681 ATCGCTTAGC GACGGTGCTG ACCGGTGAGG TTCTGCAGAC

1721 TTGGCAGGGT TTTTCTAGCC AGCAGGCCAA CACCCAGCTC

1761 ACATCACAGT TCGATCACAA GTTAACCGTC GACTCAGTTC

1801 AGCTCAGTGA CGGTGATCAA CGAGCAGTAG TCCAAGCCAA

1841 GGTCGATGAA GTTGAGCAGG TCTATCGAGG CGACCAGCTG

1881 CTCGAAACGC GCCGAGATTT GGGCTTGGTG ATCCGCTACC

1921 AGCTCGTGCG CGAGAACAAC ATCTGGAAAA TTGCTTCGAT

1961 TAGTTTGGTG CGCTAG
```

Any of the conserved amino acids and conserved domains illustrated by the sequence comparisons shown above can be expressed in cells (e.g., via a transgene or expression cassette introduced into a host cell) to increase the activity of the Ftn2 proteins described herein.

Any of the conserved amino acids and conserved domains illustrated by the sequence comparisons shown above can be deleted in cells to reduce the activity or expression of the (e.g., endogenous) Ftn2 proteins.

Overexpression of minC, minD, minE, Cdv3, DivIVA, FtsZ, Ftn2 or Combinations Thereof Populations of cyanobacteria are described herein that include cells that with increased activity and/or increased expression of minC, minD, minE, Cdv3, DivIVA, FtsZ, Ftn2, or a combination thereof. In some cases, loss of FtsZ or MinE gene expression or loss of FtsZ or MinE protein function can provide increased cell size. However, in some cases over-expression of FtsZ protein can reduce cell size. Because the Min and Cdv3 proteins can modulate FtsZ function, expression of those proteins can be used to modulate cell size.

In some cases, the mean cell length of such cyanobacterial populations can be at least 150%, or at least 200%, or at least 250%, or at least 300%, or at least 500%, or at least 750%, or at least 1000%, or at least 3000%, or at least 5000%, or at least 10000%, or at least 15000%, or at least 20000% greater than a wild type population of cyanobacteria of the same species.

In some cases, the mean cell length of cyanobacteria in the population is at least 10%, or at least 15%, or at least 20%, or at least 25%, or at least 30%, or at least 35%, or at least 40%, or at least 45%, or at least 50% less than a wild type population of cyanobacteria of the same species.

Cyanobacteria can be modified to include an expression cassette that encodes a minC, minD, minE, Cdv3 (DivIVA), FtsZ, or Ftn2 protein, and an operably linked promoter to drive such expression. In some cases, cyanobacterial cell size is modulated by recombinant expression of a combination of minC, minD, minE, Cdv3 (DivIVA), FtsZ, and/or Ftn2 polypeptides using convenient vectors, and expression systems. The invention therefore provides expression cassettes or vectors useful for expressing minC, minD, minE, Cdv3 (DivIVA), FtsZ and/or Ftn2 polypeptide(s). In general, overexpression of MinC, MinE, Cdv3, and/or Ftn2 increases cell size. Overexpression of MinD leads to a bifurcated distribution of both large and small cells. Overexpression of FtsZ can reduce cell size.

The expression cassettes or vectors can include a promoter. A promoter is a nucleotide sequence that controls expression of an operably linked nucleic acid sequence by providing a recognition site for RNA polymerase, and possibly other factors, required for proper transcription. A promoter includes a minimal promoter, consisting only of all basal elements needed for transcription initiation, such as a TATA-box and/or other sequences that serve to specify the site of transcription initiation. A promoter may be obtained from a variety of different sources. For example, a promoter may be derived entirely from a native gene, be composed of different elements derived from different promoters found in nature, or be composed of nucleic acid sequences that are entirely synthetic. A promoter may be derived from many different types of organisms and tailored for use within a given cell.

Any promoter able to direct transcription of an encoded peptide or polypeptide may be used. Accordingly, many promoters may be included within the expression cassette. Some useful promoters include constitutive promoters, inducible promoters, regulated promoters, cell specific promoters, viral promoters, and synthetic promoters. Particularly useful promoters are inducible promoters, especially those induced by inexpensive signals, or promoters that are auto-inducing under certain environmental conditions (e.g. a relatively dense cyanobacterial population).

For expression of a minC, minD, minE, Cdv3 (DivIVA), FtsZ and/or Ftn2 polypeptide in a bacterium or cyanobacterium, an expression cassette can be used that has a nucleic acid segment encoding the minC, minD, minE, Cdv3 (DivIVA), FtsZ and/or Ftn2 polypeptide and a promoter operably linked thereto. Such a promoter can be any DNA sequence capable of binding a RNA polymerase and initiating the downstream (3") transcription of a coding sequence into mRNA. A promoter has a transcription initiation region that is usually placed proximal to the 5' end of the coding sequence. This transcription initiation region usually includes an RNA polymerase binding site and a transcription initiation site. A second domain called an operator may be present and overlap an adjacent RNA polymerase binding site at which RNA synthesis begins. The operator permits negatively regulated (inducible) transcription, as a gene repressor protein may bind the operator and thereby inhibit transcription of a specific gene.

Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli* (Raibaud et al., *Ann. Rev. Genet.*, 18:173 (1984)). Regulated expression may therefore be positive or negative, thereby either enhancing or reducing transcription.

Other examples of promoters that can be employed include promoters of sugar metabolizing enzymes, such as galactose, lactose (lac) (Chang et al., *Nature*, 198:1056 (1977), and maltose. Additional examples include promoter sequences derived from biosynthetic enzymes such as tryptophan (Trp) (Goeddel et al., *Nuc. Acids Res.*, 8:4057 (1980); Yelverton et al., *Nuc. Acids Res.*, 9:731 (1981); U.S. Pat. No. 4,738,921; and EPO Publ. Nos. 036 776 and 121 775). The β-lactamase (bla) promoter system (Weissmann, "The cloning of interferon and other mistakes", in: Interferon 3 (ed. I. Gresser), 1981), and bacteriophage lambda $P_L$ (Shimatake et al., *Nature*, 292:128 (1981)) and T5 (U.S. Pat. No. 4,689,406) promoter systems also provide useful promoter sequences. A preferred promoter is the *Chlorella* virus promoter (U.S. Pat. No. 6,316,224).

Synthetic promoters that do not occur in nature also function as promoters in cyanobacterial cells. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac promoter is a hybrid trp-lac promoter comprised of both trp promoter and lac operon sequences that is regulated by the lac repressor (Amann et al., *Gene*, 25:167 (1983); de Boer et al., *Proc. Natl. Acad. Sci. USA*, 80:21 (1983)). Furthermore, a bacterial or cyanobacterial promoter can include naturally occurring promoters of non-bacterial origin that have the ability to bind RNA polymerase and initiate transcription in cyanobacteria. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al., *J. Mol. Biol.*, 189:113 (1986); Tabor et al., *Proc. Natl. Acad. Sci. USA*, 82:1074 (1985)). In addition, a hybrid promoter can also be comprised of a bacteriophage promoter and an *E. coli* operator region (EPO Publ. No. 267 851).

In some cases, quorum sensing-responsive promoters can be employed in the expression cassettes/vectors. Quorum sensing is a mechanism whereby bacteria are able to indirectly detect the concentration of neighboring cells. A quorum sensing pathway is one that is usually activated when a bacterial population becomes concentrated. For example, biofilm formation is controlled often by quorum sensing. Such quorum sensing promoters can make cyanobacteria self-induce the genes of interest when a certain cell concentration is reached (e.g., when the cells are ready, or will soon be ready, to be harvested), without the addition of chemical inducers. See, e.g., Miller, Melissa B., and Bonnie L. Bassler, "Quorum sensing in bacteria." Annual Reviews in Microbiology 55(1): 165-199 (2001).

In some cases, the promoter can become active at certain times during culture or fermentation. For example, the promoter can in some cases be active before, during, or after log phase growth of the cells during culture or fermentation.

For example, LuxI/LuxR genes are a family of genes that produce quorum sensing behavior in bacteria. See, e.g., Waters & Bassler, "Quorum sensing: cell-to-cell communication in bacteria," Annu Rev Cell Dev Biol 21: 319-46 (2005). Quorum sensing pathways in natural contexts involve a microbe that is capable of producing a diffusible molecule that can pass through the cell membrane, such as the class of molecules called acyl-homoserine lactones (AHL). These molecules can diffuse from the cell that produces them to the outside environment, and then back into other neighboring bacteria. When the concentration of AHL of a specific type becomes high enough, it can stabilize a transcription factor that turns on specific genes. Usually, quorum sensing pathways are utilized for a bacteria to sense how large its population is—the more surrounding bacteria in the environment, the higher the AHL levels. At a certain cell density, the AHL builds up to a level that it can bind a receptor protein (e.g. LuxR), stabilizing it and allowing for downstream gene regulation.

Quorum sensing-responsive promoters can be used in any of the expression cassettes or expression vectors described herein. For example, cyanobacteria expressing LuxI (or similar protein) can make an AHL signal that could then build up as the density of the cyanobacteria increases. When the cells become dense enough, they can turn on the expression of genes like Cdv3, arresting division and causing auto-induction of the elongation process.

One example of a protein that can modulate quorum sensing-responsive promoters is the LuxI from *Vibrio fishcheri*, with the following sequence (SEQ ID NO:47).

```
  1 MIKKSDFLGI PSEEYRGILS LRYQVFKRRL EWDLVSEDNL

41 ESDEYDNSNA EYIYACDDAE EVNGCWRLLP TTGDYMLKTV

81 FPELLGDQVA PRDPNIVELS RFAVGKNSSK INNSASEITM

121 KLFQAIYKHA VSQGITEYVT VTSIAIERFL KRIKVPCHRI

161 GDKEIHLLGN TRSVVLSMPI NDQFRKAVSN
```

A nucleic acid encoding this *Vibrio fishcheri* LuxI protein shown below (SEQ ID NO:48).

```
  1    ATGATAAAAA AATCGGACTT TTTGGGCATT CCATCAGAGG

41    AGTATAGAGG TATTCTTAGT CTTCGTTATC AGGTATTTAA

81    ACGAAGACTG GAGTGGGACT TGGTAAGTGA GGATAATCTT

121    GAATCAGATG AATATGATAA CTCAAATGCA GAATATATTT

161    ATGCTTGTGA TGATGCGGAA GAGGTAAATG GCTGTTGGCG

201    TTTGTTACCT ACAACGGGTG ATTACATGTT AAAAACTGTT

241    TTTCCTGAAT TGCTCGGAGA TCAAGTAGCC CCAAGAGATC

281    CAAATATAGT CGAATTAAGC CGTTTTGCTG TGGGAAAAAA

321    TAGCTCAAAA ATAAATAACT CTGCTAGTGA ATAACAATG

361    AAATTGTTTC AAGCTATATA TAAACACGCA GTTAGTCAAG

401    GTATTACAGA ATATGTAACA GTAACATCAA TAGCAATAGA
```

```
441    GCGATTTCTG AAACGTATTA AAGTTCCTTG TCATCGCATT
481    GGTGATAAGG AGATTCATTT ATTAGGTAAT ACTAGATCTG
521    TTGTATTGTC TATGCCTATT AATGATCAGT TTAGAAAAGC
561    TGTATCAAAT TAA
```

A sequence of a LuxR receptor protein from *Vibrio fishcheri* is shown below (SEQ ID NO:49).

```
  1    MIYNTQNLRQ TIGKDKEMGM KNINADDTYR IINKIKACRS
 41    NNDINQCLSD MTKMVHCEYY LLAIIYPHSM VKSDISILDN
 81    YPKKWRQYYD DANLIKYDPI VDYSNSNHSP INWNIFENNA
121    VNKKSPNVIK EAKTSGLITG FSFPIHTANN GFGMLSFAHS
161    EKDNYIDSLF LHACMNIPLI VPSLVDNYRK INIANNKSNN
201    DLTKREKECL AWACEGKSSW DISKILGCSE RTVTFHLTNA
241    QMKLNTTNRC QSISKAILTG AIDCPYFKN
```

A nucleic acid sequence for this LuxR protein from *Vibrio fishcheri* is provided below as SEQ ID NO:50.

```
  1    ATGATATATA ACACGCAAAA CTTGCGACAA ACAATAGGTA
 41    AGGATAAAGA GATGGGTATG AAAAACATAA ATGCCGACGA
 81    CACATACAGA ATAATTAATA AAATTAAAGC TTGTAGAAGC
121    AATAATGATA TTAATCAATG CTTATCTGAT ATGACTAAAA
161    TGGTACATTG TGAATATTAT TTACTCGCGA TCATTTATCC
201    TCATTCTATG GTTAAATCTG ATATTTCAAT TCTAGATAAT
241    TACCCTAAAA AATGGAGGCA ATATTATGAT GACGCTAATT
281    TAATAAAATA TGATCCTATA GTAGATTATT CTAACTCCAA
321    TCATTCACCA ATTAATTGGA ATATATTTGA AAACAATGCT
361    GTAAATAAAA AATCTCCAAA TGTAATTAAA GAAGCGAAAA
401    CATCAGGTCT TATCACTGGG TTTAGTTTCC CTATTCATAC
441    GGCTAACAAT GGCTTCGGAA TGCTTAGTTT TGCACATTCA
481    GAAAAAGACA ACTATATAGA TAGTTTATTT TTACATGCGT
521    GTATGAACAT ACCATTAATT GTTCCTTCTC TAGTTGATAA
561    TTATCGAAAA ATAAATATAG CAAATAATAA ATCAAACAAC
601    GATTTAACCA AAAGAGAAAA AGAATGTTTA GCGTGGGCAT
641    GCGAAGGAAA AAGCTCTTGG GATATTTCAA AAATATTAGG
681    CTGCAGTGAG CGTACTGTCA CTTTCCATTT AACCAATGCG
721    CAAATGAAAC TCAATACAAC AAACCGCTGC CAAAGTATTT
761    CTAAAGCAAT TTTAACAGGA GCAATTGATT GCCCATACTT
801    TAAAAATTAA
```

An example of a LuxR-responsive promoter from *Vibrio fishcheri* is shown below as (SEQ ID NO:51).

```
  1    TGTCGCAAGT TTTGCGTGTT ATATATCATT AAAACGGTAA
 41    TGGATTGACA TTTGATTCTA ATAAATTGGA TTTTTGTCAC
 81    ACTATTGTAT CGCTGGGAAT ACAATTACTT AACATAAGCA
121    CCTGTAGGAT CGTACAGGTT TACGCAAGAA AATGGTTTGT
161    TATAGTCGAA TGAATTCATT AAAGAGGAGA AAGGTACC
```

When LuxR is expressed and stabilized (because AHL is present), the LuxR protein binds to a promoter sequence like that shown above as (SEQ ID NO:51) and drives gene expression from it.

It is understood that many promoters and associated regulatory elements may be used within the expression cassette/vector to transcribe an RNA encoding a minC, minD, minE, Cdv3 (DivIVA), FtsZ and/or Ftn2 polypeptide. The promoters described above are provided merely as examples and are not to be considered as a complete list of promoters that are included within the scope of the invention.

The expression cassette of the invention may contain a nucleic acid sequence for increasing the translation efficiency of an mRNA encoding a minC, minD, minE, Cdv3 (DivIVA), FtsZ and/or Ftn2 polypeptide. Such increased translation serves to increase production of the polypeptide. The presence of an efficient ribosome binding site is useful for gene expression in prokaryotes. In bacterial mRNA, a conserved stretch of six nucleotides, the Shine-Dalgarno sequence, is usually found upstream of the initiating AUG codon. (Shine et al., *Nature*, 254:34 (1975)). This sequence is thought to promote ribosome binding to the mRNA by base pairing between the ribosome binding site and the 3' end of *Escherichia coli* 16S rRNA. (Steitz et al., "Genetic signals and nucleotide sequences in messenger RNA", in: Biological Regulation and Development: Gene Expression (ed. R. F. Goldberger), 1979)). Such a ribosome binding site, or operable derivatives thereof, are included within the expression cassette of the invention.

A translation initiation sequence can be derived from any expressed bacterial or cyanobacterial gene and can be used within an expression cassette/vector of the invention. Preferably the gene from which the translation initiation sequence is obtained is a highly expressed gene. A translation initiation sequence can be obtained via standard recombinant methods, synthetic techniques, purification techniques, or combinations thereof, which are all well known. (Ausubel et al., *Current Protocols in Molecular Biology*, Green Publishing Associates and Wiley Interscience, NY. (1989); Beaucage and Caruthers, *Tetra. Letts.*, 22:1859 (1981); VanDevanter et al., *Nucleic Acids Res.*, 12:6159 (1984). Alternatively, translational start sequences can be obtained from numerous commercial vendors. (Operon Technologies; Life Technologies Inc. Gaithersburg, Md.). In some embodiments, the T7 translation initiation sequence is used. The T7 translation initiation sequence is derived from the highly expressed T7 Gene 10 cistron and can have a sequence that includes TCTAGAAATAATTTTGTT-TAACTTTAAGAAGGAGATATA (SEQ ID NO:52). Other examples of translation initiation sequences include, but are not limited to, the maltose-binding protein (Mal E gene) start sequence (Guan et al., *Gene*, 67:21 (1997)) present in the pMalc2 expression vector (New England Biolabs, Beverly, Mass.) and the translation initiation sequence for the following genes: thioredoxin gene (Novagen, Madison, Wis.), Glutathione-S-transferase gene (Pharmacia, Piscataway, N.J.), β-galactosidase gene, chloramphenicol acetyltransferase gene and *E. coli* Trp E gene (Ausubel et al., 1989,

*Current Protocols in Molecular Biology*, Chapter 16, Green Publishing Associates and Wiley Interscience, NY).

The invention therefore provides an expression cassette or vector that includes a promoter operable in a selected host and a nucleic acid encoding one or more of the minC, minD, minE, Cdv3, (DivIVA), FtsZ and/or Ftn2 polypeptides described herein. The expression cassette can have other elements, for example, termination signals, origins of replication, enhancers, and the like as described herein. The expression cassette can also be placed in a vector for easy replication and maintenance.

An expression cassette or nucleic acid construct of the invention is thought to be particularly advantageous for inducing expression of the polypeptides.

Loss-Of-Function

Populations of cyanobacteria are also described herein that include cyanobacterial cells that with reduced activity and/or expression of minC, minD, or a combination thereof where the mean cell length of cyanobacteria in the population is at least 10%, or at least 15%, or at least 20%, or at least 25%, or at least 30%, or at least 35%, or at least 40%, or at least 45%, or at least 50% less than a wild type population of cyanobacteria of the same species. The cyanobacterial populations are modified either to reduce the expression of at least one of minC and minD, or to reduce the function or activity of at least one of minC and minD. In other words, the minC and/or minD genes in the cyanobacterial populations can have mutations in the transcriptional regulatory elements, or in the coding region of these genes. In some cases the populations of cyanobacteria have one or more genomic deletions, insertions, or substitutions in at least a portion of the coding region of the minC gene, the minD gene, or a combination thereof. Such mutations can be generated by site-specific recombination-mediated methods for deleting unwanted genetic elements from plant and animal cells. The deletions can range in size from a few base pairs to thousands of nucleotides (or any value therebetween). Deletions can be created at a desired location in the genome, for example, by selecting borders (end points) of the deletions at defined locations to control the size of the deletion.

In some cases, a native minC gene, a native minD gene, or a combination thereof is deleted, or mutated to reduce the function of the minC or minD protein, and one or more expression cassettes is introduced that includes a coding region for minC, minD, minE, Cdv3 (DivIVA), FtsZ and/or Ftn2, where each coding region is under the control of an inducible or regulatable promoter.

Non-limiting examples of methods of introducing a modification into the genome of a cell can include use of microinjection, viral delivery, recombinase technologies, homologous recombination, TALENS, CRISPR, and/or ZFN, see, e.g. Clark and Whitelaw Nature Reviews Genetics 4:825-833 (2003); which is incorporated by reference herein in its entirety.

For example, nucleases such as zinc finger nucleases (ZFNs), transcription activator like effector nucleases (TALENs), and/or meganucleases can be employed with a guide nucleic acid that allows the nuclease to target the genomic MinC and/or MinD site(s). In some cases, a targeting vector can be used to introduce a deletion or modification of one or more genomic MinC and/or MinD site(s).

A "targeting vector" is a vector generally has a 5' flanking region and a 3' flanking region homologous to segments of the gene of interest. The 5' flanking region and a 3' flanking region can surround a DNA sequence comprising a modification and/or a foreign DNA sequence to be inserted into the gene. For example, the foreign DNA sequence may encode a selectable marker. In some cases, the targeting vector does not comprise a selectable marker but such a selectable marker can facilitate identification and selection of cells with desirable mutations. Examples of suitable selectable markers include antibiotics resistance genes such as chloramphenicol resistance, gentamycin resistance, kanamycin resistance, spectinomycin resistance (SpecR), neomycin resistance gene (NEO), and/or the hygromycin β-phosphotransferase genes. The 5' flanking region and the 3' flanking region can be homologous to regions within the gene, or to regions flanking the gene to be deleted, modified, or replaced with the unrelated DNA sequence.

The targeting vector is contacted with the native gene of interest in vivo (e.g., within the cell) under conditions that favor homologous recombination. For example, the cell can be contacted with the targeting vector under conditions that result in transformation of the cyanobacterial cell(s) with the targeting vector.

A typical targeting vector contains nucleic acid fragments of not less than about 0.1 kb nor more than about 10.0 kb from both the 5' and the 3' ends of the genomic locus which encodes the gene to be modified (e.g. the genomic MinC and/or MinD site(s)). These two fragments are separated by an intervening fragment of nucleic acid which encodes the modification to be introduced. When the resulting construct recombines homologously with the chromosome at this locus, it results in the introduction of the modification, e.g. a deletion of a portion of the genomic MinC and/or MinD site(s), replacement of the genomic MinC and/or MinD promoter or coding region site(s), or the insertion of non-conserved codon or a stop codon.

In some cases, a Cas9/CRISPR system can be used to create a modification in genomic MinC and/or MinD site(s). Clustered regularly interspaced short palindromic repeats (CRISPR)/CRISPR-associated (Cas) systems are useful for, e.g. RNA-programmable genome editing (see e.g., Marraffini and Sontheimer. Nature Reviews Genetics 11: 181-190 (2010); Sorek et al. Nature Reviews Microbiology 2008 6: 181-6; Karginov and Hannon. Mol Cell 2010 1:7-19; Hale et al. Mol Cell 2010; 45:292-302; Jinek et al. Science 2012 337:815-820; Bikard and Marraffini Curr Opin Immunol 2012 24:15-20; Bikard et al. Cell Host & Microbe 2012 12: 177-186; all of which are incorporated by reference herein in their entireties). A CRISPR guide RNA can be used that can target a Cas enzyme to the desired location in the genome, where it generates a double strand break. This technique is described, for example, by Mali et al. Science 2013 339:823-6; which is incorporated by reference herein in its entirety. Kits for the design and use of CRISPR-mediated genome editing are commercially available, e.g. the PRECISION X CAS9 SMART NUCLEASE™ System (Cat No. CAS900A-1) from System Biosciences, Mountain View, Calif.

In other cases, a cre-lox recombination system of bacteriophage P1, described by Abremski et al. 1983, *Cell* 32:1301 (1983), Sternberg et al., *Cold Spring Harbor Symposia on Quantitative Biology*, Vol. XLV 297 (1981) and others, can be used to promote recombination and alteration of the genomic MinC and/or MinD site(s). The cre-lox system utilizes the cre recombinase isolated from bacteriophage P1 in conjunction with the DNA sequences that the recombinase recognizes (termed lox sites). This recombination system has been effective for achieving recombination in plant cells (see, e.g., U.S. Pat. No. 5,658,772), animal cells (U.S. Pat. Nos. 4,959,317 and 5,801,030), and in viral vectors (Hardy et al., *J. Virology* 71:1842 (1997).

The populations of cyanobacteria described herein have genomic mutations that modulate or replace the promoter regions of minC, minD, minE, Cdv3, and/or DivIVA genes.

The populations of cyanobacteria described herein have genomic mutations that alter one or more amino acids in the encoded MinC protein, the encoded MinD protein, or in both the MinC protein and the MinD protein. For example, cyanobacteria can be modified so that in the encoded MinC protein, the encoded MinD protein, or in both the MinC protein and the MinD protein is more prone to degradation, or is less stable, so that the half-life of such protein(s) is reduced. In another example, cyanobacteria can be modified so that at least one amino acid of a minC or mind polypeptide is deleted or mutated to reduce the enzymatic activity at least one of minC and minD. In some cases, a conserved amino acid or a conserved domain of the minC or mind polypeptide is modified. For example, a conserved amino acid or several amino acids in a conserved domain of the minC or mind polypeptide can be replaced with one or more amino acids having physical and/or chemical properties that are different from the conserved amino acid(s). For example, to change the physical and/or chemical properties of the conserved amino acid(s), the conserved amino acid(s) can be deleted or replaced by amino acid(s) of another class, where the classes are identified in the following Table 1.

TABLE 1

| Classification | Genetically Encoded |
| --- | --- |
| Hydrophobic | |
| Aromatic | F, Y, W |
| Apolar | M, G, P |
| Aliphatic | A, V, L, I |
| Hydrophilic | |
| Acidic | D, E |
| Basic | H, K, R |
| Polar | Q, N, S, T, Y |
| Cysteine-Like | C |

Different types of amino acids can be employed in the minC and/or mind polypeptide.

TABLE 2

| Amino Add | One-Letter Symbol | Common Abbreviation |
| --- | --- | --- |
| Alanine | A | Ala |
| Arginine | R | Arg |
| Asparagine | N | Asn |

TABLE 2-continued

| Amino Add | One-Letter Symbol | Common Abbreviation |
| --- | --- | --- |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| N-Methylglycine (sarcosine) | | MeGly |
| Ornithine | | Orn |
| Norleucine | | Nle |
| Penicillamine | | Pen |
| Homoarginine | | hArg |
| N-methylvaline | | MeVal |
| Homocysteine | | hCys |
| Homoserine | | hSer |

Types of Cyanobacteria

Any cyanobacteria can be modified to reduce cell length or to increase the cell length, either permanently or transiently. The cell sizes of any cyanobacterial species can be modulated using the methods described herein.

In some cases, the cell sizes of rod-shaped or filamentous cyanobacteria are modulated. Examples of cyanobacterial species that can be changed include *Synechococcus elongatus* sp. PCC 7942; *Synechococcus elongatus* 7002; *Synechococcus elongatus* UTEX 2973; *Anthropira platensis*; and *Leptolyngbya* sp. strain BL0902. *Synechococcus elongatus* sp. PCC 7942 is one of the dominant model organisms, providing a variety of useful genetic tools. *Synechococcus elongatus* 7002 is a well-developed model organism with improved productivity and resilience. *Synechococcus elongatus* UTEX 2973 is related to *S. elongatus* 7942, and it has greatly improved growth properties. *Anthropira platensis* is perhaps the most broadly utilized cyanobacteria in scaled applications. *Leptolyngbya* sp. strain BL0902 is a bioindustrial strain whose genetic make-up is not as well-studied as some of the model cyanobacterial species.

Further examples of cyanobacterial species that can be modified include, for example, any of those in Table 3.

TABLE 3

Types of Cyanobacteria

| Species | Lineage | Release |
| --- | --- | --- |
| *Synechococcus elongatus* sp. PCC 7942 | Cyanobacteria; Oscillatoriophycideae; Chroococcales; Synechococcus | American Type Culture Collection, ATCC accession no. 33912. |
| *Synechococcus elongatus* UTEX 2973 | Cyanobacteria; Oscillatoriophycideae; Chroococcales; Synechococcus | UTEX Culture Collection of Algae, University of Texas at Austin |
| *Anthropira platensis* | Cyanobacteria; Oscillatoriophycideae; Oscillatoriales; Arthrospira | American Type Culture Collection, ATCC accession no. 29408. |
| *Prochlorococcus marinus* str. AS9601 | Cyanobacteria; Prochlorales; Prochlorococcaceae; Prochlorococcus | The Gordon and Betty Moore Foundation Marine Microbiology Initiative (2007) |

TABLE 3-continued

Types of Cyanobacteria

| Species | Lineage | Release |
|---|---|---|
| *Acaryochloris marina* MBIC11017 | Cyanobacteria; Acaryochloris | TGen Sequencing Center (2008) |
| *Anabaena* sp. PCC 7120 | Cyanobacteria; Nostocales; Nostocaceae; Nostoc | Kazusa (2001) |
| *Anabaena variabilis* ATCC 29413 | Cyanobacteria; Nostocales; Nostocaceae; Anabaena | JGI (2007) |
| *Synechococcus* sp. CC9311 | Cyanobacteria; Chroococcales; Synechococcus | TIGR (2006) |
| *Cyanothece* sp. ATCC 51142 | Cyanobacteria; Chroococcales; Cyanothece | Washington University (2008) |
| *Chlorobium tepidum* TLS | Chlorobi; Chlorobia; Chlorobiales; Chlorobiaceae; Chlorobaculum | TIGR (2002) |
| *Synechococcus* sp. JA-3-3Ab | Cyanobacteria; Chroococcales; Synechococcus | TIGR (2007) |
| *Cyanothece* sp. PCC 7425 | Cyanobacteria; Chroococcales; Cyanothece | |
| *Synechococcus* sp. JA-2-3B'a(2-13) | Cyanobacteria; Chroococcales; Synechococcus | TIGR (2007) |
| *Gloeobacter violaceus* PCC 7421 | Cyanobacteria; Gloeobacteria; Gloeobacterales; Gloeobacter | Kazusa (2003) |
| *Prochlorococcus marinus* MED4 | Cyanobacteria; Prochlorales; Prochlorococcaceae; Prochlorococcus | JGI (2003) |
| *Microcystis aeruginosa* NIES-843 | Cyanobacteria; Chroococcales; Microcystis | Kazusa, U. Tsukuba, NIES (2007) |
| *Prochlorococcus marinus* MIT9313 | Cyanobacteria; Prochlorales; Prochlorococcaceae; Prochlorococcus | JGI (2003) |
| *Prochlorococcus marinus* str. NATL1A | Cyanobacteria; Prochlorales; Prochlorococcaceae; Prochlorococcus | The Gordon and Betty Moore Foundation Marine Microbiology Initiative (2007) |
| *Arthrospira platensis* NIES-39 | Cyanobacteria; Oscillatoriales; Arthrospira; Arthrospira platensis | |
| *Nostoc punctiforme* ATCC 29133 | Cyanobacteria; Nostocales; Nostocaceae; Nostoc | JGI (2008) |
| *Prochlorococcus marinus* str. MIT 9211 | Cyanobacteria; Prochlorales; Prochlorococcaceae; Prochlorococcus | The Gordon and Betty Moore Foundation Marine Microbiology Initiative (2008) |
| *Prochlorococcus marinus* str. MIT 9215 | Cyanobacteria; Prochlorales; Prochlorococcaceae; Prochlorococcus | JGI (2007) |
| *Prochlorococcus marinus* str. MIT 9301 | Cyanobacteria; Prochlorales; Prochlorococcaceae; Prochlorococcus | The Gordon and Betty Moore Foundation Marine Microbiology Initiative (2007) |
| *Prochlorococcus marinus* str. MIT 9303 | Cyanobacteria; Prochlorales; Prochlorococcaceae; Prochlorococcus | The Gordon and Betty Moore Foundation Marine Microbiology Initiative (2007) |
| *Prochlorococcus marinus* str. MIT 9515 | Cyanobacteria; Prochlorales; Prochlorococcaceae; Prochlorococcus | The Gordon and Betty Moore Foundation Marine Microbiology Initiative (2007) |
| *Synechococcus elongatus* PCC 6301 | Cyanobacteria; Chroococcales; Synechococcus | Nagoya U. (2007) |
| *Cyanothece* sp. PCC 7424 | Cyanobacteria; Chroococcales; Cyanothece | |
| *Cyanothece* sp. PCC 8801 | Cyanobacteria; Chroococcales; Cyanothece | |
| *Prochlorococcus marinus* str. NATL2A | Cyanobacteria; Prochlorales; Prochlorococcaceae; Prochlorococcus | JGI (2007) |
| *Prochlorococcus marinus* str. MIT 9312 | Cyanobacteria; Prochlorales; Prochlorococcaceae; Prochlorococcus | JGI (2007) |
| *Rhodopseudomonas palustris* CGA009 | Proteobacteria; Alphaproteobacteria; Rhizobiales; Bradyrhizobiaceae; Rhodopseudomonas | JGI (2003) |
| *Prochlorococcus marinus* SS120 | Cyanobacteria; Prochlorales; Prochlorococcaceae; Prochlorococcus | Genoscope (2003) |

TABLE 3-continued

Types of Cyanobacteria

| Species | Lineage | Release |
|---|---|---|
| *Synechococcus* sp. CC9605 | Cyanobacteria; Chroococcales; Synechococcus | JGI (2007) |
| *Synechococcus* sp. CC9902 | Cyanobacteria; Chroococcales; Synechococcus | JGI (2007) |
| *Synechocystis* sp. PCC 6803 | Cyanobacteria; Chroococcales; Synechocystis | Kazusa (1996, 2002, 2003) |
| *Synechococcus* sp. PCC 7002 | Cyanobacteria; Chroococcales; Synechococcus | Penn State University (2008) |
| *Synechococcus elongatus* PCC 7942 | Cyanobacteria; Chroococcales; Synechococcus | JGI (2007) |
| *Synechococcus* sp. RCC307 | Cyanobacteria; Chroococcales; Synechococeus | Genoscope (2007) |
| *Synechococcus* sp. WH 7803 | Cyanobacteria; Chroococcales; Synechococcus | Genoscope (2007) |
| *Trichodesmium erythraeum* IMS101 | Cyanobacteria; Oscillatoriales; Trichodesmium; Trichodesmium erythraeum | |
| *Thermosynechococcus elongatus* BP-1 | Cyanobacteria; Chroococcales; Thermosynechococcus | Kazusa (2002) |
| *Synechococcus* sp. WH8102 | Cyanobacteria; Chroococcales; Synechococcus | JGI (2003) |

Useful Products

Cyanobacteria can be used produce a variety of useful products. Examples include oils (fatty acids), alkenes, polyhydroxybutyrate, biomass, carbohydrates, phycocyanin, ethanol, hydrogen, isobutanol, ethylene, and combinations thereof. Products such as oils (fatty acids), alkenes, ethanol, hydrogen, isobutanol, ethylene, and combinations thereof can be used in manufacturing and as biofuels. For example, ethanol, carbohydrate feedstocks, and biomass can be used to make bioethanol. Polyhydroxybutyrate is useful, for example, in bioplastics. Biomass, carbohydrates, and ethanol can also be used in foods and food manufacturing. Ethanol, hydrogen, isobutanol, and ethylene are useful in manufacturing, as a source of energy, and/or for making fuel.

The following non-limiting Examples describe some of the experiments performed.

Example 1: Materials and Methods

This Example describes some of the materials and methods employed in the development of the invention.
Homolog Search Identification of putative Min homologs in *Synechococcus elongatus* PCC 7942 was carried out via Basic Local Alignment Search Tool (BlastP) with available Min system factors from both *Escherichia coli* str. K-12 substrain MG1655 and *Bacillus subtilis* subsp. *subtilis* str. 168. To gain insight into primary sequence conservation, *S. elongatus* MinC, MinD, MinE and DivIVA protein sequences were aligned to their homologs in *E. coli* and *B. subtilis* using MAFFT alignment v7.017 in Geneious v9.0.4 (Blossum62, open gap penalty=1.53, offset value=0.123) (FIGS. 1C-1E, 4A-4B). Secondary structure prediction for MinC/D/E was carried out using Phyre2 (see website at www.sbg.bio.ic.ac.uk/phyre2/), which performs automatic homology modeling using MinC/DIE crystal structures from *E. coli*. The resulting .pdb file was imported into PyMOL v1.76 to generate figures. Because no complete crystal structure exists for DivIVA, secondary structure prediction was carried out using JPred4 (see website at www.compbio.dundee.ac.uk/jpred/) through the automated Protein Secondary Structure Prediction Server (Jnet). Identification of the DivIVA domain was performed using general Delta-Blast (Domain Enhanced Lookup Time Accelerated Blast; see website at blast.ncbi.nlm.nih.gov/Blast.cgi). Secondary structure prediction for Cdv3 was carried out using JPred4 (see website at compbio.dundee.ac.uk/jpred/) through the automated Protein Secondary Structure Prediction Server (Jnet).
Construct Designs Deletion constructs in this study were generated using Gibson Assembly (Gibson et al., Nat Meth 6, 343-345 (2009)) from PCR fragments or synthetized dsDNA. A list of primers employed is shown in Table 4 below.

TABLE 4

Primer Sequences

| | Sequence |
|---|---|
| Knockouts | |
| ΔminC Homology Region 1 Forward | GGATCTCAAGAAGATCCTTTGATCTAGTCTAGGGATCAGCATTGGG SEQ ID NO: 53 |
| ΔminC Homology Region 1 Reverse | TTATGTCCACTGGGTTCGTGCCTTCCGGAACCACGGGGTAGAGAGC SEQ ID NO: 54 |
| ΔminC Homology Region 2 Forward | GATCACCAAGGTAGTCGGCAAATAAGGGCACATCTTGAGACGATCG SEQ ID NO: 55 |

TABLE 4-continued

Primer Sequences

| | Sequence |
|---|---|
| ΔminC Homology Region 2 Reverse | CCTATGGAAAAACGCCAGCAACGCGGAGTCCTCACGCCCGACGTAGTC SEQ ID NO: 56 |
| ΔminD Homology Region 1 Forward | GGATCTCAAGAAGATCCTTTGATCTGGCGGGCTTGGGCTTCTGTCAG SEQ ID NO: 57 |
| ΔminD Homology Region 1 Reverse | AGCGCTCGAATAAGTCAGCCAGCATAGGGTCCGAAGAGCAGGAGCGG SEQ ID NO: 58 |
| ΔminD Homology Region 2 Forward | GATCACCAAGGTAGTCGGCAAATAATAATTACTGCCTTGCCGGTGTAG SEQ ID NO: 59 |
| ΔminD Homology Region 2 Reverse | CCTATGGAAAAACGCCAGCAACGCGGCGGATCTCTGGCTGATTTGTC SEQ ID NO: 60 |
| ΔminE Homology Region 1 Forward | GGATCTCAAGAAGATCCTTTGATCTGGCGGGCTTGGGCTTCTGTCAG SEQ ID NO: 61 |
| ΔminE Homology Region 1 Reverse | AGGTGACAACAATAACGCGACTCATAGGGTCCGAAGAGCAGGAGCGG SEQ ID NO: 62 |
| ΔminE Homology Region 2 Forward | GATCACCAAGGTAGTCGGCAAATAATAATTACTGCCTTGCCGGTGTAG SEQ ID NO: 63 |
| ΔminE Homology Region 2 Reverse | CCTATGGAAAAACGCCAGCAACGCGGCGGATCTCTGGCTGATTTGTC SEQ ID NO: 64 |
| Δcdv3 Homology Region 1 Forward | GGATCTCAAGAAGATCCTTTGATCTACTTCACCGACGAAAACCGTG SEQ ID NO: 65 |
| Δcdv3 Homology Region 1 Reverse | TTATGTCCACTGGGTTCGTGCCTTCTCACGTCAGGCGATCGCGCTC SEQ ID NO: 66 |
| Δcdv3 Homology Region 2 Forward | GATCACCAAGGTAGTCGGCAAATAATTGACGACTACTCGGCTGCATC SEQ ID NO: 67 |
| Δcdv3 Homology Region 2 Reverse | CCTATGGAAAAACGCCAGCAACGCGCTTCAAGATGATCTGAGCTGAG SEQ ID NO: 68 |
| Spectinomycin Cassette Forward | GAAGGCACGAACCCAGTGGAC SEQ ID NO: 69 |
| Spectinomycin Cassette Reverse | TTATTTGCCGACTACCTTGGTG SEQ ID NO: 70 |
| Origin of Replication Forward | CGCGTTGCTGGCGTTTTCC SEQ ID NO: 71 |
| Origin of Replication Reverse | AGATCAAAGGATCTTCTTGAG SEQ ID NO: 72 |
| Riboswitch MinC and MinD Reporters | |
| mNeonGreen Forward | AGCACCCTGCTAAGGAGGCAACAAGATGGTCAGCAAAGGTGAAGAAG SEQ ID NO: 73 |
| mNeonGreen Reverse | CTTGTACAGTTCGTCCATACCC SEQ ID NO: 74 |
| MinC Forward | GATGGGTATGGACGAACTGTACAAGATGAGTGACGTAGACGCTTC SEQ ID NO: 75 |
| MinC Reverse | GCATGCCTGCAGGTCGACTCTAGAACTACTTCCCGCCAGGATCGG SEQ ID NO: 76 |
| MinD Forward | GATGGGTATGGACGAACTGTACAAGATGAGTCGCGTTATTGTTGTC SEQ ID NO: 77 |
| MinD Reverse | GCATGCCTGCAGGTCGACTCTAGAACTAGAGAATTTTTTTATTGAGG SEQ ID NO: 78 |

TABLE 4-continued

Primer Sequences

| | Sequence |
|---|---|
| Native Fluorescent Reporters | |
| minC Homology Region 1 Forward | GGATCTCAAGAAGATCCTTTGATCTAGTCTAGGGATCAGCATTGGG SEQ ID NO: 79 |
| minC Homology Region 1 Reverse | TGTCTTCTTCACCTTTGCTGACCATCGGAACCACGGGGTAGAGAGC SEQ ID NO: 80 |
| minC Homology Region 2 Forward | TTTGATGCTCGATGAGTTTTTCTAAGGGCACATCTTGAGACGATCG SEQ ID NO: 81 |
| minC Homology Region 2 Reverse | CCTATGGAAAAACGCCAGCAACGCGGAGTCCTCACGCCCGACGTAG SEQ ID NO: 82 |
| cdv3 Homology Region 1 Forward | GGATCTCAAGAAGATCCTTTGATCTGACGGTCAACTATGCGCGCCAAC SEQ ID NO: 83 |
| cdv3 Homology Region 1 Reverse | TGTCTTCTTCACCTTTGCTGACCATGCGCGATCGCCGACGGGGAGC SEQ ID NO: 84 |
| mNeonGreen Forward | ATGGTCAGCAAAGGTGAAGAAG SEQ ID NO: 85 |
| mNeonGreen Reverse | TTTTGAGACACAACGTGGCTTTCCCTCACTTGTACAGTTCGTCC SEQ ID NO: 86 |
| cdv3 Homology Region 2 Forward | TTTGATGCTCGATGAGTTTTTCTAATTGACGACTACTCGGCTGCATC SEQ ID NO: 87 |
| cdv3 Homology Region 2 Reverse | CCTATGGAAAAACGCCAGCAACGCGCTTCAAGATGATCTGAGCTGAG SEQ ID NO: 88 |
| Kanamycin Cassette Forward | GGGAAAGCCACGTTGTGTCTC SEQ ID NO: 89 |
| Kanamycin Cassette Reverse | TTAGAAAAACTCATCGAGCATC SEQ ID NO: 90 |

Additionally, all constructs contained flanking DNA from 900 to 1500 bp in length upstream and downstream of the targeted insertion site to allow homologous recombination with genomic sites. In some cases, deletion constructs for min components were designed to fully replace the coding sequence (CDS) with a selectable marker (ΔminC and ΔdivIVA). In the case of the MinD and MinE knockouts, the MinD and MinE constructs were contained in a Ferredoxin-like operon. Hence, ΔminD and ΔminE strains were generated by synthesizing a gBlock (IDT DNA) that concatenated the operon, thereby removing either the MinD or MinE coding region from the operon, and placing the resistance cassette downstream to minimize operon disruption. The development of these constructs is illustrated in FIG. 1F.

To explore the effects of altered Min activity on cell shape, cyanobacterial strains were generated with an additional integrated copy of minC, minD, minE, and cdv3 under the control of riboregulators using an inducible promoter that is turned on by the riboresponse regulator, theophylline, but that is tightly off in the absence of theophylline (Yoichi et al., Plant and Cell Physiology 54(10): 1724-1735 (2013)). Theophylline is an inexpensive commodity chemical that is generally regarded as non-toxic and is therefore a feasible inducer in scaled cultivation.

Figure 1A:
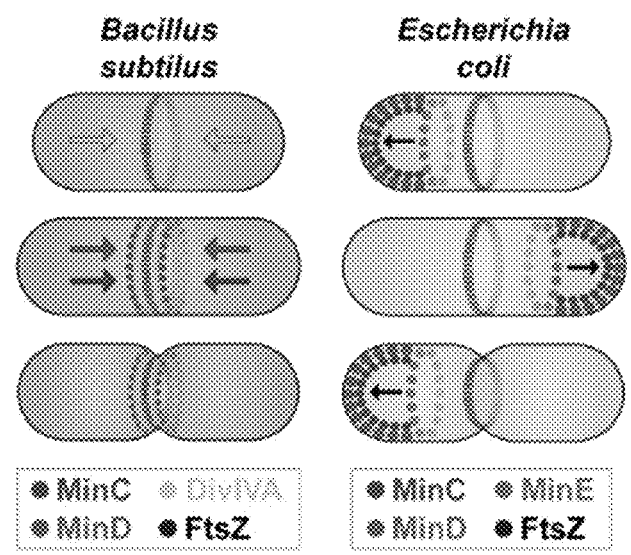
FIG. 1A-1G illustrates Cyanobacterial Min Homologs.
Figure 1B:
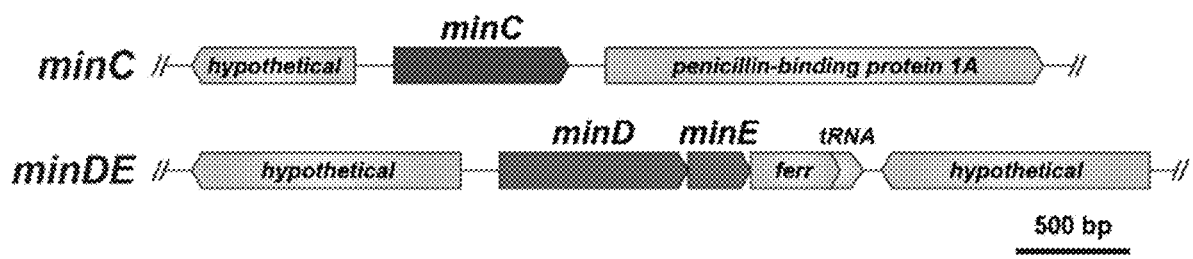
Figure 1C:
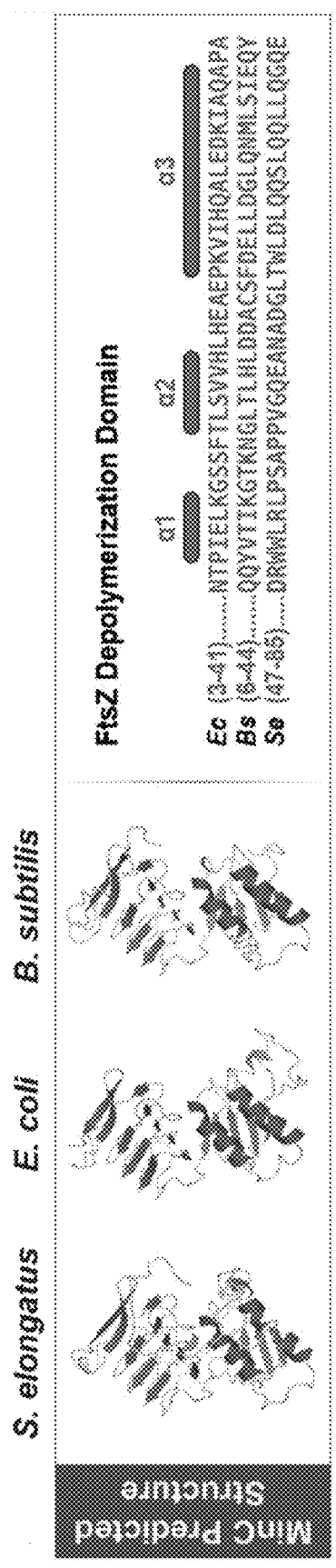
Figure 1D:
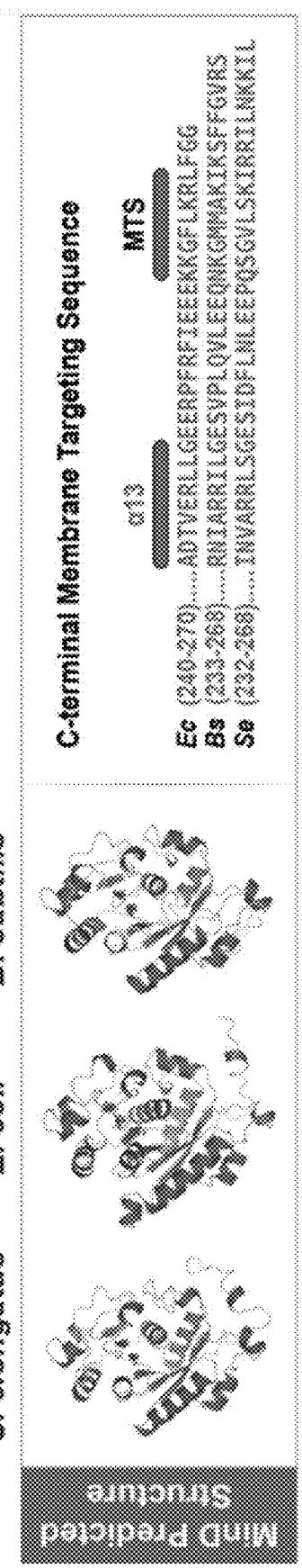
Figure 1E:
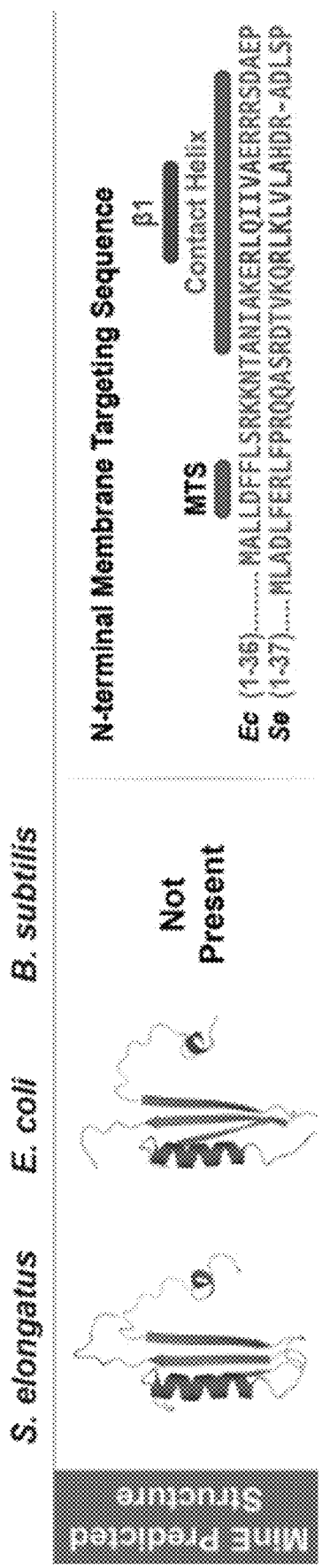
Figure 1F:
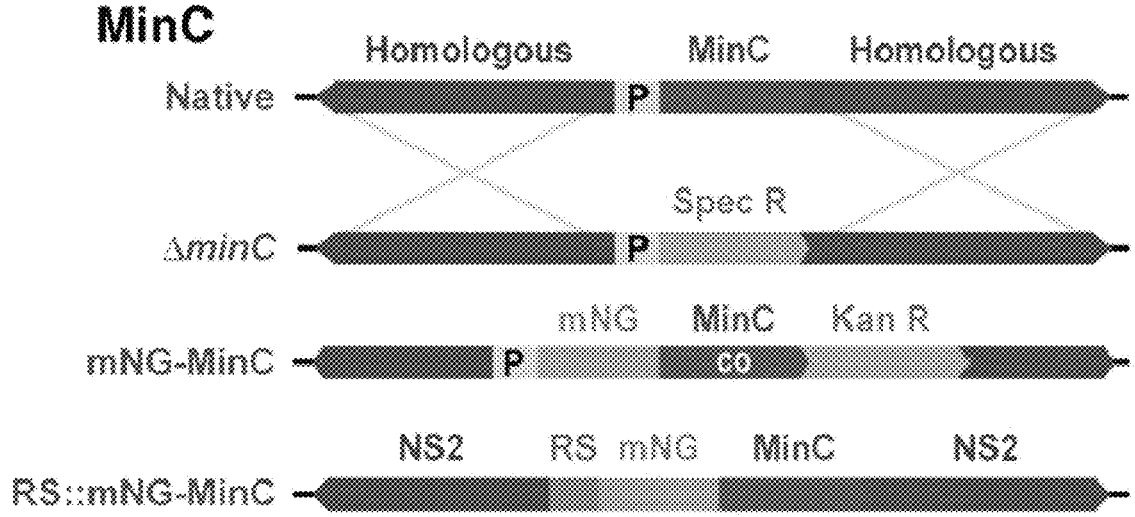
Figure 1F:
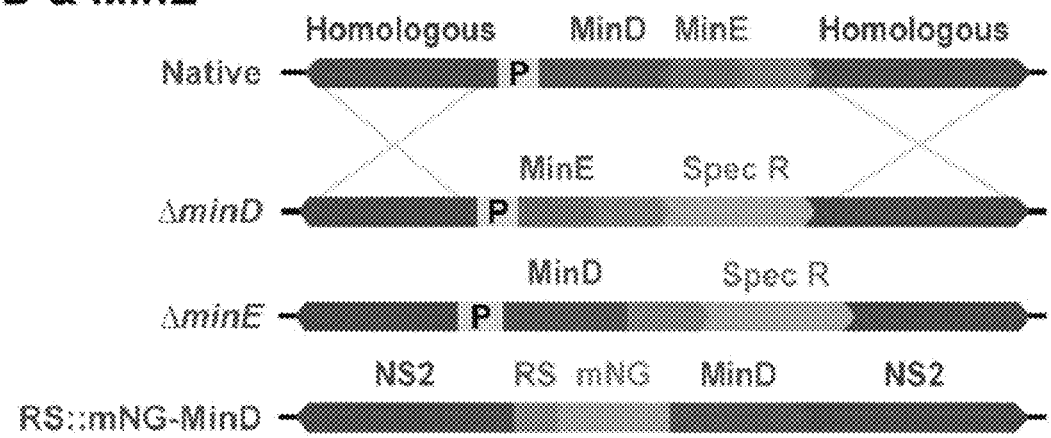
Figure 1F:
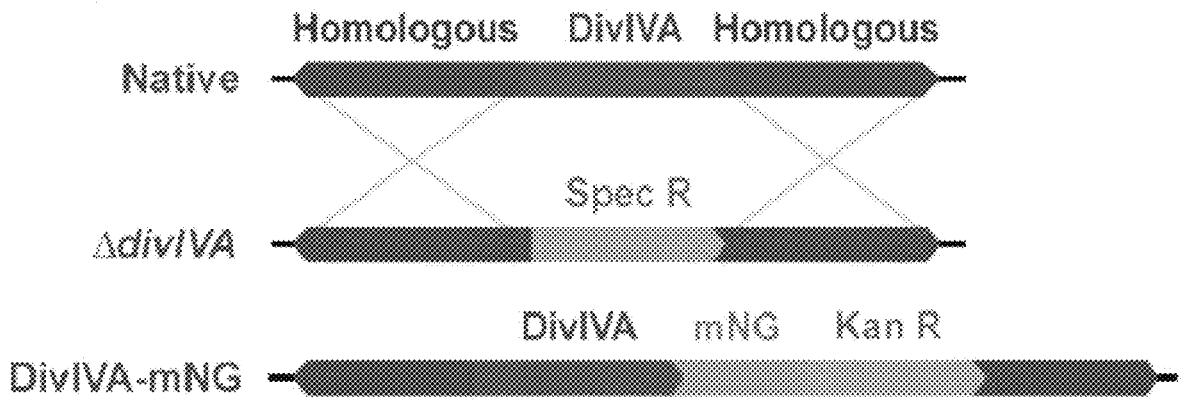

Generation of MinC/D/E, Cdv3 and DivIVA overproduction strains, as well as RS::mNG-MinC and RS::mNG-MinD fluorescent strains, was performed by insertion of the constructs into Neutral Site 2, a genomically neutral locus in S. elongatus, with an attached 5' riboswitch (RS) expressed from the Ptrc promoter (FIG. 1F). In some constructs, native Cdv3, DivIVA and MinC were fluorescently tagged by insertion of mNeonGreen (mNG) into the native genomic locus by genetic recombination (Clerico et al., Methods Mol. Biol. 362, 155-171 (2007)). Integration was verified by PCR. Special attention was given to the insertion of the selectable marker so as to minimize off-target effects in gene expression from read-through transcription potentially initiated the resistance marker's promoter (FIG. 1F).

Culture Conditions & Transformations

Cultures of S. elongatus were grown in 125 mL baffled flasks (Corning) containing 50 ml BG-11 medium (SIGMA) buffered with 1 g/L HEPES. pH 8.3. Flasks were cultured in a Multitron II (atrbiotech.com) incubation system with settings: 80 µmol m$^{-2}$ s$^{-1}$ light intensity, 32° C., 2% $CO_2$, shaking at 130 RPM unless otherwise stated. Cloning of plasmids was performed in E. coli DH5α chemically competent cells (Invitrogen). All cyanobacterial transformations were performed as described by Clerico et al. (Methods Mol. Biol. 362: 155-171 (2007)). Cells were plated on BG-11 agar with either 12.5 µg ml$^{-1}$ kanamycin (overexpression, native and riboswitch strains) or 25 g ml$^{-1}$ spectinomycin (deletion strains). Single colonies were picked into 96-well plates containing 300 µl of BG-11 with identical antibiotic concentrations and cultures were verified for complete gene replacement via PCR. Antibiotic supplementation was removed after complete gene replacement or knockout was verified.

Complete gene replacements were obtained for minC, minD, cdv3 and DivIVA.

Immunofluorescence Staining of FtsZ in Deletion and Overexpression Strains

MinCDE and Cdv3 overexpression strains were inoculated into flasks containing 50 mL BG-11 and 2 mM theophylline. The cultures were back-diluted with BG-11 and 2 mM theophylline to $OD_{750}$=0.2 whenever cultures reached $OD_{750}$≥0.7 to prevent artifacts in cell morphology due to self-shading. The cells were incubated 72 hours before fixation. Extreme filamentation was observed in DivIVA overexpression strains induced for more than 5 days. Two mL of cells were fixed with 500 µl of 2.5% glutaraldehyde/2.5% paraformaldehyde in 0.1M sodium cacodylate buffer (pH 7.4) (Electron Microscopy Sciences) for 30 minutes at room temperature and washed with PBS+ 0.01% Tween-20. After treatment with 0.05% Triton X-100 and 0.01% Tween-20 in PBS for 15 min, the cells were permeabilized for 30 min at 37° C. with 20 µg ml$^{-1}$ lysozyme dissolved in Tris-HCl, pH 7.5, 10 mM EDTA, washed, then blocked with 5% bovine serum albumin (Sigma-Aldrich) in PBS (blocking buffer) for 1 hour. Cells were incubated overnight at 4° C. with anti-Anabaena FtsZ antibodies (Agrisera Antibodies) diluted 1:250 in blocking buffer. Secondary staining was conducted with 1:1000 goat anti-rabbit IgG Alexa Fluor 488 (Life Technologies) in blocking buffer.

Fluorescence Microscopy

All live-cell microscopy was performed using exponentially growing cells. Images were captured using a Zeiss Axio Observer A1 microscope (100×, 1.46NA) with an Axiocam ICc5 camera. Cell length measurements for all deletion, overexpression and native fluorescently tagged strains were performed with live cells using manual tools in Zeiss Zen software. To induce translation of RS::mNG-MinC, cells were incubated for 30 min with 100 µM theophylline before imaging. To induce translation of RS::mNG-MinD, cells were incubated in 2 mM theophylline for 2 h. Lower induction and incubation times were used for RS::mNG-MinC imaging of oscillation because increased induction could result in relatively diffuse mNG-MinC signals, presumably due to over-saturation of MinD binding sites. Two mL of culture was spun down at 5,000 g for 30 sec and mounted on glass slides containing a square 2% agarose+BG-11 pad.

Transmission Electron Microscopy

A wild-type culture of *S. elongatus* was grown to $OD_{750}$=0.7 in BG-11. Cells were pelleted and fixed for 30 min with 2.5% paraformaldehyde/2.5% glutaraldehyde in 0.1M sodium cacodylate buffer (pH 7.4), suspended in 2% agarose and cut into 1 mm cubes. Following three washes with 0.1 M sodium cacodylate buffer, cells were suspended in 1% osmium tetroxide/1.5% potassium ferrocyanide, microwaved in a MS-9000 Laboratory Microwave Oven (Electron Microscopy Science) for 3 min, and washed three times with HPLC-quality water. Cells were then suspended in 1% uranyl acetate and microwaved for 2 minutes, decanted, and washed three times with HPLC-quality water. Cells were dehydrated in increasing acetone series (2 min at 25° C.) and then embedded in Spurr's resin (25% increments for 10 minutes each at 25° C.). Thin sections of ~70 nm were obtained using an MYX ultramicrotome (RMC Products), post-fixed with 6% uranyl acetate and Reynolds lead citrate, and visualized on a JEM 100CX II transmission electron microscope (JEOL) equipped with an Orius SC200-830 CCD camera (Gatan).

Cyanobacterial Cell Sedimentation and Lysis Quantification

Figure 6A:
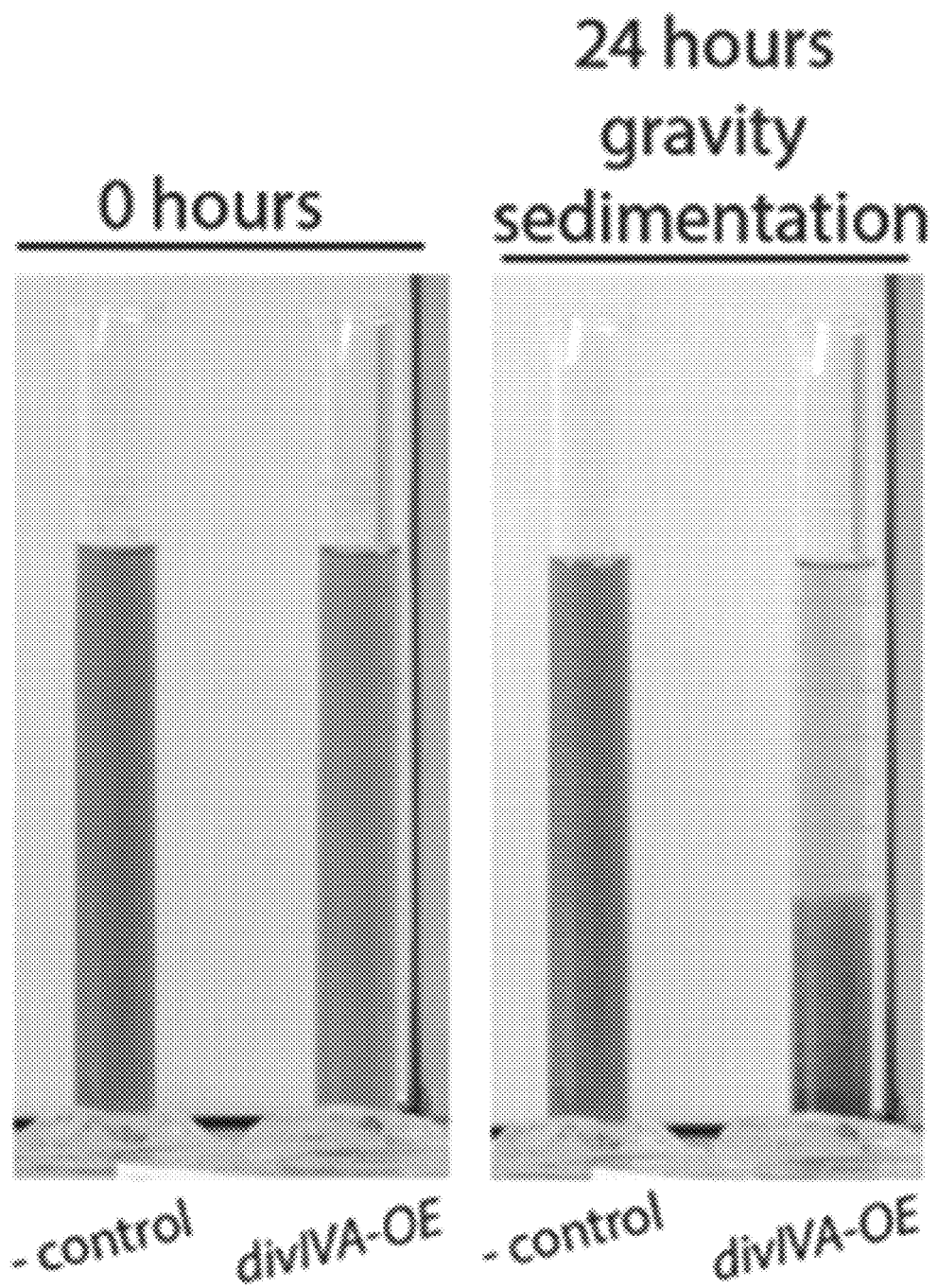
FIG. 6A-6C illustrate enhanced sedimentation of hyper-elongated cells that overexpress Cdv3 (DivIVA).
Figure 6B:
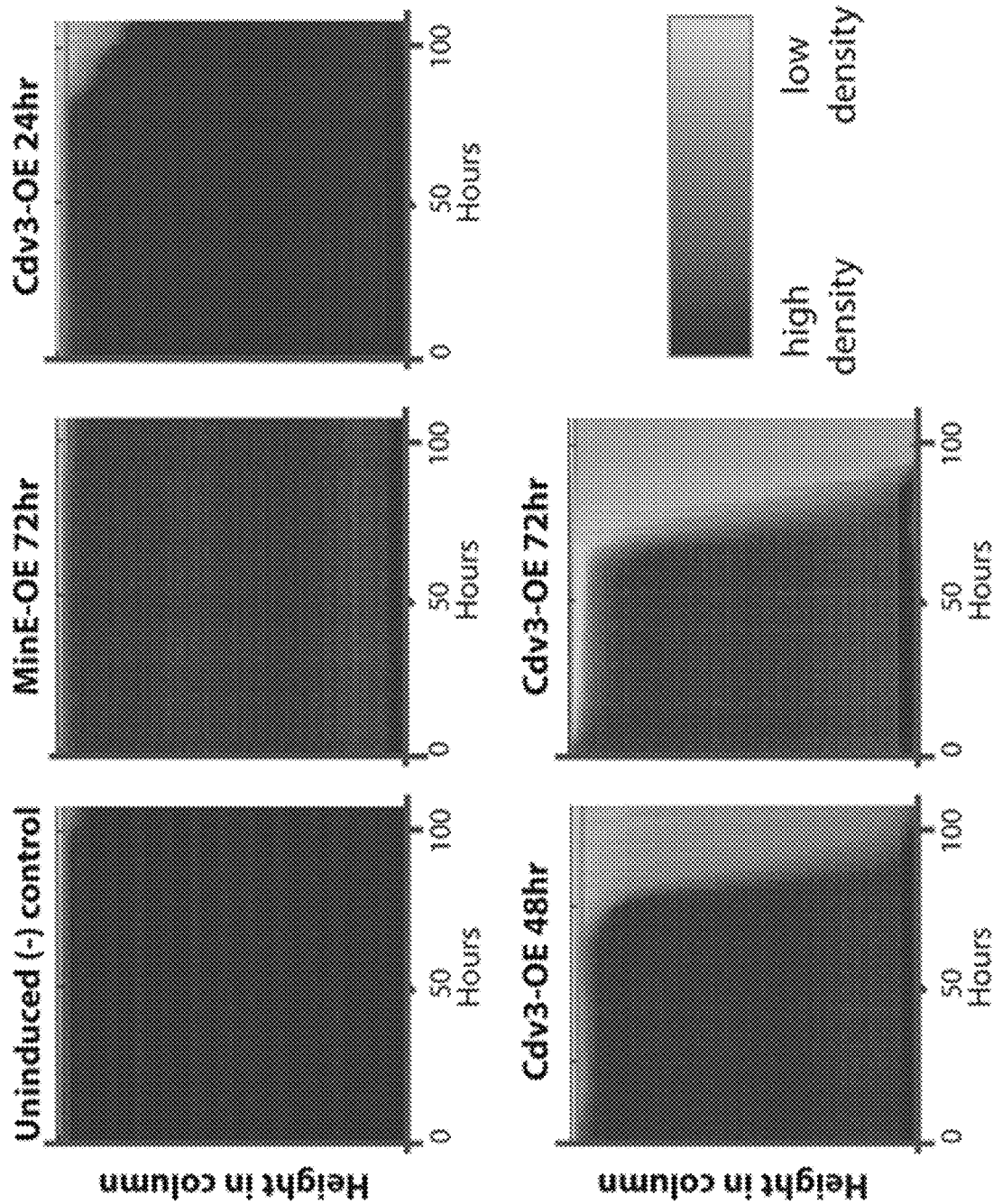

Cyanobacterial cells with a genomically-integrated copy of cdv3 or minE tagged with the fluorophore mTurquoise and driven by a theophylline inducible riboswitch were expressed as described above. The specific concentration of theophylline used, and length of time for the induction were as described in the figures and figure legends. For FIG. 6, uninduced or induced cells were suspended into 25 mL graduated cylinders and time-lapse images were captured using a standalone Nikkon Camera every 10 minutes over >100 hours. Resulting images were processed via MATLAB software to convert the still images into a heatmap of cell density as a function of height of the cylinder (FIG. 6B). Separately, 2 mL of uninduced or induced cells (as indicated) were subjected to mild centrifugation forces through the use of a benchtop centrifuge (accuSpin 17 Fischer).

The same strains were passed through a Cell Disruptor (Constant Systems) with an injection volume that can be tuned from 0 kpsi to 40 kpsi. Cells were subjected in two passes to the stated pressure (0, 4000 psi, or 8000 psi). Flow through was collected and analyzed by flow cytometry on an Acuri C6 instrument (BD Biosciences) to determine the proportion of intact and lysed cells. The indicated gates were used to discriminate between hyper-elongated cells (a result of Cdv3-OE) and normal length cells.

Example 2: Similarity of Min-Related Sequences

In two models of FtsZ regulation, MinCD is positioned in the cell by either MinE or DivIVA (FIG. 1A). To gain insight into the conservation of Min components in cyanobacteria, several comparative analyses of *S. elongatus* Min-system proteins were performed. Alignments showed that *S. elongatus* MinD is highly conserved with its homologs in other bacteria and chloroplasts. MinE exhibited lower sequence identity with the *E. coli* and *Arabidopsis thaliana* proteins, though conservation extended over the length of the protein. Table 4 shows percent amino acid identity in pairwise comparisons between *S. elongatus* MinC (YP_401018.1), MinD (YP_399913.1), MinE (YP_399914.1) and Cdv3 (YP_401023.1) and their homologs in *E. coli* (Ec) (MinC, NP_415694.1; MinD, NP_415693.1; MinE, NP_415692.1), *B. subtilis* (Bs) (MinC, NP_390678.1; MinD, NP_390677.1; DivIVA; NP_389425.1) and chloroplasts of *Arabidopsis thaliana* (At) (MinD, AED93246.1; MinE, NP_564964.1).

For example, an *E. coli* MinC (NP_415694.1) protein sequence is shown below as SEQ ID NO:91.

| | |
|---|---|
| 1 | MSNTPIELKG SSFTLSVVHL HEAEPKVIHQ ALEDKIAQAP |
| 41 | AFLKHAPVVL NVSALEDPVN WSAMHKAVSA TGLRVIGVSG |
| 81 | CKDAQLKAEI EKMGLPILTE GKEKAPRPAP TPQAPAQNTT |
| 121 | PVTKTRLIDT PVRSGQRIYA PQCDLIVTSH VSAGAELIAD |
| 161 | GNIHVYGMMR GRALAGASGD RETQIFCTNL MAELVSIAGE |
| 201 | YWLSDQIPAE FYGKAAPLQL VENALTVQPL N |

An example of a *B. subtilis* MinC protein sequence (NP_390678.1) is shown below as SEQ ID NO:92.

| | |
|---|---|
| 1 | MKTKKQQYVT IKGTKNGLTL HLDDACSFDE LLDGLQNMLS |
| 41 | IEQYTDGKGQ KISVHVKLGN RFLYKEQEEQ LTELIASKKD |
| 81 | LFVHSIDSEV ITKKEAQQIR EEAEIISVSK IVRSGQVLQV |

```
121    KGDLLLIGDV NPGGTVRAGG NIFVLGSLKG IAHAGFNGNN

161    QAVIAASEML PTQLRINHVL NRSPDHIQKG NEMECAYLDT

201    DGNMVIERLQ HLAHLRPDLT RLEGGM
```

A comparison of Min protein sequences from *E. coli*, *Bacillus subtilis*, and *Arabidopsis thaliana* is shown below.

TABLE 4

Percent Amino Acid Sequence Identity of Min Proteins from *E. coli*, *Bacillus subtilis*, and *Arabidopsis thaliana*

|  | E. coli | B. subtilis | A. thaliana |
|---|---|---|---|
| MinC | 20.8% | 27.1% | N/A |
| MinD | 46.1% | 49.8% | 53.0% |
| MinE | 27.3% | N/A | 32.2% |

An alignment of *S. elongatus* (Se; SEQ ID NO:4), *E. coli* (Ec; SEQ ID NO:91) and *B. subtilis* (Bs; SEQ ID NO:92) MinC sequences is shown below.

```
Se  MSDVDASTPSAEEAIAPDIDSDSDAAVETPAAEPAIAPPIQLEAEGDRWWLRLPSAPPVG

Ec  ••••••••••••••••••••••••••••••••••••••••••••••••MSNTPIE

Bs  ........................................................

Se  QEANADGLTWLDLQQSLQQLLQGQENFWDAGAELHLFADSWLLDGRQLE....W..LSQQ

Ec  LKGSSFTLSVVHLHEAEPKVIHQALEDKIAQAPAFLKHAPVVLNVSALEDPVNWSAMHKA

Bs  ••••••••••••••••MKTKKQQYVTIKGTKNGLTLHLDDACSFDELLDGLQNMLSIEQY

Se  LARVDLKLTRIT.TQRRQTAVAAVSLGLSI......EQPITQADPWQRKTST...SPIAA

Ec  VSATGLRVIGVSGCKDAQLKAEIEKMGLPILTEGKEKAPRPAPTPQAPAQNT...TPVTK

Bs  TDGKGQKISVHVKLGNRFLYKEQEEQLTELIASKKDLFVHSIDSEVITKKEAQQIREEAE

Se  PLYLKRTLRSGAEV.RHNGSVIVVGDVNPGSSIVASGDILVWGNLRGIAHAGAAGNSDAT

Ec  TRLIDTPVRSGQRIYAPQCDLIVTSHVSAGAELIADGNIHVYGMMRGRALAGASGDRETQ

Bs  IISVSKIVRSGQVLQVKGDLLLI.GDVNPGGTVRAGGNIFVLGSLKGIAHAGFNGNNQAV

Se  IFALSLAATQLRIGDRLARLPSSQAAGYPETA..QVIDGQIQIRRADPGGK.........

Ec  IFCTNLMAELVSIAGEYWLSDQIPAEFYGKAARLQLVENALTVQPLN.............

Bs  IAASEMLPTQLRINHVLNRSPDHIQKGNEMECAYLDTDGNMVIERLQHLAHLRPDLTRLE

Se  ...

Ec  ...

Bs  GGM
```

An example of an *E. coli* MinD protein sequence (NCBI accession number NP_415693.1) is provided below as SEQ ID NO:93.

```
1      MARIIVVTSG KGGVGKTTSS AAIATGLAQK GKKTVVIDFD

41     IGLPNLDLIM GCERRVVYDF VNVIQGDATL NQALIKDKRT

81     ENLYILPASQ TRDKDALTRE GVAKVLDDLK AMDFEFIVCD

121    SPAGIETGAL MALYFADEAI ITTNPEVSSV RDSDRILGIL

161    ASKSRRAENG EEPIKEHLLL TRYNPGRVSR GDMLSMEDVL

201    EILRIKLVGV IPEDQSVLRA SNQGEPVILD INADAGKAYA

241    DTVERLLGEE RPFRFIEEEK KGFLKRLFGG
```

An example of an *Arabidopsis thaliana* MinD protein sequence (NCBI accession number AED93246.1) is provided below as SEQ ID NO:94.

```
1      MASLRLFSTN HQSLLLPSSL SQKTLISSPR FVNNPSRRSP

41     IRSVLQFNRK PELAGETPRI VVITSGKGGV GKTTTTANVG

81     LSLARYGFSV VAIDADLGLR NLDLLLGLEN RVNYTCVEVI

121    NGDCRLDQAL VRDKRWSNFE LLCISKPRSK LPMGFGGKAL

161    EWLVDALKTR PEGSPDFIII DCPAGIDAGF ITAITPANEA

201    VLVTTPDITA LRDADRVTGL LECDGIRDIK MIVNRVRTDM

241    IKGEDMMSVL DVQEMLGLSL LGVIPEDSEV IRSTNRGFPL

281    VLNKPPTLAG LAFEQAAWRL VEQDSMKAVM VEEEPKKRGF

321    FSFFGG
```

An example of a *B. subtilis* MinD protein sequence (NCBI accession number NP_390677.1) is provided below as SEQ ID NO:95.

```
1      MGEAIVITSG KGGVGKTTTS ANLGTALAIL GKRVCLVDTD

41     IGLRNLDVVM GLENRIIYDL VDVVEGRCKM HQALVKDKRF
```

```
 81    DDLLYLMPAA QTSDKTAVAP EQIKNMVQEL KQEFDYVIID

121    CPAGIEQGYK NAVSGADKAI VVTTPEISAV RDADPIIGLL

161    EQEENIEPPR LVVNRIRNHL MKNGDTMDID EIVQHLSIDL

201    LGIVADDDEV IKASNHGEPI AMDPKNRASI AYRNIARRIL

241    GESVPLQVLE EQNKGMMAKI KSFFGVRS
```

An alignment of *S. elongatus* (Se; SEQ ID NO:14), *E. coli* (Ec; SEQ ID NO:93). *Arabidopsis thaliana* (At; SEQ ID NO:94) and *B. subtilis* (Bs; SEQ ID NO:95) MinD sequences is shown below.

```
Se  MSRVIVVTSGKGGVGKTTSSANLGMALAQLGKRLVLIDADFGLRNLDLLLGLENRIVYTA
Ec  MARIIVVTSGKGGVGKTTSSAAIATGLAQKGKKTVVIDFDIGLRNLDLIMGCERRVVYDF
At  TPRIVVITSGKGGVGKTTTTANVGLSLARYGFSVVAIDADLGLRNLDLLLGLENRVNYTC
Bs  MGEAIVITSGKGGVGKTTTSANLGTALAILGKRVCLVDTDIGLRNLDVVMGLENRIIYDL
                -----------
              P-loop  Walker A Se  QDVLAGNCRLEQALVKDKRQPN.LCLLPAANNRMK..ESVTPQQMEQLVTLLD....GQF
Ec  VNVIQGDATLNQALIKDKRTEN.LYILPASQTRDK..DALTREGVAKVLDDLKA...MDF
At  VEVINGDCRLDQALVRDKRWSN.FELLCISKPRSKLPMGFGGKALEWLVDALKTRPEGSP
Bs  VDVVEGRCKMHQALVKDKRFDDLLYLMPAAQTSDK..TAVAPEQIKNMVQELKQ....EF Se  DVILIDSPAGIEAGFQNAIAAAREAVIVTTPEIAAVRDADRVIGLLEA......HGITEI
Ec  EFIVCDSPAGIETGALMALYFADEAIITTNPEVSSVRDSDRILGILASKSRRAENGEEPI
At  DFIIIDCPAGIDAGFITAITPANEAVLVTTPPDITALRDADRVTGLLEC.....DGIRDI
Bs  DYVIIDCPAGIEQGYKNAVSGADKAIVVTTPEISAVRDADRIIGLLEQ.....EENIEPP
       -------
       SwitchII Se  R..LILNRLRPAMVKANDMMSVEDVQEILAIPLVGIIPDDEQVIISTNRGEPLVLAEAPS
Ec  KEHLLLTRYNPGRVSRGDMLSMEDVLEILRIKLVGVIPEDQSVLRASNQGEPVILDINAD
At  K..MIVNRVRTDMIKGEDMMSVLDVQEMLGLSLLGVIPEDSEVIRSTNRGFPLVLNKPPT
Bs  R..LVVNRIRNHLMKNGDTMDIDEIVQHLSIDLLGIVADDDEVIKASNHGEPIAMDPK.N
                                                               |
                                                              N222

Se  LAAKAFINVARRLSGES..IDFLNLEEPQSGVL..SKIRRILNKKIL
Ec  .AGKAYADTVERLLGEE..RPFRFIEEEKKGFL..KRLFGG......
At  LAGLAFEQAAWRLVEQDSMKAVMVEEEPKKRGF..FSFFGG......
Bs  RASIAYRNIARRILGES..VPLQVLEEQNKGMMAKIKSFFGVRS...
                                     Membrane
                                     Targeting
                                     Sequence
```

An example of an *E. coli* MinE protein sequence (NCBI accession number NP_415692.1) is shown below as SEQ ID NO:96.

```
  1    MALLDFFLSR KKNTANIAKE RLQIIVAERR RSDAEPHYLP

41    QLRKDILEVI CKYVQIDPEM VTVQLEQKDG DISILELNVT

81    LPEAEELK
```

An example of an *Arabidopsis thaliana* MinE protein sequence (NCBI accession number NP_564964.1) is shown below as SEQ ID NO:97.

```
  1    MAMSSGTLRI SATLVSPYHH HHRNRLSLPS SSSKVDFTGF

41    ISNGVNSLET QKCTPGLAIS RENTRGQVKV LARNTGDYEL

81    SPSPAEQEIE SFLYNAINMG FFDRLNLAWK IIFPSHASRR

121    SSNARIAKQR LKMILFSDRC DVSDEAKRKI VNNIIHALSD

161    FVEIESEEKV QLNVSTDGDL GTIYSVTVPV RRVKPEYQDV

201    DEAGTITNVE YKDTRDGSVD VRFDFYVPE
```

An alignment of *S. elongatus* (Se; SEQ ID NO:23), *E. coli* (Ec; SEQ ID NO:96), and *Arabidopsis thaliana* (At; SEQ ID NO:97) MinE sequences is shown below.

```
Se  ••••••••••••••••••••••••••••••••••••••••••••••••••••••••••
Ec  ••••••••••••••••••••••••••••••••••••••••••••••••••••••••••
At  SSSSKVDFTGFISNGVNSLETQKCTPGLAISRENTRGQVKVLARNTGDYELSPSPAEQEI

Se  ••••••••••••••••••••MLADLFERLFPRQQASRDTVKQRLKLVLAH•DRADLSPELLQ
Ec  ••••••••••••••••••••MALLDFFLSRKKNTANIAKERLQIIVAERRRSDAEPHYLP
At  ESFLYNAINMGFFDRLNLAWKIIFPSHASRRSSNARIAKQRLKMILFS•DRCDVSDEAKR
                       --------          =
                    Membrane Targeting    R21
                       Sequence
                                     ---------------------
                                     MinD Contact Helix Se  KMRQEILEVVSRYVELDSEG•••MELSLENDQRVTALVANLP•IRRVKPATAEG••••••
Ec  QLRKDILEVICKYVQIDPEMVTVQLEQKDGDISILELNVTLPEAEELK••••••••••••
At  KIVNNIIHALSDFVEIESEEKVQLNVSTDGDLG•TIYSVTVP•VRRVKPEYQDVDEAGTI Se  ••••••••••••••••••••••••
Ec  ••••••••••••••••••••••••
At  TNVEYKDTRDGSVDVRFDFYVPE
```

A further comparison of S. elongatus (Selong; SEQ ID NO:98) and E. coli K12 substrain MG1655 (E. coli; SEQ ID NO:99) MinE homologs is shown below, where asterisks below the sequences indicates amino acid sequence identity.

elongatus) that can be involved in interaction with MinD (Ramirez-Arcos et al, J. Bacieriol. 186: 2841-2855 (2004). MinD possessed a highly conserved N-terminal Walker A-type ATPase domain, Switch I and Switch II domains for

```
MinE: 32.8% identity in 64 residues overlap; Score: 100.0; Gap
frequency: 1.6%
Ecoli    3  LLDFFLSRKKNTANIAKERLQIIVAERRRSDAEPHYLPQLRKDILEVICKYVQIDPEMVT Selong   5  LFERLFPRQQASRDTVKQRLKLVLAHDR-ADLSPELLQKMRQEILEVVSRYVELDSEGME
              *      *    * **     *  *   *  *  *      * **      * *

Ecoli   63  VQLE

Selong  64  LSLE
              **
```

MinC proteins in bacteria are generally conserved primarily in a region near their C-termini that mediates MinC dimerization and interaction with MinD (Hu & Lutkenhaus, 2000), and this region was also conserved in S. elongatus MinC. Unlike in E. coli, where MinC, MinD and MinE are all encoded by the minB operon (de Boer et al, E. coli. Cell 56: 641-649 (1989)), genomic analysis showed that S. elongatus minD and minE reside in an operon with a ferredoxin-like gene of unknown function, while minC was located at a distant chromosomal region with its own promoter (FIG. 1B).

S. elongatus Min homologs were analyzed in greater detail using Phyre2 (Mezulis et al, Nature Protocols 10: 845-858 (2015)) to look for protein features via structural prediction. The results indicated that the Min proteins possessed secondary and tertiary structures that are highly conserved with those in the E. coli MinC, MinD and MinE crystal structures (FIG. 1C-1E, left panels). Key domains previously shown to have a role in Min protein function and dynamics in E. coli were identified in all three predicted S. elongatus structures. For example, MinC was predicted to bear multiple N-terminal alpha helices that function in binding to and depolymerizing FtsZ in E. coli, and C-terminal β-sheets important for homodimerization (FIG. 1C) (Hu & Lutkenhaus, Annu. Rev. Biochem. 76: 539-562 (2000)). Additionally, MinC possessed several conserved glycine residues involved in MinC function in E. coli, including G161 near the A-surface (G200 in S. elongatus) that can be involved in homodimerization; and G135, G154 and G171 near the B-C surface (G175, G193 and G210 in S. elongatus) that can be involved in interaction with MinD (Ramirez-Arcos et al, J. Bacieriol. 186: 2841-2855 (2004). MinD possessed a highly conserved N-terminal Walker A-type ATPase domain, Switch I and Switch II domains for binding MinC, and key residues L48, E53, and N222 (L48, E53 and N213 in S. elongatus) that are involved in interaction with MinE (Szeto et al, Proc. Natl. Acad. Sci. U.S.A. 99: 15693-15698 (2004)). Additionally, MinE possessed the R21 residue (R23 in S. elongatus), which is involved in hydrogen bond formation with E53 of MinD, and a highly conserved β1 strand concealed within a contact helix that's inserted at the MinD dimer interface, stabilized as an α-helix and involved in the stimulation of ATPase activity (FIG. 1E) (Park et al, Cell 146: 396-407 (2011)). Likewise, both MinD and MinE were predicted to possess the necessary structures for membrane-binding, which included a C-terminal amphipathic helix on MinD (FIG. 1D) and a N-terminal amphipathic helix on MinE (FIG. 1E) (Hsieh et al. Mol. Microbiol. 75: 499-512 (2010)). The hydrophobic residues of these helices typically mediate transient interactions with the non-polar environment underneath the membrane interface and facilitate binding of E. coli MinD and MinE to phospholipid membranes in vivo and in vitro (Loose et al. System. Annu. Rev. Biophys. 40: 315-336 (2011b)).

Figure 1G:
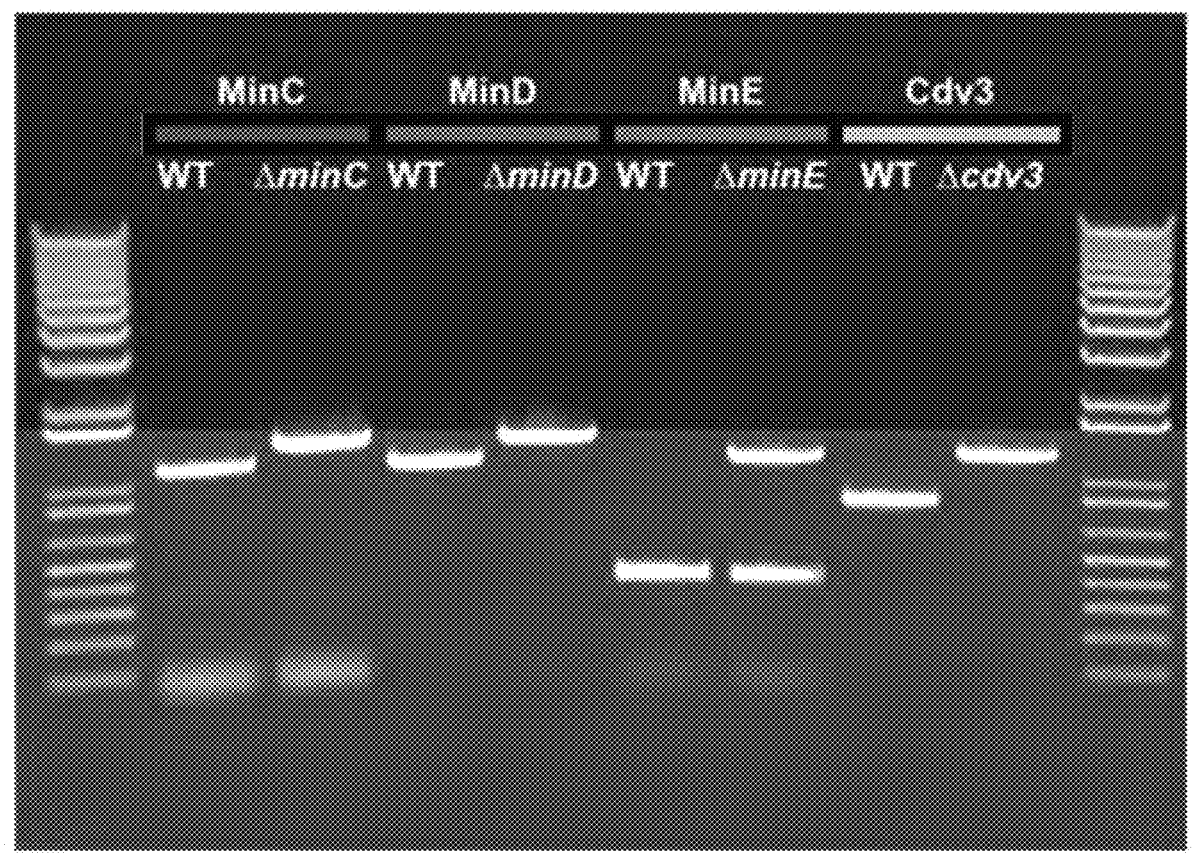

FIG. 1F is a schematic illustration of construct designs. In S. elongatus, MinC and DivIVA are expressed individually, whereas MinD and MinE are in the same operon with a putative ferredoxin-like gene (blue) of unknown function. In mNG-MinC, MinC was codon-optimized (CO) to increase transformation frequency. FIG. 1G shows PCR verification of Min gene deletions.

One example of a B. subtilis DivIVA sequence has NCBI accession number AQR85736.1, shown below as SEQ ID NO:100.

```
  1    MPLTPNDIHN KTFTKSFRGY DEDEVNEFLA QVRKDYEIVL
 41    RKKTELEAKV NELDERIGHF ANIEETLNKS ILVAQEAAED
 81    VKRNSQKEAK LIVREAEKNA DRIINESLSK SRKIAMEIEE
121    LKKQSKVFRT RFQMLIEAQL DLLKNDDWDH LLEYEVDAVF
161    EEKE
```

Example 3: Cyanobacterial Min Homologs Regulate Cell Size and Z-Ring Assembly The data described in Example 2 indicates that *S. elongatus* possesses a Min system. The inventors' screen for division-related factors in *S. elongatus* (Miyagishima et al., Mol Microbiol 56:126-43 (2005)) and preliminary studies in the spherical-shaped cyanobacterium *Synechocystis* sp. (Mazouni et al., Mol Microbiol 52:1145-58 (2004)) have provided evidence that four Min homologs from *Synechocystis* sp., *Bacillus subtilis*, *E. coli*, and *S. elongatus* function in cell division. However, there has been no systematic analysis of altered Min system expression or dynamics in cyanobacteria. Additionally, the presence of the thylakoid membrane network in cyanobacteria could influence Min system behavior, as MinD, MinE, and DivIVA all transiently associate with membranes in other bacteria through relatively small, nonpolar protein domains.

To investigate the similarities and differences in function of the cyanobacterial Min system, minC, minD, minE and divIVA deletion (Δ) and overexpression (OE) strains were generated as explained in Example 1 and as illustrated in FIG. 1F-1G. These minC, minD, minE and divIVA deletion and overexpression strains were analyzed for defects in morphology and FtsZ organization.

In wild-type (WT) cells, cell sizes fell within a narrow range of about 1.7-4.5 μm (mean cell length 3.10±0.66 μm; FIG. 2A-2B). The Z rings in wild type cells detected by immunofluorescence labeling were always positioned at the midcell (FIG. 2A-2B).

In contrast, ΔminC deletion strains exhibited a broader distribution of large and small cells with Z rings that were frequently mispositioned near the poles (FIG. 2A-2C). MinC-OE overexpression strains exhibited a high proportion of elongated cells with Z rings displaced from midcell, but generally not adjacent to cell poles (FIG. 2A blue profile for minC relative to the WT (red) distribution). Many cells contained faint FtsZ spots or rings, suggesting inhibited FtsZ polymerization (FIG. 2B-2C). A broad distribution of large and small cells was observed in both *S. elongatus* ΔminD and MinD-OE strains was observed (FIG. 2A). The *S. elongatus* ΔminD and MinD-OE strains also exhibited mispositioned polar Z rings (FIG. 2B-2C). These results demonstrate that MinC and MinD function as regulators of both assembly and positioning of the Z ring in *S. elongatus*, consistent with their roles in *E. coli*.

Because the cellular architecture of cyanobacteria could potentially interfere with the MinE-driven oscillations that are required to position MinCD in *E. coli*, cyanobacterial minE mutants were evaluated to ascertain whether they would display Z-ring assembly and positioning defects. MinE-OE overexpression strains were elongated (FIG. 2A), but exhibited well-defined, mispositioned Z rings (FIG. 2B-2C), a result highly similar to MinE overexpression in *E. coli* (de Boer et al, *E. coli. Cell* 56: 641-649 (1989)). A fully-penetrant deletion of MinE across all chromosomal copies was not obtained, indicating that deletion of MinE is lethal (FIG. 1G). However, meroploid *S. elongatus* ΔminE cells were elongated (FIG. 2A) and possessed a unique pattern of disorganized FtsZ structures throughout the cell, which occasionally formed an extended helix-like pattern (FIG. 2B-2C). Note that in *E. coli*, knockout of minE is lethal and leads to a formation of MinCD polymers along the length of the plasma membrane (de Boer et al., *Cell* 56: 641-649 (1989); Ghosal et al., *Nature Communications* 5: 1-11 (2014)).

Example 4: Theophylline Induction of Cell Growth and MinC and Cdv3 Expression The Example illustrates induction of cyanobacterial cell growth as well as expression of MinC and Cdv3 expression.

Methods mTurquoise-tagged fusions of Min factors (Cdv3-mTurq, mTurq-MinE, and mTurq-MinC) were expressed under the control of a theophylline-responsive riboswitch. Cells were exposed to increasing concentrations of theophylline (0, 200 μM, 800 μM, or 2000 μM). Average fluorescence intensity per pixel was quantified in mTurq-MinC or Cdv3-mTurq expressing *S. elongatus* cells induced with such concentrations of Theophylline.

FIGS. 2E-2F, validate that increasing theophylline concentrations increase the amount of the gene (MinC and Cdv3) that is expressed under the riboswitch element. The relationship between the inducer concentration and the expression of the gene is direct and linear.

Figure 2G:
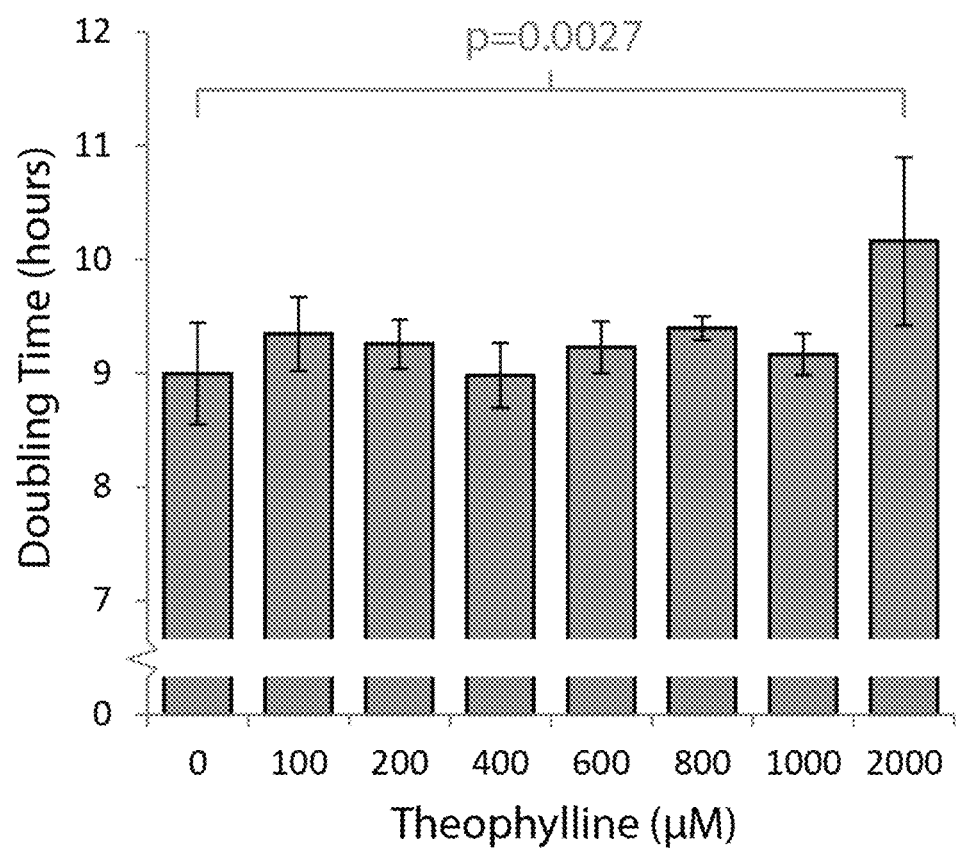

FIG. 2G illustrates the cyanobacterial growth rate in response to increasing theophylline inducer. Wild-type *S. elongatus* was incubated with increasing concentrations of theophylline and monitored for growth over 24 hours by optical density at 750 nm ($OD_{750}$). Doubling time was calculated for n≥4 independent day experiments. Error bars represent standard deviation and the p value for the only significant (p<0.05) change in doubling time is denoted, as determined from pairwise unequal variances t-tests. As illustrated in FIG. 2G, the growth (doubling time) of cyanobacteria was substantially unaffected by different concentrations of theophylline.

Hence, the addition of theophylline can induce expression of the inducible transgenes described herein without affected the growth of the cyanobacterial host cell lines.

Example 5: MinCD Oscillate from Pole-To-Pole in *S. elongatus*

In *E. coli* FtsZ assembles at the plasma membrane, which is freely-accessible to the cytosolic pool of oscillating MinCDE molecules (Lutkenhaus, *Annu. Rev. Biochem.* 76: 539-562 (2007)). However the influence of cyanobacterial internal membranes on the dynamics of Min proteins is unknown. While perforations in thylakoid membranes could facilitate sufficient diffusion of MinCDE across thylakoid layers to support emergence of MinCDE oscillations, thylakoid membranes could also pose a steric barrier that limits MinCDE access to the plasma membrane.

Figure 3A:
FIG. 3A-3I illustrate construct designs and expression patterns of MinC and MinD in various genetic backgrounds.
Figure 3A:
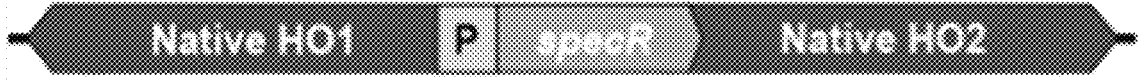
Figure 3A:
Figure 3A:
Figure 3B:
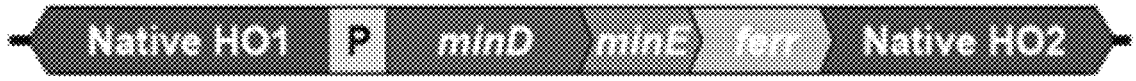
Figure 3B:
Figure 3B:
Figure 3B:
Figure 3C:
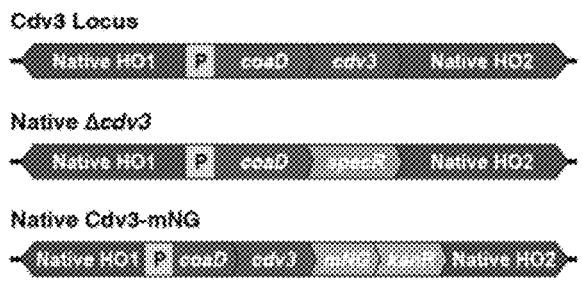

To gain insight into how Min dynamics contribute to Z-ring positioning in *S. elongatus*, N-terminal mNeonGreen (mNG) fusions were generated where mNG was fused to both MinC and MinD, and where these fusion proteins were expressed from a synthetic riboswitch at a genomic neutral site (FIG. 3A-3C). The fluorescent reporter mNG was chosen for its bright, photostable and monomeric properties, as well as its yellow-shifted excitation, highly reducing the autofluorescence generated from photosynthetic pigments in S. elongatus during imaging. In some cases, the endogenous (native) Min proteins were deleted to identify the effects of induced Min protein expression (FIG. 3A-3C).

Figure 3D:
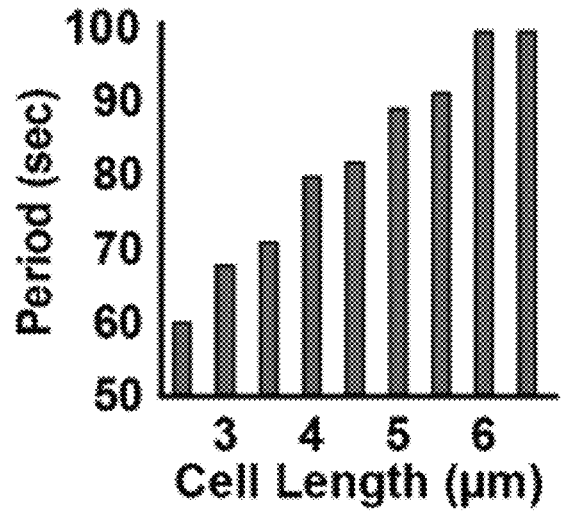
Figure 3E:
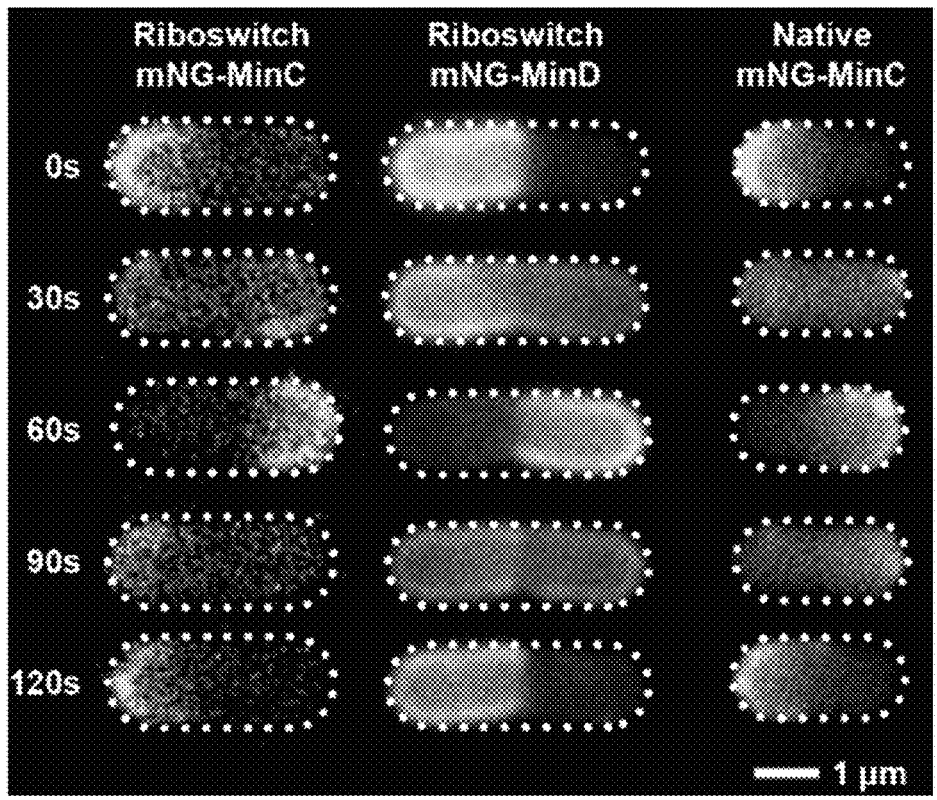

Time-lapse imaging revealed that both mNG-MinC and mNG-MinD oscillated from pole to pole (FIG. 3E). FIG. 3D graphically illustrates that the periodicity of mNG-MinC increases proportionally with cell length (n=10 cells per cell length). However, N- or C-terminal fusions to MinE were not obtained that were functional in S. elongatus.

Experiments were then performed to verify and characterize Min oscillations in a reporter strain that would mimic endogenous expression levels and minimize off-target expression effects. Modification of MinD or MinE activity can alter the periodicity of oscillations in E. coli (Lutkenhaus, 2007), but MinC is a "passenger protein" in the MinDE oscillation and is not in a larger operon in S. elongatus. Therefore, the chromosomal minC gene was completely replaced with an mNG-minC reporter fusion expressed from the native promoter at the endogenous chromosomal locus (FIG. 3A). In these strains, mNG-MinC oscillated from pole-to-pole (FIG. 3D-3E). Cell lengths and growth rates were unchanged in the native mNG-minC strain relative to wild type, indicating the fusion protein possessed WT functionally.

The mNG-MinC reporter transgene included the wild type MinC coding region linked to the mNeonGreen (mNG) fluorescent reporter fusion partner. This native MinC reporter oscillated with a periodicity that was about two times (2×) slower than in equivalently sized E. coli cells. The periodicity increased linearly as a function of increasing cell length during growth (about 10 s for each additional 1 μm of cell length) (FIG. 3D), and paused at each pole for about 10 seconds.

Figure 3F:
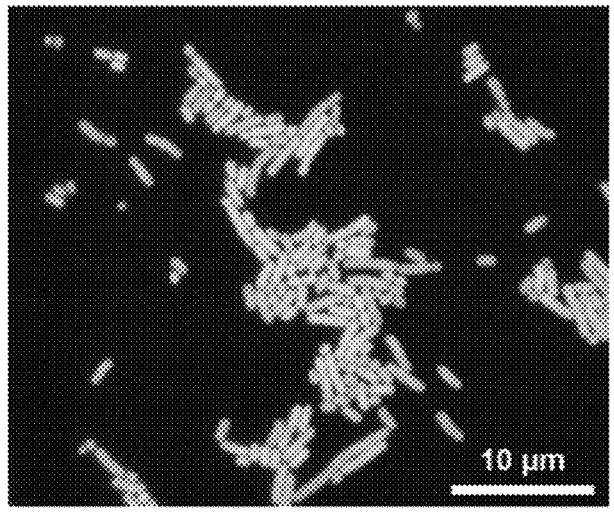
Figure 3G:
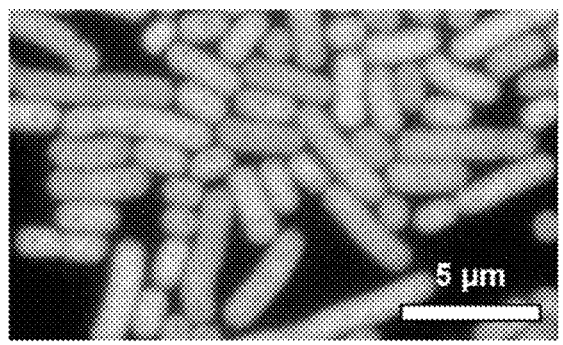
Figure 3H:
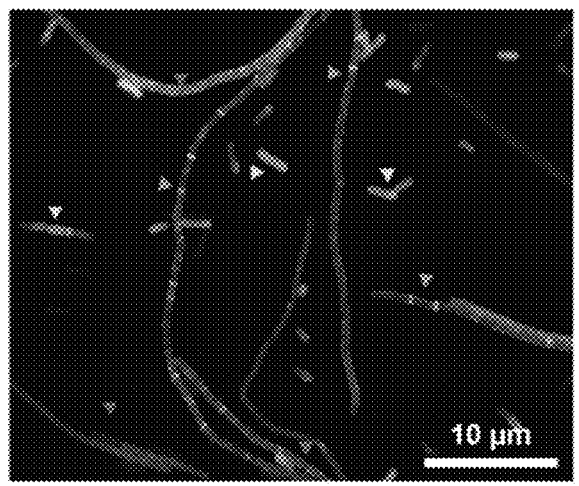
Figure 3I:
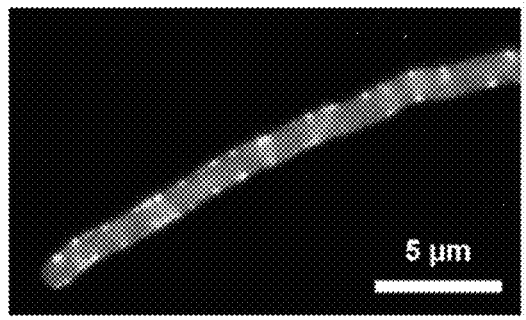

To confirm a role for MinDE in oscillation of MinC, ΔminD and ΔminE mutants were generated in this native mNG-MinC reporter line. Consistent with a role for MinD in recruitment of MinC to membranes, mNG-MinC was completely diffuse in ΔminD cells (FIG. 3F-3G). Conversely, mNG-MinC formed helical structures in incomplete minE deletion strains (FIG. 3H-3I), reminiscent of MinCD copolymer formation in E. coli and FtsZ staining in S. elongatus ΔminE cells (FIG. 2B).

MinCDE dynamics. The pool of mNG-MinC at the midcell was rapidly photobleached during time-lapse imaging, and after bleaching the signal did not recover on the same time scales (i.e. minutes) that MinCD were observed to complete an oscillation (FIG. 3E). These observations indicated that the midcell subpopulation of MinC may not readily be recycled and might be localized through an independent mechanism from MinE-driven oscillations. However, the localization of this subpopulation of MinC does resemble that observed in actively dividing B. subtilis cells, where DivIVA recruits MinCD to midcell through MinJ.

Figure 4A:
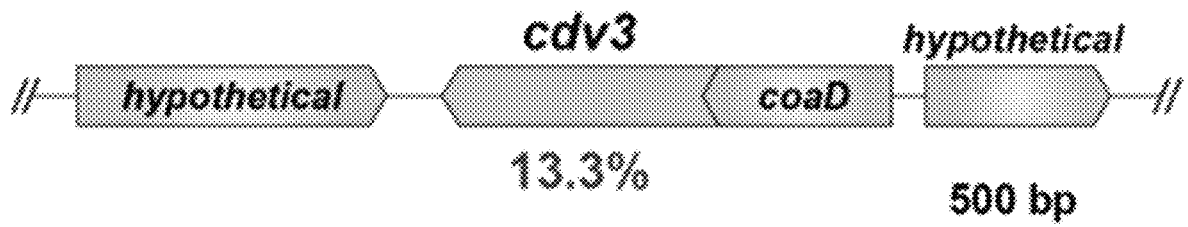
FIG. 4A-4I illustrate that Cdv3 is involved in recruiting a subpopulation of MinC to the midcell.
Figure 4B:
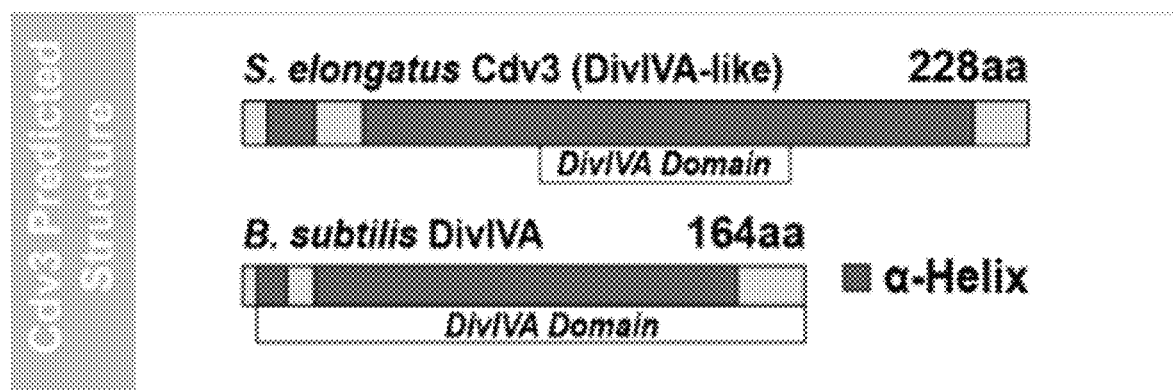

Cyanobacteria may possess a DivIVA-like protein called Cdv3, which might also function to position MinCD (Nakanishi et al., Commun Integr Biol 2: 400-402 (2009); Miyagishima et al., Mol. Microbiol. 56: 126-143 (2005)). However, Cdv3 shares low primary sequence identity with DivIVA of B. subtilis (FIG. 4A). Furthermore, while divIVA is commonly located downstream of the well-characterized division and cell wall (dcw) cluster in gram-positive bacteria, in S. elongatus, cdv3 does not cluster with cell wall or division genes but instead overlaps with the coding sequence for coaD, a gene important for Coenzyme A synthesis (FIG. 4A). Structural modeling of B. subtilis DivIVA based on separately crystallized N- and C-terminal domains suggested an extended tetramer consisting predominantly of antiparallel coiled coils (Oliva et al, EMBO J. 29: 1988-2001 (2010)). While Cdv3 could not be modeled onto this structure, JPred4 analysis indicated that there may similar coiled-coil structures spanning the majority of B. subtilis DivIVA and S. elongatus Cdv3. Furthermore, Delta-Blast identified the presence of a shared DivIVA domain in both proteins and the inventors identified conservation at residues V25 and L29 (V46 and L50 in S. elongatus) that can be important for DivIVA function in B. subtilis (Oliva et al. EMBO J 2010; 29:1988-2001 (2010) (FIG. 4B). However, Cdv3 does not have conservation of residues (S16, F17, R18, G19, Y20) reported to be required for sensing and binding of DivIVA to negatively-curved membrane regions (FIG. 4B). An alignment of S. elongatus (Se; SEQ ID NO:103) Cdv3 and B. subtilis (Bs; SEQ ID NO:104) DivIVA sequences is shown below.

```
Se MTQAQSLDVLNLLEQLEESVLDGTRVPLSGRILVRENDLLDLLDDVRAGLPAAIQQAQQI
Bs ....................MPLTPNDIHNKTFTKSFRGYDE.DEVNEFLAQVRKDYEIV
                                       -------
                                       Crossed Loops Se LERQAQILADAQQQAQAIVAQAQQE....RALLIDQNS...IRLQAERDAQQLRQTLQQE
Bs LRKTELEAKVNELDERIGHFANIEETLNKSILVAQEAAEDVKRNSQKEAKLIVREAEKN Se CDALRQQAIAEATQVRGEAQQFQLQVRQETDSLRQQTQAEIEQLRSQTQQQLSEQRQRIL
Bs ADRIINESLSKSRKIAMEIEELKKQSKVFRTRFQMLIEAQLDLLKNDDWDHLLEYEVDAV Se VECEELRRGADSYADQVLRDMEQRLTQMMQIIRNGRQALNLSENTPPPAPRRRSR
Bs FEEKE..................................................
```

Additionally, Cdv3 lacked C-terminal peptides required for interaction of DivIVA with MinJ and RacA (van Baarle et al. 2013), which are not present in cyanobacteria. Therefore, Cdv3 possesses partial conservation to DivIVA, but it has been unclear what function it may serve given the fact that the MinCDE oscillations in vivo described herein are potentially sufficient to confine FtsZ polymerization to the midcell.

Figure 4C:
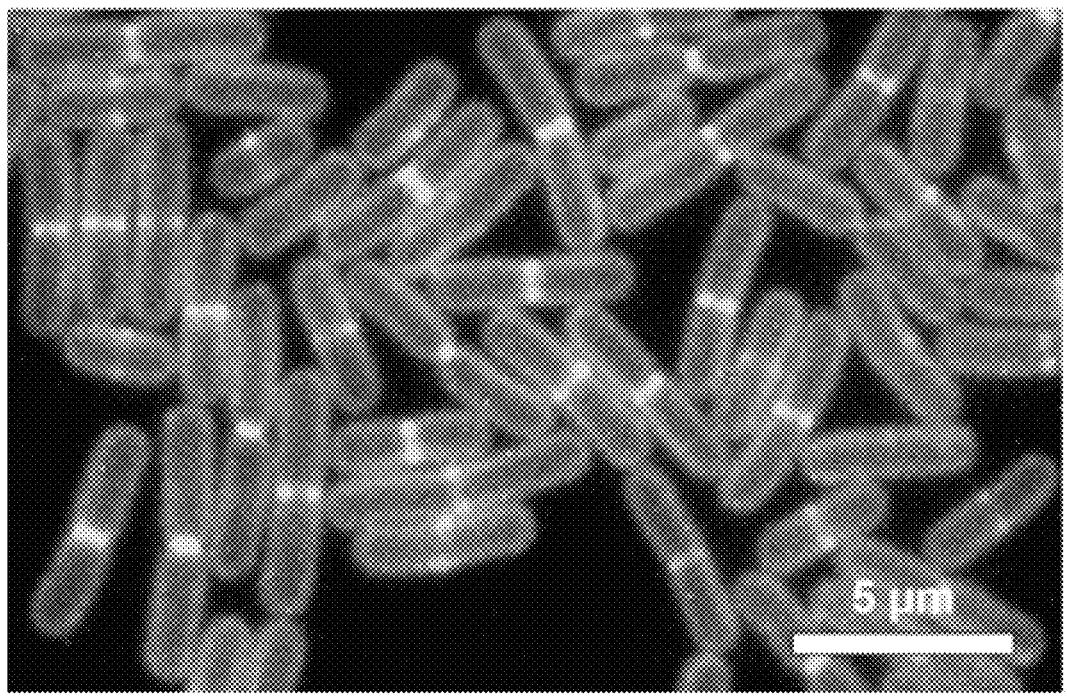

Example 6: Cdv3 Recruits MinCD to the Z Ring and is Needed for Provisioning a Functional Divisome During the in vivo imaging experiments, a subpopulation of mNG-MinC did not oscillate, but formed a ring-like structure at midcell. This midcell localization could not be readily explained from the E. coli model of emergent The role of Cdv3 and DivIVA in cell division was investigated by generating deletion, overexpression, and reporter lines (FIGS. 1F and 3C). First, a reporter strain was generated in which the native cdv3 gene was completely replaced with a C-terminal mNG fusion. Expression of such a Cdv3-mNG transgene concentrates Cdv3 to the midzone of the cell in a ring-like structure. This localization is observed prior to other signs of cell constriction and persists throughout cytokinesis (FIG. 4C). The Cdv3-mNG strains possessed wild-type growth rates and cell lengths, indicating the Cdv3-mNG fusion maintained functionality.

Figure 4D:
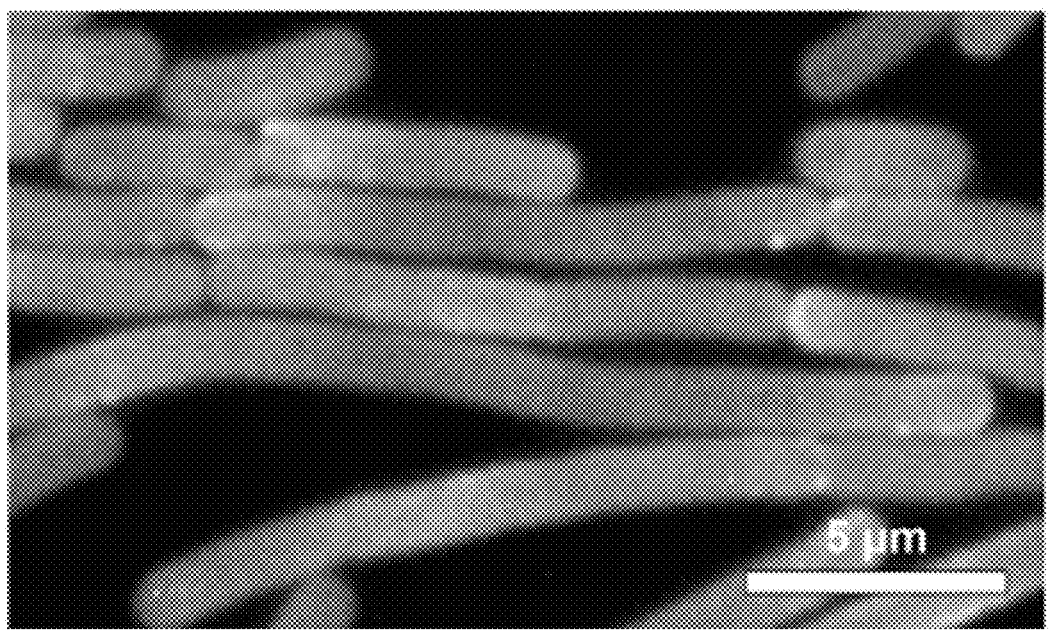
Figure 4E:
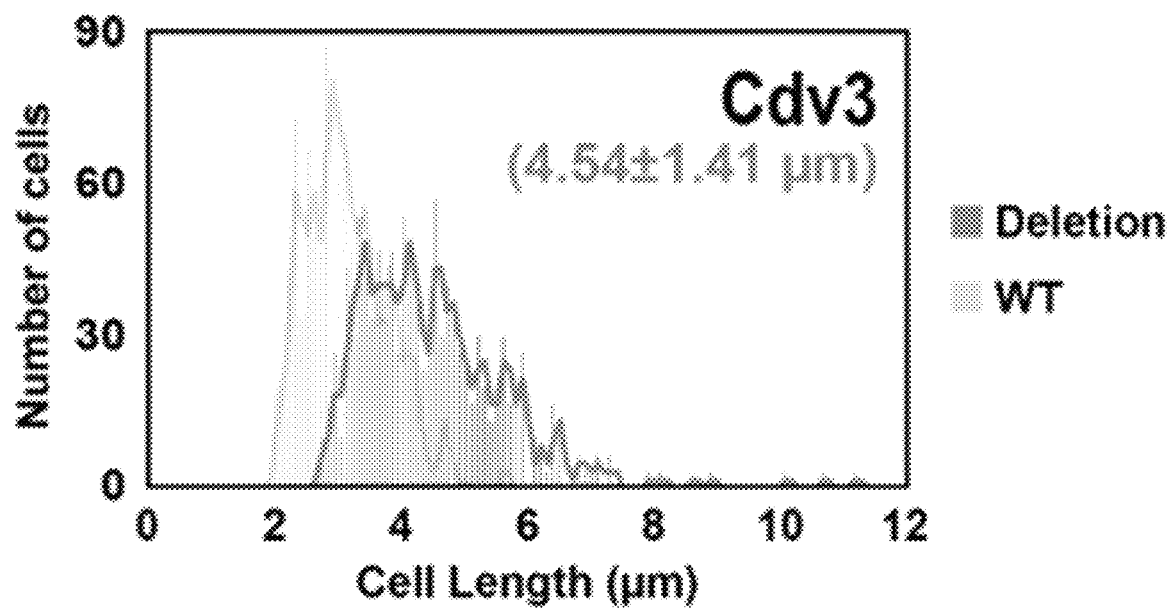
Figure 4F:
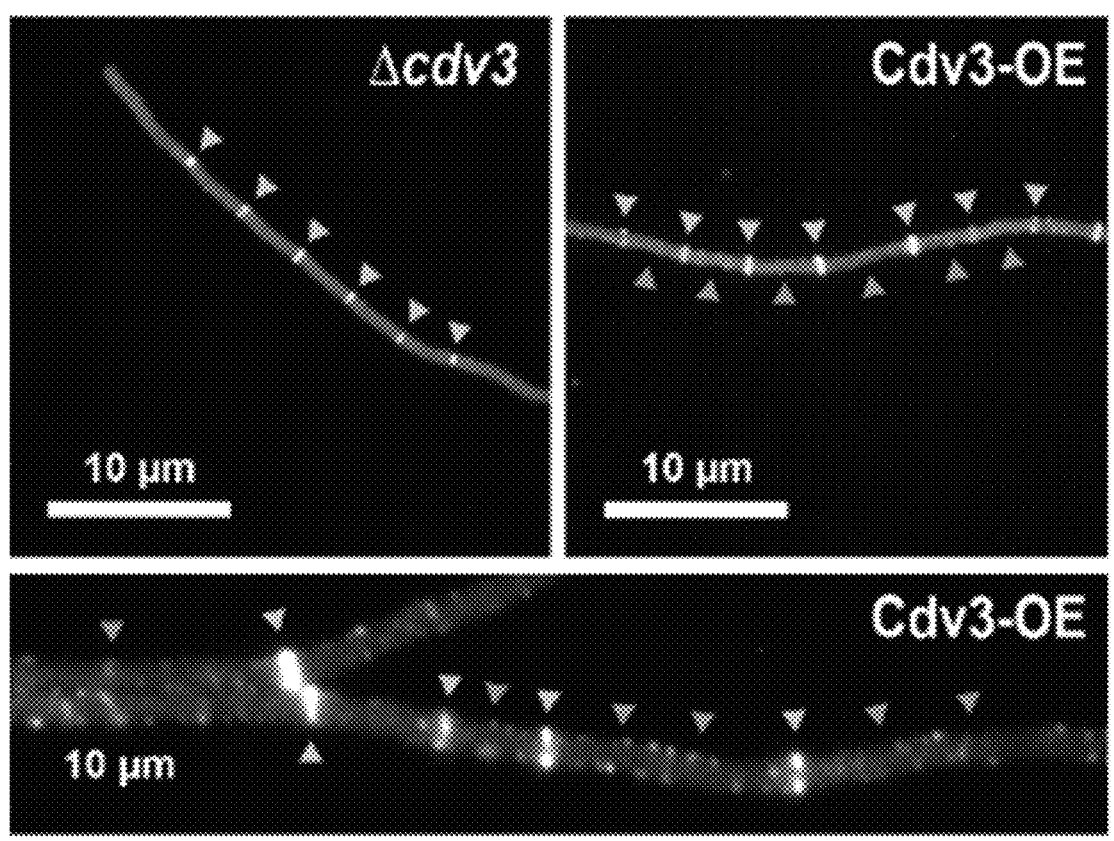

In contrast, Δcdv3 strains exhibited a highly elongated morphology (FIG. 4D-4E). FtsZ localization in such Δcdv3 strains was unlike that in ΔminE and MinE-OE strains; FtsZ was localized in regularly-spaced Z rings throughout the cell (compare FIGS. 4F and 2B). Furthermore, overexpression of Cdv3 arrested division and resulted in hyperelongation (FIG. 2C-2D) with FtsZ localizing to irregularly spaced Z rings interspersed with disorganized FtsZ filaments (FIGS. 4F and 2C). Taken together, these results indicate that Cdv3 has a function in regulating Z-ring positioning and/or constriction that is not redundant with MinE.

Figure 4G:
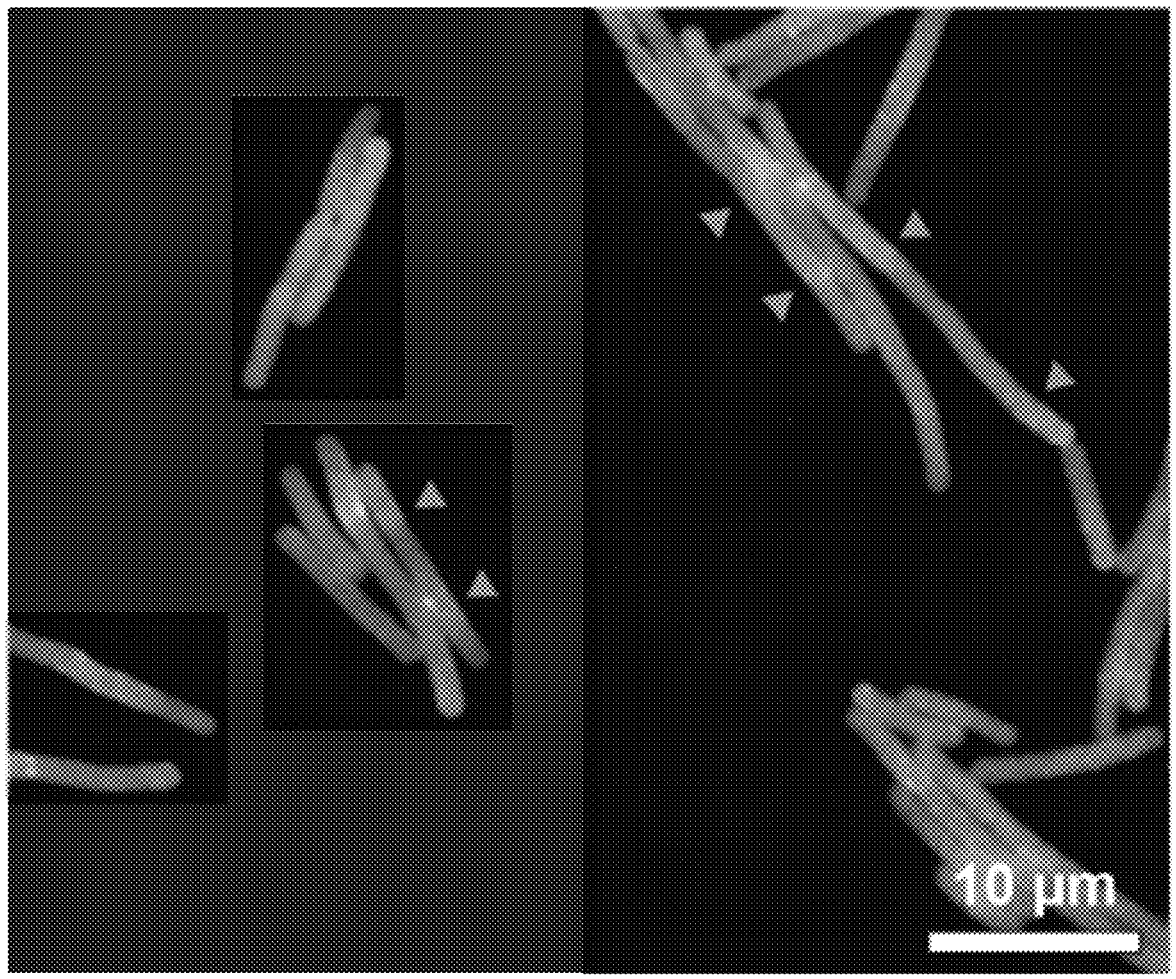

To ascertain if Cdv3 or other Min proteins have a role in recruiting the midzone-localized subpopulation of MinC, *S. elongatus* Min mutants were generated in the mNG-MinC fluorescent reporter line. The pool of midcell-localized mNG-MinC was abolished in ΔminD and Δcdv3 strains, indicative of roles for MinD and Cdv3 in the midcell recruitment of MinC (FIG. 3F-3G; FIG. 4D). Although the midcell localization of MinC was disrupted in filamentous Δcdv3 strains, these cells still exhibited oscillatory waves of mNG-MinC (FIG. 4D, 4G). These results indicate that both Cdv3 and MinE spatially regulate Z-ring assembly by providing topology to distinct pools of MinCD in cyanobacteria.

Figure 4H:
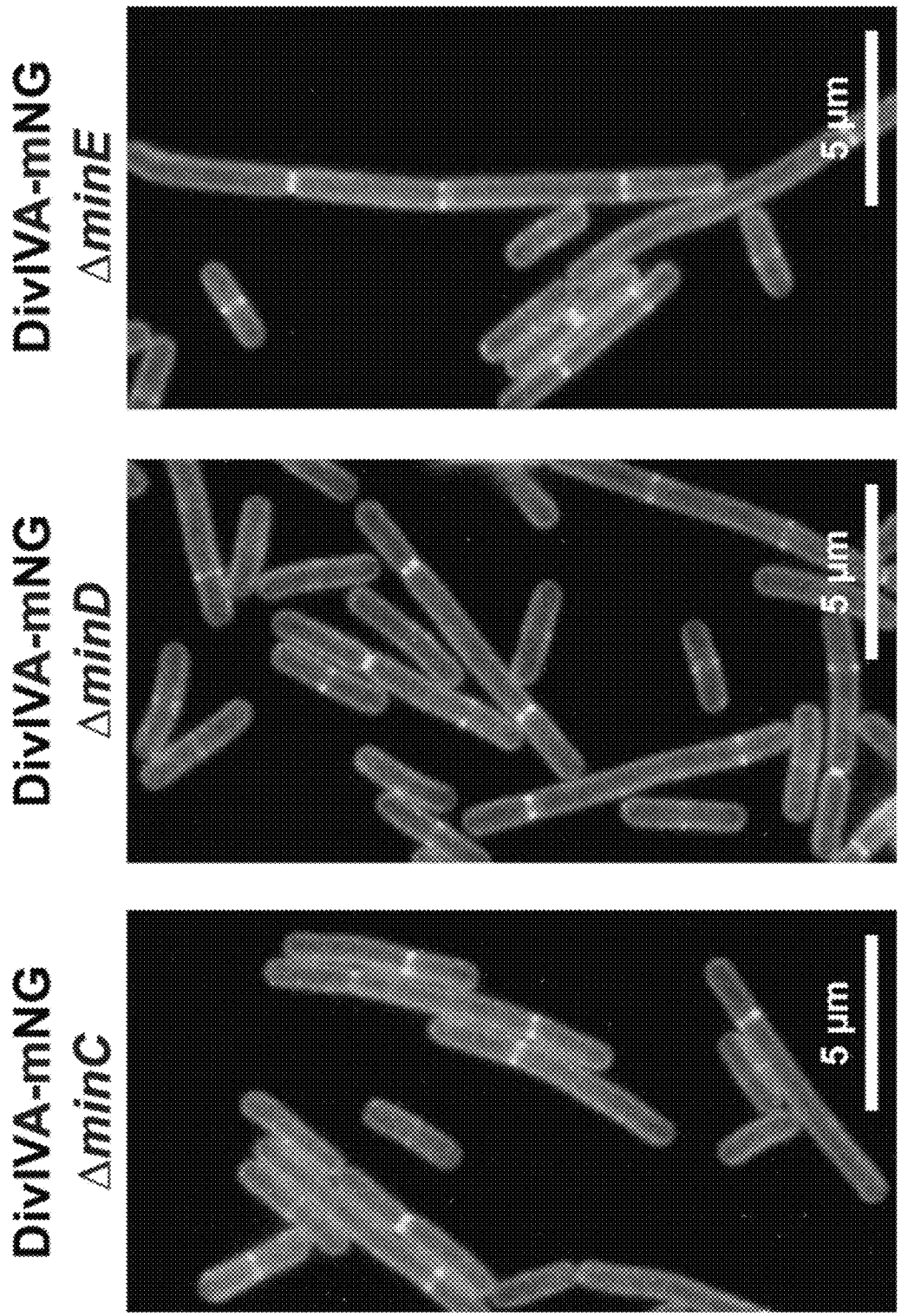

FIG. 4H illustrates that DivIVA (related to cdv3 in *S. elongatus* as described herein) localization to division planes is independent of other Min system regulators. DivIVA-mNG was imaged in ΔminC, ΔminD and ΔminE backgrounds. Upon the deletion of minC, the DivIVA signal appeared at midcell. In ΔminD backgrounds, DivIVA localization appeared in ring-like patterns that were often observed in multiple locations along the length of elongated cells, and where the ring-like structures were frequently near cell poles (FIG. 4H). These localizations are consistent with FtsZ staining in ΔminC and ΔminD cells, respectively. Interestingly, ΔminE cells displayed erratic DivIVA-mNG localization (FIG. 4H), where ring-like structures formed randomly in the cell (often at constricting sites presumed to be division planes), while also forming a helical pattern that was reminiscent of FtsZ patterning in ΔminE cells. These patterns indicate that DivIVA and FtsZ co-localize in *S. elongatus*.

Example 7: Effects of Cdv3 Expression Upon FtsZ Ring Formation

Figure 4I:
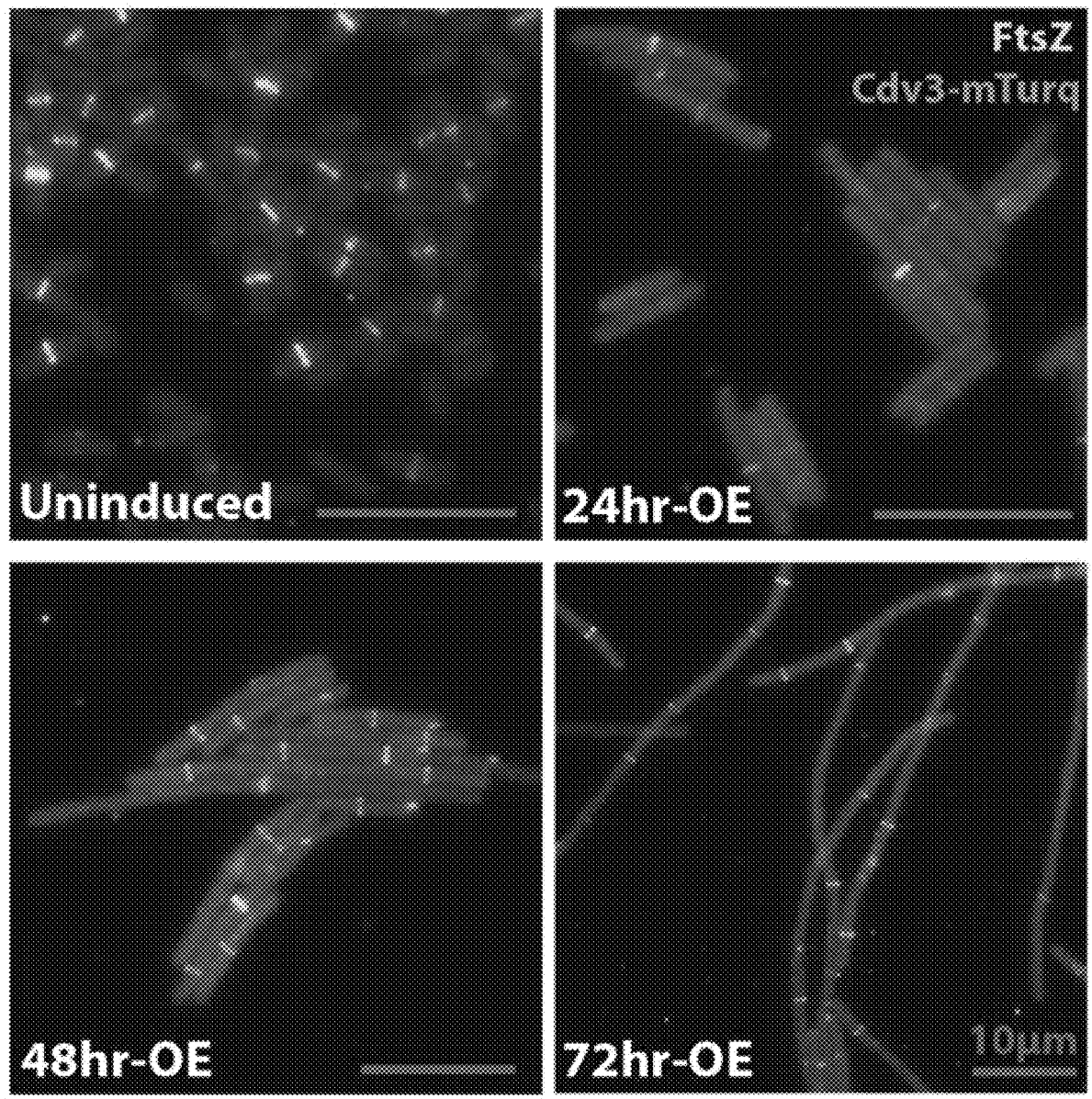

This Example illustrates that Cdv3 overexpression can elongate cells, for example, by reducing the rate of formation of FtsZ rings and impairing their capacity to constrict.
Methods
Expression of Cdv3 in riboswitch::Cdv3-mTurq strains was induced with 400 μM theophylline and representative bright-field images from each day following induction were obtained.
Results
FIG. 4I shows images of immunolocalized FtsZ (yellow) in representative cells where Cdv3 expression was induced for the indicated number of hours. As illustrated, formation of Z-rings was delayed in Cdv3-mTurq (blue) expressing lines (24 hr-OE), whereas cells of this size would normally have at least one FtsZ ring. At later time points, in severely elongated cells, multiple, mis-positioned Z-rings are evident (48-72 hours post-induction), yet there is no clear indication of FtsZ constriction in such cells.

Example 8: Cell Size Modulation by MinC, MinD, MinE, and Cdv3

This Example illustrates that cell size can be modulated in a controlled manner by regulated expression of MinC, MinD, MinE, and Cdv3.

Cyanobacterial cells that inducibly expressed MinC, MinD, MinE, or Cdv3 were generated as described in Example 1 or 2, where these genes were tagged with the fluorescent reporter mTurquoise in order to verify expression and determine localization. No fluorescence was observed in any of the cell lines when theophylline was not added to the culture, but mTurquoise fluorescence was detected in a direct relationship to the amount of theophylline added (data not shown). The cells were cultured in concentrations of theophylline varying from 0 μM to 2 mM, and the dimensions of cells were measured after 24 hours of overexpression. Cell length measurements for overexpression strains were performed with live cells using manual tools in Zeiss Zen software.

Figure 5A:
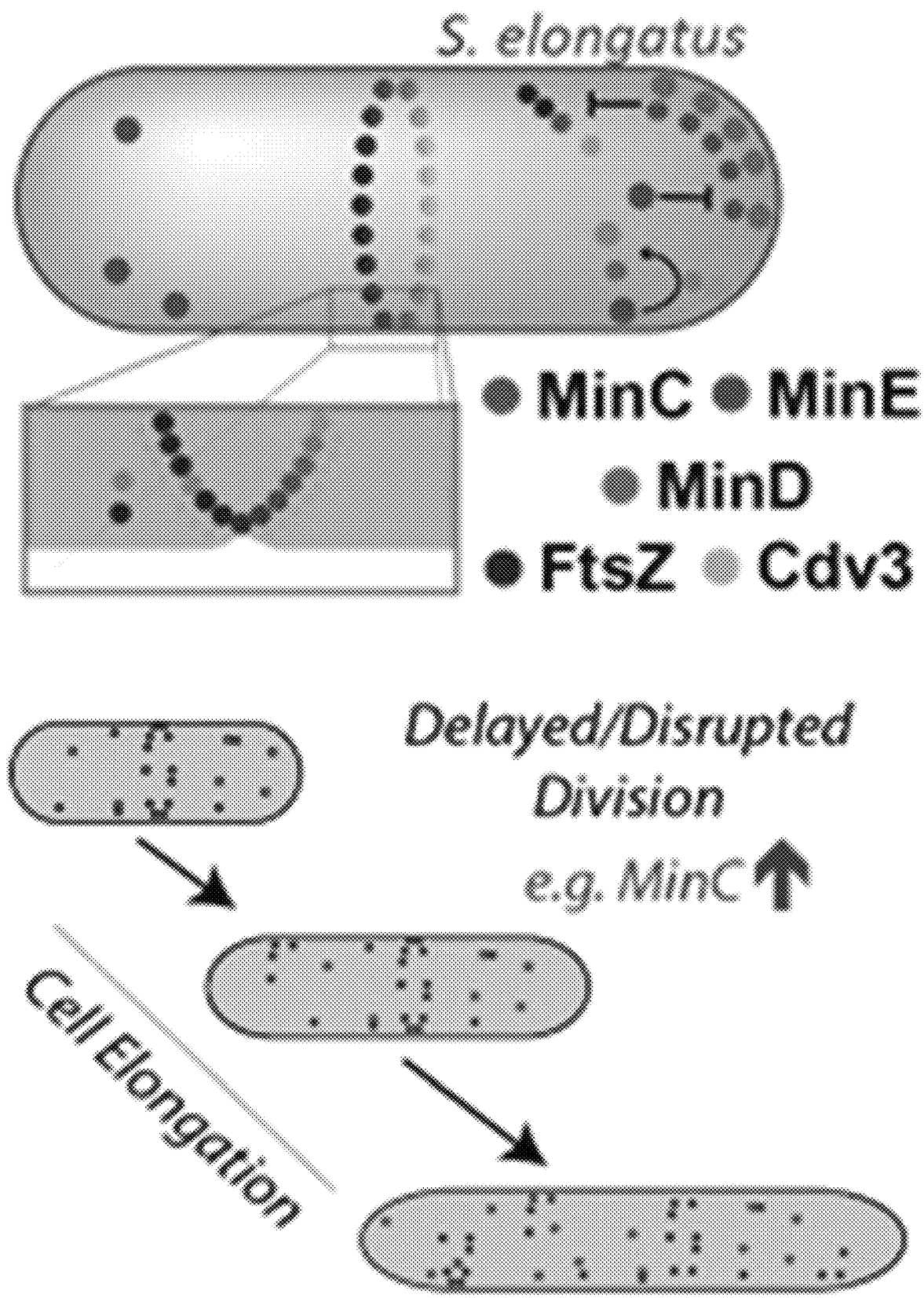
FIG. 5A-5F illustrate cyanobacterial cell elongation when MinC, MinD, MinE, and/or Cdv3 proteins are overexpressed.
Figure 5B:
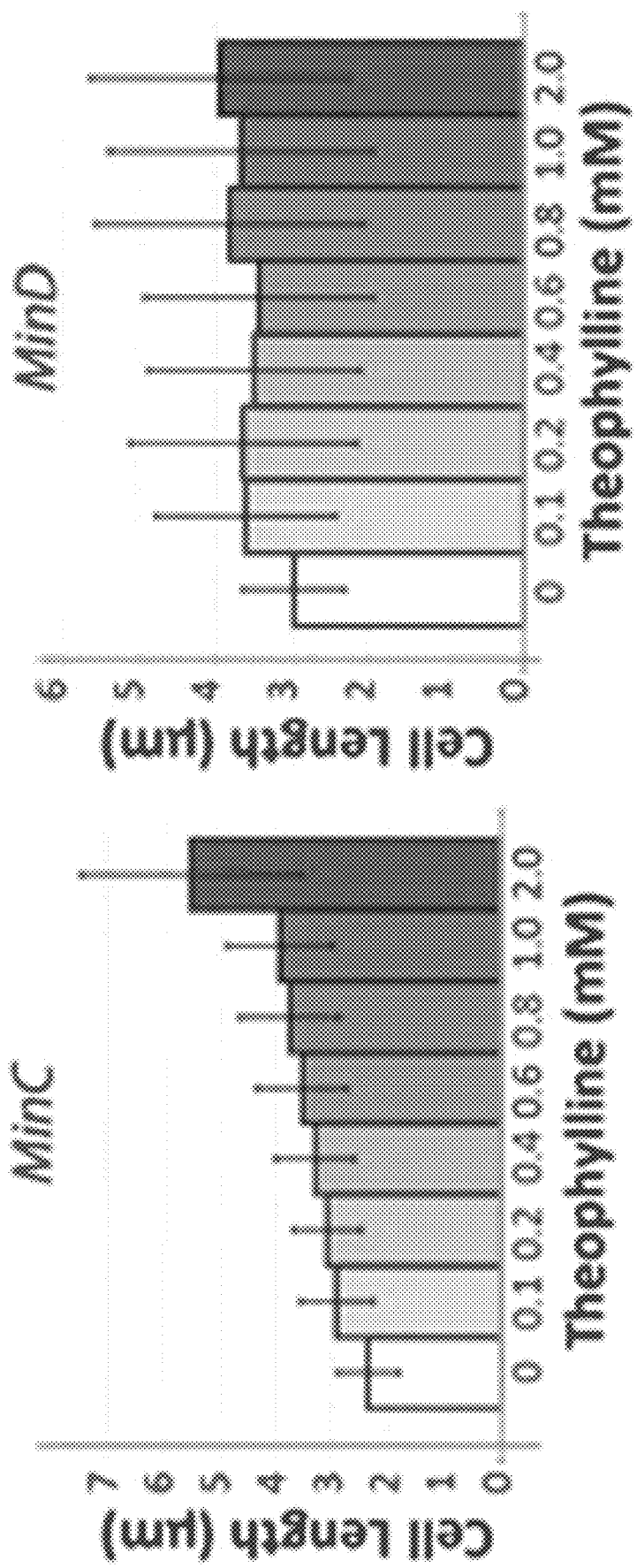
Figure 5C:
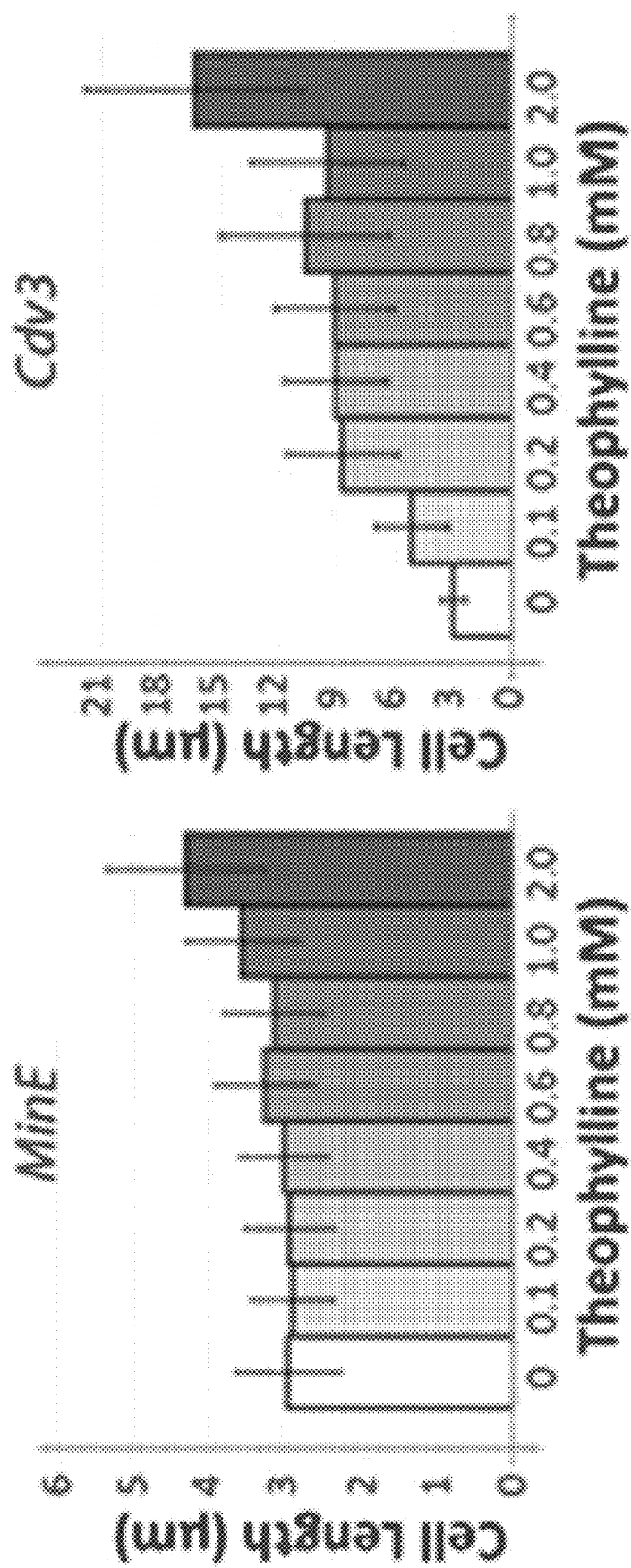

FIG. 5A-5E illustrate cyanobacterial cell elongation when MinC, MinD, MinE, and/or Cdv3 proteins are overexpressed. FIG. 5A is a schematic diagram of a cyanobacterial cell illustrating the locations of MinC, MinD, MinE, Cdv3, and FtsZ proteins, as well as the effect of overexpressing MinC protein on cell length. FIG. 5B graphically illustrates cell length upon inducing expression of MinC protein (left panel) and MinD protein (right panel) with increased amounts of the inducer (theophylline). As illustrated, greater concentrations of the theophylline inducer lead to cyanobacterial populations with increased mean cell lengths. FIG. 5C graphically illustrates cell length upon inducing expression of MinE protein (left panel) and Cdv3 protein (right panel) with increased amounts of the inducer (theophylline). As illustrated, greater concentrations of the theophylline inducer lead to cyanobacterial populations with increased mean cell lengths.

Figure 5D:
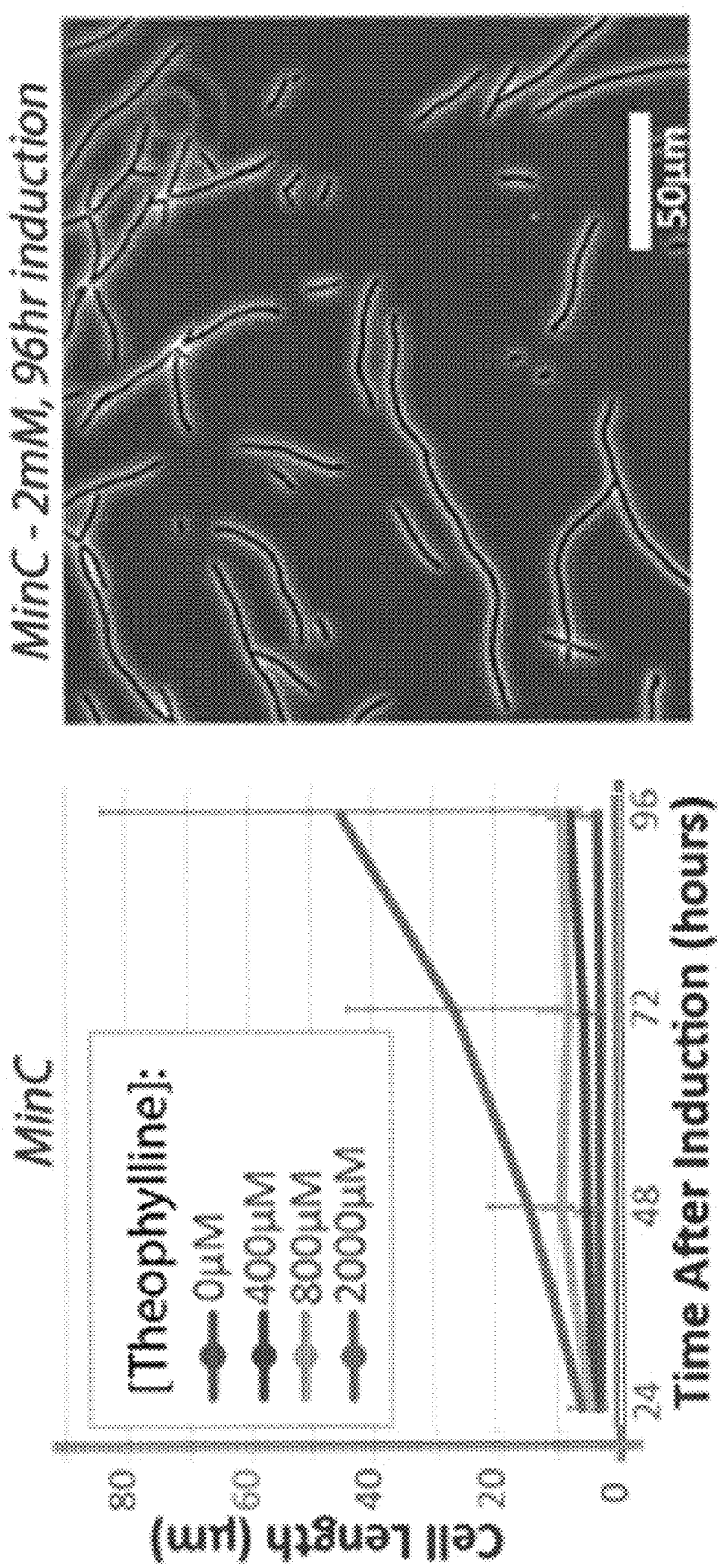

MinC cells with MinC expression induced at the highest theophylline concentrations were elongated by about 20-fold, reaching average cell lengths of 45 μm after 96 hours (FIG. 5D). These cells were hyper variable in length (FIG. 5D), in contrast to cells where MinC expression was induced at lower levels where a new steady-state cell length of about 2-3 fold larger than uninduced cells was obtained by 48 hours after induction.

Figure 5E:
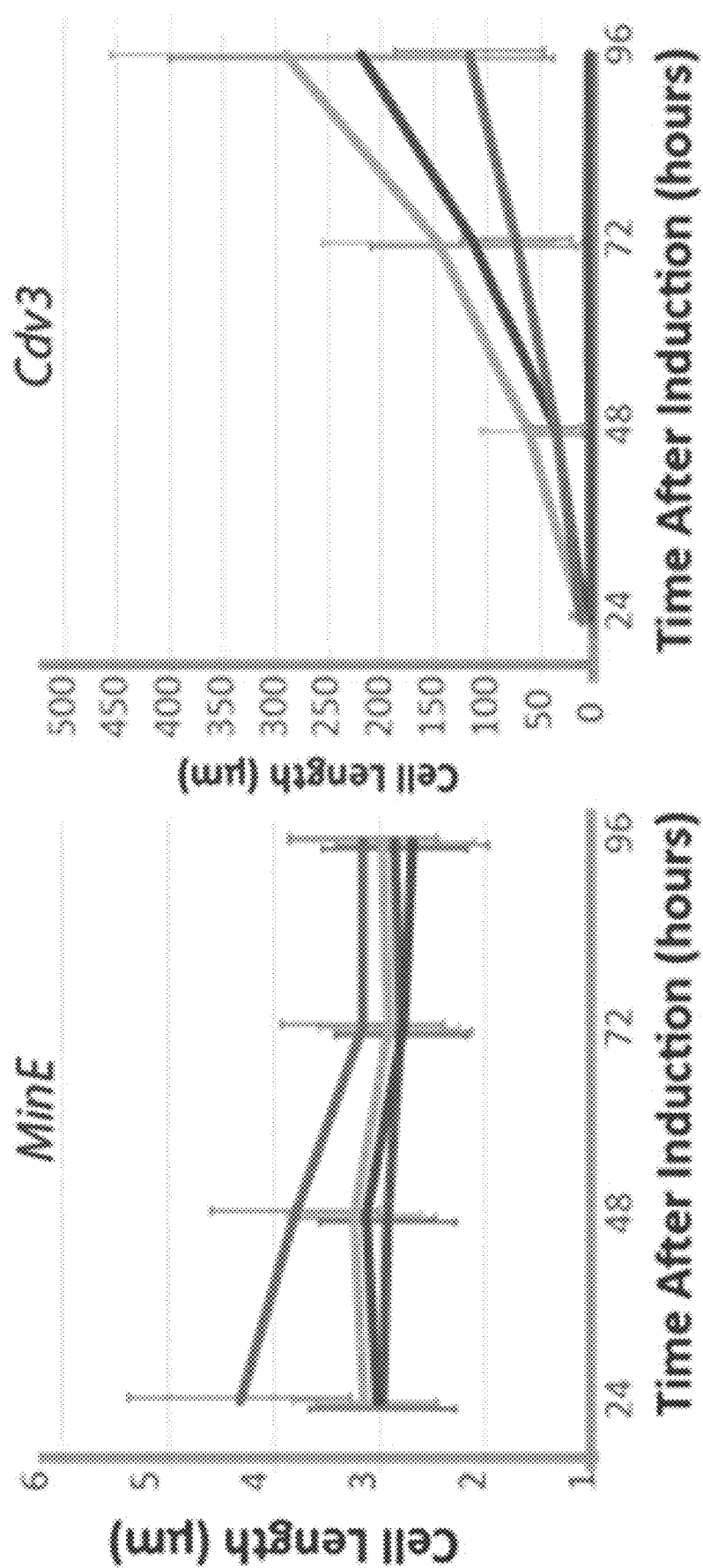

Long-term overexpression of minE did not stably increase cell lengths (FIG. 5E, left panel). At later time points all cells that overexpressed MinE returned to a baseline length of about 3 μm (FIG. 5E, right panel).

By contrast, with any additional over-expression of Cdv3, *Synechococcus elongatus* cells elongated at an accelerating rate over time. Most cells reached lengths greater than 100 μm after 3-4 days of induction (FIG. 5E). Cell division was exquisitely sensitive to overexpression of Cdv3. Similar elongation rates were observed regardless of the amount of theophylline inducer. These data indicate that even minor changes in Cdv3 activity can lead to near arrest of cell division and that cell growth is decoupled from division when Cdv3 is overexpressed.

Figure 5F:
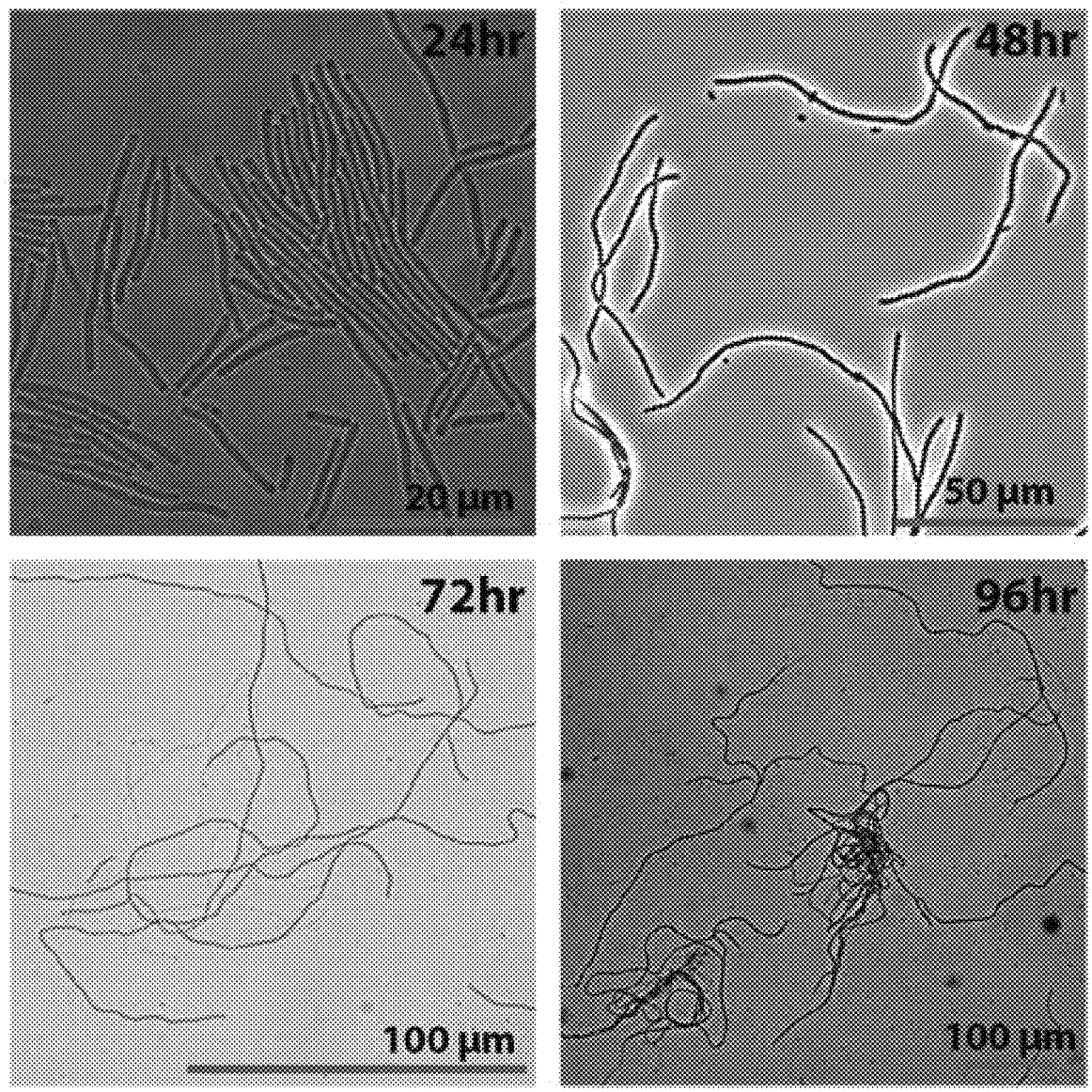

FIG. 5F shows brightfield microscopy images of elongated cyanobacterial cells that have been induced to overexpress Cdv3. The scale of these images was changed between the panels to illustrate the extreme elongation that is seen in these cells.

Example 9: Hyper-Elongated Cells are More Prone to Sediment

Figure 6C:
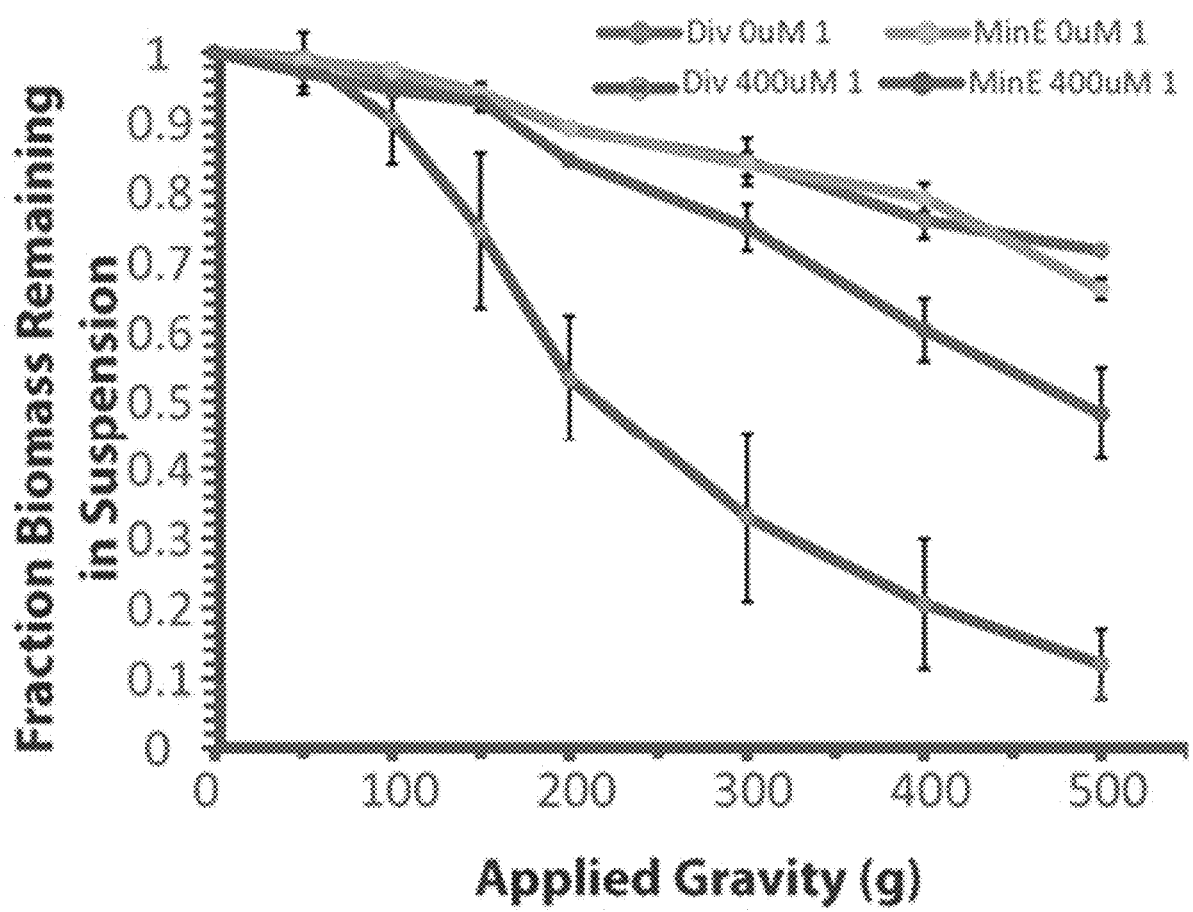

Cdv3 (DivIVA) expression was induced in cyanobacteria with the cdv3 (divIVA) overexpression transgene. The effectiveness of gravity sedimentation of the elongated cells was monitored by observing the rate at which cells fell out of a water column (FIG. 6A). Cell sedimentation was recorded over time to track the spontaneous settling via gravity and a direct correlation with the cell length and rapidity of sedimentation was observed (FIG. 6A-6C). Sedimentation took place over several hours without added gravitational forces (FIG. 6A-6B). Sedimentation occurred faster when additional gravitational forces were applied and sedimentation of Cdv3 (DivIVA) overexpressing cells was faster than MinE overexpressing cells (FIG. 6C).

Example 10: Hyper-Elongated Cells are More Readily Lysed

Cdv3 (DivIVA) expression was induced in cyanobacteria with the cdv3 (DivIVA) overexpression transgene. The vulnerability of elongated cells to lysis by mechanical forces was evaluated by subjecting the cells to torsional/shear forces that are often employed to lyse cells for bioproduct recovery. Cell elongation increases the cell surface to volume ratio. Cell elongation also increases the area over which cells can be exposed to lysing agents. In addition, torsional forces experienced by an elongated cell under sheer stress are likely greater, barring other structural changes.

Figure 7A:
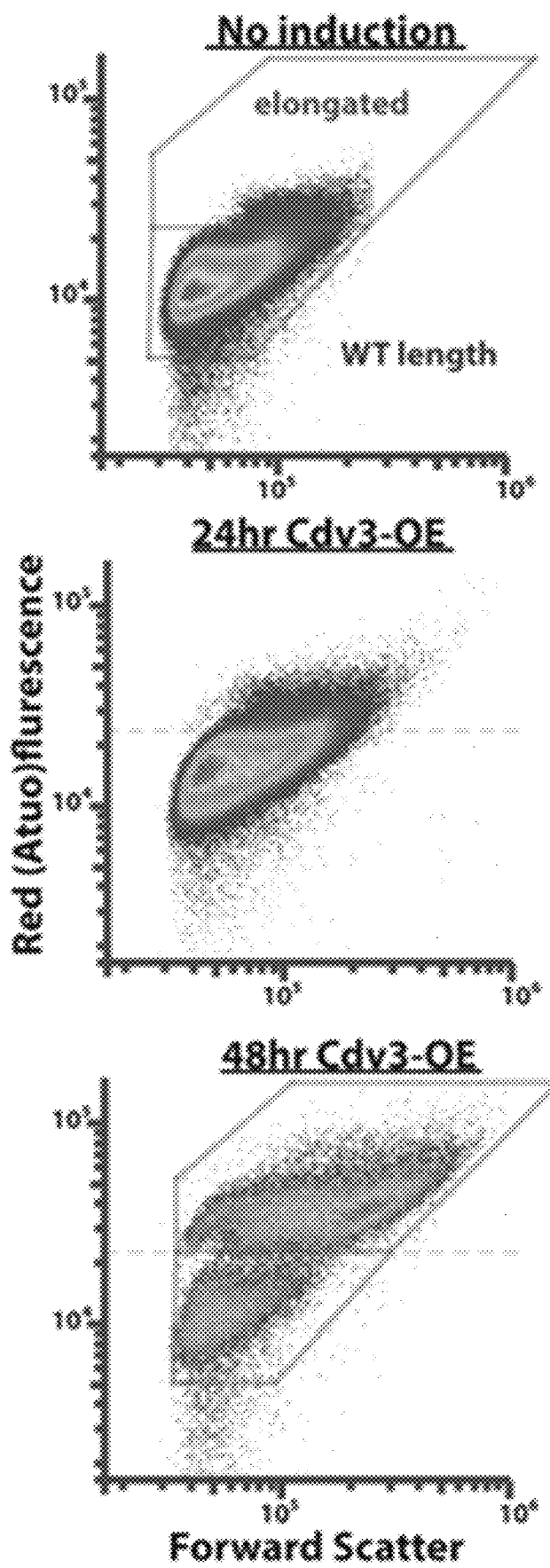
FIG. 7A-7E illustrates that hyper-elongated cells that overexpress Cdv3 (DivIVA) are more readily lysed by torsional/shear forces than control cells that do not overexpress Cdv3 (DivIVA).

The differential susceptibility of elongated cells was examined by tracking populations of cyanobacterial cells through flow cytometry, before and after passage through a cell disrupter, as described in Example 1. As shown in FIG. 7A, the cell population exhibited an increase in cell forward scatter and chlorophyll α autofluorescence following induction of Cdv3 expression through the addition of theophylline (400 µM). Such increased cell forward scatter and chlorophyll α autofluorescence correlated with increasing cell sizes (FIG. 5; FIG. 7A).

Figure 7B:
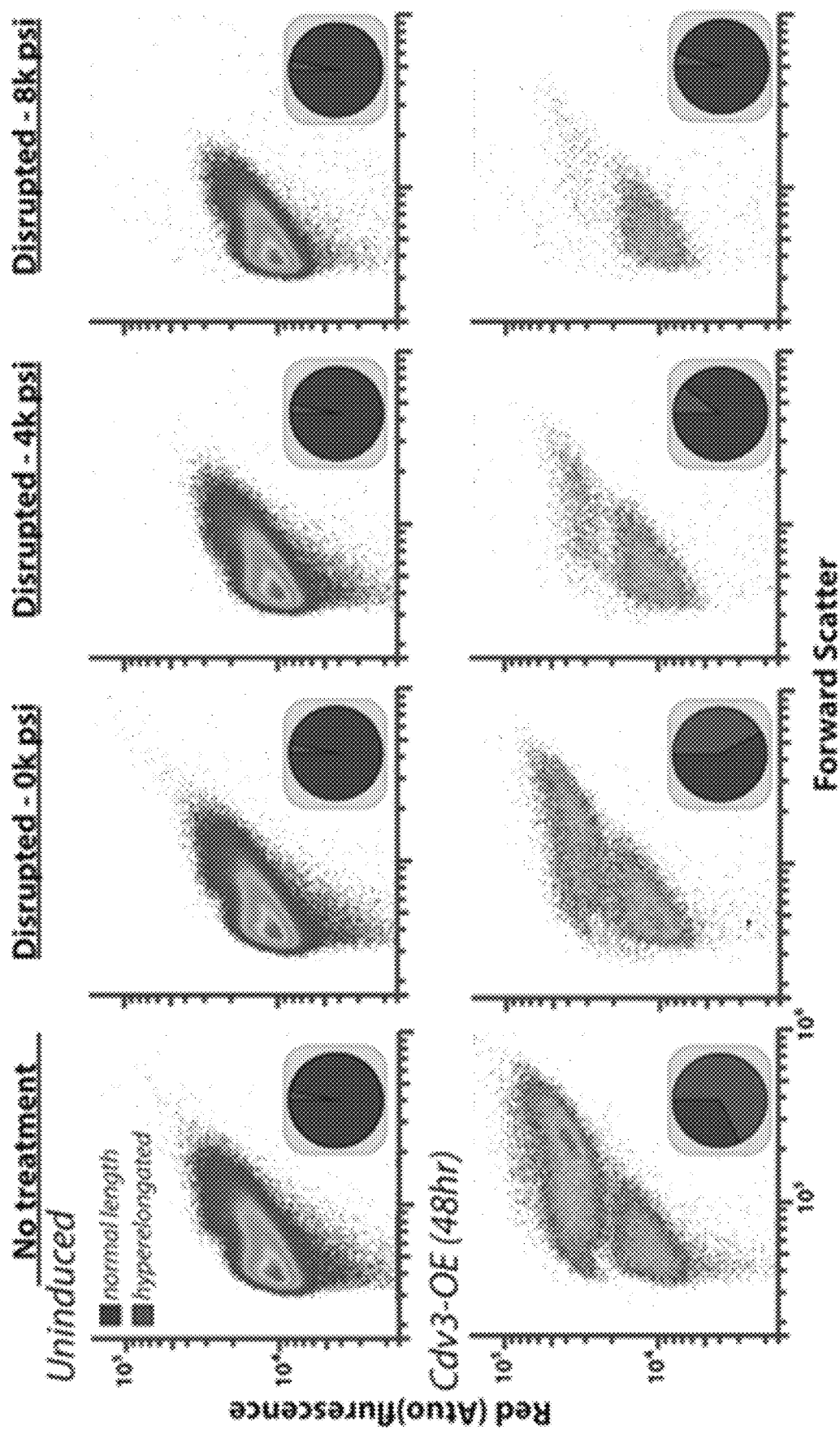
Figure 7C:
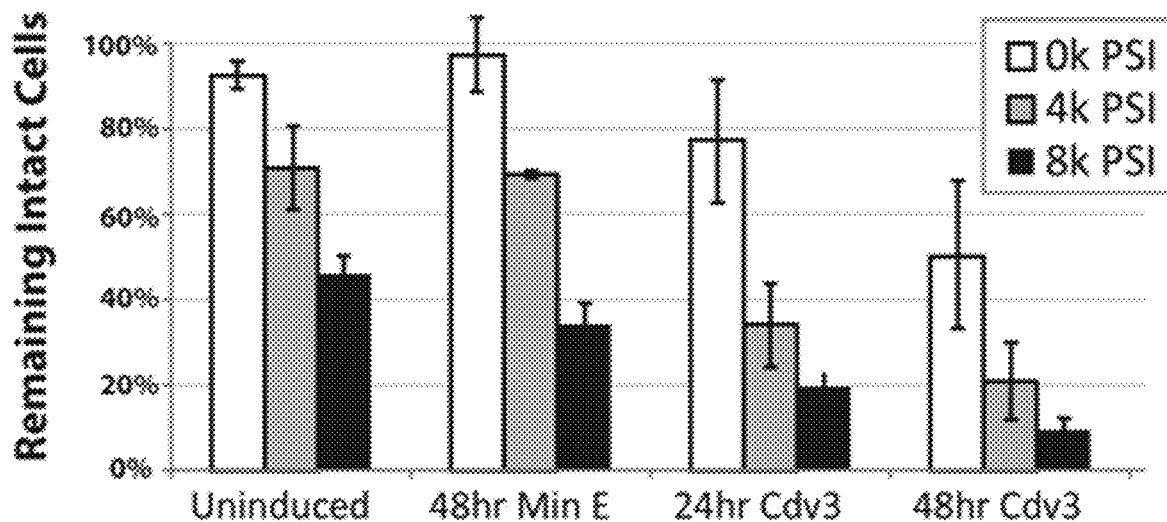
Figure 7D:
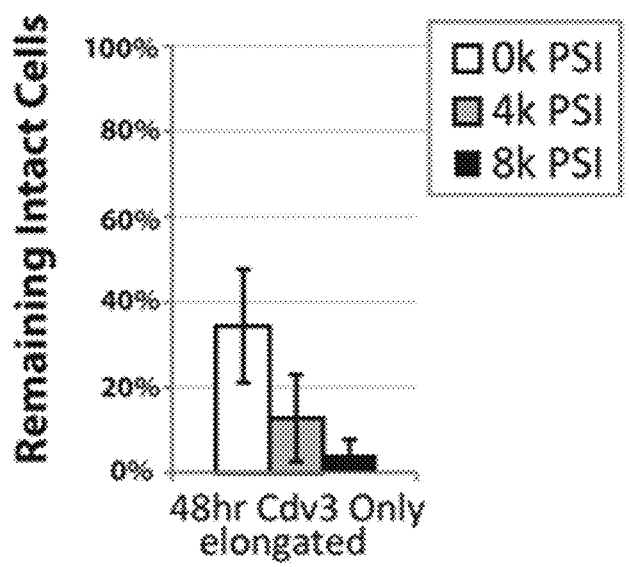

Populations of Cdv3-overexpressing cells were subjected to relatively mild pressures in a cell disrupter and examined for cell lysis through flow cytometry (FIG. 7B). Significant decreases in the proportion of elongated cells were observed following passage through the cell disrupter at the lowest pressure that could be programmed, and nearly complete lysis of the elongated population occurred at 8000 psi (FIG. 7B-7D). In contrast, uninduced cells or Cdv3-overexpressing cells were not significantly lysed at the lowest pressure tested, and were only partly disrupted at 4000 psi or at 8000 psi (FIG. 7C-7D).

Example 11: Hyperelongation of Cells by Overexpressing Cdv3 does not Reduce Biomass Produced or Cell Mass Recovered This Example shows that overexpression of Cdv3, which elongates cells, does not adversely affect the capacity of the cells to grow during the period of hyperelongation. Furthermore, the cells can still be collected without loss of biomass to cell lysis.

As illustrated in the foregoing Examples, increasing the expression level of various proteins (e.g., MinC, Cdv3) leads to increased cell length by arresting division. One concern is that, although such larger cells may be easier to harvest/process, the cells may exhibit reduced productivity during the elongation period due to the abnormal cell size or the cells could be damaged by the procedures used by the harvesting process. For example, if the cells become too sickly, if changes of the cell volume:surface area adversely impact photosynthesis, if their metabolism dramatically changes, or if their cell walls become weak, the yield of harvested cells may decline. This concern was addressed using the following procedures.

Methods

Figure 7E:
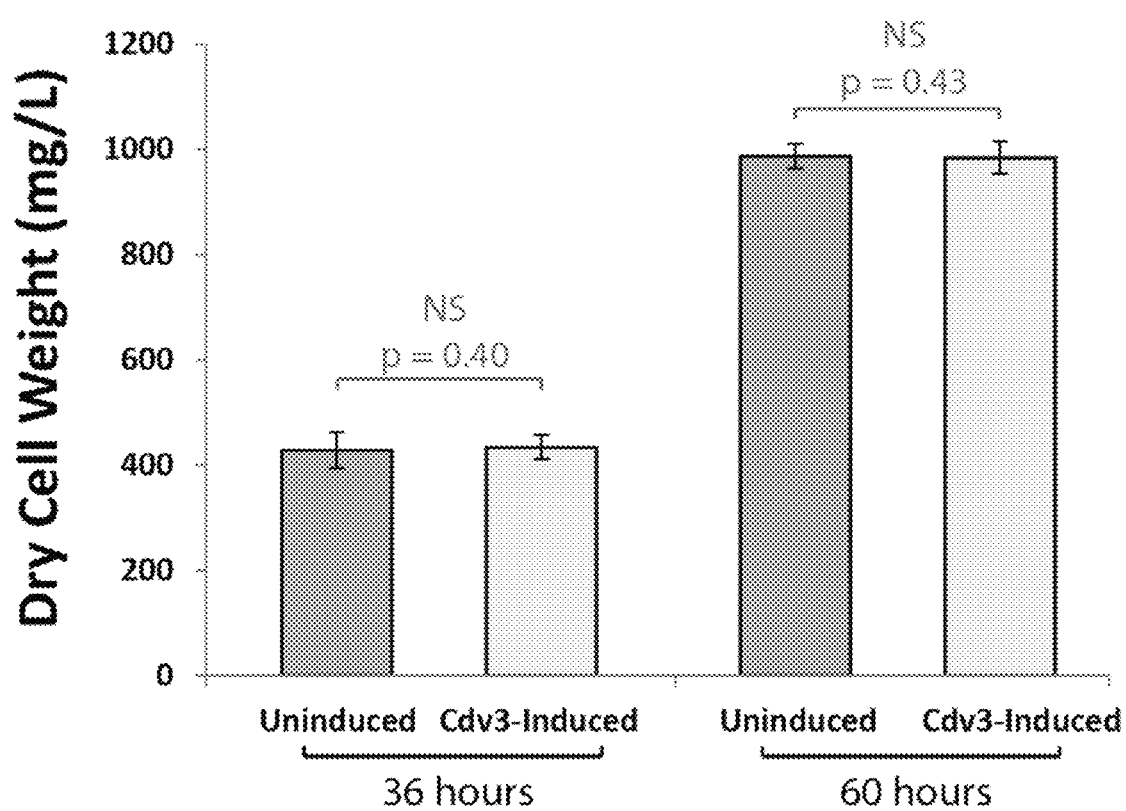
Figure 8:
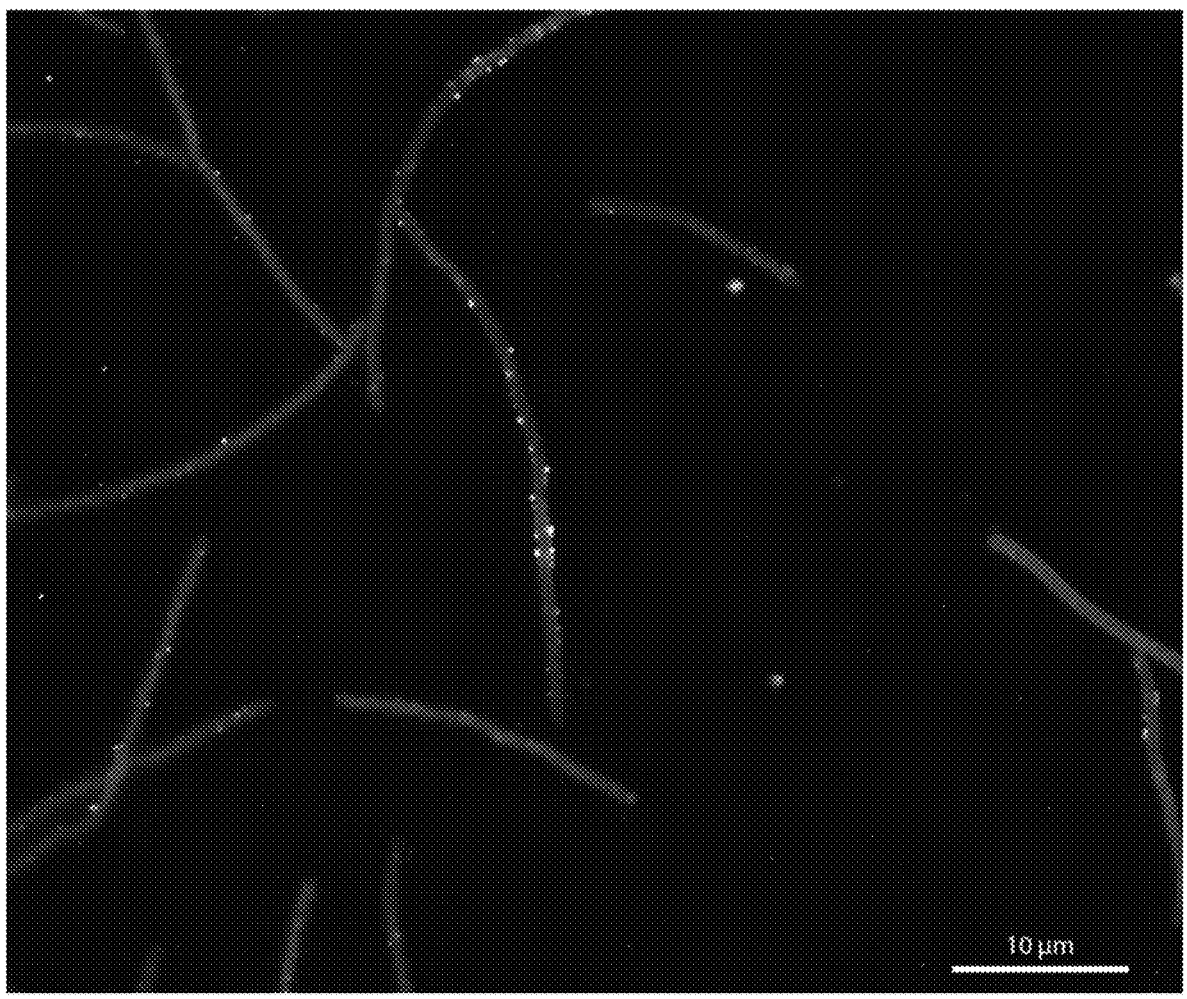
FIG. 8 illustrates cyanobacterial cell elongation when Ftn2 is overexpressed from an IPTG-inducible promoter. Representative cyanobacterial cells (red: chlorophyll fluorescence) are elongated relative to wildtype cells. Additionally, this image illustrates that FtsZ (white) localization is altered in Ftn2 overexpression (OE) cyanobacterial lines, as visualized by immunofluorescence with anti-FtsZ antibodies.

At time zero, Riboswitch::Cdv3-mTurq S. elongatus cultures were back-diluted to $OD_{750}=0.25$. Theophylline was added to a final concentration of 400 µM to induce Cdv3-mTurq expression in some cultures (Cdv3-Induced: FIG. 7E, light grey bars), while no theophylline was added to negative controls (Uninduced: FIG. 7E, dark grey bars). Cells were pelleted in a Sorvall SS-34 rotor for 10 minutes at 5000 rpm after 36 or 60 hours of incubation (induction) with theophylline. Following desiccation of the cell pellets, dry cell biomass was measured.

Results

As illustrated in FIG. 7E, there is no significant reduction in the amount of cell biomass accumulated in hyperelongated cells generated by inducing overexpression of Cdv3 even when the cells were harvested by pelleting. The dry cell mass of negative controls (Uninduced: dark grey bars in FIG. 7E) was about the same as the dry cell mass of Cdv3-expressing cells with Cdv-3 induced by theophylline (light grey bars in FIG. 7E).

REFERENCES

[1] Assembly dynamics of the bacterial MinCDE system and spatial regulation of the Z ring. Annu Rev Biochem 2007; 76:539-62. doi:10.1146/annurev.biochem.75.103004.142652.

[2] Eswaramoorthy P, Erb M L, Gregory J A, Silverman J, Pogliano K, Pogliano J, et al. Cellular Architecture Mediates DivIVA Ultrastructure and Regulates Min Activity in *Bacillus subtilis*. mBio 2011; 2:-e00257-11. doi:10.1128/mBio.00257-11.

[3] Raskin D M, de Boer P. Rapid pole-to-pole oscillation of a protein required for directing division to the middle of *Escherichia coli*. Proc Natl Acad Sci USA 1999; 96:4971-6.

[4] Nevo R, Chuartzman S G, Tsabari O. Reich Z. Charuvi D, Shimoni E. Architecture of Thylakoid Membrane Networks, vol. 30. Dordrecht: Springer Netherlands; 2009. doi:10.1007/978-90-481-2863-1_14.

[5] Osteryoung K W, Pyke K A. Division and Dynamic Morphology of Plastids 2014; 65:443-72. doi:10.1146/annurev-arplant-050213-035748.

[6] Leger M M, Petrů M, árský V, Eme L, Vlček Č, Harding T, et al. An ancestral bacterial division system is widespread in eukaryotic mitochondria. Proceedings of the National Academy of Sciences 2015; 112:10239-46. doi: 10.1073/pnas.1421392112.

[7] Miyagishima S Y, Wolk C P, Osteryoung K W. Identification of cyanobacterial cell division genes by comparative and mutational analyses. Mol Microbiol 2005; 56:126-43. doi:10.1111/j.1365-2958.2005.04548.x.

[8] Mazouni K, Domain F, Cassier-Chauvat C, Chauvat F. Molecular analysis of the key cytokinetic components of cyanobacteria: FtsZ, ZipN and MinCDE. Mol Microbiol 2004; 52:1145-58. doi:10.1111/j.1365-2958.2004.04042.x.
[9] Mezulis S, Yates C M, Wass M N, Sternberg M J E. Kelley L A. The Phyre2 web portal for protein modeling, prediction and analysis. Nature Protocols 2015; 10:845-58. doi:10.1038/nprot.2015-053.
[10] Ghosal D, Trambaiolo D, Amos L A, we J L O. MinCD cell division proteins form alternating copolymeric cytomotive filaments. Nature Communications 2014; 5:1-11. doi:10.1038/ncomms6341.
[11] King G F, Shih Y L, Maciejewski M W, Bains N P, Pan B, Rowland S L, et al. Structural basis for the topological specificity function of MinE. Nat Struct Biol 2000; 7:1013-7. doi:10.1038/80917.
[12] Drozdetskiy A, Cole C, Procter J, Barton G J. JPred4: a protein secondary structure prediction server. Nucleic Acids Res 2015; 43:W389-94. doi:10.1093/nar/gkv332.
[13] de Boer P A, Crossley R E, Rothfield L I. A division inhibitor and a topological specificity factor coded for by the minicells locus determine proper placement of the division septum in E. coli. Cell 1989; 56:641-9.
[14] Varley A W, Stewart G C. The divIVB region of the Bacillus subtilis chromosome encodes homologs of Escherichia coli septum placement (minCD) and cell shape (mreBCD) determinants. J Bacteriol 1992; 174: 6729-42.
[15] Marston A L, Thomaides H B, Edwards D H, Sharpe M E, Errington J. Polar localization of the MinD protein of Bacillus subtilis and its role in selection of the mid-cell division site. Genes Dev 1998; 12:3419-30. doi:10.1101/gad.12.21.3419.
[16] Marston A L, Errington J. Selection of the midcell division site in Bacillus subtilis through MinD-dependent polar localization and activation of MinC. Mol Microbiol 1999; 33:84-96.
[17] de Boer P A, Crossley R E, Rothfield L I. Central role for the Escherichia coli minC gene product in two different cell division-inhibition systems. Proc Natl Acad Sci USA 1990; 87:1129-33. doi:10.1073/pnas.87.3.1129.
[18] Raskin D M, de Boer P A. The MinE ring: an FtsZ-independent cell structure required for selection of the correct division site in E. coli. Cell 1997; 91:685-94.
[19] Edwards D H, Errington J. The Bacillus subtilis DivIVA protein targets to the division septum and controls the site specificity of cell division. Mol Microbiol 1997; 24:905-15.
[20] Oliva M A, Halbedel S, Freund S M, Dutow P, Leonard T A, Veprintsev D B, et al. Features critical for membrane binding revealed by DivIVA crystal structure. EMBO J 2010; 29:1988-2001. doi:10.1038/emboj.2010.99.
[21] Shaner N C, Lambert G G, Chammas A, Ni Y, Cranfill P J, Baird M A, et al. A bright monomeric green fluorescent protein derived from Branchiostoma lanceolatum. Nat Meth 2013; 10:407-9. doi:10.1038/nmeth.2413.
[22] Wu F, van Schie B G C, Keymer J E, Dekker C. Symmetry and scale orient Min protein patterns in shaped bacterial sculptures. Nature Nanotechnology 2015; 10:1-10. doi:10.1038/nnano.2015.126.
[23] Nakahira Y, Ogawa A, Asano H, Oyama T, Tozawa Y. Theophylline-dependent riboswitch as a novel genetic tool for strict regulation of protein expression in Cyanobacterium Synechococcus elongatus PCC 7942. Plant Cell Physiol 2013; 54:1724-35. doi:10.1093/pcp/pct115.
[24] Meinhardt H, de Boer P. Pattern formation in Escherichia coli: A model for the pole-to-pole oscillations of Min proteins and the localization of the division site. Proc Natl Acad Sci USA 2001; 98:14202-7. doi:10.1073/pnas.251216598.
[25] Loose M, Kruse K, Schwille P. Protein Self-Organization: Lessons from the Min System. Annu Rev Biophys 2011; 40:315-36. doi:10.1146/annurev-biophys-042910-155332.
[26] Hsieh C-W, Lin T-Y, Lai H-M, Lin C-C, Hsieh T-S, Shih Y-L. Direct MinE-membrane interaction contributes to the proper localization of MinDE in E. coli. Mol Microbiol 2010; 75:499-512. doi:10.1111/j.1365-2958.2009.07006.x.
[27] Nevo R, Charuvi D, Shimoni E, Schwarz R, Kaplan A, Ohad I, et al. Thylakoid membrane perforations and connectivity enable intracellular traffic in cyanobacteria. EMBO J 2007; 26:1467-73. doi:10.1038/sj.emboj.7601594.
[28] Varma A, Huang K C, Young K D. The Min system as a general cell geometry detection mechanism: branch lengths in Yshaped Escherichia coli cells affect Min oscillation patterns and division dynamics. J Bacteriol 2008:190:2106-17. doi:10.1128/JB.00720-07.
[29] Loose M, Fischer-Friedrich E, Ries J, Kruse K, Schwille P. Spatial regulators for bacterial cell division self-organize into surface waves in vitro. Science 2008; 320:789-92. doi:10.1126/science.1154413.
[30] Zieske K, Schwille P. Reconstitution of self-organizing protein gradients as spatial cues in cell-free systems. Elife 2014; 3. doi:10.7554/eLife.03949.
[31] Hoffmann M, Schwarz U S. Oscillations of Min-proteins in micropatterned environments: a three-dimensional particle-based stochastic simulation approach. Soft Matter 2014; 10:2388-96. doi:10.1039/c3sm52251b.
[32] Kerr R A, Levine H, Sejnowski T J, Rappel W-J. Division accuracy in a stochastic model of Min oscillations in Escherichia coli. Proc Natl Acad Sci USA 2006; 103:347-52. doi:10.1073/pnas.0505825102.
[33] Petrašek Z, Schwille P. Simple membrane-based model of the Min oscillator. New Journal of Physics 2015; 17:1-14. doi:10.1088/1367-2630/17/4/043023.
[34] Kruse K, Howard M, Margolin W. An experimentalist's guide to computational modelling of the Min system. Mol Microbiol 2007; 63:1279-84. doi:10.1111/j.1365-2958.2007.05607.x.
[35] Bonny M, Fischer-Friedrich E, Loose M, Schwille P, Kruse K. Membrane Binding of MinE Allows for a Comprehensive Description of Min-Protein Pattern Formation. PLoS Comput Biol 2013; 9:e1003347-12. doi: 10.1371/journal.pcbi.1003347.
[36] Fange D, Elf J. Noise-Induced Min Phenotypes in E. coli. PLoS Comput Biol 2006; 2:e80-12. doi:10.1371/journal.pcbi.0020080.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements:
1. A cyanobacterial population comprising cells with at least one expression cassette comprising a promoter operably linked to a nucleic acid segment encoding a MinC protein, MinD protein, MinE protein, Cdv3 (DivIVA), FtsZ or Ftn2 protein; or a combination of expression cassettes, each expression cassette comprising a promoter operably linked to a nucleic acid segment encoding a MinC protein, MinD protein, MinE protein, Cdv3 (DivIVA) protein, FtsZ protein, or Ftn2 protein.
2. The cyanobacterial population of statement 1, with a mean cell length that is at least 150%, or at least 200%, or at least 250%, or at least 300%, or at least 500%, or at least 750%, or at least 1000%, or at least 5000%, or at least 10000%, or at least 15000%, or at least 20000% greater than a wild type population of cyanobacteria of the same species.
3. The cyanobacterial population of statement 1, with a mean cell length that is at least 15%, or at least 20%, or at least 25%, or at least 30%, or at least 35%, or at least 40%, or at least 45%, or at least 50% less than the mean cell length of a wild type population of cyanobacteria of the same species.
4. The cyanobacterial population of any of statements 1-3, wherein each promoter is a constitutive promoter, inducible promoter, regulated promoter, cell specific promoter, or synthetic promoter.
5. The cyanobacterial population of any of statements 1-4, wherein the promoter is active before or during log phase growth of the cells in a culture or fermentation medium.
6. The cyanobacterial population of any of statements 1-4, wherein the promoter is active at the end, or after, log phase growth of the cells in a culture or fermentation medium.
7. The cyanobacterial population of any of statements 1-6, comprising increased expression of a MinC, MinD, MinE, Cdv3 (DivIVA), FtsZ, or Ftn2 protein relative to a wild type population of cyanobacteria of the same species.
8. The cyanobacterial population of any of statements 1-7, wherein the MinC, MinD, MinE, Cdv3 (DivIVA), FtsZ, or Ftn2 protein is expressed at levels that are at least 15%, or at least 20%, or at least 25%, or at least 30%, or at least 35%, or at least 40%, or at least 45%, or at least 50% more than a wild type population of cyanobacteria of the same species.
9. The cyanobacterial population of any of statements 1-8, wherein the MinC polypeptide has at least 70%, or at least 75%, or at least 80%, or at least 85%, or at least 90%, or at least 95%, or at least 97%, or at least 98%, or at least 99% sequence identity to any of SEQ ID NOs:4, 6-9, or 10.
10. The cyanobacterial population of any of statements 1-9, wherein the MinD polypeptide has at least 70%, or at least 75%, or at least 80%, or at least 85%, or at least 90%, or at least 95%, or at least 97%, or at least 98%, or at least 99% sequence identity to any of SEQ ID NOs:14, 15-18, or 19.
11. The cyanobacterial population of any of statements 1-10, wherein the MinE polypeptide has at least 70%, or at least 75%, or at least 80%, or at least 85%, or at least 90%, or at least 95%, or at least 97%, or at least 98%, or at least 99% sequence identity to any of SEQ ID NOs:23, 25-31, or 32.
12. The cyanobacterial population of any of statements 1-11, wherein the Cdv3 (DivIVA) polypeptide has at least 70%, or at least 75%, or at least 80%, or at least 85%, or at least 90%, or at least 95%, or at least 97%, or at least 98%, or at least 99% sequence identity to any of SEQ ID NOs:33, 35-38, or 39.
13. The cyanobacterial population of any of statements 1-12, wherein the Ftn2 polypeptide has at least 70%, or at least 75%, or at least 80%, or at least 85%, or at least 90%, or at least 95%, or at least 97%, or at least 98%, or at least 99% sequence identity to any of SEQ ID NO:45.
14. The cyanobacterial population of any of statements 1-13, wherein the FtsZ polypeptide has at least 70%, or at least 75%, or at least 80%, or at least 85%, or at least 90%, or at least 95%, or at least 97%, or at least 98%, or at least 99% sequence identity to any of SEQ ID NOs:40, 42, 43, or 44.
15. The cyanobacterial population of any of statements 1-13, wherein the population has a faster sedimentation rate than a wild type cyanobacterial population of the same population.
16. The cyanobacterial population of any of statements 1-15, wherein the extracellular or intracellular components expressed by the cells are more easily (cheaply) obtained from the population than from a wild type cyanobacterial population of the same population.
17. The cyanobacterial population of any of statements 1-16, wherein the population requires less sheer force for cell lysis than a wild type cyanobacterial population of the same population.
18. The cyanobacterial population of any of statements 1-17, wherein the population is more buoyant than a wild type cyanobacterial population of the same population.
19. The cyanobacterial population of any of statements 1-18, wherein mixing the population requires less energy than a wild type cyanobacterial population of the same population.
20. The cyanobacterial population of any of statements 1-19, wherein intracellular components expressed within the cells are more easily obtained from the population than from a wild type cyanobacterial population of the same population.
21. A cyanobacterial population comprising mutant cyanobacterial cells comprising a mutation in a MinC gene encoding a MinC polypeptide, a MinD gene encoding a MinD polypeptide, a MinE gene encoding a MinE polypeptide, cdv3 (divIVA) gene encoding a Cdv3 (DivIVA) polypeptide, a FtsZ gene encoding a FtsZ polypeptide, a Ftn2 gene encoding a Ftn2 polypeptide, or a combination thereof.
22. The cyanobacterial population of statement 21, wherein the mutant cyanobacterial cells comprise a MinC gene encoding a MinC polypeptide that has reduced MinC activity, a MinD gene encoding a MinD polypeptide that has reduced MinD activity, a MinE gene encoding a MinE polypeptide that has reduced MinE activity, a cdv3 gene encoding a Cdv3 polypeptide that has reduced Cdv3 activity, or a Ftn2 gene encoding a Ftn2 polypeptide has reduced Ftn2 activity or a FtsZ gene encoding a FtsZ polypeptide has reduced FtsZ activity.
23. The cyanobacterial population of statement 21 or 22, where the reduced MinC protein activity, reduced MinD protein activity, reduced MinE protein activity, reduced Cdv3 (DivIVA) protein activity, reduced Ftn2 activity, or reduced FtsZ activity is measured by less FtsZ polymerization than wild type cyanobacterial MinC protein activity, MinD protein activity, MinE protein activity, Cdv3 (DivIVA) protein activity, Ftn2 protein activity, or FtsZ protein activity of the same species.

24. The cyanobacterial population of any of statements 21-23, wherein the mutant cyanobacterial cells comprise a MinC gene encoding a MinC polypeptide that has less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:4, 6-9, or 10.

25. The cyanobacterial population of any of statements 21-24, wherein the mutant cyanobacterial cells comprise a MinD gene encoding a MinD polypeptide that has less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:14, 16-18, or 19.

26. The cyanobacterial population of any of statements 21-25, wherein the mutant cyanobacterial cells comprise a MinE gene encoding a MinE polypeptide that has less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:23, 25-31, or 32.

27. The cyanobacterial population of any of statements 21-26, wherein the mutant cyanobacterial cells comprise a cdv3 (divIVA) gene encoding a Cdv3 (DivIVA) polypeptide that has less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:33, 35-38, or 39.

28. The cyanobacterial population of any of statements 21-27, wherein the mutant cyanobacterial cells comprise a Ftn2 gene encoding a Ftn2 polypeptide that has less than 99%, or less than 98%, or less than 95%, or less than 90%, or less than 85%, or less than 75%, or less than 60%, or less than 50%, or less than 40%, or less than 30%, or less than 20% sequence identity to SEQ ID NO:45.

29. The cyanobacterial population of any of statements 21-28, wherein the mutant cyanobacterial cells comprise a FtsZ gene encoding a FtsZ polypeptide that has less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:40, 42, or 44.

30. The cyanobacterial population of any of statements 21-29, wherein the mutant cyanobacterial cells comprise a MinC, MinD, MinE, cdv3 (divIVA), Ftn2, or FtsZ gene comprising mutations in at least one conserved amino acid position, or at least two conserved amino acid positions, or at least three conserved amino acid positions, or at least five conserved amino acid positions, or at least seven conserved amino acid positions, or at least eight conserved amino acid positions, or at least ten conserved amino acid positions, or at least fifteen amino acid positions, or at least twenty conserved amino acid positions, or at least twenty-five amino acid positions.

31. The cyanobacterial population of any of statements 21-30, wherein the mutant cyanobacterial cells comprise a deletion or mutation in a conserved domain of a MinC, MinD, MinE, cdv3 (divIVA), Ftn2, or FtsZ gene, or a deletion or mutation in a combination of conserved domains in one or more of MinC, MinD, MinE, cdv3 (divIVA), Ftn2, and FtsZ genes.

32. The cyanobacterial population of any of statements 20-31, wherein the mutant cyanobacterial cells comprise a deletion or mutation in a MinC, MinD, MinE, cdv3 (divIVA), Ftn2, or FtsZ gene, or a combination of mutations or deletions in one or more MinC, MinD, MinE, cdv3 (divIVA), Ftn2, and FtsZ genes.

33. The cyanobacterial population of any of statements 21-32, wherein the mutant cyanobacterial cells comprise a deletion of an entire endogenous MinC, MinD, MinE, cdv3 (divIVA), or Ftn2 gene, or a combination MinC, MinD, MinE, cdv3 (divIVA), and Ftn2 genes.

34. The cyanobacterial population of any of statements 21-33, wherein the mutant cyanobacterial cells comprise a MinC gene or a MinD gene with a mutation of an operably linked MinCD promoter.

35. The cyanobacterial population of any of statements 21-34, wherein the mutant cyanobacterial cells comprise a MinC gene or a MinD gene with a deletion, insertion, or modification of an operably linked endogenous MinCD promoter.

36. The cyanobacterial population of any of statements 21-35, wherein the mutant cyanobacterial cells comprise a MinC gene or a MinD gene with a mutation of an operably linked endogenous MinCD promoter, where the mutant promoter has less than 99%, or less than 98%, or less than 95%, or less than 90%, or less than 85%, or less than 75%, or less than 60%, or less than 50%, or less than 40%, or less than 30%, or less than 20% sequence identity to SEQ ID NO:11 and/or 20.

37. The cyanobacterial population of any of statements 21-36, wherein the mutant cyanobacterial cells comprise a MinC gene, MinD gene, MinE gene, cdv3 (divIVA) gene, Ftn2 gene, or FtsZ gene with a deletion of at least one nucleotide of an operably linked endogenous promoter.

38. The cyanobacterial population of any of statements 21-37, with a mean cell length that is at least 10% smaller than a wild type population of cyanobacteria of the same species.

39. The cyanobacterial population of any of statements 21-38, with a mean cell length that is at least 15%, or at least 20%, or at least 25%, or at least 30%, or at least 35%, or at least 40%, or at least 45%, or at least 50% less than the mean cell length of a wild type population of cyanobacteria of the same species.

40. The cyanobacterial population of any of statements 21-39, with a mean cell length that is at least 150%, or at least 200%, or at least 250%, or at least 300%, or at least 500%, or at least 750%, or at least 1000%, or at least 5000%, or at least 10000%, or at least 15000%, or at least 20000% greater than a wild type population of cyanobacteria of the same species.

41. A targeting vector comprising two flanking segment, a first targeting segment that has at least 70%, or at least 75%, or at least 80%, or at least 85%, or at least 90%, or at least 95%, or at least 97%, or at least 98%, or at least 99% sequence identity to SEQ ID NO:12 and a second targeting segment that has at least 70%, or at least 75%, or at least 80%, or at least 85%, or at least 90%, or at least 95%, or at least 97%, or at least 98%, or at least 99% sequence identity to SEQ ID NO:13.

42. A targeting vector comprising two flanking segment, a first targeting segment that has at least 70%, or at least 75%, or at least 80%, or at least 85%, or at least 90%, or at least 95%, or at least 97%, or at least 98%, or at least 99% sequence identity to SEQ ID NO:21 and a second targeting segment that has at least 70%, or at least 75%, or at least 80%, or at least 85%, or at least 90%, or at least 95%, or at least 97%, or at least 98%, or at least 99% sequence identity to SEQ ID NO:22.

43. A method comprising (a) expressing a MinC, MinD, MinE, Cdv3 (DivIVA), FtsZ, or Ftn2 protein from a heterologous promoter, or a combination of two or more MinC, MinD, MinE, Cdv3 (DivIVA), FtsZ, or Ftn2 proteins from one or more heterologous promoter(s) in a cyanobacteria to generate a transformed cyanobacteria; and (b) establishing a cyanobacterial population comprising the transformed cyanobacteria.

44. The method of any statement 43, wherein each promoter is a constitutive promoter, inducible promoter, regulated promoter, cell specific promoter, or synthetic promoter.

45. The method of any statement 43 or 44, wherein one or more promoter is active before or during log phase growth of the cells in a culture or fermentation medium.

46. The method of any of statements 43-45, wherein the promoter is active at the end, or after, log phase growth of the cells in a culture or fermentation medium.

47. The method of any of statements 43-46, wherein the cyanobacterial population has a mean cell length of at least 10% larger than a wild type population of cyanobacteria of the same species.

48. The method of any of statements 43-47, where the population has a mean cell length that is at least 150%, or at least 200%, or at least 250%, or at least 300%, or at least 500%, or at least 750%, or at least 1000%, or at least 5000%, or at least 10000%, or at least 15000%, or at least 20000% greater than a wild type population of cyanobacteria of the same species.

49. The method of any of statements 43-48, where the population has a mean cell length that is at least 10% smaller than a wild type population of cyanobacteria of the same species.

50. The method of any of statements 43-46 or 49, where the population has a mean cell length that is at least 15%, or at least 20%, or at least 25%, or at least 30%, or at least 35%, or at least 40%, or at least 45%, or at least 50% less than the mean cell length of a wild type population of cyanobacteria of the same species.

51. A method comprising (a) deleting or mutating a genomic MinC site, a genomic MinD site, a genomic MinE site, a genomic cdv3 (divIVA) site, a genomic Ftn2 site, or a combination of one or more genomic MinC site, genomic MinD site, genomic MinE site, genomic cdv3 (divIVA) site, genomic Ftn2 site(s) in a cyanobacteria to generate a mutant cyanobacteria; (b) establishing a cyanobacterial population comprising the mutant cyanobacteria, wherein the cyanobacterial population has a mean cell length of at least 10% smaller than a wild type population of cyanobacteria of the same species.

52. A method comprising expressing a MinC, MinD, MinE, Cdv3 (DivIVA), FtsZ, or Ftn2 protein from a heterologous promoter, or a combination of two or more MinC, MinD, MinE, Cdv3 (DivIVA), FtsZ, or Ftn2 proteins from one or more heterologous promoter(s) in a cyanobacteria.

53. The method of statement 52, wherein the cyanobacteria is a population of cyanobacteria in culture medium or fermentation medium.

54. The method of statement 52 or 53, wherein each promoter is a constitutive promoter, inducible promoter, regulated promoter, cell specific promoter, or synthetic promoter.

55. The method of any of statements 52-54, wherein the promoter is active before or during log phase growth of the cells in a culture or fermentation medium.

56. The method of any of statements 52-55, wherein the promoter is active at the end, or after, log phase growth of the cells in a culture or fermentation medium.

57. The method of any of statements 52-55, wherein the cyanobacteria also produces an oil (e.g., one or more fatty acids), alkene, polyhydroxybutyrate, biomass, carbohydrate, phycocyanin, ethanol, hydrogen, isobutanol, ethylene, or a combination thereof.

58. The method of any of statements 52-57, further comprising harvesting the cyanobacteria.

59. The method of any of statements 52-58, further comprising isolating an oil (e.g., one or more fatty acids), alkene, polyhydroxybutyrate, biomass, carbohydrate, phycocyanin, ethanol, hydrogen, isobutanol, ethylene, or a combination thereof from the cyanobacteria.

60. The method of any of statements 52-59, where a native gene encoding a MinC, MinD, MinE, Cdv3 (DivIVA), FtsZ, or Ftn2 protein, or a combination of two or more native genes encoding a MinC, MinD, MinE, Cdv3 (DivIVA), FtsZ, or Ftn2 protein, in the cyanobacteria are mutated or deleted so that expression of the MinC, MinD, MinE, Cdv3 (DivIVA), FtsZ, and/or Ftn2 protein in the cyanobacteria is from the heterologous promoter.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential.

The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a promoter" includes a plurality of such nucleic acids or promoters (for example, a solution of nucleic acids or a series of promoters), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

What is claimed:

1. A cyanobacterial population comprising cells with at least one expression cassette comprising a heterologous promoter operably linked to a nucleic acid segment encoding a Cdv3 protein comprising at least 95% identity to SEQ ID NO:33 or a DivIVA protein comprising at least 95% identity to SEQ ID NO:100, and at least one expression cassette comprising a heterologous promoter operably linked to a nucleic acid segment encoding a FtsZ protein and a Ftn2 protein.

2. The cyanobacterial population of claim 1, wherein one or more of the heterologous promoters is a constitutive promoter, inducible promoter, regulated promoter, cell specific promoter, or synthetic promoter.

3. The cyanobacterial population of claim 1, wherein the promoter is active before or during log phase growth of the cells in a culture or fermentation medium.

4. The cyanobacterial population of claim 1, wherein the promoter is active at the end, or after, log phase growth of the cells in a culture or fermentation medium.

5. The cyanobacterial population of claim 1, wherein the promoter is heterologous, and not a native promoter that would express the MinC protein, MinD protein, MinE protein, FtsZ protein, or Ftn2 protein in a wild type cyanobacteria.

6. The cyanobacterial population of claim 1, with a mean cell length that is at least 150% greater than a wild type population of cyanobacteria of the same species.

7. The cyanobacterial population of claim 1, with a mean cell length that is at least 10% less than a wild type population of cyanobacteria of the same species.

8. A method comprising expressing a DivIVA protein comprising at least 95% identity to SEQ ID NO:100 or Cdv3 protein comprising at least 95% identity to SEQ ID NO:33 from a heterologous promoter, or a combination of the DivIVA and Cdv3 proteins from one or more heterologous promoter(s) in a cyanobacteria to thereby generate modified cyanobacteria with faster sedimentation rates than a wild type cyanobacteria.

9. The method of claim 8, wherein each promoter is a constitutive promoter, inducible promoter, regulated promoter, cell specific promoter, or synthetic promoter.

10. The method of claim 8, wherein the promoter is active before or during log phase growth of the cells in a culture or fermentation medium.

11. The method of claim 8, wherein the promoter is active at the end, or after, log phase growth of the cells in a culture or fermentation medium.

12. The method of claim 8, wherein the DivIVA or Cdv3 protein is expressed with a Ftn2 protein.

13. The method of claim 8, further comprising selecting at least one cyanobacteria that expresses at least one of the DivIVA protein or Cdv3 protein from the heterologous promoter(s) and culturing the at least one cyanobacteria to generate a cyanobacterial population.

14. The method of claim 13, wherein the cyanobacterial population has a mean cell length that is at least 150% greater than a wild type population of cyanobacteria of the same species.

15. The method of claim 13, wherein the cyanobacterial population synthesizes a product comprising oil, alkene, polyhydroxybutyrate, biomass, carbohydrate, phycocyanin, ethanol, hydrogen, isobutanol, ethylene, or a combination thereof.

16. The method of claim 13, further comprising harvesting the cyanobacteria.

17. The method of claim 13, further comprising isolating the oil, alkene, polyhydroxybutyrate, biomass, carbohydrate, phycocyanin, ethanol, hydrogen, isobutanol, ethylene, or a combination thereof from the cyanobacterial population.

18. The method of claim 14, wherein the mean cell length facilitates harvesting of the cyanobacterial population.

19. The method of claim 13, wherein less energy is needed for obtaining extracellular or intracellular components expressed by the cyanobacterial population than a wild type cyanobacterial population of the same population.

20. The method of claim 13, wherein the population requires less sheer force for cell lysis than a wild type cyanobacterial population of the same population.

21. The method of claim 13, wherein the population is more buoyant than a wild type cyanobacterial population of the same population.

22. The method of claim 13, wherein mixing the population requires less energy than a wild type cyanobacterial population of the same population.

\* \* \* \* \*

SEQUENCE LISTING

```
<160> NUMBER OF SEQ ID NOS: 112

<210> SEQ ID NO 1
<211> LENGTH: 36
<212> TYPE: PRT
<213> ORGANISM: B. subtilis

<400> SEQUENCE: 1

Met Pro Leu Thr Pro Asn Asp Ile His Asn Lys Thr Phe Thr Lys Ser
1               5                   10                  15

Phe Arg Gly Tyr Asp Glu Asp Glu Val Asn Glu Phe Leu Ala Gln Val
            20                  25                  30

Arg Lys Asp Tyr
        35

<210> SEQ ID NO 2
<211> LENGTH: 37
<212> TYPE: PRT
<213> ORGANISM: S. elongatus

<400> SEQUENCE: 2

Leu Asp Gly Thr Arg Val Pro Leu Ser Gly Arg Ile Leu Val Arg Glu
1               5                   10                  15

Asn Asp Leu Leu Asp Leu Leu Asp Asp Val Arg Ala Phe Leu Pro Ala
            20                  25                  30

Ala Ile Gln Gln Ala
        35

<210> SEQ ID NO 3

<400> SEQUENCE: 3

000

<210> SEQ ID NO 4
<211> LENGTH: 272
<212> TYPE: PRT
<213> ORGANISM: Synechococcus elongatus

<400> SEQUENCE: 4

Met Ser Asp Val Asp Ala Ser Thr Pro Ser Ala Glu Glu Ala Ile Ala
1               5                   10                  15

Pro Asp Ile Asp Ser Asp Ser Asp Ala Ala Val Glu Thr Pro Ala Ala
            20                  25                  30

Glu Pro Ala Ile Ala Pro Pro Ile Gln Leu Glu Ala Glu Gly Asp Arg
        35                  40                  45

Trp Trp Leu Arg Leu Pro Ser Ala Pro Pro Val Gly Gln Glu Ala Asn
    50                  55                  60

Ala Asp Gly Leu Thr Trp Leu Asp Leu Gln Gln Ser Leu Gln Gln Leu
65                  70                  75                  80
```

Leu Gln Gly Gln Glu Asn Phe Trp Asp Ala Gly Ala Glu Leu His Leu
                 85                  90                  95

Phe Ala Asp Ser Trp Leu Leu Asp Gly Arg Gln Leu Glu Trp Leu Ser
            100                 105                 110

Gln Gln Leu Ala Arg Val Asp Leu Lys Leu Thr Arg Ile Thr Thr Gln
        115                 120                 125

Arg Arg Gln Thr Ala Val Ala Ala Val Ser Leu Gly Leu Ser Ile Glu
    130                 135                 140

Gln Pro Ile Thr Gln Ala Asp Pro Trp Gln Lys Thr Ser Thr Ser
145                 150                 155                 160

Pro Ile Ala Ala Pro Leu Tyr Leu Lys Arg Thr Leu Arg Ser Gly Ala
                165                 170                 175

Glu Val Arg His Asn Gly Ser Val Ile Val Val Gly Asp Val Asn Pro
            180                 185                 190

Gly Ser Ser Ile Val Ala Ser Gly Asp Ile Leu Val Trp Gly Asn Leu
        195                 200                 205

Arg Gly Ile Ala His Ala Gly Ala Ala Gly Asn Ser Asp Ala Thr Ile
    210                 215                 220

Phe Ala Leu Ser Leu Ala Ala Thr Gln Leu Arg Ile Gly Asp Arg Leu
225                 230                 235                 240

Ala Arg Leu Pro Ser Ser Gln Ala Ala Gly Tyr Pro Glu Thr Ala Gln
                245                 250                 255

Val Ile Asp Gly Gln Ile Gln Ile Arg Arg Ala Asp Pro Gly Gly Lys
            260                 265                 270

<210> SEQ ID NO 5
<211> LENGTH: 819
<212> TYPE: DNA
<213> ORGANISM: Synechococcus elongatus

<400> SEQUENCE: 5

```
atgagtgacg tagacgcttc taccccctcg gcagaggagg cgatcgcacc tgacatcgac      60
agtgacagcg atgcggcagt tgagacacct gctgctgaac ccgcgatcgc accgccaatc     120
cagctcgaag cggagggcga tcgctggtgg ttgaggctgc aagtgcaccc ccggttggt      180
caagaagcca atgcggacgg cttgacttgg ctagatttgc aacagtcgct ccaacaattg     240
ctgcaaggtc aggaaaactt ctgggatgcg ggagctgagc tccacctctt tgccgatagt     300
tggctactgg atgggcgtca gttggaatgg ctaagccagc agctagcgcg ggttgacctg     360
aaattgacac ggatcacaac ccagcgccgg cagacggcag tggcagccgt gagccttggg     420
ctctcgattg aacagccaat cacccaggcc gatccttggc agcgcaagac ctcgaccagc     480
cccattgccg cgccgctcta cctcaaacgc accctgcgat cgggagctga ggtacgccat     540
aacggctcag tgattgtggt gggagatgtc aaccccggca gcagcattgt ggccagtggc     600
gacattcttg tttggggtaa cctgcggggc attgcccatg cgggggctgc cggtaattca     660
gacgcgacaa ttttttgccct gtcgctggcg gccacccaac tgcggattgg cgatcgtcta     720
gccagactgc ccagtagcca agcagccggc tatcccgaaa cggcccaagt gattgatggt     780
caaattcaga ttcgccgcgc cgatcctggc gggaagtag                             819
```

<210> SEQ ID NO 6
<211> LENGTH: 272
<212> TYPE: PRT
<213> ORGANISM: Synechococcus elongatus

<400> SEQUENCE: 6

Met Ser Asp Val Asp Ala Ser Thr Pro Ser Ala Glu Glu Ala Ile Ala
1               5                   10                  15

Pro Asp Ile Asp Ser Asp Ser Asp Ala Ala Val Glu Pro Ala Ala
            20                  25                  30

Glu Pro Ala Ile Ala Pro Pro Ile Gln Leu Glu Ala Glu Gly Asp Arg
                35                  40                  45

Trp Trp Leu Arg Leu Pro Ser Ala Pro Pro Val Gly Gln Glu Ala Asn
50                  55                  60

Ala Asp Gly Leu Thr Trp Leu Asp Leu Gln Gln Ser Leu Gln Gln Leu
65                  70                  75                  80

Leu Gln Gly Gln Glu Asn Phe Trp Asp Ala Gly Ala Glu Leu His Leu
                85                  90                  95

Phe Ala Asp Ser Trp Leu Leu Asp Gly Arg Gln Leu Glu Trp Leu Ser
                100                 105                 110

Gln Gln Leu Ala Arg Ala Asp Leu Lys Leu Thr Arg Ile Thr Thr Gln
                115                 120                 125

Arg Arg Gln Thr Ala Val Ala Ala Val Ser Leu Gly Leu Ser Ile Glu
130                 135                 140

Gln Pro Ile Thr Gln Ala Asp Pro Trp Gln Arg Lys Thr Ser Thr Ser
145                 150                 155                 160

Pro Ile Ala Ala Pro Leu Tyr Leu Lys Arg Thr Leu Arg Ser Gly Ala
                165                 170                 175

Glu Val Arg His Asn Gly Ser Val Ile Val Val Gly Asp Val Asn Pro
                180                 185                 190

Gly Ser Ser Ile Val Ala Ser Gly Asp Ile Leu Val Trp Gly Asn Leu
                195                 200                 205

Arg Gly Ile Ala His Ala Gly Ala Ala Gly Asn Ser Asp Ala Thr Ile
210                 215                 220

Phe Ala Leu Ser Leu Ala Ala Thr Gln Leu Arg Ile Gly Asp Arg Leu
225                 230                 235                 240

Ala Arg Leu Pro Ser Ser Gln Ala Ala Gly Tyr Pro Glu Thr Ala Gln
                245                 250                 255

Val Ile Asp Gly Gln Ile Gln Ile Arg Arg Ala Asp Pro Gly Gly Lys
                260                 265                 270

<210> SEQ ID NO 7
<211> LENGTH: 287
<212> TYPE: PRT
<213> ORGANISM: Leptolyngbya sp. NIES-3755

<400> SEQUENCE: 7

Met Thr Ser Asp Thr Ser Leu Ser Pro Leu Ser Asn Asp Pro Thr Pro
1               5                   10                  15

Ile Ser Pro Glu Ala Val Ser Ser Pro Asp Val Asp Ala Asp Leu Leu
                20                  25                  30

Asp Leu Pro Pro Leu Glu Thr Pro Glu Val Pro Lys Ile Ala Ile Glu
                35                  40                  45

Asp Leu Gln Val Arg Leu Lys Ala Lys Asp Gly Val Leu Ser Leu Ile
                50                  55                  60

Leu Pro Pro Glu Ser Glu Ala Ala Ser Lys Val Ala Leu Ala Trp Gly
65                  70                  75                  80

Glu Leu Trp Gln Gln Leu Lys Gln Leu Leu Met Gly Arg Glu Arg Gln
                85                  90                  95

Trp Gln Pro Asn Thr Ile Val His Leu Ile Ala Asp Asp Arg Leu Leu

```
            100                 105                 110
Asp Thr Arg Gln Leu Ser Ala Ile Ala Glu Ala Leu Thr Asp Val Gln
        115                 120                 125

Leu Gln Leu Lys Ser Val His Thr Arg Arg Gln Thr Ala Val Val
130                 135                 140

Ala Ala Thr Ala Gly Tyr Ser Val Glu Gln Ile Thr Ala Val Asp Pro
145                 150                 155                 160

Leu Ala Ala Lys Gln Glu Thr Ala Val Ala Met Glu Glu Pro Leu Tyr
                165                 170                 175

Ile Gln Met Thr Leu Arg Ser Gly Thr Glu Ile Arg His Asn Gly Thr
            180                 185                 190

Val Val Val Met Gly Asp Leu Asn Pro Gly Ser Thr Ile Ile Ala Glu
        195                 200                 205

Gly Asp Ile Leu Val Trp Gly Arg Leu Arg Gly Val Ala His Ala Gly
210                 215                 220

Cys Lys Gly Asn Val Lys Ser Leu Ile Met Ala Leu Gln Leu Glu Pro
225                 230                 235                 240

Thr Gln Ile Arg Ile Ala Asp Tyr Val Ala Arg Ala Pro Glu Thr Pro
                245                 250                 255

Pro Ala Gln Tyr Phe Pro Glu Val Ala Tyr Val Ser Pro Gln Gly Ser
            260                 265                 270

Ile Arg Ile Ala Arg Ala Thr Asp Phe Ser Met Arg Lys Asp Asp
        275                 280                 285

<210> SEQ ID NO 8
<211> LENGTH: 263
<212> TYPE: PRT
<213> ORGANISM: Gloeocapsa sp. PCC 7428

<400> SEQUENCE: 8

Met Thr Asp Ser Ala Pro Pro Glu Ile Glu Thr Thr Leu Thr Pro Pro
1               5                   10                  15

Thr Asn Ile Ala Asn Ser Asn Leu Gln Val Arg Leu Lys Gly Glu Gly
            20                  25                  30

Glu His Leu Leu Leu Ile Leu Pro Thr Glu Val Glu Ser Ser Ala Thr
        35                  40                  45

Ala Thr Thr Trp Ser Asp Leu Trp Gln Gln Leu Lys Gln Arg Leu Asn
    50                  55                  60

Gly Gly Asp Arg Phe Trp Gln Pro Asn Thr Ile Val His Leu Met Ala
65                  70                  75                  80

Thr Asp Arg Leu Leu Asp Thr Arg Gln Leu Gln Ala Ile Ala Asp Ala
                85                  90                  95

Leu Ser Glu Ala Gln Leu Gln Leu Thr His Val Phe Thr Ser Arg Arg
            100                 105                 110

Gln Thr Ala Val Ala Ala Ala Thr Ala Gly Tyr Ser Val Glu Gln Gln
        115                 120                 125

Ala Pro Ile Thr Gly Leu Asn Gln Thr Val Asn Ala Ala Pro Thr Pro
    130                 135                 140

Leu Ala Glu Pro Leu Tyr Leu Gln Met Thr Val Arg Ser Gly Ile Glu
145                 150                 155                 160

Ile Arg His Ala Gly Ser Val Ile Val Leu Gly Asp Leu Asn Pro Gly
                165                 170                 175

Gly Thr Val Val Ala Asn Gly Asp Ile Leu Val Trp Gly Arg Leu Arg
            180                 185                 190
```

```
Gly Val Ala His Ala Gly Ala Gly Asn Ser Lys Cys Leu Ile Met
            195                 200                 205

Ala Leu Gln Met Glu Pro Thr Gln Leu Arg Ile Ala Glu Phe Val Ala
210                 215                 220

Arg Ala Pro Thr Asn Ile Pro Ser Gln Phe Tyr Pro Glu Val Ala Tyr
225                 230                 235                 240

Val Thr Pro Glu Gly Ile Arg Ile Ala Lys Ala Ala Asp Phe Ser Lys
                245                 250                 255

Ser Gln Phe Ser Leu Pro Ser
            260

<210> SEQ ID NO 9
<211> LENGTH: 319
<212> TYPE: PRT
<213> ORGANISM: Leptolyngbya boryana

<400> SEQUENCE: 9

Met Thr Pro Asp Thr Ser Val Ser Pro Thr Pro Ile Asp Pro Leu Ser
1               5                   10                  15

Val Thr Ser Asp Ser Thr Leu Glu Lys Pro Leu Glu Ala Pro Thr Pro
                20                  25                  30

Ser Ser Asp Thr Pro Thr Ala Glu Asn Pro Lys Thr Asp Val Thr Ala
            35                  40                  45

Ser Ser Asp Ala His Ala Ser Ser Glu Ile Thr Asp Ser Ser Leu Ser
        50                  55                  60

Thr Ser Ser Glu Leu Ser Pro Gln Thr Val Ala Ile Ala Asp Leu Gln
65                  70                  75                  80

Val Arg Leu Lys Thr Lys Glu Gly Glu Leu His Leu Ile Leu Pro Pro
                85                  90                  95

Glu Ser Glu Asn Ser Lys Ile Ala Leu Ala Trp Val Glu Leu Trp Gln
            100                 105                 110

Gln Phe Lys Gln Leu Leu Met Gly Gln Glu Arg Phe Trp Gln Pro Asn
        115                 120                 125

Thr Pro Val His Leu Val Ser Asp Asp Arg Leu Leu Asp Thr Arg Gln
130                 135                 140

Ile Ser Ala Ile Ala Glu Ala Leu Ala Glu Val Gln Leu Gln Leu Lys
145                 150                 155                 160

Trp Val His Thr Arg Arg Gln Thr Ala Val Val Ala Ala Thr Ala
                165                 170                 175

Gly Tyr Ser Val Glu Gln Ile Thr Ala Ala Ser Pro Leu Leu Pro Asn
            180                 185                 190

Ser Glu Pro Ala Thr Ala Met Glu Asp Pro Leu Tyr Ile Gln Met Thr
        195                 200                 205

Leu Arg Ser Gly Ala Glu Ile Arg His Asn Gly Thr Val Val Val Val
210                 215                 220

Gly Asp Leu Asn Pro Gly Ser Ser Ile Ile Ala Glu Gly Asp Ile Leu
225                 230                 235                 240

Val Trp Gly Arg Leu Arg Gly Val Ala His Ala Gly Cys Lys Gly Asn
                245                 250                 255

Ala Lys Cys Leu Ile Met Ala Leu Gln Met Glu Pro Thr Gln Ile Arg
            260                 265                 270

Ile Ala Asp Tyr Val Ala Arg Ala Pro Glu Thr Pro Leu Ala Gln Tyr
        275                 280                 285

Phe Pro Glu Val Ala Tyr Val Ser Pro Gln Gly Ser Ile Arg Ile Ala
290                 295                 300
```

Arg Ala Ala Asp Phe Ala Ala Arg Lys Glu Glu Pro Asn Phe Ser
305                 310                 315

<210> SEQ ID NO 10
<211> LENGTH: 262
<212> TYPE: PRT
<213> ORGANISM: Leptolyngbya boryana

<400> SEQUENCE: 10

Met Thr Asp Ser Ser Leu Ser Thr Ser Ser Glu Leu Ser Pro Gln Thr
1               5                   10                  15

Val Ala Ile Ala Asp Leu Gln Val Arg Leu Lys Thr Lys Glu Gly Glu
            20                  25                  30

Leu His Leu Ile Leu Pro Pro Glu Ser Glu Asn Ser Lys Ile Ala Leu
        35                  40                  45

Ala Trp Val Glu Leu Trp Gln Gln Phe Lys Gln Leu Leu Met Gly Gln
    50                  55                  60

Glu Arg Phe Trp Gln Pro Asn Thr Pro Val His Leu Val Ser Asp Asp
65                  70                  75                  80

Arg Leu Leu Asp Thr Arg Gln Ile Ser Ala Ile Ala Glu Ala Leu Ala
                85                  90                  95

Glu Val Gln Leu Gln Leu Lys Trp Val His Thr Arg Arg Arg Gln Thr
            100                 105                 110

Ala Val Val Ala Ala Thr Ala Gly Tyr Ser Val Glu Gln Ile Thr Ala
        115                 120                 125

Ala Ser Pro Leu Leu Pro Asn Ser Glu Pro Ala Thr Ala Met Glu Asp
    130                 135                 140

Pro Leu Tyr Ile Gln Met Thr Leu Arg Ser Gly Ala Glu Ile Arg His
145                 150                 155                 160

Asn Gly Thr Val Val Val Gly Asp Leu Asn Pro Gly Ser Ser Ile
                165                 170                 175

Ile Ala Glu Gly Asp Ile Leu Val Trp Gly Arg Leu Arg Gly Val Ala
            180                 185                 190

His Ala Gly Cys Lys Gly Asn Ala Lys Cys Leu Ile Met Ala Leu Gln
        195                 200                 205

Met Glu Pro Thr Gln Ile Arg Ile Ala Asp Tyr Val Ala Arg Ala Pro
    210                 215                 220

Glu Thr Pro Leu Ala Gln Tyr Phe Pro Glu Val Ala Tyr Val Ser Pro
225                 230                 235                 240

Gln Gly Ser Ile Arg Ile Ala Arg Ala Ala Asp Phe Ala Ala Arg Lys
                245                 250                 255

Glu Glu Pro Asn Phe Ser
            260

<210> SEQ ID NO 11
<211> LENGTH: 56
<212> TYPE: DNA
<213> ORGANISM: Synechococcus elongatus

<400> SEQUENCE: 11
aaatattctg aaatgagctg ttgacaatta atcatccggc tcgtataatg tgtgga         56

<210> SEQ ID NO 12
<211> LENGTH: 1000
<212> TYPE: DNA
<213> ORGANISM: Synechococcus elongatus

```
<400> SEQUENCE: 12
agtctaggga tcagcattgg gaaaaaacct gaatggatag ggctcgtggg gttgagtgct      60
ctaagcagac tcataggggg tacgaaccca attcggtttt ggatgcatcg atcgctggca     120
attaatccga acgagttgcg gtgacagggg gttgcgatcg ccgacgaggc ttgggccgaa     180
aggggaccag cagttctgcc tcaacaatcc gcaactgacc gtaccgagtc acctcgcagt     240
caaactgcca ccaccctgga cgcagttgct caggtgcccc gcgcaattgc agtcgtttga     300
ttttccaggc tggcttgtcg atctgtccgg gtggcgcggc ctcattgcga ccaatccaga     360
cctgcacggc cccgttttga tccttccagc ttttgacaaa accgcagatc cgtacccgac     420
cagcttgtag atctgcggga gcctgatttt gccagccccg caaccaaaat tgcagatgct     480
tgtggcgttg cagcggccag ctgacccagt agtgaggggt ttgcatgagc tgctgcagct     540
gctggggatg gcgttgtagg gtcgcttgca ccaatccact cagcgctaca ttcaggctgt     600
gattgtccgt aatctgcaga gtggctgttt ctccctgttg gtcccaagcc aagctgcctt     660
ggaaacaagc aaccgcccga taggtgacgc tgtcgggctt cggggcagt tccgtgcggc     720 ggggtggctt gcggctggga cgcgatcgcg acgcagcagg gctagaacgg gtgatcggtc     780
gcgcagggcg tggacgacca ctcggcaaag gggatggggg aggcgtagcc atggatggca     840
ctgggcaagg gcgatcactg ttattctggc ggctcccgct cgacttgccc gtactcttta     900
atttgttttg ggctaaatat cgggccaagt ctgcttgggc agcggatctc tggatccatc     960
ccagcccaat tgctaacctg ctctctaccc cgtggttccg                          1000

<210> SEQ ID NO 13
<211> LENGTH: 1000
<212> TYPE: DNA
<213> ORGANISM: Synechococcus elongatus

<400> SEQUENCE: 13
gggcacatct tgagacgatc gcccgatgcg accgcttcgc ggagtgaacc ttcgactgaa      60
ccttagcgcc cgccaaaatg caaaactgac agagagcctg tcctgctctg tcctacttcc     120
gtttcaatac tgtttcacct gcaaaggtgc ttttcctagg ttggcagatg agcgatcgcc     180
cgcagccggc acccaccgtc ctgaaacgcc tgacccaatt ggcaacgcag gttcagcgac     240
gggccaagtt tgataatctc aacctgcgtg actctgactc agttccccaa ttgacggtct     300
gtcagggaga ccgccggcag tcttatccgc tgcttgggga ctattaccgc ctgggccgag     360
gccgtgactg tgacatcccg attgatagcc cgatcgtcag caagcttcac ctcagcctcg     420
gtcgctcggg caaagagcgc ggtgactttg tcctgcaaga cgaaaactcg accaacggcg     480
tcttttggcg gggccgccgt gtcgatcgct tggaattaca gcatggcgat cgcatctacc     540
tggggccacc agagctgacc gatcgcgttg agctgctcta tgaaaacgct cctcctctct     600
ggcaggactg gctgaaacga ggggtgacta tcactacagc tgtggtcgga gcgatcgcga     660
tcggcattac cctcgaggcc agccgagtct ccgtgcgatc gctggggacg gtgcaaggac     720
cgatcgctgc ctatgccgct gatggcgagc ccctacaaac tctgcgcagt agtagccacg     780
tcgaattacc ggccctctca gattttcgc ccgttctccc caaagccctg cttgcctccg      840
aagacagtcg cttctactgg catctgggta tcgatcccta cggcacggcg cgtgcgattc     900
tgactaactt ccgcagtggc gaagttcgcg aaggcgccag cacctcacc cagcagattg      960 ctcgcagcct atttagcgac tacgtcgggc gtgaggactc                          1000
```

```
<210> SEQ ID NO 14
<211> LENGTH: 268
<212> TYPE: PRT
<213> ORGANISM: Synechococcus elongatus

<400> SEQUENCE: 14
```

Met Ser Arg Val Ile Val Val Thr Ser Gly Lys Gly Val Gly Lys
1               5                   10                  15

Thr Thr Ser Ser Ala Asn Leu Gly Met Ala Leu Ala Gln Leu Gly Lys
            20                  25                  30

Arg Leu Val Leu Ile Asp Ala Asp Phe Gly Leu Arg Asn Leu Asp Leu
        35                  40                  45

Leu Leu Gly Leu Glu Asn Arg Ile Val Tyr Thr Ala Gln Asp Val Leu
    50                  55                  60

Ala Gly Asn Cys Arg Leu Glu Gln Ala Leu Val Lys Asp Lys Arg Gln
65                  70                  75                  80

Pro Asn Leu Cys Leu Leu Pro Ala Ala Asn Asn Arg Met Lys Glu Ser
                85                  90                  95

Val Thr Pro Gln Gln Met Glu Gln Leu Val Thr Leu Leu Asp Gly Gln
            100                 105                 110

Phe Asp Val Ile Leu Ile Asp Ser Pro Ala Gly Ile Glu Ala Gly Phe
        115                 120                 125

Gln Asn Ala Ile Ala Ala Ala Arg Glu Ala Val Ile Val Thr Thr Pro
    130                 135                 140

Glu Ile Ala Ala Val Arg Asp Ala Asp Arg Val Ile Gly Leu Leu Glu
145                 150                 155                 160

Ala His Gly Ile Thr Glu Ile Arg Leu Ile Leu Asn Arg Leu Arg Pro
                165                 170                 175

Ala Met Val Lys Ala Asn Asp Met Met Ser Val Glu Asp Val Gln Glu
            180                 185                 190

Ile Leu Ala Ile Pro Leu Val Gly Ile Ile Pro Asp Asp Glu Gln Val
        195                 200                 205

Ile Ile Ser Thr Asn Arg Gly Glu Pro Leu Val Leu Ala Glu Ala Pro
    210                 215                 220

Ser Leu Ala Ala Lys Ala Phe Ile Asn Val Ala Arg Arg Leu Ser Gly
225                 230                 235                 240

Glu Ser Ile Asp Phe Leu Asn Leu Glu Glu Pro Gln Ser Gly Val Leu
                245                 250                 255

Ser Lys Ile Arg Arg Ile Leu Asn Lys Lys Ile Leu
            260                 265

```
<210> SEQ ID NO 15
<211> LENGTH: 807
<212> TYPE: DNA
<213> ORGANISM: Synechococcus elongatus

<400> SEQUENCE: 15
```
atgagtcgcg ttattgttgt cacctccggt aagggaggcg tgggcaaaac cacctccagc        60
gccaacttgg gtatggcctt agcccagctg gtaaacgcc tcgtgctcat cgatgcggac       120
tttggcttgc gcaatctcga cctgctgctg gggctggaga tcggattgt ctacaccgct       180 caggatgttt tagcgggcaa ttgccgcctc gagcaagcat tggtcaaaga caagcgccaa       240
ccgaatctct gcctgctgcc tgcggccaac aaccgcatga aggagtcggt gaccccccag       300
cagatggagc agttggtgac gctgctcgat ggtcagttcg acgtgatctt gatcgactca       360
cccgctggaa ttgaagccgg attccagaat gcgatcgcgg ccgcccgcga agccgtaatt       420

```
gttacgacgc cggagattgc ggctgtccga gacgccgatc gcgttattgg attgctagaa      480
gcccatggca tcacagagat tcggctgatt ttgaaccggc tgcggccagc gatggtcaag      540
gccaacgaca tgatgagtgt cgaagatgtg caggaaatcc tcgcgatccc tcttgtcggc      600
atcattcccg atgacgagca ggtgattatt ccaccaacc gtggcgagcc gttggtccta       660
gccgaggcac cttccttggc ggccaaggca ttcatcaatg tggcgcggcg cctgagtggt      720
gaaagcatcg acttcctcaa tcttgaggaa cccccagagcg tgtgctcag taagattcgc      780 cgcatcctca ataaaaaaat tctctag                                          807
```

```
<210> SEQ ID NO 16
<211> LENGTH: 273
<212> TYPE: PRT
<213> ORGANISM: Oscillatoriales cyanobacterium

<400> SEQUENCE: 16

Met Ser Arg Val Ile Val Thr Ser Gly Lys Gly Val Gly Lys
 1               5                  10                  15

Thr Thr Thr Thr Ala Asn Leu Gly Met Ala Leu Ala Lys Arg Gly Arg
                20                  25                  30

Lys Val Ile Val Ile Asp Ala Asp Phe Gly Leu Arg Asn Leu Asp Leu
            35                  40                  45

Leu Leu Gly Leu Glu Asn Arg Val Val Tyr Thr Ala Val Asp Val Leu
        50                  55                  60

Ala Gly Gln Cys Arg Leu Glu Gln Ala Leu Val Lys Asp Lys Arg His
65                  70                  75                  80

Pro Asn Leu Met Leu Leu Pro Ala Ala Gln Asn Arg Thr Lys Asp Ala
                85                  90                  95

Val Lys Pro Asp Gln Met Lys Gln Leu Val Asn Ala Leu Ala Lys Ala
            100                 105                 110

Phe Asn Tyr Val Leu Val Asp Cys Pro Ala Gly Ile Glu Met Gly Phe
        115                 120                 125

Gln Asn Ala Ile Ala Ala Ala Lys Glu Ala Leu Ile Val Thr Thr Pro
    130                 135                 140

Glu Ile Ala Ala Val Arg Asp Ala Asp Arg Val Val Gly Leu Leu Glu
145                 150                 155                 160

Ala Asn Asn Ile Lys Gln Ile Arg Leu Ile Val Asn Arg Leu Arg Pro
                165                 170                 175

Ala Met Val Gln Ala Asn Asp Met Met Thr Val Glu Asp Val Gln Glu
            180                 185                 190

Ile Leu Ala Val Pro Leu Ile Gly Ile Val Pro Asp Asp Glu Arg Val
        195                 200                 205

Ile Val Ser Thr Asn Lys Gly Glu Pro Leu Val Leu Ala Glu Thr Pro
    210                 215                 220

Ser Leu Ala Gly Thr Ala Phe Asp Asn Ile Ala Arg Arg Leu Glu Gly
225                 230                 235                 240

Glu Ser Val Glu Phe Leu Asp Phe Thr Ala Pro Asn Asp Gly Phe Phe
                245                 250                 255

Ser Arg Leu Arg Arg Val Leu Thr Thr Pro Ile Gly Lys Lys Pro Ser
            260                 265                 270

Lys

<210> SEQ ID NO 17
<211> LENGTH: 268
```

<212> TYPE: PRT
<213> ORGANISM: Kamptonema

<400> SEQUENCE: 17

Met Ala Arg Ile Ile Val Val Thr Ser Gly Lys Gly Val Gly Lys
1               5                   10                  15

Thr Thr Ser Thr Ala Asn Leu Gly Met Ala Leu Ala Lys Leu Gly Arg
            20                  25                  30

Ser Val Ala Val Val Asp Ala Asp Phe Gly Leu Arg Asn Leu Asp Leu
        35                  40                  45

Leu Leu Gly Leu Glu Asn Arg Ile Val Tyr Thr Ala Val Glu Val Ile
    50                  55                  60

Ala Gly Glu Cys Arg Leu Glu Gln Ala Leu Val Lys Asp Lys Arg Gln
65                  70                  75                  80

Pro Asn Leu Val Leu Leu Pro Ala Ala Gln Asn Arg Met Lys Asp Ala
                85                  90                  95

Val Ser Ala Glu Gln Met Lys Gln Leu Val Asn Val Leu Ala Glu Lys
            100                 105                 110

Tyr Asp Tyr Ile Leu Ile Asp Ser Pro Ala Gly Ile Glu Gln Gly Phe
        115                 120                 125

Gln Asn Ala Ile Ala Ala Gln Glu Gly Val Ile Val Thr Thr Pro
    130                 135                 140

Glu Ile Ala Ala Val Arg Asp Ala Asp Arg Val Val Gly Leu Leu Glu
145                 150                 155                 160

Ala His Asn Val Lys Arg Ile His Leu Ile Val Asn Arg Ile Arg Pro
                165                 170                 175

Leu Met Val Gln Ala Asn Asp Met Met Ser Val Gln Asp Val Arg Glu
            180                 185                 190

Ile Leu Ala Ile Pro Leu Leu Gly Val Val Pro Asp Asp Glu Arg Val
        195                 200                 205

Ile Val Ser Thr Asn Arg Gly Glu Pro Leu Val Leu Ser Glu Thr Pro
    210                 215                 220

Ser Leu Ala Gly Thr Ala Tyr Glu Asn Ile Ala Arg Arg Leu Glu Gly
225                 230                 235                 240

Glu Lys Val Glu Phe Leu Glu Leu Asn Pro Pro Gln Asp Asn Phe Phe
                245                 250                 255

Thr Arg Leu Arg Arg Leu Leu Thr Ala Lys Ile Met
            260                 265

<210> SEQ ID NO 18
<211> LENGTH: 268
<212> TYPE: PRT
<213> ORGANISM: Geitlerinema sp. PCC 7407

<400> SEQUENCE: 18

Met Ser Arg Val Ile Val Val Thr Ser Gly Lys Gly Val Gly Lys
1               5                   10                  15

Thr Thr Cys Thr Ala Asn Leu Gly Met Ala Leu Ala Gln Gln Gly Arg
            20                  25                  30

Arg Val Ile Val Val Asp Ala Asp Phe Gly Leu Arg Asn Leu Asp Leu
        35                  40                  45

Leu Leu Gly Leu Glu Asn Arg Ile Val Tyr Thr Ala Leu Glu Val Leu
    50                  55                  60

Ala Gly Glu Cys Arg Leu Glu Gln Ala Ile Val Lys Asp Lys Arg Gln
65                  70                  75                  80

```
Asn Arg Leu Ala Leu Leu Pro Ala Ala Gln Asn Arg Thr Lys Asp Ala
                85                  90                  95

Val Arg Pro Glu Gln Met Lys Gln Leu Ile Ala Ala Leu Thr Gly Lys
            100                 105                 110

Tyr Asp Tyr Ile Leu Val Asp Cys Pro Ala Gly Ile Glu Met Gly Phe
        115                 120                 125

Gln Asn Ala Ile Val Ala Ala Arg Glu Ala Leu Val Val Thr Thr Pro
130                 135                 140

Glu Ile Ser Ala Val Arg Asp Ala Asp Arg Val Val Gly Leu Leu Glu
145                 150                 155                 160

Ala Gln Gly Ile Lys Gln Met Arg Leu Ile Ile Asn Arg Ile Arg Pro
                165                 170                 175

Asn Met Val Gln Val Asn Asp Met Met Ser Val Glu Asp Val Gln Glu
            180                 185                 190

Ile Leu Ala Ile Pro Leu Ile Gly Val Ile Pro Asp Asp Glu Arg Val
        195                 200                 205

Ile Val Ser Thr Asn Arg Gly Glu Pro Leu Val Leu Ser Glu Thr Pro
210                 215                 220

Ser Met Ala Gly Thr Ala Phe Glu Asn Val Ala Arg Arg Leu Glu Gly
225                 230                 235                 240

Gln Lys Val Glu Phe Leu Asp Leu Asn Gly Pro Gly Asp Ser Phe Phe
                245                 250                 255

Ser Arg Ile Lys Arg Leu Leu Ser Thr Lys Ile Leu
            260                 265

<210> SEQ ID NO 19
<211> LENGTH: 268
<212> TYPE: PRT
<213> ORGANISM: Planktothricoides sp. SR001

<400> SEQUENCE: 19

Met Ser Arg Ile Ile Val Ile Thr Ser Gly Lys Gly Gly Val Gly Lys
1               5                   10                  15

Thr Thr Ser Thr Ala Asn Leu Gly Met Ala Leu Ala Lys Arg Gly Arg
            20                  25                  30

Lys Val Ala Leu Ile Asp Ala Asp Phe Gly Leu Arg Asn Leu Asp Leu
        35                  40                  45

Leu Leu Gly Leu Glu Asn Arg Ile Val Tyr Thr Ala Val Glu Val Ile
    50                  55                  60

Ala Gly Gln Cys Arg Leu Glu Gln Ala Leu Val Lys Asp Lys Arg Gln
65                  70                  75                  80

```
Ile Leu Ala Ile Pro Leu Ile Gly Val Ile Pro Asp Asp Glu Arg Val
        195                 200                 205

Ile Val Ser Thr Asn Arg Gly Glu Pro Leu Val Leu Gly Glu Glu Gln
        210                 215                 220

Thr Leu Ala Gly Lys Ala Phe Asp Asn Ile Ala Arg Arg Leu Glu Gly
225                 230                 235                 240

Glu Lys Val Glu Leu Leu Asp Leu Ser Leu Pro Ser Asp Asn Phe Phe
                245                 250                 255

Ser Arg Ile Arg Lys Leu Phe Phe Thr Lys Ile Met
            260                 265
```

```
<210> SEQ ID NO 20
<211> LENGTH: 56
<212> TYPE: DNA
<213> ORGANISM: Synechococcus elongatus

<400> SEQUENCE: 20
aaatattctg aaatgagctg ttgacaatta atcatccggc tcgtataatg tgtgga      56

<210> SEQ ID NO 21
<211> LENGTH: 1000
<212> TYPE: DNA
<213> ORGANISM: Synechococcus elongatus

<400> SEQUENCE: 21
ggcgggcttg gcttctgtc agtcctacct gagctgccgc cggatccatc tctaaaactt    60 gctgcgggc tagagctgat tgctgacgcg gccaaccgaa cagaccgtgt tgcgcgatcg   120
cacggacttc tgccggactg agattggctg cgatcgcccg actccccggc agcagcggca   180
gcggatcagg ttgaaataa ttgagactca gctcgcagga atccgtctga cgagttgact    240
gctccagcag atggatgccc tcagcctgac attgagcttg cagccgttga caatcgtag    300 gctcccaact cgaccagatt gcaggcgttg ccaagccgac atcccaacca tgacgggtca   360
gggcttgggc aactccaatc gcgattgtgc gatcgccagt aaccgtcaca gattgcggtt   420
gtggatcggg ggtcagtaag tcccagagcg gcgttgcttc tgcccctgtc ggttgagcct   480
gccagatctg ccgcgcctcc agtcggcgat cgctacagtc caccacccga cgcgatcgtg   540
tcgctttcca gtgactggca acaatatcaa ttccctgttg ctgcagagcg atcgggcctt   600
gcagtagctc aaggcgttcg tagagagcct gccctgaggc cagtgcttct gggacagaag   660
tggacttcaa caagcaacgc atcaacaggc gatcgcgatc gatcgcgccc caactctctg   720
gcagatagat caaggccaca cgagcctgcc agcgccgtgc ctgttgtgcc agcgcgatcg   780
ctgccggtgt cgcccccaga atcagtaagt tatagtccgc tgtcattcaa gttgggagtg   840
aaagccccgc tgcattgtct ttccatcgtc aggcagaaca gccctgtcat gaagggtgaa   900
tatagaaagc ctttggcagt ctaggggggat ttgacgacac ggtttaagat gagtcagcga   960
ttgccggctg agcgatcgcc gctcctgctc ttcggaccct                       1000

<210> SEQ ID NO 22
<211> LENGTH: 1000
<212> TYPE: DNA
<213> ORGANISM: Synechococcus elongatus

<400> SEQUENCE: 22
taattactgc cttgccggtg tagctcaggg gtagagcagc tgttttgtaa acagccggtc    60
gcaggttcga atccggtcac cggctctgag ctcaaaccca gtcttcttgt tggaggctgg   120
```

```
gttttttgttt gtcgtagctg actagacgtt ccctgccgta accacggatt gctgactgaa      180
tcaagccgct tcagagatgt catccgtgcg agtcagtgtc agggcgtaac ggtagagcgc      240
gatcggacga tcgccaactt gaaagtagct ggggtcctgc ggcgtcagat agatggcggt      300
aatttgatcc gccgtaatca aattgggcga tcgcagctgg tagcgagctg tggtttctac      360
gctgttgaac tgagggcgac cctgaccccg aaaaatctgg cggctcagtt cgctagcaat      420
gaaaacgaag tcgtgggct gttcccaggc tcggcctgtc atccgcatta gcagactatc      480
gccattcacc aactggacga gttgttgatt gggatcagga gctttgacgg tggcaacagc      540
ctccccaaga taggcgcggg cgatcgcaag gccattaaaa gcgcgatcgg cgacgacggg      600
ggctgcttga ggccgtaaat ctggtagcgg ttttgcagcg gcagcgtagg tcggggtgcc      660
aaagcgcaca ggaaactcca gcggttgatc cagccagcgg cgattgctgt caaagcctgg      720
tgtgatgatt tccggcgcga ggggtgcttg taaatccacc aaggtgctgg tgacttgcca      780
cgttcctgcc atccaatcgg ggtagggcag atccggtgca ttggttttta gggatggtga      840
gcttgaccaa gccggatacg acgcaacgcg atcgctcaag gttgccgcct gtgctggtgt      900
gatcacagtc agccaacagc cgagggcaat cgctccgatt aacagcgatc gcagtaaccc      960
aacaggaaca cacgcacga caaatcagcc agagatccgc                           1000
```

<210> SEQ ID NO 23
<211> LENGTH: 91
<212> TYPE: PRT
<213> ORGANISM: Synechococcus elongatus

<400> SEQUENCE: 23

```
Met Leu Ala Asp Leu Phe Glu Arg Leu Phe Pro Arg Gln Gln Ala Ser
1               5                   10                  15

Arg Asp Thr Val Lys Gln Arg Leu Lys Leu Val Leu Ala His Asp Arg
            20                  25                  30

Ala Asp Leu Ser Pro Glu Leu Leu Gln Lys Met Arg Gln Glu Ile Leu
        35                  40                  45

Glu Val Val Ser Arg Tyr Val Glu Leu Asp Ser Glu Gly Met Glu Leu
    50                  55                  60

Ser Leu Glu Asn Asp Gln Arg Val Thr Ala Leu Val Ala Asn Leu Pro
65                  70                  75                  80

Ile Arg Arg Val Lys Pro Ala Thr Ala Glu Gly
                85                  90
```

<210> SEQ ID NO 24
<211> LENGTH: 276
<212> TYPE: DNA
<213> ORGANISM: Synechococcus elongatus

<400> SEQUENCE: 24

```
atgctggctg acttattcga gcgcttgttc ccccggcaac aggccagtcg agacaccgtg       60
aagcagcgcc ttaagcttgt gctggctcac gatcgtgctg acctcagccc tgagctgttg      120
caaaagatgc gccaagagat tttagaagtg gtctctcgct acgttgagct ggactctgag      180
ggaatggaac tctcgctaga aaatgaccag cgagtcacag cacttgtcgc caatttaccg      240
attcgtcgtg tcaaacccgc aactgctgaa ggatga                               276
```

<210> SEQ ID NO 25
<211> LENGTH: 104
<212> TYPE: PRT

<213> ORGANISM: Synechococcus sp. PCC 6312

<400> SEQUENCE: 25

Met Ile Thr Asp Leu Leu Glu Arg Ile Phe Pro Arg Gln Gln Thr Ser
1               5                   10                  15

Arg Gln Gln Val Lys Gln Arg Leu Lys Leu Val Leu Ala His Asp Arg
            20                  25                  30

Cys Asp Leu Asn Pro Glu Ile Leu Glu His Leu Arg Gln Asp Ile Leu
        35                  40                  45

Glu Val Val Ser Arg Tyr Val Glu Leu Asp Leu Asp Ala Leu Asp Phe
    50                  55                  60

Ser Leu Glu Ser Asp Gln Arg Thr Thr Ala Leu Ile Ala Asn Leu Pro
65                  70                  75                  80

Ile Arg Arg Val Lys Leu Pro Thr Pro Thr Glu Glu Ser Pro Val Pro
                85                  90                  95

Met Gln Pro Asp Gly Leu Glu Leu
            100

<210> SEQ ID NO 26
<211> LENGTH: 90
<212> TYPE: PRT
<213> ORGANISM: Leptolyngbya sp. O-77

<400> SEQUENCE: 26

Met Leu Ser Glu Leu Leu Asp Arg Leu Phe Pro Arg Gln Pro Glu Val
1               5                   10                  15

Ser Ser Arg Glu Thr Val Lys Gln Arg Leu Gln Leu Val Leu Ala His
            20                  25                  30

Asp Arg Thr Asp Leu Pro Pro Ala Thr Ile Glu Lys Met Arg Gln Glu
        35                  40                  45

Ile Leu Glu Val Val Ser Arg Tyr Val Glu Ile Asp Gln Glu Gly Thr
    50                  55                  60

Glu Phe Met Leu Glu Asn Asn Gln Arg Ala Thr Ala Leu Ile Ala Asn
65                  70                  75                  80

Leu Pro Ile Arg Arg Ile Lys Ser Asp Val
                85                  90

<210> SEQ ID NO 27
<211> LENGTH: 103
<212> TYPE: PRT
<213> ORGANISM: Lyngbya aestuarii

<400> SEQUENCE: 27

Met Lys Leu Asn Glu Leu Leu Glu Arg Leu Phe Pro Arg Ser Thr Asn
1               5                   10                  15

Ser Arg Glu Asp Val Lys Arg Arg Leu Lys Leu Val Leu Ala His Asp
            20                  25                  30

Arg Ala Asp Leu Thr Pro Glu Leu Ile Glu Ala Met Arg Gln Glu Ile
        35                  40                  45

Leu Glu Val Leu Ser Arg Tyr Val Glu Ile Asp Thr Glu Asp Ser Glu
    50                  55                  60

Phe Gly Leu Glu Ser Asp Gln Arg Ala Thr Ala Leu Ile Ala Asn Leu
65                  70                  75                  80

Pro Ile Arg Arg Val Lys Asn Thr Pro Asp Val Asn Gln Thr Ser Pro
                85                  90                  95

Thr Ser Pro Asp Ala Pro Leu
            100

-continued

<210> SEQ ID NO 28
<211> LENGTH: 99
<212> TYPE: PRT
<213> ORGANISM: Calothrix sp. PCC 7103

<400> SEQUENCE: 28

Met Ile Leu Glu Phe Ile Glu Arg Leu Phe Ser Arg Ser Asn Asp Thr
1               5                   10                  15

Ser Arg Ser Glu Val Lys Arg Arg Leu Gln Leu Val Ile Ala His Asp
            20                  25                  30

Arg Ala Asp Leu Ser Pro Gln Met Ile Glu Lys Met Arg Gln Glu Ile
        35                  40                  45

Leu Glu Ile Val Cys Arg Tyr Val Glu Val Glu Thr Glu Gly Leu Glu
    50                  55                  60

Phe Ser Leu Glu Ser Asn Gln Arg Thr Thr Ala Leu Ile Ala Asn Leu
65                  70                  75                  80

Pro Ile Arg Arg Val Lys Glu Ser Thr Ser Glu Glu Glu Ala Asn Ser
                85                  90                  95

Glu Lys Val

<210> SEQ ID NO 29
<211> LENGTH: 129
<212> TYPE: PRT
<213> ORGANISM: Leptolyngbya sp. Heron Island J

<400> SEQUENCE: 29

Met Ile Ser Asp Phe Phe Glu Arg Leu Phe Gly Ser Arg Glu Pro Val
1               5                   10                  15

Ser Arg Asp Thr Ala Lys Gln Arg Leu Arg Phe Val Leu Ala His Asp
            20                  25                  30

Arg Ser Asp Ile Ser Pro Gln Asn Leu Glu Lys Leu Arg Gln Glu Ile
        35                  40                  45

Leu Glu Val Val Ser Arg Tyr Val Glu Leu Asp Phe Asp Gly Leu Glu
    50                  55                  60

Phe Ser Leu Glu Ser Asp Gln Arg Met Thr Ala Leu Met Ala Asn Leu
65                  70                  75                  80

Pro Ile Arg Arg Val Arg Ser Asn Pro Leu Glu Pro Asp Ser Pro Val
                85                  90                  95

Glu Glu Thr Glu Ala Lys Asn Leu Gly Leu Thr Asp Glu Ser Ile Ala
            100                 105                 110

Leu Asp Asp Glu Val Glu Glu Val Ser Glu Thr Ala Asp Ile Pro Leu
        115                 120                 125

Asp

<210> SEQ ID NO 30
<211> LENGTH: 91
<212> TYPE: PRT
<213> ORGANISM: Scytonema millei

<400> SEQUENCE: 30

Met Phe Ser Asp Leu Phe Asp Lys Ile Phe Ser Ser Asn Pro Asn Asp
1               5                   10                  15

Asn Asn Ser Arg Ser Gln Val Lys Gln Arg Leu Gln Leu Val Ile Ser
            20                  25                  30

His Asp Arg Ser Asp Leu Ser Pro Gln Thr Ile Glu Lys Met Arg Arg
        35                  40                  45

```
Glu Ile Leu Glu Val Val Gly Arg Tyr Val Glu Leu Asp Val Glu Gly
             50                  55                  60

Met Glu Phe Ser Leu Glu Asn Asn Gln Arg Ala Thr Ala Leu Ile Ala
 65                  70                  75                  80

Asn Leu Pro Ile Arg Arg Val Lys Thr Asp Glu
                 85                  90

<210> SEQ ID NO 31
<211> LENGTH: 105
<212> TYPE: PRT
<213> ORGANISM: Microcoleus sp. PCC 7113

<400> SEQUENCE: 31

Met Ile Ser Asp Leu Leu Glu Arg Leu Phe Pro Trp Thr Ser Ala Ser
 1               5                  10                  15

Asn Ser Arg Ala Glu Val Lys Arg Arg Leu Gln Leu Val Ile Ala His
                 20                  25                  30

Asp Arg Ala Asp Leu Thr Pro Gln Met Ile Glu Lys Met Arg Asn Glu
             35                  40                  45

Ile Leu Glu Val Val Ser Arg Tyr Val Glu Ile Glu Thr Glu Gly Leu
         50                  55                  60

Glu Ile Ala Leu Glu Ser Asn Gln Arg Val Thr Ala Leu Ile Ala Asn
 65                  70                  75                  80

Leu Pro Ile Arg Arg Val Lys Glu Glu Ala Pro Val Ala Ser Gly Gly
                 85                  90                  95

Val Glu Pro Gly Ile Asp Leu Ile Gly
            100                 105

<210> SEQ ID NO 32
<211> LENGTH: 197
<212> TYPE: PRT
<213> ORGANISM: Synechococcus elongatus PCC 7942

<400> SEQUENCE: 32

Met Thr Gln Ala Gln Ser Leu Asp Val Leu Asn Leu Leu Glu Gln Leu
 1               5                  10                  15

Glu Glu Ser Val Leu Asp Gly Thr Arg Val Pro Leu Ser Gly Arg Ile
                 20                  25                  30

Leu Val Arg Glu Asn Asp Leu Leu Asp Leu Leu Asp Asp Val Arg Ala
             35                  40                  45

Gly Leu Pro Ala Ala Ile Gln Gln Ala Gln Gln Ile Leu Glu Arg Gln
         50                  55                  60

Ala Gln Ile Leu Ala Asp Ala Gln Gln Ala Gln Ala Ile Val Ala
 65                  70                  75                  80

Gln Ala Gln Gln Glu Arg Ala Leu Leu Ile Asp Gln Asn Ser Ile Arg
                 85                  90                  95

Leu Gln Ala Glu Arg Asp Ala Ser Ser Ser Ala Lys Pro Phe Asn Arg
                100                 105                 110

Asn Val Met Pro Phe Gly Asn Arg Arg Ser Arg Lys Gln His Lys Cys
             115                 120                 125

Gly Ala Arg Pro Asn Ser Ser Ser Lys Ser Ala Arg Lys Pro Thr
         130                 135                 140

Val Phe Ala Ser Arg Pro Lys Pro Lys Ser Ser Ser Cys Ala Ala Lys
145                 150                 155                 160

Leu Asn Ser Ser Tyr Leu Ser Ser Ala Lys Gly Phe Trp Ser Asn Val
                165                 170                 175
```

Arg Ser Cys Gly Gly Val Leu Thr Ala Met Leu Thr Lys Phe Cys Gly
                180                 185                 190

Thr Trp Ser Ser Asp
        195

<210> SEQ ID NO 33
<211> LENGTH: 228
<212> TYPE: PRT
<213> ORGANISM: Synechococcus elongatus

<400> SEQUENCE: 33

Met Thr Gln Ala Gln Ser Leu Asp Val Leu Asn Leu Leu Glu Gln Leu
1               5                   10                  15

Glu Glu Ser Val Leu Asp Gly Thr Arg Val Pro Leu Ser Gly Arg Ile
            20                  25                  30

Leu Val Arg Glu Asn Asp Leu Leu Asp Leu Leu Asp Asp Val Arg Ala
        35                  40                  45

Gly Leu Pro Ala Ala Ile Gln Gln Ala Gln Ile Leu Glu Arg Gln
    50                  55                  60

Ala Gln Ile Leu Ala Asp Ala Gln Gln Gln Ala Gln Ala Ile Val Ala
65                  70                  75                  80

Gln Ala Gln Gln Glu Arg Ala Leu Leu Ile Asp Gln Asn Ser Ile Arg
                85                  90                  95

Leu Gln Ala Glu Arg Asp Ala Gln Gln Leu Arg Gln Thr Leu Gln Gln
            100                 105                 110

Glu Cys Asp Ala Leu Arg Gln Gln Ala Ile Ala Glu Ala Thr Gln Val
        115                 120                 125

Arg Gly Glu Ala Gln Gln Phe Gln Leu Gln Val Arg Gln Glu Thr Asp
    130                 135                 140

Ser Leu Arg Gln Gln Thr Gln Ala Glu Ile Glu Gln Leu Arg Ser Gln
145                 150                 155                 160

Thr Gln Gln Gln Leu Ser Glu Gln Arg Gln Arg Ile Leu Val Glu Cys
                165                 170                 175

Glu Glu Leu Arg Arg Gly Ala Asp Ser Tyr Ala Asp Gln Val Leu Arg
            180                 185                 190

Asp Met Glu Gln Arg Leu Thr Gln Met Met Gln Ile Ile Arg Asn Gly
        195                 200                 205

Arg Gln Ala Leu Asn Leu Ser Glu Asn Thr Pro Pro Ala Pro Arg
    210                 215                 220

Arg Arg Ser Arg
225

<210> SEQ ID NO 34
<211> LENGTH: 687
<212> TYPE: DNA
<213> ORGANISM: Synechococcus elongatus

<400> SEQUENCE: 34
gtgacccaag cccaatcact cgatgtcttg aacttgctag agcagctcga agagtctgtg      60
ctcgacggga ctcgcgtgcc gctttcgggg cgcattctgg ttcgagaaaa cgacctgctc     120
gacctgttag atgacgtgcg tgccgggttg cccgctgcga ttcaacaagc tcagcaaatc     180
ctcgagcgcc aagcccaaat tttggctgac gcccaacagc aagcacaggc gatcgtggcg     240
caggcgcagc aagaacgggc cctgctgatt gaccaaaaca gtattcggct tcaagctgag     300
cgcgatgcgc agcagctccg ccaaacccct caacaggaat gtgatgccct tcggcaacag     360

```
gcgatcgcgg aagcaacaca agtgcggggc gaggcccaac agttccagct ccaagtccgc    420
caggaaaccg acagtcttcg ccagcagacc caagccgaaa tcgagcagct gcgcagccaa    480
actcaacagc agctatctga gcagcgccaa aggatttttgg tcgaatgtga ggagttgcgg    540
cggggtgctg acagctatgc tgaccaagtt ctgcgggaca tggagcagcg attgacccag    600
atgatgcaga tcatccgcaa tggtcgtcag gccctgaact tgagcgaaaa tacgccgccc    660
cctgctcccc gtcggcgatc gcgctaa                                        687

<210> SEQ ID NO 35
<211> LENGTH: 295
<212> TYPE: PRT
<213> ORGANISM: Leptolyngbya sp. Heron Island J

<400> SEQUENCE: 35
```

Met Val Arg Gln Glu Pro Pro Ile Asn Asp Pro Arg Leu Ile Asn Asp
1               5                   10                  15

Pro Arg Leu Asn Gly Gln Val Asp Val Leu Ala Gln Gln Ile
            20                  25                  30

Gly Asn Val Thr Pro Gly Pro Val Ala Gly Phe Asp Ile Gln Asp Ala
        35                  40                  45

Leu Asn Gln Ile Glu Glu Ala Val Leu Asp Ser Pro Arg Leu Pro Val
    50                  55                  60

Met Gly Arg Thr Met Ile Asn Glu Asp Asp Leu Leu Asp Gln Leu Asp
65                  70                  75                  80

Ala Val Arg Leu Asn Leu Pro Gly Ala Phe Gln Glu Ala Gln Gln Leu
                85                  90                  95

Leu Glu Gln Arg Asp Asp Ile Leu Ser Glu Ala Glu Arg Tyr Ala Gln
            100                 105                 110

Asp Ile Val Thr Thr Ala Glu Lys Gln Ala Ala Ile Leu Asn Glu
        115                 120                 125

Thr Thr Ile Leu Arg Gln Ala Glu Gln Gln Ala Gln Gln Leu Arg Leu
    130                 135                 140

Gln Val Glu Gln Glu Cys Ala Ala Leu Arg Ser Gln Thr Met Met Glu
145                 150                 155                 160

Ile Glu Gln Leu Gln Ala Gln Thr Asn Gln Glu Cys Asp Glu Met Arg
                165                 170                 175

Lys Ser Ala Ile Thr Glu Cys His Ala Ile Gln Thr Asp Ala Asp Thr
            180                 185                 190

Tyr Ala Asp Gln Val Leu Gln Arg Met Glu Thr Gln Phe Ser Glu Met
        195                 200                 205

Leu Asp Val Ile Ser Asn Gly Arg Gln Gln Leu Tyr Glu Arg Gln Gln
    210                 215                 220

Arg Ala Arg Gln Thr Ala Pro Thr Pro Pro Ser Ser Ala Ser Ser Gly
225                 230                 235                 240

Asp Val Pro Val Ala Pro Leu Ser Arg Arg Pro Ile Ser Gln Arg Pro
                245                 250                 255

Pro Gly Gln Gln Ser Tyr Ile Gln Pro Pro Ser Thr Pro Pro Ser
            260                 265                 270

Arg Pro Gln Gln Gln Pro Pro Arg Gln Gln Pro Arg Pro Gln
        275                 280                 285

Gln Arg Pro Pro Arg Lys Phe
    290                 295

<210> SEQ ID NO 36
<211> LENGTH: 308
<212> TYPE: PRT
<213> ORGANISM: Leptolyngbya sp. PCC 7375

<400> SEQUENCE: 36

Met Val Arg Gln Glu Pro Pro Leu Asn Asp Pro Arg Leu Val Asn Asp
1               5                   10                  15

Pro Arg Leu Val Asn Asp Pro Arg Leu Asn Gly Gln Ala Ala Gln Val
            20                  25                  30

Asp Asp Val Leu Ala Gln Gln Gln Ile Gly Lys Ala Gly Pro Ala Pro
        35                  40                  45

Met Ala Gly Phe Asp Ile Gln Asp Ala Leu Asn Gln Ile Glu Glu Ser
    50                  55                  60

Val Leu Asp Ser Pro Arg Leu Pro Val Met Gly Arg Thr Met Ile Asn
65                  70                  75                  80

Glu Asp Asp Leu Leu Asp Gln Leu Asp Ala Val Arg Leu Asn Leu Pro
                85                  90                  95

Ser Ala Phe Gln Glu Ala Gln Gln Leu Val Glu Gln Arg Asp Asp Ile
            100                 105                 110

Leu Asn Glu Ala Glu Arg Tyr Ala Gln Asn Ile Val Thr Ala Ala Glu
        115                 120                 125

Lys Gln Ala Ala Thr Ile Leu Asn Glu Thr Ser Ile Leu Arg Gln Ala
    130                 135                 140

Glu Gln Gln Ala Gln Gln Leu Arg Leu Gln Val Gln Glu Cys Ala
145                 150                 155                 160

Ala Leu Arg Ser Gln Thr Met Leu Glu Ile Glu Gln Leu Gln Thr Gln
                165                 170                 175

Thr Lys Gln Glu Cys Glu Asp Leu Arg Gln Asn Ala Ile Ala Glu Cys
            180                 185                 190

His Ala Ile Gln Thr Asp Ala Asp Thr Tyr Ala Asp Gln Val Leu Gln
        195                 200                 205

Arg Met Glu Thr Gln Phe Ser Glu Met Leu Gly Val Ile Ser Asn Gly
    210                 215                 220

Arg Gln Gln Leu Tyr Glu Arg Gln Arg Ala Arg Gln Thr Ala Pro
225                 230                 235                 240

Pro Ser Met Pro Ala Ala Ser Asp Val Val Ala Pro Asn Pro Leu
                245                 250                 255

Asn Arg Cys Pro Ala Thr Gln Arg Pro Ser Ser Thr Gln Gln Ser Tyr
            260                 265                 270

Ile Gln Pro Pro Gln Gln Gln Pro Thr Arg Ser Pro Gln Gln Gln
        275                 280                 285

Pro Pro Thr Arg Pro Pro Gln Gln Pro Pro Arg Pro Gln Gln Arg Pro
    290                 295                 300

Pro Arg Lys Phe
305

<210> SEQ ID NO 37
<211> LENGTH: 226
<212> TYPE: PRT
<213> ORGANISM: Neosynechococcus sphagnicola

<400> SEQUENCE: 37

Met Gln His Pro Ala Glu Ala Leu Asp Val Gln Arg Glu Leu Asn Lys
1               5                   10                  15

Leu Glu Glu Met Ile Leu Asp Ser Pro Arg Leu Pro Phe Ser Gly Arg

```
                20                  25                  30
Thr Leu Val Asp Glu Glu His Ile Leu Asp Gln Val Asp Leu Ile Arg
            35                  40                  45
Leu Ser Leu Pro Ala Ala Phe His Glu Ala Glu Met Val Arg Arg
        50                  55                  60
Lys Asp Glu Leu Leu Ser Gln Ala Glu His Tyr Ala Gln Glu Arg Ile
65                  70                  75                  80
Asp Gln Ala Glu Arg Gln Ala Ala Gln Ile Leu Asp Glu Ile Gly Ile
                85                  90                  95
Ile Gln Gln Ala Glu Gln Glu Ala Arg Gln Ile Arg Gln Arg Val Gln
            100                 105                 110
Gln Glu Cys Glu Ala Ala Gln Thr His Thr Met Ala Glu Ile Glu Arg
        115                 120                 125
Met His Arg Gln Ala Gln Gln Glu Leu Glu Glu Met Arg Arg Leu Ala
            130                 135                 140
Ile Ser Glu Cys His Asp Ile Gln His Glu Ala Asp Val Tyr Ala Asp
145                 150                 155                 160
Arg Val Leu Lys Ser Met Glu Gln Gln Leu Gly Glu Met Met Arg Val
                165                 170                 175
Ile Arg Asn Gly Arg Gln Leu Gln Pro Glu Pro Pro Ser Arg
            180                 185                 190
Arg Glu Gln Arg Glu Asp Gly Thr Thr Thr Asn Pro Gly Arg Pro Thr
            195                 200                 205
Pro Pro Ala Val His Thr Gln Thr Gln Thr Arg Met Pro Glu Arg Ile
        210                 215                 220
Lys Gly
225

<210> SEQ ID NO 38
<211> LENGTH: 214
<212> TYPE: PRT
<213> ORGANISM: Planktothrix

<400> SEQUENCE: 38

Met Leu Arg Gln Glu Ser Thr Pro Arg Leu Pro Glu Gln Asn Gly
1               5                   10                  15
Leu Arg Val Glu Pro Glu Thr Thr Val Ser Asn Ser Pro Gly Ile Asp
            20                  25                  30
Ile Gln Arg Glu Leu Asn Arg Leu Glu Glu Met Ile Leu Asp Ser Pro
            35                  40                  45
Arg Ile Pro Leu Thr Arg Arg Thr Leu Val Asp Glu Glu Gln Leu Leu
        50                  55                  60
Asp Gln Leu Asp Leu Ile Arg Leu Asn Leu Pro Ser Ala Phe Gln Glu
65                  70                  75                  80
Ser Asp Ile Ile Val Arg His Lys Asp Glu Ile Leu Gln Glu Ala Glu
                85                  90                  95
Glu Tyr Ala Gln Glu Ile Val Thr Met Ala Glu Gln Arg Ala Ala Arg
            100                 105                 110
Ile Leu Asn Glu Met Gly Leu Ile Gln Gln Ala Lys Ser Glu Ala Asp
        115                 120                 125
Gln Leu Arg Gln Gln Val Gln Asn Glu Cys Asp Thr Leu Gln Gln Gln
            130                 135                 140
Thr Leu Ser Glu Ile Glu Gln Ile Arg Tyr Arg Leu Gln Gln Glu Leu
145                 150                 155                 160
```

```
Glu Glu Met Arg Ser Arg Thr Met Ala Glu Cys Glu Glu Ile Gln Asn
            165                 170                 175

Gly Ala Asp Asp Tyr Ala Asp His Val Leu Gly Ser Ile Glu Gln Gln
        180                 185                 190

Leu Asn Glu Met Met Arg Val Ile Arg Asn Gly Arg Gln Gln Val Gln
    195                 200                 205

Gly Asn Asn Pro Thr Arg
    210

<210> SEQ ID NO 39
<211> LENGTH: 238
<212> TYPE: PRT
<213> ORGANISM: Geitlerinema sp. PCC 7105

<400> SEQUENCE: 39

Met Leu Arg Gln Asp Ser Ala Gly Ile Asp Pro Lys Ser Asp Ser Pro
1               5                   10                  15

Gln Pro Gln Gly Glu Pro Ala Gly Thr Val Ala Pro Glu Gln Arg Gln
            20                  25                  30

Glu Gly Ala Asn Gln Gly Ser Val Asn Val Gln Gln Ala Leu Asn Arg
        35                  40                  45

Leu Glu Glu Ala Ile Leu Asp Ser Pro Arg Ile Pro Phe Thr Gly Arg
    50                  55                  60

Thr Leu Val Asp Glu Glu Pro Leu Leu Asp Ile Leu Asp Ala Ile Arg
65                  70                  75                  80

Leu Asn Leu Pro Ala Ala Phe Gln Glu Ala Glu Val Ile Arg Gln
                85                  90                  95

Lys Asp Glu Ile Leu Arg Gln Ala Glu Gln Tyr Gly Arg Glu Ile Val
            100                 105                 110

Asp Ala Ala Glu Gln Gln Ala Ala Ser Ile Leu Asp Glu Met Gly Leu
        115                 120                 125

Val Arg Gln Ala Lys Val Glu Ala Asp Arg Leu Arg Gln Gln Val Gln
    130                 135                 140

Ala Asp Cys Glu Val Ala Arg Glu Arg Ala Ile Ser Glu Ile Glu Gln
145                 150                 155                 160

Met Gln Arg Gln Ala Gln Glu Leu Glu Glu Val Arg Ala Arg Ala
            165                 170                 175

Leu Ala Glu Ala Glu Gln Ile Glu Ala Gly Ala Asp Glu Tyr Ala Asp
        180                 185                 190

Arg Val Leu Arg Asn Ile Glu Gln Gln Leu Ser Asp Met Met Arg Val
    195                 200                 205

Ile Arg Asn Gly Arg Gln Gln Leu Gln Gln Glu Val Ala Tyr Arg Ala
    210                 215                 220

His Gln Lys Glu Pro Lys Val Asn Pro Asn Val Arg Arg Tyr
225                 230                 235

<210> SEQ ID NO 40
<211> LENGTH: 393
<212> TYPE: PRT
<213> ORGANISM: Synechococcus elongatus

<400> SEQUENCE: 40

Met Thr Asp Pro Met Pro Ile Asn Asn Ser Tyr Gly Phe Asn Arg Asp
1               5                   10                  15

Gly Ser Leu Ser Gly Phe Asp Ala Leu Gly Gln Pro Glu Glu Leu Ile
            20                  25                  30
```

```
Ile Pro Ser Ser Val Ala Arg Ile Lys Val Ile Gly Val Gly Gly Gly
            35                  40                  45
Gly Ser Asn Gly Val Asn Arg Met Ile Ser Ser Asp Val Ser Gly Val
 50                  55                  60
Glu Phe Trp Ala Leu Asn Thr Asp Ala Gln Ala Leu Leu His Ser Ala
 65                  70                  75                  80
Ala Pro Lys Arg Met Gln Leu Gly Gln Lys Leu Thr Arg Gly Leu Gly
                 85                  90                  95
Ala Gly Gly Asn Pro Ala Ile Gly Met Lys Ala Ala Glu Glu Ser Arg
                100                 105                 110
Glu Glu Leu Ile Ala Ala Leu Glu Gly Ala Asp Leu Val Phe Ile Thr
            115                 120                 125
Ala Gly Met Gly Gly Gly Thr Gly Thr Gly Ala Ala Pro Ile Val Ala
130                 135                 140
Glu Val Ala Lys Glu Val Gly Ala Leu Thr Val Gly Ile Val Thr Lys
145                 150                 155                 160
Pro Phe Thr Phe Glu Gly Arg Arg Arg Met Lys Gln Ala Glu Glu Gly
                165                 170                 175
Thr Ala Ala Leu Gln Ser Ser Val Asp Thr Leu Ile Thr Ile Pro Asn
                180                 185                 190
Asp Arg Leu Leu His Ala Ile Ser Glu Gln Thr Pro Ile Gln Glu Ala
            195                 200                 205
Phe Arg Val Ala Asp Asp Ile Leu Arg Gln Gly Val Gln Gly Ile Ser
            210                 215                 220
Asp Ile Ile Thr Ile Pro Gly Leu Val Asn Val Asp Phe Ala Asp Val
225                 230                 235                 240
Arg Ala Val Met Ala Asp Ala Gly Ser Ala Leu Met Gly Ile Gly Ser
                245                 250                 255
Gly Ser Gly Lys Ser Arg Ala Arg Glu Ala Ala His Ala Ala Ile Ser
                260                 265                 270
Ser Pro Leu Leu Glu Ser Ser Ile Glu Gly Ala Arg Gly Val Val Phe
            275                 280                 285
Asn Ile Thr Gly Gly Arg Asp Met Thr Leu His Glu Val Asn Ala Ala
290                 295                 300
Ala Asp Ala Ile Tyr Glu Val Val Asp Pro Glu Ala Asn Ile Ile Phe
305                 310                 315                 320
Gly Ala Val Ile Asp Asp Arg Leu Glu Gly Glu Leu Arg Ile Thr Val
                325                 330                 335
Ile Ala Thr Gly Phe Ser Thr Asp Arg Pro Asn Leu Asn Thr Ile Ser
                340                 345                 350
Thr Ser Thr Ser Gln Pro Thr Ser Gln Pro Ser Val Ser Pro Asn Pro
            355                 360                 365
Ala Ser Ala Pro Pro Ala Ser Gly Gly Leu Asp Ile Pro Ala Phe
            370                 375                 380
Leu Gln Arg Lys Ile Gln Asn Arg Pro
385                 390

<210> SEQ ID NO 41
<211> LENGTH: 1182
<212> TYPE: DNA
<213> ORGANISM: Synechococcus elongatus

<400> SEQUENCE: 41
atgaccgacc ctatgccgat caacaattcc tatggcttca accgtgacgg ctctctgtcg      60
```

```
gggttcgatg cactagggca gccagaagaa ctaatcatcc ccagcagcgt tgcccgcatc    120
aaagtaattg gcgttggcgg tggcggcagc aacggggtca accgcatgat tagcagcgat    180
gtcagcgggg ttgaattttg ggccctcaac actgatgctc aagctttgct ccactctgca    240
gcccccaagc ggatgcagtt gggacagaaa ctaacgcgag gctaggcgc aggtggcaac    300 cctgcgatcg gcatgaaagc cgctgaagaa tcgcgggaag aactaatcgc cgccttggaa    360
ggggctgacc tcgtctttat cacggcgggg atgggcggtg gaaccggcac tggagctgcc    420
ccgatcgtgg cagaagtcgc caaagaagtg ggtgcgctga cggttgggat tgtcaccaaa    480
cccttcacct tcgaagggcg tcgccgaatg aagcaggcgg aagaaggaac agccgcactg    540
caaagctcag tcgacacttt tgatcactat tcctaatgacc gcctactcca cgccatatct    600
gagcagacgc cgattcaaga agctttccgg gtcgccgacg atattctccg gcagggtgtg    660
caagggattt ctgacatcat cacgatccca ggtctggtca acgtcgactt tgccgacgtt    720
cgcgccgtca tggccgatgc tggatcagcc ctgatgggca tcggtagcgg ctctggcaag    780
tcccgcgctc gggaagccgc tcatgcagcc attagctcac cgctgctgga gtcttcgatc    840 gaagggcgc gcggcgttgt cttcaacatc acaggcggcc gcgatatgac cctgcatgag    900
gtcaacgcag cagcggatgc gatttacgaa gtcgtcgatc ctgaagccaa tatcattttc    960
ggcgccgtga ttgacgatcg attggaagga gagctgcgga tcaccgtgat cgccacgggc   1020
ttcagcaccg atcgccccaa cctcaacacg atttccacca gcacgtccca gccgaccagc   1080
caacccagcg tgagtcccaa cccagctagt gccccaccgg cgagcggcgg cggcctcgac   1140
attccggcct tcctacaacg gaaaattcaa aaccgaccct ag                      1182
```

<210> SEQ ID NO 42
<211> LENGTH: 383
<212> TYPE: PRT
<213> ORGANISM: Escherichia coli

<400> SEQUENCE: 42

```
Met Phe Glu Pro Met Glu Leu Thr Asn Asp Ala Val Ile Lys Val Ile
1               5                   10                  15

Gly Val Gly Gly Gly Gly Gly Asn Ala Val Glu His Met Val Arg Glu
            20                  25                  30

Arg Ile Glu Gly Val Glu Phe Phe Ala Val Asn Thr Asp Ala Gln Ala
        35                  40                  45

Leu Arg Lys Thr Ala Val Gly Gln Thr Ile Gln Ile Gly Ser Gly Ile
    50                  55                  60

Thr Lys Gly Leu Gly Ala Gly Ala Asn Pro Glu Val Gly Arg Asn Ala
65                  70                  75                  80

Ala Asp Glu Asp Arg Asp Ala Leu Arg Ala Ala Leu Glu Gly Ala Asp
                85                  90                  95

Met Val Phe Ile Ala Ala Gly Met Gly Gly Gly Thr Gly Thr Gly Ala
            100                 105                 110

Ala Pro Val Val Ala Glu Val Ala Lys Asp Leu Gly Ile Leu Thr Val
        115                 120                 125

Ala Val Val Thr Lys Pro Phe Asn Phe Glu Gly Lys Lys Arg Met Ala
    130                 135                 140

Phe Ala Glu Gln Gly Ile Thr Glu Leu Ser Lys His Val Asp Ser Leu
145                 150                 155                 160

Ile Thr Ile Pro Asn Asp Lys Leu Leu Lys Val Leu Gly Arg Gly Ile
                165                 170                 175
```

Ser Leu Leu Asp Ala Phe Gly Ala Ala Asn Asp Val Leu Lys Gly Ala
            180                 185                 190

Val Gln Gly Ile Ala Glu Leu Ile Thr Arg Pro Gly Leu Met Asn Val
        195                 200                 205

Asp Phe Ala Asp Val Arg Thr Val Met Ser Glu Met Gly Tyr Ala Met
    210                 215                 220

Met Gly Ser Gly Val Ala Ser Gly Glu Asp Arg Ala Glu Glu Ala Ala
225                 230                 235                 240

Glu Met Ala Ile Ser Ser Pro Leu Leu Glu Ile Asp Leu Ser Gly
                245                 250                 255

Ala Arg Gly Val Leu Val Asn Ile Thr Ala Gly Phe Asp Leu Arg Leu
            260                 265                 270

Asp Glu Phe Glu Thr Val Gly Asn Thr Ile Arg Ala Phe Ala Ser Asp
        275                 280                 285

Asn Ala Thr Val Val Ile Gly Thr Ser Leu Asp Pro Asp Met Asn Asp
    290                 295                 300

Glu Leu Arg Val Thr Val Ala Thr Gly Ile Gly Met Asp Lys Arg
305                 310                 315                 320

Pro Glu Ile Thr Leu Val Thr Asn Lys Gln Val Gln Gln Pro Val Met
                325                 330                 335

Asp Arg Tyr Gln Gln His Gly Met Ala Pro Leu Thr Gln Glu Gln Lys
            340                 345                 350

Pro Val Ala Lys Val Val Asn Asp Asn Ala Pro Gln Thr Ala Lys Glu
        355                 360                 365

Pro Asp Tyr Leu Asp Ile Pro Ala Phe Leu Arg Lys Gln Ala Asp
    370                 375                 380

<210> SEQ ID NO 43
<211> LENGTH: 1152
<212> TYPE: DNA
<213> ORGANISM: Escherichia coli

<400> SEQUENCE: 43

| | | |
|---|---|---|
| atgtttgaac caatggaact taccaatgac gcggtgatta aagtcatcgg cgtcggcggc | 60 |
| ggcggcggta atgctgttga acacatggtg cgcgagcgca ttgaaggtgt tgaattcttc | 120 |
| gcggtaaaata ccgatgcaca agcgctgcgt aaaacagcgg ttggacagac gattcaaatc | 180 |
| ggtagcggta tcaccaaagg actgggcgct ggcgctaatc cagaagttgg ccgcaatgcg | 240 |
| gctgatgagg atcgcgatgc attgcgtgcg gcgctggaag gtgcagacat ggtctttatt | 300 |
| gctgcgggta tgggtggtgg taccggtaca ggtgcagcac cagtcgtcgc tgaagtggca | 360 |
| aaagatttgg gtatcctgac cgttgctgtc gtcactaagc ctttcaactt gaaggcaag | 420 |
| aagcgtatgg cattcgcgga gcaggggatc actgaactgt ccaagcatgt ggactctctg | 480 |
| atcactatcc cgaacgacaa actgctgaaa gttctgggcc gcggtatctc cctgctggat | 540 |
| gcgtttggcg cagcgaacga tgtactgaaa ggcgctgtgc aaggtatcgc tgaactgatt | 600 |
| actcgtccgg gtttgatgaa cgtggacttt gcagacgtac gcaccgtaat gtctgagatg | 660 |
| ggctacgcaa tgatgggttc tggcgtggcg agcggtgaag accgtgcgga agaagctgct | 720 |
| gaaatggcta tctcttctcc gctgctgaa gatatcgacc tgtctggcgc gcgcggcgtg | 780 |
| ctggttaaca tcacggcggg cttcgacctg cgtctggatg agttcgaaac ggtaggtaac | 840 |
| accatccgtg catttgcttc cgacaacgcg actgtggtta tcggtacttc tcttgacccg | 900 |
| gatatgaatg acgagctgcg cgtaaccgtt gttgcgacag gtatcggcat ggacaaacgt | 960 |

```
cctgaaatca ctctggtgac caataagcag gttcagcagc cagtgatgga tcgctaccag    1020
cagcatggga tggctccgct gacccaggag cagaagccgg ttgctaaagt cgtgaatgac    1080
aatgcgccgc aaactgcgaa agagccggat tatctggata tcccagcatt cctgcgtaag    1140
caagctgatt aa                                                        1152
```

<210> SEQ ID NO 44
<211> LENGTH: 434
<212> TYPE: PRT
<213> ORGANISM: Planktothricoides sp. SR001

<400> SEQUENCE: 44

```
Met Thr Leu Asn Asn Ser Leu Gly Pro Val His Glu Ser Pro His Ala
1               5                   10                  15

Gln Glu Thr Thr Ser Leu Pro Pro Ala Asn Ala Glu Asn Ser Asn Pro
            20                  25                  30

Phe Asn Asn Val Gly Leu Tyr Gly Gly Gln Asn Leu Asp Pro Ile Trp
        35                  40                  45

Arg Glu Lys Thr Pro Pro Lys Glu Glu Pro Arg Ser Arg Glu Ile Val
    50                  55                  60

Pro Ser Ser Ile Ala Arg Ile Lys Val Ile Gly Val Gly Gly Gly Gly
65                  70                  75                  80

Cys Asn Ala Val Asn Arg Met Ile Ala Ser Glu Val Ser Gly Val Glu
                85                  90                  95

Phe Trp Gly Ile Asn Thr Asp Ala Gln Ala Leu Thr Gln Ala Asn Ala
            100                 105                 110

Pro Lys Arg Leu Gln Ile Gly Gln Lys Leu Thr Arg Gly Leu Gly Ala
        115                 120                 125

Gly Gly Asn Pro Ala Ile Gly Gln Lys Ala Ala Glu Glu Ser Arg Asp
    130                 135                 140

Glu Ile Ala Ala Ala Leu Asp Gly Ser Asp Leu Val Phe Ile Thr Ala
145                 150                 155                 160

Gly Met Gly Gly Gly Thr Gly Thr Gly Ala Ala Pro Ile Val Ala Glu
                165                 170                 175

Ala Ala Lys Glu Val Gly Ala Leu Thr Val Gly Val Val Thr Arg Pro
            180                 185                 190

Phe Asn Phe Glu Gly Arg Arg Arg Thr Ser Gln Ala Glu Glu Gly Ile
        195                 200                 205

Ala Ala Leu Gln Gly Arg Val Asp Thr Leu Ile Ile Pro Asn Asp
    210                 215                 220

Arg Leu Leu His Val Ile Ser Glu Gln Thr Pro Val Gln Glu Ala Phe
225                 230                 235                 240

Arg Val Ala Asp Asp Ile Leu Arg Gln Gly Val Gln Gly Ile Ser Asp
                245                 250                 255

Ile Ile Thr Ile Pro Gly Met Val Asn Val Asp Phe Ala Asp Val Arg
            260                 265                 270

Ala Ile Met Ala Asp Ala Gly Ser Ala Leu Met Gly Ile Gly Thr Gly
        275                 280                 285

Ser Gly Lys Ser Arg Ala Arg Glu Ala Ala Met Ala Ala Ile Ser Ser
    290                 295                 300

Pro Leu Met Glu Ala Ser Ile Glu Gly Ala Lys Gly Val Val Phe Asn
305                 310                 315                 320

Ile Thr Gly Gly Gly Asp Leu Thr Leu His Glu Val Ser Ala Ala Ala
                325                 330                 335
```

```
Asp Ile Ile Tyr Glu Val Val Asp Pro Asn Ala Asn Ile Ile Phe Gly
            340                 345                 350

Ala Val Ile Asp Glu Arg Leu Gln Gly Glu Ile Arg Met Thr Val Ile
        355                 360                 365

Ala Thr Gly Phe Ser Asn Glu Pro Gln Pro Leu Pro Gln Lys Ser Arg
    370                 375                 380

Thr Val Pro Pro Pro Pro Ser Phe Arg Arg Glu Ala Ser Ala Pro
385                 390                 395                 400

Arg Thr Val Asn Pro Val Glu Pro Ser Pro Gln Pro Lys Pro Pro Thr
                405                 410                 415

Gln Thr Gly Gly Leu Asp Ile Pro Glu Phe Leu Gln Arg Arg Arg Pro
            420                 425                 430

Pro Lys

<210> SEQ ID NO 45
<211> LENGTH: 631
<212> TYPE: PRT
<213> ORGANISM: Synechococcus elongatus

<400> SEQUENCE: 45

Val Arg Ile Pro Leu Asp Tyr Tyr Arg Ile Leu Cys Val Gly Val Gln
1               5                   10                  15

Ala Ser Ala Asp Lys Leu Ala Glu Ser Tyr Arg Asp Arg Leu Asn Gln
            20                  25                  30

Ser Pro Ser His Glu Phe Ser Glu Leu Ala Leu Gln Ala Arg Arg Gln
        35                  40                  45

Leu Leu Glu Ala Ala Ile Ala Glu Leu Ser Asp Pro Glu Gln Arg Asp
    50                  55                  60

Arg Tyr Asp Arg Arg Phe Phe Gln Gly Gly Leu Glu Ala Ile Glu Pro
65                  70                  75                  80

Ser Leu Glu Leu Glu Asp Trp Gln Arg Ile Gly Ala Leu Leu Ile Leu
                85                  90                  95

Leu Glu Leu Gly Glu Tyr Asp Arg Val Ser Gln Leu Ala Glu Glu Leu
            100                 105                 110

Leu Pro Asp Tyr Asp Ala Ser Ala Glu Val Arg Asp Gln Phe Ala Arg
        115                 120                 125

Gly Asp Ile Ala Leu Ala Ile Ala Leu Ser Gln Gln Ser Leu Gly Arg
    130                 135                 140

Glu Cys Arg Gln Gln Gly Leu Tyr Glu Gln Ala Ala Gln His Phe Gly
145                 150                 155                 160

Arg Ser Gln Ser Ala Leu Ala Asp His Gln Arg Phe Pro Glu Leu Ser
                165                 170                 175

Arg Thr Leu His Gln Glu Gln Gly Gln Leu Arg Pro Tyr Arg Ile Leu
            180                 185                 190

Glu Arg Leu Ala Gln Pro Leu Thr Ala Asp Ser Asp Arg Gln Gln Gly
        195                 200                 205

Leu Leu Leu Leu Gln Ala Met Leu Asp Asp Arg Gln Gly Ile Glu Gly
    210                 215                 220

Pro Gly Asp Asp Gly Ser Gly Leu Thr Leu Asp Asn Phe Leu Met Phe
225                 230                 235                 240

Leu Gln Gln Ile Arg Gly Tyr Leu Thr Leu Ala Glu Gln Leu Leu
                245                 250                 255

Phe Glu Ser Glu Ala Arg Arg Pro Ser Pro Ala Ala Ser Phe Phe Ala
            260                 265                 270
```

-continued

```
            Cys Tyr Thr Leu Ile Ala Arg Gly Phe Cys Asp His Gln Pro Ser Leu
                275                 280                 285

Ile His Arg Ala Ser Leu Leu His Glu Leu Lys Ser Arg Met Asp
                290                 295                 300

Val His Ile Glu Gln Ala Ile Ala Ser Leu Leu Leu Gly Gln Pro Glu
            305                 310                 315                 320

Glu Ala Glu Ala Leu Leu Val Gln Ser Gln Asp Glu Thr Leu Ser
                            325                 330                 335

Gln Ile Arg Ala Leu Ala Gln Gly Glu Ala Leu Ile Val Gly Leu Cys
                                340                 345                 350

Arg Phe Thr Glu Thr Trp Leu Ala Thr Lys Val Phe Pro Asp Phe Arg
                            355                 360                 365

Asp Leu Lys Glu Arg Thr Ala Pro Leu Gln Pro Tyr Phe Asp Asp Pro
                370                 375                 380

Asp Val Gln Thr Tyr Leu Asp Ala Ile Val Glu Leu Pro Ser Asp Leu
            385                 390                 395                 400

Met Pro Thr Pro Leu Pro Val Glu Pro Leu Glu Val Arg Ser Ser Leu
                            405                 410                 415

Leu Ala Lys Glu Leu Pro Thr Pro Ala Thr Pro Gly Val Ala Pro Pro
                            420                 425                 430

Pro Arg Arg Arg Arg Arg Asp Arg Ser Glu Arg Pro Ala Arg Thr Ala
                            435                 440                 445

Lys Arg Leu Pro Leu Pro Trp Ile Gly Leu Gly Val Val Val Val Leu
                            450                 455                 460

Gly Gly Gly Thr Gly Val Trp Ala Trp Arg Ser Arg Ser Asn Ser Thr
            465                 470                 475                 480

Pro Pro Thr Pro Pro Val Val Gln Thr Leu Pro Glu Ala Val Pro
                            485                 490                 495

Ala Pro Ser Pro Ala Pro Val Thr Val Ala Leu Asp Arg Ala Gln Ala
                            500                 505                 510

Glu Thr Val Leu Gln Asn Trp Leu Ala Ala Lys Ala Ala Ala Leu Gly
                            515                 520                 525

Pro Gln Tyr Asp Arg Asp Arg Leu Ala Thr Val Leu Thr Gly Glu Val
                            530                 535                 540

Leu Gln Thr Trp Gln Gly Phe Ser Ser Gln Gln Ala Asn Thr Gln Leu
            545                 550                 555                 560

Thr Ser Gln Phe Asp His Lys Leu Thr Val Asp Ser Val Gln Leu Ser
                            565                 570                 575

Asp Gly Asp Gln Arg Ala Val Gln Ala Lys Val Asp Glu Val Glu
                        580                 585                 590

Gln Val Tyr Arg Gly Asp Gln Leu Leu Glu Thr Arg Arg Asp Leu Gly
                            595                 600                 605

Leu Val Ile Arg Tyr Gln Leu Val Arg Glu Asn Asn Ile Trp Lys Ile
                        610                 615                 620

Ala Ser Ile Ser Leu Val Arg
            625                 630

<210> SEQ ID NO 46
<211> LENGTH: 1896
<212> TYPE: DNA
<213> ORGANISM: Synechococcus elongatus

<400> SEQUENCE: 46
gtgcgtattc ctctcgatta ctaccgaatt ctctgtgttg gcgtgcaagc ctcggcagac       60
```

-continued

```
aaacttgccg aaagctaccg cgatcgcctc aaccaatcgc cctcccatga gttttcagag       120
ctggcattgc aggcgcggcg gcaactcctc gaagcagcga ttgctgagct gagtgatccc       180
gaacagcgcg atcgctacga tcgccgcttt tttcagggcg gtctggaagc gattgaacca       240
agcctagaac tcgaagactg gcagcgaatt ggagccctgc tgatcctgct ggaattgggg       300
gaatacgatc gcgtttcgca actggctgag gaactcctgc cagactacga cgcgagcgca       360
gaagtacgcg atcagttcgc gcggggtgat atcgccttgg cgatcgcact atcccagcaa       420
tccctcggtc gagaatgccg tcagcagggt ctgtacgaac aggccgccca gcactttggc       480
cgcagccagt ctgccctagc cgatcatcag cgctttcctg aactgagtcg aaccctgcac       540
caagaacaag gacagctacg gccctatcgc attttggagc ggttggccca gcccttgact       600
gccgatagcg atcgccagca gggttttgct tgttgcaggg cgatgttgga cgaccggcag       660
ggcattgaag gccctgggga tgatggctcg ggctgaccc ttgataactt tttgatgttt       720
ctccagcaaa ttcgcggcta tctgaccctg gctgaacagc agttgctgtt tgaatcggaa       780
gcgcgtcggc cctcgccggc tgcgagcttt tttgcctgct acaccctgat gcgcggggc       840 ttttgcgatc accaaccctc gttgatccat cgcgccagct tgctcttgca tgaactcaag       900
agccgcatgg atgtgcacat cgaacaggcg atcgccagcc tattgctcgg acagcccgaa       960
gaagctgagg cgctactcgt ccagagccaa gatgaggaaa ccctcagcca aatccgtgcc      1020
ctagcccaag gggaagccct gatcgtcggt ttgtgccgat tcacggaaac ctggctagcg      1080
accaaggtat ttccggattt ccgcgacctc aaggaaagga ctgcgccgct gcagccctac      1140
tttgacgacc ccgatgtcca gacctatctg gatgcgatcg tggagttgcc gtccgatttg      1200
atgccaacgc cgctacccgt tgagccgctt gaggtgcgat cgtcgttgct ggccaaggaa      1260
ctgccgaccc cagcaacgcc tggtgtagct ccaccccctc gccgccgtcg ccgcgatcgc      1320
tccgaacgtc ctgctcgcac ggccaaacgc ttgcccttgc cctggattgg tttgggggtt      1380
gtggtggttc tcggcggtgg aacaggggtt gggcttggc gatcgcgttc caattccacc      1440
ccgccgaccc cgcccccccgt ggttcaaacg ctgcctgagg cggtacctgc cccttcgccc      1500
gcgcagttta ccgttgccct cgatcgggct caggctgaaa ctgtgtttgca aaactggttg      1560 gccgctaaag ctgcagcctt ggggcctcaa tacgatcgcg atcgcttagc gacggtgctg      1620
accggtgagt tctgcagac ttggcagggt ttttctagcc agcaggccaa cacccagctc      1680
acatcacagt tcgatcacaa gttaaccgtc gactcagttc agctcagtga cggtgatcaa      1740
cgagcagtag tccaagccaa ggtcgatgaa gttgagcagg tctatcgagg cgaccagctg      1800
ctcgaaacgc gccgagattt gggcttggtg atccgctacc agctcgtgcg cgagaacaac      1860
atctggaaaa ttgcttcgat tagtttggtg cgctag                                1896
```

<210> SEQ ID NO 47
<211> LENGTH: 190
<212> TYPE: PRT
<213> ORGANISM: Vibrio fishcheri

<400> SEQUENCE: 47

Met Ile Lys Lys Ser Asp Phe Leu Gly Ile Pro Ser Glu Glu Tyr Arg
1               5                   10                  15

Gly Ile Leu Ser Leu Arg Tyr Gln Val Phe Lys Arg Arg Leu Glu Trp
            20                  25                  30

Asp Leu Val Ser Glu Asp Asn Leu Glu Ser Asp Glu Tyr Asp Asn Ser
        35                  40                  45

```
Asn Ala Glu Tyr Ile Tyr Ala Cys Asp Asp Ala Glu Val Asn Gly
    50                  55                  60

Cys Trp Arg Leu Leu Pro Thr Thr Gly Asp Tyr Met Leu Lys Thr Val
 65                  70                  75                  80

Phe Pro Glu Leu Leu Gly Asp Gln Val Ala Pro Arg Asp Pro Asn Ile
                 85                  90                  95

Val Glu Leu Ser Arg Phe Ala Val Gly Lys Asn Ser Ser Lys Ile Asn
            100                 105                 110

Asn Ser Ala Ser Glu Ile Thr Met Lys Leu Phe Gln Ala Ile Tyr Lys
        115                 120                 125

His Ala Val Ser Gln Gly Ile Thr Glu Tyr Val Thr Val Thr Ser Ile
130                 135                 140

Ala Ile Glu Arg Phe Leu Lys Arg Ile Lys Val Pro Cys His Arg Ile
145                 150                 155                 160

Gly Asp Lys Glu Ile His Leu Leu Gly Asn Thr Arg Ser Val Val Leu
                165                 170                 175

Ser Met Pro Ile Asn Asp Gln Phe Arg Lys Ala Val Ser Asn
            180                 185                 190

<210> SEQ ID NO 48
<211> LENGTH: 573
<212> TYPE: DNA
<213> ORGANISM: Vibrio fishcheri

<400> SEQUENCE: 48
atgataaaaa aatcggactt tttgggcatt ccatcagagg agtatagagg tattcttagt      60
cttcgttatc aggtatttaa cgaagactg gagtgggact tggtaagtga ggataatctt     120
gaatcagatg aatatgataa ctcaaatgca gaatatattt atgcttgtga tgatgcggaa     180
gaggtaaatg gctgttggcg tttgttacct acaacgggtg attacatgtt aaaaactgtt     240
tttcctgaat tgctcggaga tcaagtagcc caagagatc caaatatagt cgaattaagc      300
cgttttgctg tgggaaaaaa tagctcaaaa ataaataact ctgctagtga aataacaatg     360
aaattgtttc aagctatata taaacacgca gttagtcaag gtattacaga atatgtaaca     420
gtaacatcaa tagcaataga gcgatttctg aaacgtatta agttccttg tcatcgcatt      480 ggtgataagg agattcattt attaggtaat actagatctg ttgtattgtc tatgcctatt     540
aatgatcagt ttagaaaagc tgtatcaaat taa                                  573

<210> SEQ ID NO 49
<211> LENGTH: 269
<212> TYPE: PRT
<213> ORGANISM: Vibrio fishcheri

<400> SEQUENCE: 49

Met Ile Tyr Asn Thr Gln Asn Leu Arg Gln Thr Ile Gly Lys Asp Lys
  1               5                  10                  15

Glu Met Gly Met Lys Asn Ile Asn Ala Asp Thr Tyr Arg Ile Ile
             20                  25                  30

Asn Lys Ile Lys Ala Cys Arg Ser Asn Asn Asp Ile Asn Gln Cys Leu
         35                  40                  45

Ser Asp Met Thr Lys Met Val His Cys Glu Tyr Tyr Leu Leu Ala Ile
    50                  55                  60

Ile Tyr Pro His Ser Met Val Lys Ser Asp Ile Ser Ile Leu Asp Asn
 65                  70                  75                  80

Tyr Pro Lys Lys Trp Arg Gln Tyr Tyr Asp Asp Ala Asn Leu Ile Lys
```

|     |     |     |     |     | 85  |     |     |     |     | 90  |     |     |     |     | 95  |     |
| --- | --- | --- | --- | --- | --- | --- | --- | --- | --- | --- | --- | --- | --- | --- | --- | --- |

Tyr Asp Pro Ile Val Asp Tyr Ser Asn Ser Asn His Ser Pro Ile Asn
           100                       105                   110

Trp Asn Ile Phe Glu Asn Asn Ala Val Asn Lys Lys Ser Pro Asn Val
           115                       120                   125

Ile Lys Glu Ala Lys Thr Ser Gly Leu Ile Thr Gly Phe Ser Phe Pro
   130                    135                     140

Ile His Thr Ala Asn Asn Gly Phe Gly Met Leu Ser Phe Ala His Ser
145                  150                   155               160

Glu Lys Asp Asn Tyr Ile Asp Ser Leu Phe Leu His Ala Cys Met Asn
           165                       170                   175

Ile Pro Leu Ile Val Pro Ser Leu Val Asp Asn Tyr Arg Lys Ile Asn
           180                       185                   190

Ile Ala Asn Asn Lys Ser Asn Asn Asp Leu Thr Lys Arg Glu Lys Glu
   195                    200                   205

Cys Leu Ala Trp Ala Cys Glu Gly Lys Ser Ser Trp Asp Ile Ser Lys
   210                    215                   220

Ile Leu Gly Cys Ser Glu Arg Thr Val Thr Phe His Leu Thr Asn Ala
225                  230                   235               240

Gln Met Lys Leu Asn Thr Thr Asn Arg Cys Gln Ser Ile Ser Lys Ala
           245                       250                   255

Ile Leu Thr Gly Ala Ile Asp Cys Pro Tyr Phe Lys Asn
   260                    265

<210> SEQ ID NO 50
<211> LENGTH: 810
<212> TYPE: DNA
<213> ORGANISM: Vibrio fishcheri

<400> SEQUENCE: 50

| | | | | | |
|---|---|---|---|---|---|
| atgatatata | acacgcaaaa | cttgcgacaa | acaataggta | aggataaaga | gatgggtatg | 60 |
| aaaaacataa | atgccgacga | cacatacaga | ataattaata | aaattaaagc | ttgtagaagc | 120 |
| aataatgata | ttaatcaatg | cttatctgat | atgactaaaa | tggtacattg | tgaatattat | 180 |
| ttactcgcga | tcatttatcc | tcattctatg | gttaaatctg | atatttcaat | tctagataat | 240 |
| taccctaaaa | aatggaggca | atattatgat | gacgctaatt | taataaaata | tgatcctata | 300 |
| gtagattatt | ctaactccaa | tcattcacca | attaattgga | atatatttga | aaacaatgct | 360 |
| gtaaataaaa | aatctccaaa | tgtaattaaa | gaagcgaaaa | catcaggtct | tatcactggg | 420 |
| tttagtttcc | ctattcatac | ggctaacaat | ggcttcggaa | tgcttagttt | tgcacattca | 480 |
| gaaaaagaca | actatataga | tagtttatttt | ttacatgcgt | gtatgaacat | accattaatt | 540 |
| gttccttctc | tagttgataa | ttatcgaaaa | ataaatatag | caataataa | atcaaacaac | 600 |
| gatttaacca | aaagagaaaa | agaatgttta | gcgtgggcat | gcgaaggaaa | aagctcttgg | 660 |
| gatatttcaa | aaatattagg | ctgcagtgag | cgtactgtca | ctttccattt | aaccaatgcg | 720 |
| caaatgaaac | tcaatacaac | aaaccgctgc | caaagtattt | ctaaagcaat | tttaacagga | 780 |
| gcaattgatt | gcccatactt | taaaaattaa | | | | 810 |

<210> SEQ ID NO 51
<211> LENGTH: 198
<212> TYPE: DNA
<213> ORGANISM: Vibrio fishcheri

<400> SEQUENCE: 51

```
tgtcgcaagt tttgcgtgtt atatatcatt aaaacggtaa tggattgaca tttgattcta      60
ataaattgga tttttgtcac actattgtat cgctgggaat acaattactt aacataagca     120
cctgtaggat cgtacaggtt tacgcaagaa atggtttgt tatagtcgaa tgaattcatt      180
aaagaggaga aaggtacc                                                    198
```

```
<210> SEQ ID NO 52
<211> LENGTH: 39
<212> TYPE: DNA
<213> ORGANISM: Artificial Sequence
<220> FEATURE:
<223> OTHER INFORMATION: A synthetic oligonucleotide

<400> SEQUENCE: 52
tctagaaata attttgttta actttaagaa ggagatata                              39

<210> SEQ ID NO 53
<211> LENGTH: 46
<212> TYPE: DNA
<213> ORGANISM: Artificial Sequence
<220> FEATURE:
<223> OTHER INFORMATION: A synthetic primer

<400> SEQUENCE: 53
ggatctcaag aagatccttt gatctagtct agggatcagc attggg                      46

<210> SEQ ID NO 54
<211> LENGTH: 46
<212> TYPE: DNA
<213> ORGANISM: Artificial Sequence
<220> FEATURE:
<223> OTHER INFORMATION: A synthetic primer

<400> SEQUENCE: 54
ttatgtccac tgggttcgtg ccttccggaa ccacgggta gagagc                       46

<210> SEQ ID NO 55
<211> LENGTH: 46
<212> TYPE: DNA
<213> ORGANISM: Artificial Sequence
<220> FEATURE:
<223> OTHER INFORMATION: A synthetic primer

<400> SEQUENCE: 55
gatcaccaag gtagtcggca aataagggca catcttgaga cgatcg                      46

<210> SEQ ID NO 56
<211> LENGTH: 48
<212> TYPE: DNA
<213> ORGANISM: Artificial Sequence
<220> FEATURE:
<223> OTHER INFORMATION: A synthetic primer

<400> SEQUENCE: 56
cctatggaaa aacgccagca acgcggagtc ctcacgcccg acgtagtc                    48

<210> SEQ ID NO 57
<211> LENGTH: 47
<212> TYPE: DNA
<213> ORGANISM: Artificial Sequence
<220> FEATURE:
<223> OTHER INFORMATION: A synthetic primer

<400> SEQUENCE: 57
ggatctcaag aagatccttt gatctggcgg gcttgggctt ctgtcag                     47
```

<210> SEQ ID NO 58
<211> LENGTH: 47
<212> TYPE: DNA
<213> ORGANISM: Artificial Sequence
<220> FEATURE:
<223> OTHER INFORMATION: A synthetic primer

<400> SEQUENCE: 58
agcgctcgaa taagtcagcc agcatagggt ccgaagagca ggagcgg                47

<210> SEQ ID NO 59
<211> LENGTH: 48
<212> TYPE: DNA
<213> ORGANISM: Artificial Sequence
<220> FEATURE:
<223> OTHER INFORMATION: A synthetic primer

<400> SEQUENCE: 59
gatcaccaag gtagtcggca aataataatt actgccttgc cggtgtag               48

<210> SEQ ID NO 60
<211> LENGTH: 47
<212> TYPE: DNA
<213> ORGANISM: Artificial Sequence
<220> FEATURE:
<223> OTHER INFORMATION: A synthetic primer

<400> SEQUENCE: 60
cctatggaaa aacgccagca acgcggcgga tctctggctg atttgtc                47

<210> SEQ ID NO 61
<211> LENGTH: 47
<212> TYPE: DNA
<213> ORGANISM: Artificial Sequence
<220> FEATURE:
<223> OTHER INFORMATION: A synthetic primer

<400> SEQUENCE: 61
ggatctcaag aagatccttt gatctggcgg gcttgggctt ctgtcag                47

<210> SEQ ID NO 62
<211> LENGTH: 47
<212> TYPE: DNA
<213> ORGANISM: Artificial Sequence
<220> FEATURE:
<223> OTHER INFORMATION: A synthetic primer

<400> SEQUENCE: 62
aggtgacaac aataacgcga ctcatagggt ccgaagagca ggagcgg                47

<210> SEQ ID NO 63
<211> LENGTH: 48
<212> TYPE: DNA
<213> ORGANISM: Artificial Sequence
<220> FEATURE:
<223> OTHER INFORMATION: A synthetic primer

<400> SEQUENCE: 63
gatcaccaag gtagtcggca aataataatt actgccttgc cggtgtag               48

<210> SEQ ID NO 64
<211> LENGTH: 47
<212> TYPE: DNA
<213> ORGANISM: Artificial Sequence
<220> FEATURE:

<223> OTHER INFORMATION: A synthetic primer

<400> SEQUENCE: 64
cctatggaaa aacgccagca acgcggcgga tctctggctg atttgtc                    47

<210> SEQ ID NO 65
<211> LENGTH: 46
<212> TYPE: DNA
<213> ORGANISM: Artificial Sequence
<220> FEATURE:
<223> OTHER INFORMATION: A synthetic primer

<400> SEQUENCE: 65
ggatctcaag aagatccttt gatctacttc accgacgaaa accgtg                     46

<210> SEQ ID NO 66
<211> LENGTH: 46
<212> TYPE: DNA
<213> ORGANISM: Artificial Sequence
<220> FEATURE:
<223> OTHER INFORMATION: A synthetic primer

<400> SEQUENCE: 66
ttatgtccac tgggttcgtg ccttctcacg tcaggcgatc gcgctc                     46

<210> SEQ ID NO 67
<211> LENGTH: 47
<212> TYPE: DNA
<213> ORGANISM: Artificial Sequence
<220> FEATURE:
<223> OTHER INFORMATION: A synthetic primer

<400> SEQUENCE: 67
gatcaccaag gtagtcggca ataattgac gactactcgg ctgcatc                     47

<210> SEQ ID NO 68
<211> LENGTH: 47
<212> TYPE: DNA
<213> ORGANISM: Artificial Sequence
<220> FEATURE:
<223> OTHER INFORMATION: A synthetic primer

<400> SEQUENCE: 68
cctatggaaa aacgccagca acgcgcttca agatgatctg agctgag                    47

<210> SEQ ID NO 69
<211> LENGTH: 21
<212> TYPE: DNA
<213> ORGANISM: Artificial Sequence
<220> FEATURE:
<223> OTHER INFORMATION: A synthetic primer

<400> SEQUENCE: 69
gaaggcacga acccagtgga c                                                21

<210> SEQ ID NO 70
<211> LENGTH: 22
<212> TYPE: DNA
<213> ORGANISM: Artificial Sequence
<220> FEATURE:
<223> OTHER INFORMATION: A synthetic primer

<400> SEQUENCE: 70
ttatttgccg actaccttgg tg                                               22

```
<210> SEQ ID NO 71
<211> LENGTH: 20
<212> TYPE: DNA
<213> ORGANISM: Artificial Sequence
<220> FEATURE:
<223> OTHER INFORMATION: A synthetic primer

<400> SEQUENCE: 71
cgcgttgctg gcgtttttcc                                               20

<210> SEQ ID NO 72
<211> LENGTH: 21
<212> TYPE: DNA
<213> ORGANISM: Artificial Sequence
<220> FEATURE:
<223> OTHER INFORMATION: A synthetic primer

<400> SEQUENCE: 72
agatcaaagg atcttcttga g                                             21

<210> SEQ ID NO 73
<211> LENGTH: 47
<212> TYPE: DNA
<213> ORGANISM: Artificial Sequence
<220> FEATURE:
<223> OTHER INFORMATION: A synthetic primer

<400> SEQUENCE: 73
agcaccctgc taaggaggca acaagatggt cagcaaaggt gaagaag                 47

<210> SEQ ID NO 74
<211> LENGTH: 22
<212> TYPE: DNA
<213> ORGANISM: Artificial Sequence
<220> FEATURE:
<223> OTHER INFORMATION: A synthetic primer

<400> SEQUENCE: 74
cttgtacagt tcgtccatac cc                                            22

<210> SEQ ID NO 75
<211> LENGTH: 45
<212> TYPE: DNA
<213> ORGANISM: Artificial Sequence
<220> FEATURE:
<223> OTHER INFORMATION: A synthetic primer

<400> SEQUENCE: 75
gatgggtatg gacgaactgt acaagatgag tgacgtagac gcttc                   45

<210> SEQ ID NO 76
<211> LENGTH: 45
<212> TYPE: DNA
<213> ORGANISM: Artificial Sequence
<220> FEATURE:
<223> OTHER INFORMATION: A synthetic primer

<400> SEQUENCE: 76
gcatgcctgc aggtcgactc tagaactact tcccgccagg atcgg                   45

<210> SEQ ID NO 77
<211> LENGTH: 46
<212> TYPE: DNA
<213> ORGANISM: Artificial Sequence
<220> FEATURE:
<223> OTHER INFORMATION: A synthetic primer
```

<400> SEQUENCE: 77
gatgggtatg gacgaactgt acaagatgag tcgcgttatt gttgtc        46

<210> SEQ ID NO 78
<211> LENGTH: 47
<212> TYPE: DNA
<213> ORGANISM: Artificial Sequence
<220> FEATURE:
<223> OTHER INFORMATION: A synthetic primer

<400> SEQUENCE: 78
gcatgcctgc aggtcgactc tagaactaga gaattttttt attgagg       47

<210> SEQ ID NO 79
<211> LENGTH: 46
<212> TYPE: DNA
<213> ORGANISM: Artificial Sequence
<220> FEATURE:
<223> OTHER INFORMATION: A synthetic primer

<400> SEQUENCE: 79
ggatctcaag aagatccttt gatctagtct agggatcagc attggg        46

<210> SEQ ID NO 80
<211> LENGTH: 46
<212> TYPE: DNA
<213> ORGANISM: Artificial Sequence
<220> FEATURE:
<223> OTHER INFORMATION: A synthetic primer

<400> SEQUENCE: 80
tgtcttcttc acctttgctg accatcggaa ccacggggta gagagc        46

<210> SEQ ID NO 81
<211> LENGTH: 46
<212> TYPE: DNA
<213> ORGANISM: Artificial Sequence
<220> FEATURE:
<223> OTHER INFORMATION: A synthetic primer

<400> SEQUENCE: 81
tttgatgctc gatgagtttt tctaagggca catcttgaga cgatcg        46

<210> SEQ ID NO 82
<211> LENGTH: 46
<212> TYPE: DNA
<213> ORGANISM: Artificial Sequence
<220> FEATURE:
<223> OTHER INFORMATION: A synthetic primer

<400> SEQUENCE: 82
cctatggaaa aacgccagca acgcggagtc ctcacgcccg acgtag        46

<210> SEQ ID NO 83
<211> LENGTH: 48
<212> TYPE: DNA
<213> ORGANISM: Artificial Sequence
<220> FEATURE:
<223> OTHER INFORMATION: A synthetic primer

<400> SEQUENCE: 83
ggatctcaag aagatccttt gatctgacgg tcaactatgc gcgccaac      48

<210> SEQ ID NO 84
<211> LENGTH: 46

```
<212> TYPE: DNA
<213> ORGANISM: Artificial Sequence
<220> FEATURE:
<223> OTHER INFORMATION: A synthetic primer

<400> SEQUENCE: 84
tgtcttcttc acctttgctg accatgcgcg atcgccgacg gggagc            46

<210> SEQ ID NO 85
<211> LENGTH: 22
<212> TYPE: DNA
<213> ORGANISM: Artificial Sequence
<220> FEATURE:
<223> OTHER INFORMATION: A synthetic primer

<400> SEQUENCE: 85
atggtcagca aaggtgaaga ag                                      22

<210> SEQ ID NO 86
<211> LENGTH: 44
<212> TYPE: DNA
<213> ORGANISM: Artificial Sequence
<220> FEATURE:
<223> OTHER INFORMATION: A synthetic primer

<400> SEQUENCE: 86
ttttgagaca caacgtggct ttccctcact tgtacagttc gtcc              44

<210> SEQ ID NO 87
<211> LENGTH: 47
<212> TYPE: DNA
<213> ORGANISM: Artificial Sequence
<220> FEATURE:
<223> OTHER INFORMATION: A synthetic primer

<400> SEQUENCE: 87
tttgatgctc gatgagtttt tctaattgac gactactcgg ctgcatc           47

<210> SEQ ID NO 88
<211> LENGTH: 47
<212> TYPE: DNA
<213> ORGANISM: Artificial Sequence
<220> FEATURE:
<223> OTHER INFORMATION: A synthetic primer

<400> SEQUENCE: 88
cctatggaaa aacgccagca acgcgcttca agatgatctg agctgag           47

<210> SEQ ID NO 89
<211> LENGTH: 21
<212> TYPE: DNA
<213> ORGANISM: Artificial Sequence
<220> FEATURE:
<223> OTHER INFORMATION: A synthetic primer

<400> SEQUENCE: 89
gggaaagcca cgttgtgtct c                                       21

<210> SEQ ID NO 90
<211> LENGTH: 22
<212> TYPE: DNA
<213> ORGANISM: Artificial Sequence
<220> FEATURE:
<223> OTHER INFORMATION: A synthetic primer

<400> SEQUENCE: 90
```
ttagaaaaac tcatcgagca tc                                              22

<210> SEQ ID NO 91
<211> LENGTH: 231
<212> TYPE: PRT
<213> ORGANISM: E. coli

<400> SEQUENCE: 91

Met Ser Asn Thr Pro Ile Glu Leu Lys Gly Ser Ser Phe Thr Leu Ser
1               5                   10                  15

Val Val His Leu His Glu Ala Glu Pro Lys Val Ile His Gln Ala Leu
            20                  25                  30

Glu Asp Lys Ile Ala Gln Ala Pro Ala Phe Leu Lys His Ala Pro Val
        35                  40                  45

Val Leu Asn Val Ser Ala Leu Glu Asp Pro Val Asn Trp Ser Ala Met
    50                  55                  60

His Lys Ala Val Ser Ala Thr Gly Leu Arg Val Ile Gly Val Ser Gly
65                  70                  75                  80

Cys Lys Asp Ala Gln Leu Lys Ala Glu Ile Glu Lys Met Gly Leu Pro
                85                  90                  95

Ile Leu Thr Glu Gly Lys Glu Lys Ala Pro Arg Pro Ala Pro Thr Pro
            100                 105                 110

Gln Ala Pro Ala Gln Asn Thr Thr Pro Val Thr Lys Thr Arg Leu Ile
        115                 120                 125

Asp Thr Pro Val Arg Ser Gly Gln Arg Ile Tyr Ala Pro Gln Cys Asp
    130                 135                 140

Leu Ile Val Thr Ser His Val Ser Ala Gly Ala Glu Leu Ile Ala Asp
145                 150                 155                 160

Gly Asn Ile His Val Tyr Gly Met Met Arg Gly Arg Ala Leu Ala Gly
                165                 170                 175

Ala Ser Gly Asp Arg Glu Thr Gln Ile Phe Cys Thr Asn Leu Met Ala
            180                 185                 190

Glu Leu Val Ser Ile Ala Gly Glu Tyr Trp Leu Ser Asp Gln Ile Pro
        195                 200                 205

Ala Glu Phe Tyr Gly Lys Ala Ala Arg Leu Gln Leu Val Glu Asn Ala
    210                 215                 220

Leu Thr Val Gln Pro Leu Asn
225                 230

<210> SEQ ID NO 92
<211> LENGTH: 226
<212> TYPE: PRT
<213> ORGANISM: B. subtilis

<400> SEQUENCE: 92

Met Lys Thr Lys Lys Gln Gln Tyr Val Thr Ile Lys Gly Thr Lys Asn
1               5                   10                  15

Gly Leu Thr Leu His Leu Asp Asp Ala Cys Ser Phe Asp Glu Leu Leu
            20                  25                  30

Asp Gly Leu Gln Asn Met Leu Ser Ile Glu Gln Tyr Thr Asp Gly Lys
        35                  40                  45

Gly Gln Lys Ile Ser Val His Val Lys Leu Gly Asn Arg Phe Leu Tyr
    50                  55                  60

Lys Glu Gln Glu Gln Leu Thr Glu Leu Ile Ala Ser Lys Lys Asp
65                  70                  75                  80

Leu Phe Val His Ser Ile Asp Ser Glu Val Ile Thr Lys Lys Glu Ala

```
            85                  90                  95
Gln Gln Ile Arg Glu Glu Ala Glu Ile Ile Ser Val Ser Lys Ile Val
            100                 105                 110

Arg Ser Gly Gln Val Leu Gln Val Lys Gly Asp Leu Leu Ile Gly
            115                 120                 125

Asp Val Asn Pro Gly Gly Thr Val Arg Ala Gly Gly Asn Ile Phe Val
            130                 135                 140

Leu Gly Ser Leu Lys Gly Ile Ala His Ala Gly Phe Asn Gly Asn Asn
145                 150                 155                 160

Gln Ala Val Ile Ala Ala Ser Glu Met Leu Pro Thr Gln Leu Arg Ile
            165                 170                 175

Asn His Val Leu Asn Arg Ser Pro Asp His Ile Gln Lys Gly Asn Glu
            180                 185                 190

Met Glu Cys Ala Tyr Leu Asp Thr Asp Gly Asn Met Val Ile Glu Arg
            195                 200                 205

Leu Gln His Leu Ala His Leu Arg Pro Asp Leu Thr Arg Leu Glu Gly
            210                 215                 220

Gly Met
225

<210> SEQ ID NO 93
<211> LENGTH: 270
<212> TYPE: PRT
<213> ORGANISM: E. coli

<400> SEQUENCE: 93

Met Ala Arg Ile Ile Val Val Thr Ser Gly Lys Gly Gly Val Gly Lys
1               5                   10                  15

Thr Thr Ser Ser Ala Ala Ile Ala Thr Gly Leu Ala Gln Lys Gly Lys
            20                  25                  30

Lys Thr Val Val Ile Asp Phe Asp Ile Gly Leu Arg Asn Leu Asp Leu
            35                  40                  45

Ile Met Gly Cys Glu Arg Arg Val Val Tyr Asp Phe Val Asn Val Ile
50                  55                  60

Gln Gly Asp Ala Thr Leu Asn Gln Ala Leu Ile Lys Asp Lys Arg Thr
65                  70                  75                  80

Glu Asn Leu Tyr Ile Leu Pro Ala Ser Gln Thr Arg Asp Lys Asp Ala
            85                  90                  95

Leu Thr Arg Glu Gly Val Ala Lys Val Leu Asp Asp Leu Lys Ala Met
            100                 105                 110

Asp Phe Glu Phe Ile Val Cys Asp Ser Pro Ala Gly Ile Glu Thr Gly
            115                 120                 125

Ala Leu Met Ala Leu Tyr Phe Ala Asp Glu Ala Ile Ile Thr Thr Asn
130                 135                 140

Pro Glu Val Ser Ser Val Arg Asp Ser Asp Arg Ile Leu Gly Ile Leu
145                 150                 155                 160

Ala Ser Lys Ser Arg Arg Ala Glu Asn Gly Glu Glu Pro Ile Lys Glu
            165                 170                 175

His Leu Leu Leu Thr Arg Tyr Asn Pro Gly Arg Val Ser Arg Gly Asp
            180                 185                 190

Met Leu Ser Met Glu Asp Val Leu Glu Ile Leu Arg Ile Lys Leu Val
            195                 200                 205

Gly Val Ile Pro Glu Asp Gln Ser Val Leu Arg Ala Ser Asn Gln Gly
210                 215                 220
```

Glu Pro Val Ile Leu Asp Ile Asn Ala Asp Ala Gly Lys Ala Tyr Ala
225                 230                 235                 240

Asp Thr Val Glu Arg Leu Leu Gly Glu Glu Arg Pro Phe Arg Phe Ile
                245                 250                 255

Glu Glu Glu Lys Lys Gly Phe Leu Lys Arg Leu Phe Gly Gly
            260                 265                 270

<210> SEQ ID NO 94
<211> LENGTH: 326
<212> TYPE: PRT
<213> ORGANISM: Arabidopsis thaliana

<400> SEQUENCE: 94

Met Ala Ser Leu Arg Leu Phe Ser Thr Asn His Gln Ser Leu Leu Leu
1               5                   10                  15

Pro Ser Ser Leu Ser Gln Lys Thr Leu Ile Ser Ser Pro Arg Phe Val
            20                  25                  30

Asn Asn Pro Ser Arg Arg Ser Pro Ile Arg Ser Val Leu Gln Phe Asn
        35                  40                  45

Arg Lys Pro Glu Leu Ala Gly Glu Thr Pro Arg Ile Val Val Ile Thr
50                  55                  60

Ser Gly Lys Gly Gly Val Gly Lys Thr Thr Thr Ala Asn Val Gly
65                  70                  75                  80

Leu Ser Leu Ala Arg Tyr Gly Phe Ser Val Val Ala Ile Asp Ala Asp
                85                  90                  95

Leu Gly Leu Arg Asn Leu Asp Leu Leu Leu Gly Leu Glu Asn Arg Val
            100                 105                 110

Asn Tyr Thr Cys Val Glu Val Ile Asn Gly Asp Cys Arg Leu Asp Gln
        115                 120                 125

Ala Leu Val Arg Asp Lys Arg Trp Ser Asn Phe Glu Leu Leu Cys Ile
    130                 135                 140

Ser Lys Pro Arg Ser Lys Leu Pro Met Gly Phe Gly Gly Lys Ala Leu
145                 150                 155                 160

Glu Trp Leu Val Asp Ala Leu Lys Thr Arg Pro Glu Gly Ser Pro Asp
                165                 170                 175

Phe Ile Ile Ile Asp Cys Pro Ala Gly Ile Asp Ala Gly Phe Ile Thr
            180                 185                 190

Ala Ile Thr Pro Ala Asn Glu Ala Val Leu Val Thr Thr Pro Asp Ile
        195                 200                 205

Thr Ala Leu Arg Asp Ala Asp Arg Val Thr Gly Leu Leu Glu Cys Asp
    210                 215                 220

Gly Ile Arg Asp Ile Lys Met Ile Val Asn Arg Val Arg Thr Asp Met
225                 230                 235                 240

Ile Lys Gly Glu Asp Met Met Ser Val Leu Asp Val Gln Glu Met Leu
                245                 250                 255

Gly Leu Ser Leu Leu Gly Val Ile Pro Glu Asp Ser Glu Val Ile Arg
            260                 265                 270

Ser Thr Asn Arg Gly Phe Pro Leu Val Leu Asn Lys Pro Pro Thr Leu
        275                 280                 285

Ala Gly Leu Ala Phe Glu Gln Ala Ala Trp Arg Leu Val Glu Gln Asp
    290                 295                 300

Ser Met Lys Ala Val Met Val Glu Glu Glu Pro Lys Lys Arg Gly Phe
305                 310                 315                 320

Phe Ser Phe Phe Gly Gly
                325

<210> SEQ ID NO 95
<211> LENGTH: 268
<212> TYPE: PRT
<213> ORGANISM: B. subtilis

<400> SEQUENCE: 95

Met Gly Glu Ala Ile Val Ile Thr Ser Gly Lys Gly Val Gly Lys
1               5                   10                  15

Thr Thr Thr Ser Ala Asn Leu Gly Thr Ala Leu Ala Ile Leu Gly Lys
            20                  25                  30

Arg Val Cys Leu Val Asp Thr Asp Ile Gly Leu Arg Asn Leu Asp Val
        35                  40                  45

Val Met Gly Leu Glu Asn Arg Ile Ile Tyr Asp Leu Val Asp Val Val
    50                  55                  60

Glu Gly Arg Cys Lys Met His Gln Ala Leu Val Lys Asp Lys Arg Phe
65                  70                  75                  80

Asp Asp Leu Leu Tyr Leu Met Pro Ala Ala Gln Thr Ser Asp Lys Thr
                85                  90                  95

Ala Val Ala Pro Glu Gln Ile Lys Asn Met Val Gln Glu Leu Lys Gln
            100                 105                 110

Glu Phe Asp Tyr Val Ile Ile Asp Cys Pro Ala Gly Ile Glu Gln Gly
        115                 120                 125

Tyr Lys Asn Ala Val Ser Gly Ala Asp Lys Ala Ile Val Val Thr Thr
    130                 135                 140

Pro Glu Ile Ser Ala Val Arg Asp Ala Asp Arg Ile Ile Gly Leu Leu
145                 150                 155                 160

Glu Gln Glu Glu Asn Ile Glu Pro Pro Arg Leu Val Val Asn Arg Ile
                165                 170                 175

Arg Asn His Leu Met Lys Asn Gly Asp Thr Met Asp Ile Asp Glu Ile
            180                 185                 190

Val Gln His Leu Ser Ile Asp Leu Leu Gly Ile Val Ala Asp Asp
        195                 200                 205

Glu Val Ile Lys Ala Ser Asn His Gly Glu Pro Ile Ala Met Asp Pro
    210                 215                 220

Lys Asn Arg Ala Ser Ile Ala Tyr Arg Asn Ile Ala Arg Arg Ile Leu
225                 230                 235                 240

Gly Glu Ser Val Pro Leu Gln Val Leu Glu Gln Asn Lys Gly Met
                245                 250                 255

Met Ala Lys Ile Lys Ser Phe Phe Gly Val Arg Ser
            260                 265

<210> SEQ ID NO 96
<211> LENGTH: 88
<212> TYPE: PRT
<213> ORGANISM: E. coli

<400> SEQUENCE: 96

Met Ala Leu Leu Asp Phe Phe Leu Ser Arg Lys Lys Asn Thr Ala Asn
1               5                   10                  15

Ile Ala Lys Glu Arg Leu Gln Ile Ile Val Ala Glu Arg Arg Arg Ser
            20                  25                  30

Asp Ala Glu Pro His Tyr Leu Pro Gln Leu Arg Lys Asp Ile Leu Glu
        35                  40                  45

Val Ile Cys Lys Tyr Val Gln Ile Asp Pro Glu Met Val Thr Val Gln
    50                  55                  60

```
Leu Glu Gln Lys Asp Gly Asp Ile Ser Ile Leu Glu Leu Asn Val Thr
 65                  70                  75                  80

Leu Pro Glu Ala Glu Glu Leu Lys
                85

<210> SEQ ID NO 97
<211> LENGTH: 229
<212> TYPE: PRT
<213> ORGANISM: Arabidopsis thaliana

<400> SEQUENCE: 97

Met Ala Met Ser Ser Gly Thr Leu Arg Ile Ser Ala Thr Leu Val Ser
  1               5                  10                  15

Pro Tyr His His His His Arg Asn Arg Leu Ser Leu Pro Ser Ser Ser
                 20                  25                  30

Ser Lys Val Asp Phe Thr Gly Phe Ile Ser Asn Gly Val Asn Ser Leu
             35                  40                  45

Glu Thr Gln Lys Cys Thr Pro Gly Leu Ala Ile Ser Arg Glu Asn Thr
 50                  55                  60

Arg Gly Gln Val Lys Val Leu Ala Arg Asn Thr Gly Asp Tyr Glu Leu
 65                  70                  75                  80

Ser Pro Ser Pro Ala Glu Gln Glu Ile Glu Ser Phe Leu Tyr Asn Ala
                 85                  90                  95

Ile Asn Met Gly Phe Phe Asp Arg Leu Asn Leu Ala Trp Lys Ile Ile
                100                 105                 110

Phe Pro Ser His Ala Ser Arg Arg Ser Ser Asn Ala Arg Ile Ala Lys
            115                 120                 125

Gln Arg Leu Lys Met Ile Leu Phe Ser Asp Arg Cys Asp Val Ser Asp
130                 135                 140

Glu Ala Lys Arg Lys Ile Val Asn Asn Ile Ile His Ala Leu Ser Asp
145                 150                 155                 160

Phe Val Glu Ile Glu Ser Glu Glu Lys Val Gln Leu Asn Val Ser Thr
                165                 170                 175

Asp Gly Asp Leu Gly Thr Ile Tyr Ser Val Thr Val Pro Val Arg Arg
            180                 185                 190

Val Lys Pro Glu Tyr Gln Asp Val Asp Glu Ala Gly Thr Ile Thr Asn
        195                 200                 205

Val Glu Tyr Lys Asp Thr Arg Asp Gly Ser Val Asp Val Arg Phe Asp
210                 215                 220

Phe Tyr Val Pro Glu
225

<210> SEQ ID NO 98
<211> LENGTH: 63
<212> TYPE: PRT
<213> ORGANISM: S. elongatus

<400> SEQUENCE: 98

Leu Phe Glu Arg Leu Phe Pro Arg Gln Gln Ala Ser Arg Asp Thr Val
  1               5                  10                  15

Lys Gln Arg Leu Lys Leu Val Leu Ala His Asp Arg Ala Asp Leu Ser
                 20                  25                  30

Pro Glu Leu Leu Gln Lys Met Arg Gln Glu Ile Leu Glu Val Val Ser
             35                  40                  45

Arg Tyr Val Glu Leu Asp Ser Glu Gly Met Glu Leu Ser Leu Glu
 50                  55                  60
```

<210> SEQ ID NO 99
<211> LENGTH: 64
<212> TYPE: PRT
<213> ORGANISM: E. coli

<400> SEQUENCE: 99

Leu Leu Asp Phe Phe Leu Ser Arg Lys Lys Asn Thr Ala Asn Ile Ala
1               5                   10                  15

Lys Glu Arg Leu Gln Ile Ile Val Ala Glu Arg Arg Ser Asp Ala
            20                  25                  30

Glu Pro His Tyr Leu Pro Gln Leu Arg Lys Asp Ile Leu Glu Val Ile
        35                  40                  45

Cys Lys Tyr Val Gln Ile Asp Pro Glu Met Val Thr Val Gln Leu Glu
50                  55                  60

<210> SEQ ID NO 100
<211> LENGTH: 164
<212> TYPE: PRT
<213> ORGANISM: B. subtilis

<400> SEQUENCE: 100

Met Pro Leu Thr Pro Asn Asp Ile His Asn Lys Thr Phe Thr Lys Ser
1               5                   10                  15

Phe Arg Gly Tyr Asp Glu Asp Glu Val Asn Glu Phe Leu Ala Gln Val
            20                  25                  30

Arg Lys Asp Tyr Glu Ile Val Leu Arg Lys Lys Thr Glu Leu Glu Ala
        35                  40                  45

Lys Val Asn Glu Leu Asp Glu Arg Ile Gly His Phe Ala Asn Ile Glu
50                  55                  60

Glu Thr Leu Asn Lys Ser Ile Leu Val Ala Gln Glu Ala Ala Glu Asp
65                  70                  75                  80

Val Lys Arg Asn Ser Gln Lys Glu Ala Lys Leu Ile Val Arg Glu Ala
            85                  90                  95

Glu Lys Asn Ala Asp Arg Ile Ile Asn Glu Ser Leu Ser Lys Ser Arg
        100                 105                 110

Lys Ile Ala Met Glu Ile Glu Glu Leu Lys Lys Gln Ser Lys Val Phe
    115                 120                 125

Arg Thr Arg Phe Gln Met Leu Ile Glu Ala Gln Leu Asp Leu Leu Lys
    130                 135                 140

Asn Asp Asp Trp Asp His Leu Leu Glu Tyr Glu Val Asp Ala Val Phe
145                 150                 155                 160

Glu Glu Lys Glu

<210> SEQ ID NO 101

<400> SEQUENCE: 101

000

<210> SEQ ID NO 102

<400> SEQUENCE: 102

000

<210> SEQ ID NO 103
<211> LENGTH: 228
<212> TYPE: PRT

<213> ORGANISM: S. elongatus

<400> SEQUENCE: 103

```
Met Thr Gln Ala Gln Ser Leu Asp Val Leu Asn Leu Leu Glu Gln Leu
1               5                   10                  15

Glu Glu Ser Val Leu Asp Gly Thr Arg Val Pro Leu Ser Gly Arg Ile
            20                  25                  30

Leu Val Arg Glu Asn Asp Leu Leu Asp Leu Leu Asp Asp Val Arg Ala
        35                  40                  45

Gly Leu Pro Ala Ala Ile Gln Gln Ala Gln Gln Ile Leu Glu Arg Gln
    50                  55                  60

Ala Gln Ile Leu Ala Asp Ala Gln Gln Ala Gln Ala Ile Val Ala
65                  70                  75                  80

Gln Ala Gln Gln Glu Arg Ala Leu Leu Ile Asp Gln Asn Ser Ile Arg
                85                  90                  95

Leu Gln Ala Glu Arg Asp Ala Gln Gln Leu Arg Gln Thr Leu Gln Gln
            100                 105                 110

Glu Cys Asp Ala Leu Arg Gln Gln Ala Ile Ala Glu Ala Thr Gln Val
        115                 120                 125

Arg Gly Glu Ala Gln Gln Phe Gln Leu Gln Val Arg Gln Glu Thr Asp
    130                 135                 140

Ser Leu Arg Gln Gln Thr Gln Ala Glu Ile Glu Gln Leu Arg Ser Gln
145                 150                 155                 160

Thr Gln Gln Gln Leu Ser Gln Arg Gln Arg Ile Leu Val Glu Cys
                165                 170                 175

Glu Glu Leu Arg Arg Gly Ala Asp Ser Tyr Ala Asp Gln Val Leu Arg
            180                 185                 190

Asp Met Glu Gln Arg Leu Thr Gln Met Met Gln Ile Ile Arg Asn Gly
        195                 200                 205

Arg Gln Ala Leu Asn Leu Ser Glu Asn Thr Pro Pro Pro Ala Pro Arg
    210                 215                 220

Arg Arg Ser Arg
225
```

<210> SEQ ID NO 104
<211> LENGTH: 163
<212> TYPE: PRT
<213> ORGANISM: B. subtilis

<400> SEQUENCE: 104

```
Met Pro Leu Thr Pro Asn Asp Ile His Asn Lys Thr Phe Thr Lys Ser
1               5                   10                  15

Phe Arg Gly Tyr Asp Glu Asp Glu Val Asn Glu Phe Leu Ala Gln Val
            20                  25                  30

Arg Lys Asp Tyr Glu Ile Val Leu Arg Lys Thr Glu Leu Glu Ala Lys
        35                  40                  45

Val Asn Glu Leu Asp Glu Arg Ile Gly His Phe Ala Asn Ile Glu Glu
    50                  55                  60

Thr Leu Asn Lys Ser Ile Leu Val Ala Gln Glu Ala Glu Asp Val
65                  70                  75                  80

Lys Arg Asn Ser Gln Lys Glu Ala Lys Leu Ile Val Arg Glu Ala Glu
                85                  90                  95

Lys Asn Ala Asp Arg Ile Ile Asn Glu Ser Leu Ser Lys Ser Arg Lys
            100                 105                 110

Ile Ala Met Glu Ile Glu Glu Leu Lys Lys Gln Ser Lys Val Phe Arg
```

```
            115                 120                 125
Thr Arg Phe Gln Met Leu Ile Glu Ala Gln Leu Asp Leu Leu Lys Asn
    130                 135                 140

Asp Asp Trp Asp His Leu Leu Glu Tyr Glu Val Asp Ala Val Phe Glu
145                 150                 155                 160

Glu Lys Glu

<210> SEQ ID NO 105
<211> LENGTH: 39
<212> TYPE: PRT
<213> ORGANISM: S. elongatus

<400> SEQUENCE: 105

Asp Arg Trp Trp Leu Arg Leu Pro Ser Ala Pro Pro Val Gly Gln Glu
1               5                   10                  15

Ala Asn Ala Asp Gly Leu Thr Trp Leu Asp Leu Gln Gln Ser Leu Gln
            20                  25                  30

Gln Leu Leu Gln Gly Gln Glu
        35

<210> SEQ ID NO 106
<211> LENGTH: 39
<212> TYPE: PRT
<213> ORGANISM: E. coli

<400> SEQUENCE: 106

Asn Thr Pro Ile Glu Leu Lys Gly Ser Ser Phe Thr Leu Ser Val Val
1               5                   10                  15

His Leu His Glu Ala Glu Pro Lys Val Ile His Gln Ala Leu Glu Asp
            20                  25                  30

Lys Ile Ala Gln Ala Pro Ala
        35

<210> SEQ ID NO 107
<211> LENGTH: 39
<212> TYPE: PRT
<213> ORGANISM: B. subtilis

<400> SEQUENCE: 107

Gln Gln Tyr Val Thr Ile Lys Gly Thr Lys Asn Gly Leu Thr Leu His
1               5                   10                  15

Leu Asp Asp Ala Cys Ser Phe Asp Glu Leu Leu Asp Gly Leu Gln Asn
            20                  25                  30

Met Leu Ser Ile Glu Gln Tyr
        35

<210> SEQ ID NO 108
<211> LENGTH: 37
<212> TYPE: PRT
<213> ORGANISM: S. elongatus

<400> SEQUENCE: 108

Ile Asn Val Ala Arg Arg Leu Ser Gly Glu Ser Ile Asp Phe Leu Asn
1               5                   10                  15

Leu Glu Glu Pro Gln Ser Gly Val Leu Ser Lys Ile Arg Arg Ile Leu
            20                  25                  30

Asn Lys Lys Ile Leu
        35
```

```
<210> SEQ ID NO 109
<211> LENGTH: 31
<212> TYPE: PRT
<213> ORGANISM: E. coli

<400> SEQUENCE: 109

Ala Asp Thr Val Glu Arg Leu Leu Gly Glu Glu Arg Pro Phe Arg Phe
1               5                   10                  15

Ile Glu Glu Glu Lys Lys Gly Phe Leu Lys Arg Leu Phe Gly Gly
                20                  25                  30

<210> SEQ ID NO 110
<211> LENGTH: 36
<212> TYPE: PRT
<213> ORGANISM: B. subtilis

<400> SEQUENCE: 110

Arg Asn Ile Ala Arg Arg Ile Leu Gly Glu Ser Val Pro Leu Gln Val
1               5                   10                  15

Leu Glu Glu Gln Asn Lys Gly Met Met Ala Lys Ile Lys Ser Phe Phe
                20                  25                  30

Gly Val Arg Ser
            35

<210> SEQ ID NO 111
<211> LENGTH: 37
<212> TYPE: PRT
<213> ORGANISM: S. elongatus

<400> SEQUENCE: 111

Met Leu Ala Asp Leu Phe Glu Arg Leu Phe Pro Arg Gln Gln Ala Ser
1               5                   10                  15

Arg Asp Thr Val Lys Gln Arg Leu Lys Leu Val Leu Ala His Asp Arg
                20                  25                  30

Ala Asp Leu Ser Pro
            35

<210> SEQ ID NO 112
<211> LENGTH: 36
<212> TYPE: PRT
<213> ORGANISM: E. coli

<400> SEQUENCE: 112

Met Ala Leu Leu Asp Phe Phe Leu Ser Arg Lys Lys Asn Thr Ala Asn
1               5                   10                  15

Ile Ala Lys Glu Arg Leu Gln Ile Ile Val Ala Glu Arg Arg Arg Ser
                20                  25                  30

Asp Ala Glu Pro
            35
```